(12) United States Patent
Aslanian et al.

(10) Patent No.: US 7,884,080 B2
(45) Date of Patent: *Feb. 8, 2011

(54) AZETIDINONE DERIVATIVES AND METHODS OF USE THEREOF

(75) Inventors: Robert G. Aslanian, Rockaway, NJ (US); Chad E. Bennett, Metuchen, NJ (US); Duane A. Burnett, Bernardsville, NJ (US); Tin-Yau Chan, Edison, NJ (US); Eugenia Y. Kiselgof, Flemington, NJ (US); Chad E. Knutson, Garwood, NJ (US); Joel M. Harris, Summit, NJ (US); Brian A. McKittrick, New Vernon, NJ (US); Anandan Palani, Bridgewater, NJ (US); Elizabeth M. Smith, Verona, NJ (US); Henry M. Vaccaro, South Plainfield, NJ (US); Dong Xiao, Warren, NJ (US); Hyunjin M. Kim, Livingston, NJ (US)

(73) Assignee: Schering Plough Corporation, Kenilworth, NJ (US)

( * ) Notice: Subject to any disclaimer, the term of this patent is extended or adjusted under 35 U.S.C. 154(b) by 640 days.

This patent is subject to a terminal disclaimer.

(21) Appl. No.: 11/854,754

(22) Filed: Sep. 13, 2007

(65) Prior Publication Data

US 2008/0076751 A1 Mar. 27, 2008

Related U.S. Application Data

(60) Provisional application No. 60/845,075, filed on Sep. 15, 2006.

(51) Int. Cl.
C07D 471/10 (2006.01)
A61K 31/397 (2006.01)
A61P 3/06 (2006.01)
A61P 3/10 (2006.01)

(52) U.S. Cl. .................... 514/23; 514/210.05; 540/203; 536/29.2

(58) Field of Classification Search ................ 540/203; 514/210.05
See application file for complete search history.

(56) References Cited

U.S. PATENT DOCUMENTS

| | | | |
|---|---|---|---|
| 4,692,515 A * | 9/1987 | Georgiev et al. ............ 540/203 |
| 5,130,425 A * | 7/1992 | Malamas .................... 540/203 |
| 5,215,994 A | 6/1993 | Oku et al. |
| 5,354,759 A | 10/1994 | Oku et al. |
| 5,624,920 A | 4/1997 | McKittrick et al. |
| 5,631,356 A | 5/1997 | Smeets et al. |
| 5,633,246 A | 5/1997 | McKittrick et al. |
| 5,648,484 A * | 7/1997 | Wu ............................ 540/203 |
| 5,656,624 A | 8/1997 | Vaccaro et al. |
| 5,688,787 A | 11/1997 | Burnett et al. |
| 5,698,548 A * | 12/1997 | Dugar et al. ........... 514/210.02 |
| 5,756,470 A | 5/1998 | Yumibe et al. |
| 5,767,115 A | 6/1998 | Rosenblum et al. |
| 5,846,966 A | 12/1998 | Rosenblum et al. |
| 6,022,409 A | 2/2000 | Coquerel et al. |
| 6,140,317 A | 10/2000 | Traxler et al. |
| 6,302,837 B1 | 10/2001 | De Nanteuil et al. |
| 6,992,067 B2 | 1/2006 | Glombik et al. |
| 7,045,515 B2 | 5/2006 | Tomiyama et al. |
| 7,165,943 B2 | 1/2007 | Suzuki et al. |
| 7,291,728 B2 * | 11/2007 | Marin et al. ................. 540/203 |
| 7,297,788 B2 * | 11/2007 | Marin et al. ................. 540/203 |
| 7,342,039 B2 | 3/2008 | Havran et al. |
| 7,638,526 B2 * | 12/2009 | McKittrick et al. ......... 514/278 |
| 2004/0122033 A1 | 6/2004 | Nargund et al. |
| 2004/0229844 A1 | 11/2004 | Cheng et al. |
| 2005/0089935 A1 | 4/2005 | Cai et al. |
| 2005/0096307 A1 | 5/2005 | Graziano |
| 2005/0239820 A1 | 10/2005 | Borzilleri et al. |
| 2008/0070888 A1 * | 3/2008 | McKittrick et al. .... 514/210.02 |
| 2008/0070889 A1 * | 3/2008 | Burnett et al. ......... 514/210.04 |
| 2008/0070890 A1 * | 3/2008 | Burnett et al. ......... 514/210.05 |
| 2008/0070892 A1 * | 3/2008 | Harris et al. ........... 514/210.16 |
| 2008/0076750 A1 * | 3/2008 | Aslanian et al. ........ 514/210.02 |

FOREIGN PATENT DOCUMENTS

| | | |
|---|---|---|
| JP | 3239506 | 10/2001 |
| WO | WO 94/17038 | 8/1994 |
| WO | WO 95/08522 A1 | 3/1995 |

(Continued)

OTHER PUBLICATIONS

Alonso et al., "Spiro β-Lactams as β-Turn Mimetics. Design, Synthesis, and NMR Conformational Analysis", J. Org. Chem. 66(19):6333-6338, (2001).

(Continued)

Primary Examiner—Mark L Berch
(74) Attorney, Agent, or Firm—Sylvia A. Ayler; Gerard M. Devlin

(57) ABSTRACT

The present invention relates to Azetidinone Derivatives of structural formula 1:

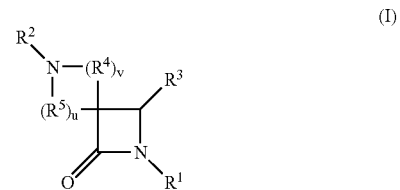

(I)

and compositions comprising an Azetidinone Derivative and methods for treating or preventing a disorder of lipid metabolism, pain, diabetes, a vascular condition, demyelination or nonalcoholic fatty liver disease, comprising administering to a patient an effective amount of an Azetidinone Derivative.

23 Claims, No Drawings

FOREIGN PATENT DOCUMENTS

| WO | WO 96/19450 A1 | 6/1996 |
| --- | --- | --- |
| WO | WO 02/30695 A1 | 4/2002 |
| WO | WO 02/066464 A1 | 8/2002 |
| WO | WO 03/010140 A2 | 2/2003 |
| WO | WO 2004/087714 A1 | 10/2004 |
| WO | WO 2004/110375 A2 | 12/2004 |
| WO | WO 2005/000217 A2 | 1/2005 |
| WO | WO 2005/105213 A2 | 11/2005 |
| WO | WO 2006/019831 A1 | 2/2006 |

OTHER PUBLICATIONS

Bittermann et al., "Chirospecific Synthesis of Spirocyclic β-Lactams and Their Characterization as Potent Type II β-Turn Inducing Peptide Mimetics", J. Org. Chem. 71:97-102, (2006).

Cignarella et al., "Synthesis of a new series of 2,7-diazaspiro[3.5]nonan-1-ones and study of their cholinergic properties", Eur J Med Chem 29:115-120, (1994).

Clayden et al., "Cyclization of Lithiated Pyridine and Quinoline Carboxamides: Synthesis of Partially Saturated Pyrrolopyridines and Spirocyclic β-Lactams", Organic Letters 7 (l7):3673-3676, (2005).

Khasanov et al., "Novel Asymmetric Approach to Proline-Derived Spiro-β-Lactams", J. Org. Chem. 69(17):5766-5769, (2004).

Macias et al., "Diastereoselective [2+2]-Cycloaddition Reactions of Unsymmetrical Cyclic ketenes with Imines: Synthesis of Modified Prolines and Theoretical Study of the Reaction Mechanism", J. Org. Chem. 69:7004-7012, (2004).

Macias et al., "Synthesis of Enantiopure Pyrrolidine-Derived Peptidomimetics and Oligo-β-peptides via Nucleophilic Ring-Opening of β-Lactams", J. Org. Chem. 71:7721-7730, (2004).

Overman et al., "A Convenient Synthesis of 4-Unsubstituted β-Lactams", J. Am. Chem. Soc. 107:1698-1701, (1985).

PCT International Search Report dated Mar. 31, 2008 for corresponding PCT Application No. PCT/US2007/019930.

* cited by examiner

AZETIDINONE DERIVATIVES AND METHODS OF USE THEREOF

REFERENCE TO PRIOR APPLICATIONS

This application claims the benefit of priority from U.S. provisional patent application No. 60/845,075, filed Sep. 15, 2006, which is incorporated herein by reference in its entirety.

FIELD OF THE INVENTION

The present invention relates to Azetidinone Derivatives, compositions comprising an Azetidinone Derivative, and methods for treating or preventing a disorder of lipid metabolism, pain, diabetes, a vascular condition, demyelination or nonalcoholic fatty liver disease, comprising administering to a patient an effective amount of an Azetidinone Derivative.

BACKGROUND

Treatment of chronic pain, particularly inflammatory and neuropathic pain, is an area of unmet medical need. Neuropathic pain is nerve injury resulting in hyperexcitability of neurons involved in pain sensation. T-currents are present in neurons of pain pathways. T-type calcium channel blockers are effective in preclinical models of neuropathic pain. Transient receptor potential V1 (TRPV1) is a nonspecific cation channel, activation of which can lead to pain, in particular inflammatory pain, and hyperalgesia, as well as playing a role in cough and bladder function.

Type II diabetes, also known as non-insulin dependent diabetes mellitus, is a progressive disease characterized by impaired glucose metabolism resulting in elevated blood glucose levels. Patients with type II diabetes exhibit impaired pancreatic beta-cell function resulting in failure of the pancreatic beta-cells to secrete an appropriate amount of insulin in response to a hyperglycemic signal, and resistance to the action of insulin at its target tissues (insulin resistance).

Current treatments of type II diabetes aim to reverse insulin resistance, control intestinal glucose absorption, normalise hepatic glucose productions and improve beta-cell glucose sensing and insulin secretion. The sulfonylurea class of oral antihyperglycemic agents promote insulin secretion from pancreatic beta-islet cells, but have the potential to cause hypoglycemia as their action is independent of glucose levels. Antihyperglycemic agents include: insulin sensitizers that reduce hepatic glucose production by inhibiting gluconeogenesis; α-glucosidase inhibitors that inhibit breakdown of complex carbohydrates thus delaying glucose absorption and dampening postprandial glucose and insulin peaks; and thiazolidinediones that improve the action of insulin and reduce insulin resistance. Over time approximately one-half of type II diabetes patients lose their response to these agents. Because of the shortcomings of current treatments, new treatments for type II diabetes are highly desirable.

GPR119 is a constitutively active G-protein coupled receptor expressed predominantly in pancreatic beta-islet cells. Activation of GPR119 by an agonist increases insulin release from pancreatic beta-islet cells in a glucose dependent manner. Thus an agonist of GPR119 offers the potential to normalize blood glucose levels in a type II diabetic patient in response to post-prandial blood glucose elevation, but would not be expected to stimulate insulin release in the pre-prandial or fasted state.

Niemann-Pick C1-like (NPC1L1) has been identified as a critical mediator of cholesterol absorption. It has been determined that the cholesterol absorption inhibitor ezetimibe targets NPC1 L1.

The treatment of disorders of lipid metabolism, diabetes, vascular conditions, demyelination and nonalcoholic fatty liver disease with azetidinone derivatives has been disclosed. Azetidinone derivatives that inhibit cholesterol absorption in the small intestine are well known in the art and are described, for example, in U.S. RE 37,721; U.S. Pat. No. 5,631,356; U.S. Pat. No. 5,767,115; U.S. Pat. No. 5,846,966; U.S. Pat. No. 5,698,548; U.S. Pat. No. 5,633,246; U.S. Pat. No. 5,656,624; U.S. Pat. No. 5,624,920; U.S. Pat. No. 5,688,787; U.S. Pat. No. 5,756,470; US Publication No. 2002/0137689; WO 02/066464; WO 95/08522 and WO96/19450. Each of the aforementioned publications is incorporated by reference. The art indicates that these compounds are useful in treating, for example, atherosclerotic coronary disease, either by administrating these compounds alone or with a second compound such as a cholesterol biosynthesis inhibitor.

WO 2005/000217 describes combination therapies for the treatment of dyslipidemia comprising the administration of a combination of an anti-obesity agent and an anti-dyslipidemic agent. WO 2004/110375 describes combination therapies for the treatment of diabetes comprising the administration of a combination of an anti-obesity agent and an anti-diabetic agent. US 2004/0122033 describes combination therapies for the treatment of obesity comprising the administration of a combination of an appetite suppressant and/or metabolic rate enhancers and/or nutrient absorption inhibitors. US 2004/0229844 describes combination therapies for treating atherosclerosis comprising the administration of a combination of nicotinic acid or another nicotinic acid receptor agonist and a DP receptor antagonist. Also known is a method for treating nonalcoholic fatty liver disease in a mammal by administering an effective amount of therapeutic composition comprising at least one cholesterol lowering agent and/or at least one $H_3$ receptor antagonist/inverse agonist.

SUMMARY OF THE INVENTION

The present invention is related to Azetidinone Derivatives, compositions comprising an Azetidinone Derivative, and methods for using the Azetidinone Derivatives.

Accordingly, in one aspect, the invention provides compounds having the formula:

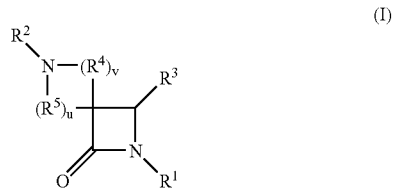

(I)

and pharmaceutically acceptable salts, solvates, esters, prodrugs or stereoisomers thereof, wherein:

$R^1$ is H, alkyl, aryl, arylalkyl, heteroaryl, heteroarylalkyl, diphenylmethyl, cycloalkylalkyl, cycloalkyl, cycloalkenyl, heterocycloalkyl, heterocycloalkenyl or -alkylene-C(O)N(alkyl)$_2$, wherein an alkyl aryl or heteroaryl group can be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH$_2$, —SO$_2$NH(alkyl), —SO$_2$N(alkyl)$_2$, —CF$_3$, —OH, -halo, —CN, -alkoxy, —CO(O)-alkyl, —S(O)alkyl, —SO$_2$-alkyl, or —P(O)(O-alkyl)$_2$, and an aryl group may further be optionally and independently substituted with one or more alkyl groups;

$R^2$ is H, alkyl, cycloalkyl, aryl, arylalkyl, heteroarylalkyl, heterocycloalkyl, heterocycloalkylalkyl, $R^6$-A-, alkyl-O—C(O)—, (alkyl)$_2$N-alkylene-C(O)—, (alkyl)$_2$-N—C(O)-alkylene-C(O)—, CN-alkylene-C(O)—, alkyl-O-alkylene-C(O)—, alkyl-C(O)-alkylene-C(O)—, alkyl-C(O)—NH-alkylene-C(O)—, alkyl-NH—C(O)—, aryl-NH—C(O)—, alkyl-O—C(O)-alkylene-C(O)—, alkyl-O—C(O)-cycloalkylene-alkylene-, NH$_2$—C(O)—NH-alkylene-C(O)—, NH$_2$—C(O)-alkylene-C(O)—, alkyl-C(O)—NH-alkylene-S-alkylene-C(O)—, alkyl-O—C(O)-alkylene-C(O)—, alkyl-S-alkylene-C(O)—, alkyl-C(O)-cycloalkylene-alkylene-C(O)—, alkyl-S-alkylene-, (—NHC(O)alkyl)-C(O)—, alkyl(-C(O)Oalkyl)-NH—C(O)—, or —C(O)-alkylene-N(R$^6$)$_2$—; or alkyl-S-alkylene(-NHC(O)alkyl)-C(O)—, wherein an alkyl or aryl group can be optionally and independently substituted with one or more of the following groups: —(C=N—O-alkyl)CH$_3$, —NH—C(O)NH-alkyl, —C(O)NH$_2$, —CN, —C(O)NH-alkyl, —C(O)O-alkyl, —C(O)H, —C(O)OH, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, haloalkyl, —CN, -alkoxy, —C(O)O-alkyl, —S(O)alkyl, —SO$_2$-alkyl, or —P(O)(O-alkyl)$_2$, and an aryl group may further be optionally and independently substituted with one or more alkyl groups;

$R^3$ is H, alkyl, aryl, arylalkyl, arylalkenyl, arylalkynyl, NH-arylalkyl, arylalkoxy, arylthio, arylalkylthio, arylcarbonyl, aryloxy, cycloalkyl, arylsulfonyl, heteroaryl, heteroarylalkyl, heteroarylalkenyl, heteroarylalkynyl, heteroarylalkoxy, heteroaryloxy or heteroarylsulfonyl, wherein an alkyl or aryl group can be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$, an aryl group can be optionally and independently substituted with one or more alkyl groups, and a heteroaryl group can be optionally and independently substituted with one or more aryl or heteroaryl groups.

each occurrence of $R^4$ and $R^5$ is independently —C(R$^7$)$_2$—, wherein the ring carbon atom of one $R^4$ group and the ring carbon atom of one $R^5$ group may optionally be joined by a —CH$_2$—CH$_2$— group;

each occurrence of $R^6$ is independently alkyl, alkenyl, aryl, heteroaryl, cycloalkyl, cycloalkylalkyl, heterocycloalkyl, cycloalkenyl, heterocycloalkenyl, benzofused cycloalkyl, benzofused heterocycloalkyl, or benzofused heterocycloalkenyl;

each occurrence of $R^7$ is independently —H, -alkyl, —CN, or —OH;

A is —C(O)—, —OC(O)—, -alkylene-C(O)—, —O-alkylene-C(O)—, —C(O)-alkylene-C(O)—, —C(O)—NHCH$_2$—C(O)—, —C(O)—N(alkyl)-CH$_2$—C(O)—, -alkylene-, -alkenylene-, -alkenylene-C(O)—, —O—C(O)-alkylene-C(O), -cycloalkylene-NH—C(O)—, —NHC(O)—, -alkylene-NHC(O)—, -alkylene-C(O)NH-alkylene-C(O)—, -alkylene-C(O)NH-alkylene-C(O)—, —C(O)—NH-alkylene-C(O)—, -alkylene-O-alkylene-C(O)—, -alkylene(alkoxy)-C(O)— or —S-alkylene-C(O)—, wherein an A group is joined to the nitrogen atom to which it is attached via a terminal C(O) group;

u is an integer ranging from 0 to 3; and v is an integer ranging from 0 to 3; such that the sum of u and V is from 3 to 5, such that the compound of formula (I) is not a compound of formula (IA), (IB), (IC) or (ID) as set forth below:

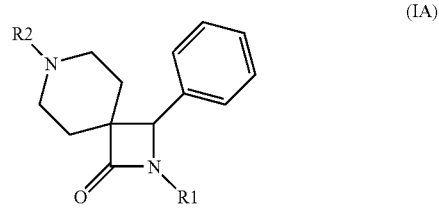

(IA)

wherein $R^1$ and $R^2$ are denoted using an "X" as set forth below in Table 1, and defined below in Tables 5 and 6, respectively.

TABLE 1

| R2 | R1 | | | | | | | | | | | |
|---|---|---|---|---|---|---|---|---|---|---|---|---|
|  | 1 | 2 | 3 | 4 | 5 | 6 | 8 | 9 | 10 | 11 | 7 | 12 |
| 1 | X | X | X | X | X | X | X | X | X | X | X | X |
| 2 | X | X | X | X | X | X | X | X | | | | |
| 3 | X | X | X | X | X | X | X | X | | | | |
| 4 | X | X | X | X | X | X | X | X | X | | X | X |
| 5 | X | X | | X | X | | X | X | | | | |
| 6 | X | X | X | X | X | X | X | X | X | X | X | X |
| 7 | X | X | X | X | X | X | X | X | | | | |
| 8 | X | X | X | X | | | X | X | X | X | X | X |
| 9 | X | X | | | X | X | X | X | | | | |
| 10 | X | X | X | X | | X | X | X | | | | |
| 11 | X | X | X | X | X | X | X | X | | | | |
| 12 | X | X | X | X | | X | X | X | | | | |
| 13 | X | X | | | X | | X | X | | | | |
| 14 | X | X | | X | X | X | X | X | | | | |
| 15 | X | X | X | X | X | X | X | X | | | | |
| 16 | X | X | X | X | X | | X | X | | | | |
| 17 | X | X | X | | X | X | X | X | | | | |
| 18 | X | X | | X | X | X | X | X | | | | |
| 19 | X | X | X | X | X | X | X | X | | | | |
| 20 | X | X | X | X | X | X | X | X | | | | |
| 21 | X | X | X | X | X | X | X | X | | | | |
| 22 | X | X | X | X | X | X | X | X | X | X | X | X |
| 23 | X | X | X | X | X | X | X | X | | | | |
| 24 | X | X | X | X | X | X | X | X | | | | |
| 25 | X | X | X | X | X | X | X | X | | | | |
| 26 | X | X | X | X | X | X | X | X | X | X | X | X |
| 27 | X | X | X | X | X | X | X | X | | | | |
| 28 | X | X | X | X | X | X | X | X | X | X | X | X |
| 29 | X | X | X | X | X | X | X | X | | | | |
| 30 | X | X | | | X | | X | X | X | X | X | X |
| 31 | X | X | X | X | X | | X | X | | | | |
| 32 | X | X | X | X | X | | X | X | | | | |
| 33 | X | X | X | | | X | X | X | | | | |
| 34 | X | X | | X | X | X | X | X | | | | |
| 35 | X | X | X | X | X | X | X | X | X | X | X | X |
| 36 | X | X | X | X | X | X | X | X | | | | |
| 37 | X | X | X | X | X | X | X | X | | | | |
| 38 | X | X | X | X | X | X | X | X | X | X | X | X |
| 39 | X | X | X | X | X | X | X | X | | | | |
| 40 | X | X | X | X | X | X | X | X | | | | |
| 41 | X | X | X | X | X | X | X | X | | | | |
| 42 | X | X | X | | X | X | X | X | | | | |
| 43 | X | X | | X | X | | X | X | X | | X | X |
| 44 | X | X | X | X | X | X | X | X | | | | |
| 45 | X | X | X | X | X | X | X | X | | | | |
| 46 | X | X | X | X | X | X | X | X | | | | |
| 47 | X | X | X | X | X | X | X | X | | | | |

TABLE 1-continued

| R2 | 1 | 2 | 3 | 4 | 5 | 6 | 8 | 9 | 10 | 11 | 7 | 12 |
|---|---|---|---|---|---|---|---|---|---|---|---|---|
| 48 | X | X | X | X | X | X | X | X | | | | |
| 49 | X | X | X | | X | X | X | X | | | | |
| 50 | X | X | X | | X | X | X | X | | | | |
| 51 | X | X | X | X | X | X | X | X | | | | |
| 52 | X | X | X | X | X | X | X | X | X | X | X | X |
| 53 | X | X | X | X | X | X | X | X | | | | |
| 54 | X | X | | X | | | X | X | | | | |
| 55 | X | X | X | X | X | | X | X | X | X | X | X |
| 56 | X | X | X | X | | X | X | X | X | X | X | X |
| 57 | X | X | | | X | X | X | X | | | | |
| 58 | X | X | X | X | X | X | X | X | | | | |
| 59 | X | X | | X | X | X | X | X | | | | |
| 60 | X | X | | X | X | X | X | X | | | | |
| 61 | X | X | X | X | X | X | X | X | | | | |
| 62 | X | X | X | X | X | X | X | X | | | | |
| 63 | X | X | X | X | X | X | X | X | X | X | X | X |
| 64 | X | X | X | X | X | X | X | X | | | | |
| 65 | X | X | X | X | X | X | X | X | | | | |
| 66 | X | X | X | X | X | X | X | X | | | | |
| 67 | X | X | X | X | X | X | X | X | X | X | X | X |
| 68 | X | X | X | X | X | X | X | X | X | X | X | X |
| 69 | X | X | X | X | X | X | X | X | | | | |
| 70 | X | X | X | X | X | X | X | X | | | | |
| 71 | X | X | X | X | X | X | X | X | | | | |
| 72 | X | X | X | X | X | X | X | X | X | X | X | X |
| 73 | X | X | X | X | X | X | X | X | | | | |
| 74 | X | X | X | X | X | X | X | X | | | | |
| 75 | X | X | X | X | X | X | X | X | | | | |
| 76 | X | X | X | X | X | X | X | X | X | X | X | X |
| 77 | X | X | X | X | X | X | X | X | | | | |
| 78 | X | X | X | X | X | X | X | X | | | | |
| 79 | X | X | X | X | X | X | X | X | | | | |
| 80 | X | X | X | X | X | X | X | X | | | | |
| 81 | X | X | X | X | X | X | X | X | | | | |
| 82 | X | X | X | X | X | X | X | X | | | | |
| 83 | X | X | X | X | X | X | X | X | | | | |
| 84 | X | X | X | X | X | X | X | X | | | | |
| 85 | X | X | X | X | X | X | X | X | | | | |
| 86 | X | X | X | X | X | X | X | X | | | | |
| 87 | X | X | X | X | X | X | X | X | | | | |
| 88 | X | X | X | X | X | X | X | X | | | | |
| 133 | X | X | X | X | X | X | X | X | | X | | X |
| 134 | X | X | X | X | X | X | X | X | | X | X | X |
| 135 | X | X | X | X | X | X | X | X | | X | X | X |
| 136 | X | X | X | X | | X | | X | X | | | |
| 137 | X | X | X | X | | X | X | X | X | X | X | X |
| 138 | X | X | X | X | | | X | X | X | X | X | X |
| 139 | X | X | X | | X | | X | X | | | | |
| 140 | X | X | X | X | | X | X | X | | | | |
| 141 | X | X | X | | X | X | X | X | | | | |
| 142 | X | X | X | X | | X | X | X | | | | |
| 143 | X | X | X | X | X | X | X | X | X | X | X | X |
| 144 | X | X | X | X | X | X | X | X | | | | |
| 145 | X | X | X | X | X | X | X | X | | | | |
| 146 | X | X | X | X | X | X | X | X | X | X | X | X |
| 147 | X | X | X | X | | | X | X | X | X | X | X |
| 148 | X | X | X | X | | X | X | X | X | X | X | X |
| 149 | X | X | X | | X | X | X | X | | | | |
| 150 | X | X | X | X | X | X | X | X | X | X | X | X |
| 151 | X | X | X | X | X | X | X | X | | | | |
| 152 | X | X | X | X | X | X | X | X | | | | |
| 153 | X | X | X | X | X | X | X | X | X | X | X | X |
| 154 | X | X | X | X | X | X | X | X | X | X | X | X |
| 155 | X | X | X | X | X | X | X | X | | | | |
| 156 | X | X | X | X | X | X | X | X | | | | |
| 157 | X | X | X | X | X | X | X | X | | | | |
| 158 | X | X | X | | X | X | X | X | | | | |
| 159 | X | X | X | | X | X | X | X | | | | |
| 160 | X | X | X | X | X | X | X | X | | | | |
| 161 | X | X | X | X | X | X | X | X | | | | |
| 162 | X | X | X | X | X | X | X | X | | | | |
| 163 | X | X | X | X | X | X | X | X | X | X | X | X |
| 164 | X | X | X | X | X | X | X | X | | | | |
| 165 | X | X | X | X | X | X | X | X | | | | |
| 166 | X | X | X | X | X | X | X | X | | | | |
| 167 | X | X | X | X | X | X | X | X | | | | |
| 168 | X | X | X | X | X | X | X | X | | | | |
| 169 | X | X | X | X | X | X | X | X | | | | |
| 170 | X | X | X | X | X | X | X | X | | | | |
| 171 | X | X | X | | X | X | X | X | | | | |
| 172 | X | X | X | X | X | X | X | X | X | X | X | X |
| 173 | X | X | X | X | X | X | X | X | | | | |
| 174 | X | X | X | | X | X | X | X | | | | |
| 175 | X | X | X | | X | X | X | X | | | | |
| 176 | X | X | X | X | X | X | X | X | | | | |
| 177 | X | X | | X | X | X | X | X | X | X | X | X |
| 178 | X | | | | X | X | | X | | X | X | X |
| 179 | X | | X | X | X | X | X | X | | X | X | X |
| 180 | X | X | X | | | | | X | X | X | X | X |
| 181 | X | X | X | X | X | X | X | X | | X | X | X |
| 182 | X | X | X | X | X | X | X | X | X | X | X | X |
| 183 | X | X | X | X | | X | X | X | X | X | X | X |
| 184 | X | X | X | X | X | X | X | X | X | X | X | X |
| 185 | X | X | X | | | X | X | | | X | X | |
| 186 | X | X | X | X | X | X | X | X | X | X | X | X |
| 187 | X | X | | X | | | X | X | | X | X | X |
| 188 | X | X | X | X | | X | X | X | | X | X | X |
| 189 | X | X | X | X | X | X | X | X | X | X | X | X |
| 190 | X | X | X | X | X | X | X | X | X | X | X | X |
| 191 | X | X | X | X | X | X | X | X | | X | X | X |
| 192 | X | X | X | X | | X | X | X | X | X | X | X |
| 193 | X | X | X | X | | X | X | X | | | X | |
| 194 | X | X | X | X | | X | X | X | X | X | X | X |
| 195 | X | X | X | X | | X | X | X | | X | X | |
| 196 | X | X | X | X | X | X | X | X | | X | X | X |
| 197 | X | X | X | X | | X | X | X | X | X | X | X |
| 198 | X | X | | | | X | X | | | | X | |
| 199 | X | X | X | X | | X | X | X | | | X | X |
| 200 | X | X | | X | X | X | X | X | | X | X | X |
| 201 | X | X | X | X | | X | X | X | X | X | X | X |
| 202 | X | X | X | X | | X | X | X | | X | X | X |
| 203 | X | X | X | X | X | X | X | X | | X | X | X |
| 204 | X | X | X | X | X | X | X | X | X | X | X | X |
| 205 | X | X | | X | | | X | | | | X | X |
| 206 | X | X | | X | | | X | X | | | X | |
| 207 | X | X | | X | | | X | | | | X | |
| 208 | X | X | | X | | X | X | X | | | X | X |
| 209 | | X | | X | | | X | | | X | X | |
| 213 | | | | X | | X | X | | | X | | X |
| 214 | | | X | X | X | | | X | | X | X | X |
| 210 | | | X | X | X | | X | X | | X | X | X |
| 211 | | X | | | | | X | X | | | X | |
| 215 | | X | | | X | X | | X | X | | X | X |
| 216 | | X | | X | | | X | X | X | | X | X |
| 212 | | | | | | | | | | | X | X |
| 217 | X | X | X | X | X | X | X | X | X | X | X | X |
| 218 | X | X | X | X | X | X | X | X | X | X | X | X |
| 219 | X | X | X | X | X | X | X | X | X | X | X | X |
| 220 | X | X | X | | X | X | X | X | X | X | X | X |
| 221 | X | X | X | | X | X | X | X | X | X | X | X |
| 222 | X | X | X | X | | X | X | | X | X | X | X |
| 223 | X | | | | | | X | | | X | X | X |
| 224 | X | | | X | | | X | | | X | X | X |
| 225 | X | | | | | | X | | | X | X | X |
| 233 | | | | | | | | | | X | | X |
| 227 | | | X | | X | X | | X | | X | X | X |
| 228 | | | X | | | X | | X | | X | X | X |
| 230 | | | X | | X | X | X | | | X | | X |
| 232 | | | X | | X | X | | | | X | | X |
| 229 | | | | | X | X | | | | X | X | X |
| 231 | | | X | | | X | | | | X | | X |
| 234 | | | | X | X | X | X | X | | X | | |
| 226 | | X | | | X | | | X | | | X | X |
| 235 | | X | | | | | | | | | | |
| 236 | | | | | X | X | X | | | | X | |
| 237 | | | | | | | | | X | X | X | X |
| 238 | | | | | | | | | X | X | X | X |
| 239 | | | | | | | | | X | X | X | X |
| 240 | | | | | | | | | X | X | X | X |
| 242 | | | | | | | | | X | X | X | X |

TABLE 1-continued

| R2 | \multicolumn{12}{c}{R1} |
|---|---|---|---|---|---|---|---|---|---|---|---|---|
| | 1 | 2 | 3 | 4 | 5 | 6 | 8 | 9 | 10 | 11 | 7 | 12 |
| 243 | | | | | | | | | X | X | X | X |
| 244 | | | | | | | | | X | X | X | X |
| 245 | | | | | | | | | X | X | X | X |
| 246 | | | | | | | | | X | X | X | X |
| 247 | | | | | | | | | X | X | X | X |
| 248 | | | | | | | | | X | X | X | X |
| 249 | | | | | | | | | X | X | X | X |
| 250 | | | | | | | | | X | X | X | X |
| 299 | | | | | | | | | X | X | X | X |
| 251 | | | | | | | | | X | X | X | X |
| 300 | | | | | | | | | X | | X | X |
| 252 | | | | | | | | | X | X | X | X |
| 253 | | | | | | | | | X | X | X | X |
| 254 | | | | | | | | | X | X | X | X |
| 255 | | | | | | | | | X | X | X | X |
| 256 | | | | | | | | | X | X | X | X |
| 257 | | | | | | | | | X | X | X | X |
| 258 | | | | | | | | | X | X | X | X |
| 259 | | | | | | | | | X | X | X | X |
| 260 | | | | | | | | | X | X | X | X |
| 261 | | | | | | | | | X | X | X | X |
| 262 | | | | | | | | | X | X | X | X |
| 263 | | | | | | | | | X | X | X | X |
| 264 | | | | | | | | | X | X | X | X |
| 265 | | | | | | | | | X | X | X | X |
| 286 | | | | | | | | | X | X | X | X |
| 267 | | | | | | | | | X | X | X | X |
| 268 | | | | | | | | | X | X | X | X |
| 269 | | | | | | | | | X | X | X | X |
| 270 | | | | | | | | | X | X | X | X |
| 271 | | | | | | | | | X | X | X | X |
| 272 | | | | | | | | | X | X | X | X |
| 273 | | | | | | | | | X | X | X | X |
| 274 | | | | | | | | | X | X | X | X |
| 276 | | | | | | | | | X | X | X | X |
| 277 | | | | | | | | | X | X | X | X |
| 278 | | | | | | | | | X | X | X | X |
| 279 | | | | | | | | | X | X | X | X |
| 280 | | | | | | | | | X | X | X | X |
| 281 | | | | | | | | | X | X | X | X |
| 282 | | | | | | | | | X | X | X | X |
| 283 | | | | | | | | | X | X | X | X |
| 285 | | | | | | | | | X | X | X | X |
| 286 | | | | | | | | | X | X | X | X |
| 287 | | | | | | | | | X | X | X | X |
| 288 | | | | | | | | | X | X | X | X |
| 289 | | | | | | | | | X | X | X | X |
| 290 | | | | | | | | | X | X | X | X |
| 291 | | | | | | | | | X | X | X | X |
| 292 | | | | | | | | | X | X | x | x |
| 293 | | | | | | | | | X | X | X | X |
| 294 | | | | | | | | | X | X | X | X |
| 295 | | | | | | | | | X | X | X | X |
| 296 | | | | | | | | | X | X | X | X |
| 297 | | | | | | | | | X | X | X | X |
| 298 | | | | | | | | | X | X | X | X |
| 241 | | | | | | | | | | X | X | X |
| 303 | | | | | | | | | | X | X | X |
| 284 | | | | | | | | | | X | X | X |
| 301 | | | | | | | | | | | X | X |
| 275 | | | | | | | | | | | X | X |
| 302 | | | | | | | | | | | X | X |
| 304 | | | | | | | | | | | X | X |
| 305 | | | | | | | | | | | X | X |
| 334 | | | | | | X | | | X | X | X | X |
| 360 | | | | | | X | | | X | X | X | |
| 335 | | | | | | X | | | X | X | X | X |
| 336 | | | | | | X | | | X | X | X | X |
| 337 | | | | | | X | | | X | X | X | X |
| 338 | | | | | | X | | | X | X | X | X |
| 339 | | | | | | X | | | X | X | X | X |
| 340 | | | | | | X | | | X | X | X | X |
| 341 | | | | | | X | | | X | X | X | X |
| 342 | | | | | | X | | | X | X | X | X |
| 343 | | | | | | X | | | X | X | X | X |
| 344 | | | | | | X | | | X | X | X | X |
| 345 | | | | | | X | | | X | X | X | X |
| 346 | | | | | | X | | | X | X | X | |
| 347 | | | | | | X | | | X | X | X | X |
| 348 | | | | | | X | | | X | X | X | X |
| 349 | | | | | | X | | | X | X | X | X |
| 350 | | | | | | X | | | X | X | X | X |
| 351 | | | | | | X | | | X | X | X | X |
| 352 | | | | | | X | | | X | X | X | X |
| 353 | | | | | | X | | | X | X | X | X |
| 354 | | | | | | X | | | X | X | X | X |
| 355 | | | | | | X | | | X | X | X | X |
| 356 | | | | | | X | | | X | X | X | |
| 361 | | | | | | X | | | X | X | | X |
| 362 | | | | | | | | | X | X | X | X |
| 357 | | | | | | X | | | X | X | X | X |
| 358 | | | | | | X | | | X | X | X | X |
| 359 | | | | | | X | | | X | X | X | X |
| 363 | | | | | | X | | | | X | | X |
| 364 | X | X | X | X | X | X | X | X | X | X | X | X |
| 365 | X | X | X | X | X | X | X | X | X | X | X | X |
| 366 | X | X | X | X | X | X | X | X | X | X | X | X |
| 367 | X | X | X | X | X | X | X | X | X | X | X | X |
| 368 | X | X | X | X | X | X | X | X | X | X | X | X |
| 369 | X | X | X | X | X | X | X | X | X | X | X | X |
| 370 | X | X | X | X | X | X | X | X | X | X | X | X |
| 371 | X | X | X | X | X | X | X | X | X | X | X | X |
| 372 | X | X | X | X | X | X | X | X | X | X | X | X |
| 373 | X | X | X | X | X | X | X | X | X | X | X | X |
| 374 | X | X | X | X | X | X | X | X | X | X | X | X |
| 375 | X | X | X | X | X | X | X | | | X | X | X |
| 376 | X | X | X | X | X | X | X | X | X | X | X | X |
| 377 | X | X | X | X | X | X | X | | X | X | X | X |
| 378 | X | X | X | X | X | X | X | X | X | X | X | X |
| 379 | X | X | X | X | X | X | X | X | X | X | X | X |
| 380 | X | X | X | X | X | X | X | X | X | X | X | X |
| 381 | X | X | X | X | X | X | X | X | X | X | X | X |
| 382 | X | X | X | X | X | X | X | | X | | X | X |
| 383 | X | X | X | X | X | X | X | X | X | X | X | X |
| 384 | X | X | X | X | X | X | X | X | X | X | X | X |
| 385 | X | X | X | X | X | X | X | X | X | X | X | X |
| 386 | X | X | X | X | X | X | X | X | X | X | X | X |
| 387 | X | X | X | X | X | X | X | X | X | X | X | X |
| 388 | X | X | X | X | X | X | X | X | X | X | X | X |
| 389 | X | X | X | X | X | X | X | X | X | X | X | X |
| 390 | X | X | X | X | X | X | X | X | X | X | X | X |
| 391 | X | X | X | X | X | X | X | X | X | X | X | X |
| 392 | X | X | X | X | X | X | X | X | X | X | X | X |
| 393 | X | X | X | X | X | | X | X | X | X | X | X |
| 394 | X | X | X | X | X | X | X | X | X | X | X | X |
| 395 | X | X | X | X | X | X | | X | X | X | X | X |
| 396 | X | | X | X | X | X | X | X | X | X | X | X |
| 397 | X | X | X | X | X | X | X | X | X | X | X | X |
| 398 | X | X | X | X | X | X | X | X | X | X | X | X |
| 399 | X | X | X | X | X | X | X | X | X | X | X | X |
| 400 | X | X | X | X | X | X | X | X | X | X | X | X |
| 401 | X | X | X | X | X | X | X | X | X | X | X | X |
| 402 | X | X | X | X | X | X | X | X | X | X | X | X |
| 403 | X | X | X | X | X | X | X | X | X | X | X | X |
| 404 | X | X | X | X | X | X | X | X | X | X | X | X |
| 405 | X | X | X | X | X | X | X | X | X | X | X | X |

TABLE 1-continued

| R2 | \multicolumn{12}{c}{R1} |
|---|---|---|---|---|---|---|---|---|---|---|---|---|
|  | 1 | 2 | 3 | 4 | 5 | 6 | 8 | 9 | 10 | 11 | 7 | 12 |
| 406 | X | X | X | X | X | X | X | X | X | X | X | X |
| 407 | X | X | X | X | X | X | X | X | X | X | X | X |

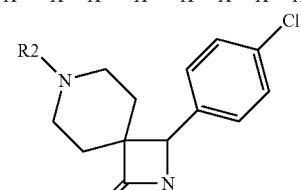

(IB)

wherein $R^5$ and $R^2$ are denoted using an "X" as set forth below in Table 2, and defined below in Tables 5 and 6, respectively.

TABLE 2

| R2 | \multicolumn{11}{c}{R1} |
|---|---|---|---|---|---|---|---|---|---|---|---|
|  | 1 | 3 | 4 | 6 | 7 | 8 | 2 | 11 | 5 | 12 | 9 | 10 |
| 1 | X | X | X | X | X | X | X | X | X | X |  |  |
| 2 | X | X | X | X | X | X |  |  |  |  | X |  |
| 3 | X | X | X | X | X | X |  |  |  |  | X |  |
| 4 | X | X |  | X | X | X | X |  | X |  |  |  |
| 5 | X | X |  | X | X | X |  |  |  |  |  |  |
| 6 | X | X |  | X | X | X | X | X | X | X | X |  |
| 7 | X | X | X | X | X | X |  |  |  |  | X |  |
| 8 | X | X | X | X | X | X | X | X | X | X | X |  |
| 9 | X | X |  | X | X | X |  |  |  |  |  |  |
| 10 | X | X | X | X | X | X |  |  |  |  | X |  |
| 11 | X | X | X | X | X | X |  |  |  |  | X |  |
| 12 | X | X | X | X | X | X |  |  |  |  | X |  |
| 13 | X | X |  | X | X | X |  |  |  |  |  |  |
| 14 | X | X |  | X | X | X |  |  |  |  | X |  |
| 15 | X | X |  | X | X | X |  |  |  |  | X |  |
| 16 | X | X |  | X | X | X |  |  |  |  | X |  |
| 17 | X | X |  | X | X | X |  |  |  |  | X |  |
| 18 | X | X |  | X | X | X |  |  |  |  | X |  |
| 19 | X | X |  | X | X | X |  |  |  |  | X |  |
| 20 | X | X |  | X | X | X |  |  |  |  | X |  |
| 21 | X | X |  | X | X | X |  |  |  |  | X |  |
| 22 | X | X |  | X | X | X | X | X | X | X | X |  |
| 23 | X | X |  | X | X | X |  |  |  |  | X |  |
| 24 | X | X |  | X | X | X |  |  |  |  | X |  |
| 25 | X | X |  | X | X | X |  |  |  |  | X |  |
| 26 | X | X |  | X | X | X | X | X | X | X | X |  |
| 27 | X | X |  | X | X | X |  |  |  |  | X |  |
| 28 | X | X |  | X | X | X | X | X | X | X | X |  |
| 29 | X | X |  | X | X | X |  |  |  |  | X |  |
| 30 | X | X |  | X | X | X | X | X | X | X |  |  |
| 31 | X | X | X | X | X | X |  |  |  |  | X |  |
| 32 | X | X | X | X | X | X |  |  |  |  | X |  |
| 33 | X | X | X | X | X | X |  |  |  |  | X |  |
| 34 | X | X | X | X | X | X |  |  |  |  | X |  |
| 35 | X | X | X | X | X | X | X | X | X | X | X |  |
| 36 | X | X | X | X | X | X |  |  |  |  | X |  |
| 37 | X | X | X | X | X | X |  |  |  |  |  |  |
| 38 | X | X | X | X | X | X | X | X | X | X | X |  |
| 39 | X | X | X | X | X | X |  |  |  |  | X |  |
| 40 | X | X | X | X | X | X |  |  |  |  | X |  |
| 41 | X | X | X | X | X | X |  |  |  |  | X |  |
| 42 | X | X | X | X | X | X |  |  |  |  | X |  |
| 43 | X | X | X | X | X | X | X | X | X |  | X |  |
| 44 | X | X | X | X | X | X |  |  |  |  | X |  |
| 45 | X | X | X | X | X | X |  |  |  |  | X |  |
| 46 | X | X | X | X | X | X |  |  |  |  | X |  |
| 47 | X | X | X | X | X | X |  |  |  |  | X |  |

TABLE 2-continued

| R2 | \multicolumn{11}{c}{R1} |
|---|---|---|---|---|---|---|---|---|---|---|---|
|  | 1 | 3 | 4 | 6 | 7 | 8 | 2 | 11 | 5 | 12 | 9 | 10 |
| 48 | X | X | X | X | X | X |  |  |  |  | X |  |
| 49 | X | X | X | X | X | X |  |  |  |  | X |  |
| 50 | X | X | X | X | X | X |  |  |  |  | X |  |
| 51 | X | X | X | X | X | X |  |  |  |  | X |  |
| 52 | X | X | X | X | X | X | X | X | X | X | X |  |
| 53 | X | X | X | X | X | X |  |  |  |  | X |  |
| 54 | X | X | X | X | X | X |  |  |  |  |  |  |
| 55 | X | X | X | X | X | X | X | X | X | X |  |  |
| 56 | X | X | X | X | X | X | X | X | X | X | X |  |
| 57 | X | X | X | X | X | X |  |  |  |  | X |  |
| 58 | X | X | X | X | X | X |  |  |  |  | X |  |
| 59 | X | X | X | X | X | X |  |  |  |  | X |  |
| 60 | X | X | X | X | X | X |  |  |  |  | X |  |
| 61 | X | X | X | X | X | X |  |  |  |  | X |  |
| 62 | X | X | X | X | X | X |  |  |  |  | X |  |
| 63 | X | X | X | X | X | X | X | X | X | X | X |  |
| 64 | X | X | X | X | X | X |  |  |  |  | X |  |
| 65 | X | X | X | X | X | X |  |  |  |  | X |  |
| 66 | X | X | X | X | X | X |  |  |  |  | X |  |
| 67 | X | X | X | X | X | X | X | X | X | X | X |  |
| 68 | X | X | X | X | X | X | X | X | X | X | X |  |
| 69 | X | X | X | X | X | X |  |  |  |  | X |  |
| 70 | X | X | X | X | X | X |  |  |  |  | X |  |
| 71 | X | X | X | X | X | X |  |  |  |  | X |  |
| 72 | X | X | X | X | X | X | X | X | X | X | X |  |
| 73 | X | X | X | X | X | X |  |  |  |  | X |  |
| 74 | X | X | X | X | X | X |  |  |  |  | X |  |
| 75 | X | X | X | X | X | X |  |  |  |  | X |  |
| 76 | X | X | X | X | X | X | X | X | X | X | X |  |
| 77 | X | X | X | X | X | X |  |  |  |  | X |  |
| 78 | X | X | X | X | X | X |  |  |  |  | X |  |
| 79 | X | X | X | X | X | X |  |  |  |  | X |  |
| 80 | X | X | X | X | X | X |  |  |  |  | X |  |
| 81 | X | X | X | X | X | X |  |  |  |  | X |  |
| 82 | X | X | X | X | X | X |  |  |  |  | X |  |
| 83 | X | X | X | X | X | X |  |  |  |  | X |  |
| 84 | X | X | X | X | X | X |  |  |  |  | X |  |
| 85 | X | X | X | X | X | X |  |  |  |  | X |  |
| 86 | X | X | X | X | X | X |  |  |  |  | X |  |
| 87 | X | X | X | X | X | X |  |  |  |  | X |  |
| 88 | X | X | X | X | X | X |  |  |  |  | X | X |
| 133 | X | X | X | X | X | X |  |  | X | X |  | X |
| 134 | X | X | X | X | X | X | X | X | X | X |  | X |
| 135 | X | X | X | X | X | X | X | X | X |  |  |  |
| 136 | X | X | X | X | X | X |  |  |  |  |  | X |
| 137 | X | X | X | X | X | X | X | X | X | X |  | X |
| 138 | X | X | X | X | X | X | X | X | X | X |  |  |
| 140 | X | X | X | X | X | X |  |  |  |  |  |  |
| 141 | X | X | X | X | X | X |  |  |  |  |  |  |
| 142 | X | X | X | X | X | X |  |  |  |  |  | X |
| 143 | X | X | X | X | X | X | X | X | X | X |  |  |
| 144 | X | X | X | X | X | X |  |  |  |  |  |  |
| 145 | X | X | X | X | X | X |  |  |  |  |  | X |
| 146 | X | X | X | X | X | X | X | X | X | X |  | X |
| 147 | X | X | X | X | X | X | X | X | X | X |  | X |
| 148 | X | X | X | X | X | X | X | X | X | X |  | X |
| 150 | X | X | X | X | X | X | X | X | X | X |  |  |
| 151 | X | X | X | X | X | X |  |  |  |  |  |  |
| 152 | X | X | X | X | X | X |  |  |  |  |  | X |
| 153 | X | X | X | X | X | X |  | X | X | X |  | X |
| 154 | X | X | X | X | X | X |  | X | X | X |  |  |
| 155 | X | X | X | X | X | X |  |  |  |  |  |  |
| 156 | X | X | X | X | X | X |  |  |  |  |  |  |
| 157 | X | X | X | X | X | X |  |  |  |  |  |  |
| 159 | X | X | X | X | X | X |  |  |  |  |  |  |
| 160 | X | X | X | X | X | X |  |  |  |  |  |  |
| 161 | X | X | X | X | X | X |  |  |  |  |  |  |
| 162 | X | X | X | X | X | X |  |  |  |  |  | X |
| 163 | X | X | X | X | X | X |  | X | X | X |  |  |
| 164 | X | X | X | X | X | X |  |  |  |  |  |  |
| 165 | X | X | X | X | X | X |  |  |  |  |  |  |
| 166 | X | X | X | X | X | X |  |  |  |  |  |  |
| 167 | X | X | X | X | X | X |  |  |  |  |  |  |
| 168 | X | X | X | X | X | X |  |  |  |  |  |  |
| 170 | X | X | X | X | X | X |  |  |  |  |  | X |

TABLE 2-continued

|  | R1 | | | | | | | | | | | |
|---|---|---|---|---|---|---|---|---|---|---|---|---|
| R2 | 1 | 3 | 4 | 6 | 7 | 8 | 2 | 11 | 5 | 12 | 9 | 10 |
| 172 | X | X | X | X | X | X | X | X | X | X | | |
| 173 | X | X | X | X | X | X | | | | | | |
| 176 | X | X | X | X | X | X | | | | | | |
| 139 | | X | X | | X | X | | | | | | |
| 149 | | X | X | | X | X | | | | | | |
| 158 | | X | X | | X | X | | | | | | |
| 169 | | X | X | X | X | X | | | | | | |
| 171 | | X | X | X | X | X | | | | | | |
| 174 | | X | X | X | X | X | | | | | | |
| 175 | | X | X | | X | X | | | | | | X |
| 177 | X | X | X | X | X | X | X | X | X | X | X | X |
| 179 | X | X | X | X | X | X | X | X | X | X | | X |
| 180 | X | X | X | X | X | X | X | X | X | X | | X |
| 181 | X | X | X | X | | X | X | X | X | X | | X |
| 182 | X | X | X | X | X | X | X | X | X | X | | X |
| 183 | X | X | X | X | X | X | X | X | X | X | | X |
| 184 | X | X | X | X | X | X | X | X | X | X | | |
| 185 | X | X | X | X | X | X | X | X | X | | | |
| 209 | X | X | X | X | | X | X | X | | X | | X |
| 186 | X | X | X | X | | X | X | X | X | X | | X |
| 187 | X | X | X | | | X | X | X | X | | | X |
| 188 | X | X | X | X | | X | X | X | X | X | | X |
| 189 | X | X | X | X | | X | X | X | X | | | X |
| 190 | X | X | X | X | | X | X | X | X | X | | X |
| 191 | X | X | X | X | | X | X | X | X | | | X |
| 192 | X | X | X | X | | X | X | X | X | | | |
| 193 | X | X | X | X | | | | X | X | X | | X |
| 194 | X | X | X | X | | X | X | X | X | | | X |
| 195 | X | X | X | X | | X | X | X | X | | | |
| 196 | X | X | X | X | | X | X | X | | X | | X |
| 197 | X | X | X | X | | X | X | X | X | | | X |
| 198 | X | X | | X | | X | X | X | X | | | X |
| 201 | X | X | X | X | | X | X | X | X | X | | X |
| 202 | X | X | X | X | | X | X | X | X | X | | X |
| 203 | X | X | X | X | | X | X | X | X | X | | X |
| 204 | X | X | X | X | | X | X | X | X | X | | X |
| 205 | X | | | X | X | X | X | | | X | | X |
| 210 | X | X | | X | X | X | X | X | X | X | | X |
| 206 | X | | X | | X | X | X | | | | | |
| 207 | X | | X | | X | X | X | | | X | | |
| 208 | X | | X | | X | X | X | | X | | | X |
| 178 | | | | X | X | | | X | X | | | X |
| 212 | | X | | X | X | | | X | X | | | X |
| 215 | | X | X | X | X | X | X | X | X | | | |
| 199 | | | | X | X | | | | X | | | X |
| 200 | | X | X | X | X | X | X | X | X | | | X |
| 213 | | | | | | | | X | | | | X |
| 214 | | X | X | X | | X | | X | | | | X |
| 211 | | X | | X | X | X | X | X | X | | | |
| 216 | | X | X | X | X | | X | X | | | | |
| 217 | X | X | X | X | X | X | | | X | | | X |
| 218 | X | X | X | X | X | X | | | X | | | X |
| 226 | X | X | X | X | X | X | | | X | | | X |
| 219 | X | | | X | X | X | X | X | X | | | X |
| 220 | X | | | | X | X | X | X | X | | | X |
| 227 | X | X | | | X | X | X | | X | X | | X |
| 228 | X | X | | | X | X | X | | X | X | | |
| 221 | X | X | X | X | X | X | X | X | X | | | X |
| 222 | X | X | X | X | X | X | | | X | X | | |
| 229 | X | | | | | | | | X | X | | |
| 223 | X | X | X | X | X | X | X | X | X | X | | |
| 224 | X | X | | | X | X | X | X | | X | | |
| 234 | | | X | | X | X | | | | | X | |
| 233 | | | | X | | X | | | | X | | X |
| 230 | | X | X | | | | | | | | | X |
| 232 | | X | X | | | | X | X | | | | X |
| 225 | | X | | | X | X | | | X | X | X | |
| 236 | | | | | X | X | X | | | X | X | |
| 231 | | | | | X | | | | | X | X | |
| 237 | | | | | | | X | X | X | X | | |
| 238 | | | | | | | X | X | X | X | | |
| 239 | | | | | | | X | X | X | X | | |
| 240 | | | | | | | X | X | X | X | | |
| 241 | | | | | | | X | | X | X | | |
| 242 | | | | | | | X | X | X | X | | |
| 243 | | | | | | | X | X | X | X | | |
| 244 | | | | | | | X | X | X | X | | |
| 245 | | | | | | | X | X | X | X | | |
| 246 | | | | | | | X | X | X | X | | |
| 301 | | | | | | | X | | | | | |
| 247 | | | | | | | X | X | X | X | | |
| 248 | | | | | | | X | X | X | X | | |
| 249 | | | | | | | X | X | X | X | | |
| 250 | | | | | | | X | X | X | X | | |
| 299 | | | | | | | X | X | | X | | |
| 251 | | | | | | | X | X | X | X | | |
| 300 | | | | | | | X | | | X | | |
| 252 | | | | | | | X | X | X | X | | |
| 253 | | | | | | | X | X | X | X | | |
| 254 | | | | | | | X | X | X | X | | |
| 255 | | | | | | | X | X | X | X | | |
| 256 | | | | | | | X | X | | X | | |
| 257 | | | | | | | X | X | X | X | | |
| 258 | | | | | | | X | X | X | X | | |
| 259 | | | | | | | X | X | X | X | | |
| 260 | | | | | | | X | X | X | X | | |
| 261 | | | | | | | X | X | X | X | | |
| 262 | | | | | | | X | X | X | X | | |
| 263 | | | | | | | X | X | X | X | | |
| 264 | | | | | | | X | X | X | X | | |
| 265 | | | | | | | X | X | X | X | | |
| 266 | | | | | | | X | X | X | X | | |
| 267 | | | | | | | X | X | X | X | | |
| 268 | | | | | | | X | X | X | X | | |
| 269 | | | | | | | X | X | X | X | | |
| 270 | | | | | | | X | X | X | X | | |
| 271 | | | | | | | X | X | X | X | | |
| 272 | | | | | | | X | X | X | X | | |
| 273 | | | | | | | X | X | X | X | | |
| 274 | | | | | | | X | | X | X | | |
| 275 | | | | | | | X | | | | | |
| 276 | | | | | | | X | X | X | X | | |
| 277 | | | | | | | X | X | X | X | | |
| 278 | | | | | | | X | X | X | X | | |
| 279 | | | | | | | X | X | X | X | | |
| 280 | | | | | | | X | X | X | X | | |
| 302 | | | | | | | X | | | | | |
| 281 | | | | | | | X | X | X | X | | |
| 282 | | | | | | | X | X | X | X | | |
| 303 | | | | | | | X | X | | | | |
| 283 | | | | | | | X | | X | X | | |
| 304 | | | | | | | X | | X | | | |
| 284 | | | | | | | X | X | X | X | | |
| 285 | | | | | | | X | X | X | X | | |
| 286 | | | | | | | X | X | X | X | | |
| 287 | | | | | | | X | X | X | X | | |
| 288 | | | | | | | X | X | X | X | | |
| 289 | | | | | | | X | X | X | X | | |
| 290 | | | | | | | X | X | X | X | | |
| 291 | | | | | | | X | X | X | X | | |
| 292 | | | | | | | X | X | X | X | | |
| 293 | | | | | | | X | X | X | X | | |
| 294 | | | | | | | X | X | X | X | | |
| 295 | | | | | | | X | X | X | X | | |
| 296 | | | | | | | X | X | | X | | |
| 305 | | | | | | | X | | | | | |
| 297 | | | | | | | X | X | X | X | | |
| 298 | | | | | | | X | X | X | X | | |
| 312 | | | | | | | | | X | X | X | |
| 324 | | | | | | | | | X | X | X | |
| 334 | | | | | | | X | X | X | X | | X |
| 360 | | | | | | | X | X | X | X | | X |
| 335 | | | | | | | X | X | X | X | | X |
| 336 | | | | | | | X | X | X | X | | X |
| 337 | | | | | | | X | X | X | X | | X |
| 338 | | | | | | | X | X | X | X | | X |
| 339 | | | | | | | X | X | X | X | | X |
| 340 | | | | | | | X | X | X | X | | X |
| 341 | | | | | | | X | X | X | X | | X |
| 342 | | | | | | | X | X | X | X | | X |

TABLE 2-continued

| R2 | R1 1 | 3 | 4 | 6 | 7 | 8 | 2 | 11 | 5 | 12 | 9 | 10 |
|---|---|---|---|---|---|---|---|---|---|---|---|---|
| 343 | | | | | | | | X | X | X | X | X |
| 344 | | | | | | | | X | X | X | X | X |
| 345 | | | | | | | | X | X | X | X | X |
| 346 | | | | | | | | X | X | X | X | X |
| 347 | | | | | | | | X | X | X | X | X |
| 348 | | | | | | | | X | X | X | X | X |
| 361 | | | | | | | | X | X | X | X | X |
| 349 | | | | | | | | X | X | X | X | X |
| 350 | | | | | | | | X | X | X | X | X |
| 351 | | | | | | | | X | X | X | X | X |
| 352 | | | | | | | | X | X | X | X | X |
| 363 | | | | | | | | | X | X | X | X |
| 353 | | | | | | | | X | X | X | X | X |
| 354 | | | | | | | | X | X | X | X | X |
| 355 | | | | | | | | X | X | X | X | X |
| 356 | | | | | | | | X | X | X | X | X |
| 362 | | | | | | | | X | X | X | X | X |
| 357 | | | | | | | | | X | X | | X |
| 358 | | | | | | | | X | X | X | | X |
| 359 | | | | | | | | | X | X | X | X |
| 364 | X | X | X | X | X | X | X | X | X | X | X | X |
| 365 | X | X | X | X | X | X | X | X | X | X | X | X |
| 366 | X | X | X | X | X | X | X | X | X | X | X | X |
| 367 | X | X | X | X | X | X | X | X | X | X | X | X |
| 368 | X | X | X | X | X | X | X | X | X | X | X | X |
| 369 | X | X | X | X | X | X | X | X | X | X | X | X |
| 370 | X | X | X | X | X | X | X | X | X | X | X | X |
| 371 | X | X | X | X | X | X | X | X | X | X | X | X |
| 372 | X | X | X | X | X | X | X | X | X | X | X | X |
| 373 | X | X | X | X | X | X | X | X | X | X | X | X |
| 374 | X | X | X | X | X | X | X | X | X | X | X | X |
| 375 | X | X | X | X | X | X | X | X | X | X | X | X |
| 376 | X | X | X | X | X | X | X | X | X | X | X | X |
| 377 | X | X | X | X | X | X | X | X | X | X | X | X |
| 378 | X | X | X | X | X | X | X | X | X | X | X | X |
| 379 | X | X | X | X | X | X | X | X | X | X | X | X |
| 380 | X | X | X | X | X | X | X | X | X | X | X | X |
| 381 | X | X | X | X | X | X | X | X | X | X | X | X |
| 382 | X | X | X | X | X | X | X | X | X | X | X | X |
| 383 | X | X | X | X | X | X | X | X | X | X | X | X |
| 384 | X | X | X | X | X | X | X | X | X | X | X | X |
| 385 | X | X | X | X | X | X | X | X | X | X | X | X |
| 386 | X | X | X | X | X | X | X | X | X | X | X | X |
| 387 | X | X | X | X | X | X | X | X | X | X | X | X |
| 388 | X | X | X | X | X | X | X | X | X | X | X | X |
| 389 | X | X | X | X | X | X | X | X | X | X | X | X |
| 390 | X | X | X | X | X | X | X | X | X | X | X | X |
| 391 | X | X | X | X | X | X | X | X | X | X | X | X |
| 392 | X | X | X | X | X | X | X | X | X | X | X | X |
| 393 | X | X | X | X | X | | | | X | X | X | X |
| 394 | X | X | X | X | X | | | X | X | X | X | X |
| 395 | X | X | X | X | X | | X | | X | X | X | X |
| 396 | X | X | X | X | X | X | X | | X | X | X | X |
| 397 | X | X | X | X | X | X | X | | X | X | X | X |
| 398 | X | X | X | X | X | X | X | | X | X | X | X |
| 399 | X | X | X | X | X | X | X | X | X | X | X | X |
| 400 | X | X | X | X | X | X | X | | X | X | X | X |
| 401 | X | X | X | X | X | X | X | | X | X | X | X |
| 402 | X | X | X | X | X | X | X | | X | X | X | X |
| 403 | X | X | X | X | X | X | X | | X | X | X | X |
| 404 | X | X | X | X | X | X | X | X | X | X | X | X |
| 405 | X | X | X | X | X | X | X | X | X | X | X | X |
| 406 | X | X | X | X | X | X | X | X | X | X | X | X |
| 407 | X | X | X | X | X | X | X | X | X | X | X | X |

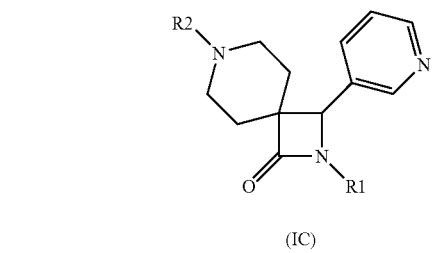

(IC)

wherein $R^1$ and $R^2$ are denoted using an "X" as set forth below in Table 3, and defined below in Tables 5 and 6, respectively.

TABLE 3

| R2 | R1 1 | 2 | 3 | 4 | 8 | 12 | 11 | 7 | 6 | 5 | 10 |
|---|---|---|---|---|---|---|---|---|---|---|---|
| 177 | X | X | X | X | X | X | | | | | |
| 178 | X | X | | | X | X | X | | | | |
| 179 | | X | | X | X | X | | | | | |
| 180 | X | X | X | | X | X | | X | | | |
| 181 | | X | | X | X | X | | X | | | |
| 182 | X | X | X | X | X | X | | X | | | |
| 183 | X | X | X | X | X | X | | X | | | |
| 184 | X | X | X | | X | X | | | | | |
| 185 | | X | | X | X | | | | | | |
| 186 | X | X | | X | X | X | | X | | | |
| 187 | | | X | | X | X | | | | | |
| 188 | X | X | X | X | X | X | | X | X | | |
| 189 | | X | X | X | X | X | | | | | |
| 190 | X | X | X | X | X | X | | X | | | |
| 191 | X | X | X | X | X | X | | | | | |
| 192 | X | X | X | X | X | X | | | | | |
| 193 | X | | | X | X | | | | | | |
| 194 | X | X | X | X | X | X | | X | | | |
| 195 | X | | X | X | X | X | | | | | |
| 196 | | | | X | X | X | | | | | |
| 197 | X | X | X | X | X | X | | | | | |
| 198 | | | | X | X | | | | | | |
| 199 | | X | | X | | | | X | | | |
| 200 | | X | | X | | | | | | | |
| 201 | X | X | | X | X | X | | X | | | |
| 202 | | X | | X | X | | | | | | |
| 203 | | X | X | X | | | | | | | |
| 204 | X | X | X | X | X | X | | X | | | |
| 205 | | X | | X | | | | | | | |
| 207 | | | | | X | | | | | | |
| 208 | | X | | X | | | | | | | |
| 209 | | X | | X | | | | X | | | |
| 210 | X | | X | X | X | | | X | | | |
| 211 | | X | | X | X | | | | | | |
| 212 | X | | | | | | | | | | |
| 213 | | | X | | X | | | | | X | |
| 214 | | | X | | | | | | | | |
| 215 | | X | X | X | | | | | | | |
| 216 | | | X | | X | | | | X | | |
| 26 | X | X | X | X | X | X | | X | X | X | X |
| 30 | X | X | | X | X | X | | X | X | | X |
| 38 | X | X | X | X | X | X | | X | X | X | X |
| 43 | X | X | X | X | X | X | | X | X | X | X |
| 52 | X | X | X | X | X | X | | X | X | X | X |
| 63 | X | X | X | X | X | | | X | X | X | X |
| 68 | X | X | X | X | X | X | | X | X | X | X |
| 217 | | X | X | X | X | | X | | | | |
| 218 | X | | | X | X | | | X | | | |

TABLE 3-continued

| R2 | 1 | 2 | 3 | 4 | 8 | 12 | 11 | 7 | 6 | 5 | 10 |
|---|---|---|---|---|---|---|---|---|---|---|---|
| 219 |   |   |   | X | X |   |   |   |   |   |   |
| 220 | X |   | X | X | X | X |   |   | X |   |   |
| 221 | X |   |   | X | X |   |   |   |   |   |   |
| 222 | X |   | X | X | X | X |   |   | X | X |   |
| 223 |   |   |   |   | X |   |   |   |   |   |   |
| 224 |   |   |   |   | X |   |   |   |   |   |   |
| 225 |   |   |   |   | X |   |   |   |   |   |   |
| 226 |   | X |   |   | X | X |   |   |   |   |   |
| 227 |   |   |   | X | X | X | X |   |   | X | X |
| 228 |   |   |   | X |   | X |   |   |   |   |   |
| 229 | X |   |   | X | X |   | X |   |   |   |   |
| 230 | X | X |   | X | X |   |   |   |   |   |   |
| 231 |   |   |   |   | X |   |   |   |   |   |   |
| 232 | X | X |   | X | X |   |   |   |   |   |   |
| 233 |   |   |   |   | X |   |   |   |   |   |   |
| 234 |   |   | X | X | X | X |   |   |   | X | X |
| 236 |   |   |   |   | X |   | X |   |   |   |   |
| 237 | X | X | X | X | X | X |   | X | X | X | X |
| 238 | X | X | X | X | X | X |   | X | X | X | X |
| 239 | X | X | X | X | X | X |   | X | X | X | X |
| 240 | X | X | X |   | X | X |   | X | X | X | X |
| 241 | X | X | X | X | X | X |   | X | X | X | X |
| 242 | X | X | X | X | X | X |   | X | X | X | X |
| 243 | X | X | X | X | X | X |   | X | X | X | X |
| 244 | X | X | X | X | X | X |   | X | X | X | X |
| 245 | X | X | X | X | X | X |   | X | X | X | X |
| 246 | X | X | X | X | X | X |   | X | X | X | X |
| 247 | X | X | X | X | X | X |   | X | X | X | X |
| 248 | X | X | X | X | X | X |   | X | X | X | X |
| 6 | X | X | X | X | X | X |   | X | X | X | X |
| 8 | X | X | X | X | X | X |   | X | X | X | X |
| 22 | X | X | X | X | X | X |   | X | X | X | X |
| 28 | X | X | X | X | X | X |   | X | X | X | X |
| 56 | X | X | X | X | X | X |   | X | X | X | X |
| 76 | X | X | X | X | X | X |   | X | X | X | X |
| 249 | X | X | X | X | X | X |   | X | X | X | X |
| 250 | X | X | X | X | X | X |   | X | X | X | X |
| 251 | X | X | X | X | X | X |   | X | X | X | X |
| 252 | X | X | X | X | X | X |   | X | X | X | X |
| 253 | X | X | X | X | X | X |   | X | X | X | X |
| 254 | X | X | X | X | X | X |   | X | X | X | X |
| 255 | X | X | X | X | X | X |   | X | X | X | X |
| 256 | X | X | X | X | X | X |   | X | X | X | X |
| 257 | X | X | X | X | X | X |   | X | X | X | X |
| 258 | X | X | X | X | X | X |   | X | X | X | X |
| 259 | X | X | X | X | X | X |   | X | X | X | X |
| 260 | X | X | X | X | X | X |   | X | X |   | X |
| 261 | X | X | X | X | X | X |   | X | X | X | X |
| 262 | X | X | X | X | X | X |   | X | X | X | X |
| 263 | X | X |   | X | X | X |   | X | X | X | X |
| 264 | X | X |   | X | X | X |   | X | X | X | X |
| 265 | X | X | X | X | X | X |   | X | X | X | X |
| 266 | X | X | X | X | X | X |   | X | X | X | X |
| 267 | X | X | X | X | X | X |   | X | X | X | X |
| 268 | X | X | X | X | X | X |   | X | X | X | X |
| 269 | X | X | X | X | X | X |   | X | X | X | X |
| 270 | X | X | X | X | X | X |   | X | X | X | X |
| 271 | X | X | X |   | X | X |   | X | X | X | X |
| 272 | X | X | X | X | X | X |   | X |   | X | X |
| 273 | X | X | X | X | X | X |   | X |   | X | X |
| 274 | X | X | X | X | X | X |   | X | X | X | X |
| 275 | X |   |   |   | X | X |   | X |   |   | X |
| 276 | X |   | X | X | X | X |   | X | X | X | X |
| 277 | X | X | X | X | X | X |   | X | X | X | X |
| 278 | X | X | X | X | X | X |   | X | X | X | X |
| 279 | X | X | X | X | X | X |   | X | X | X | X |
| 280 | X | X | X | X | X | X |   | X | X | X | X |
| 281 | X | X | X | X | X | X |   | X | X | X | X |
| 1 | X | X |   |   |   |   |   |   |   |   |   |
| 4 |   |   |   |   | X | X |   | X |   |   | X |
| 35 | X | X | X |   | X | X |   |   | X |   | X |
| 55 | X | X | X |   | X | X |   | X | X |   | X |
| 67 | X | X | X | X | X | X |   | X | X |   | X |
| 72 | X | X | X |   | X | X |   | X | X | X | X |
| 282 | X | X | X | X | X | X |   | X | X | X | X |
| 283 | X | X | X | X | X | X |   | X | X | X | X |
| 284 | X |   | X | X | X | X |   | X | X |   | X |
| 285 | X | X | X | X | X | X |   | X | X | X | X |
| 286 | X | X | X | X | X | X |   | X | X | X | X |
| 287 | X | X | X | X | X | X |   | X | X | X | X |
| 288 | X | X | X | X | X | X |   | X | X | X | X |
| 289 | X | X | X | X | X | X |   | X | X | X | X |
| 290 | X | X | X | X | X | X |   | X | X |   | X |
| 291 | X | X | X | X | X | X |   | X | X |   | X |
| 292 | X | X | X | X | X | X |   | X | X |   | X |
| 293 | X | X | X | X | X | X |   | X | X |   | X |
| 294 | X | X | X | X | X | X |   | X |   | X | X |
| 295 | X | X | X | X | X | X |   | X |   | X | X |
| 296 | X | X | X | X | X | X |   | X |   | X | X |
| 297 | X | X | X | X | X | X |   | X |   | X | X |
| 298 | X | X | X | X | X | X |   | X |   | X | X |
| 299 |   | X | X | X | X | X |   | X | X |   | X |
| 300 |   |   | X |   | X | X |   | X | X | X | X |
| 301 |   |   |   |   | X | X |   | X |   | X | X |
| 302 |   |   |   |   | X | X |   | X |   |   | X |
| 303 |   | X |   |   | X | X |   | X | X | X | X |
| 304 |   |   |   | X | X | X |   | X | X | X | X |
| 305 |   |   |   |   | X | X |   | X |   |   | X |
| 146 | X | X |   |   | X | X | X | X |   | X | X |
| 147 | X | X |   |   | X | X | X | X |   | X | X |
| 148 | X | X |   |   | X | X | X | X |   | X | X |
| 334 | X | X |   |   | X | X | X | X |   | X | X |
| 335 | X | X |   | X | X | X | X | X |   | X | X |
| 133 | X | X |   |   | X |   |   |   |   | X | X |
| 134 | X | X |   |   | X | X |   | X |   | X | X |
| 135 | X | X |   |   | X | X |   | X |   | X | X |
| 137 | X | X |   |   | X | X |   | X |   | X | X |
| 138 | X | X |   |   | X | X |   | X |   | X | X |
| 143 | X | X |   |   | X | X | X | X |   |   | X |
| 150 | X | X |   |   | X | X |   |   |   | X | X |
| 153 | X | X |   |   | X | X |   | X |   | X |   |
| 154 | X | X |   |   | X | X |   | X |   | X |   |
| 163 | X | X |   |   | X | X |   |   |   |   | X |
| 172 | X | X |   |   | X | X |   | X |   | X | X |
| 336 | X | X |   | X | X | X |   | X |   |   | X |
| 337 | X | X |   | X |   | X |   | X |   | X | X |
| 338 | X | X |   |   | X | X |   | X |   | X | X |
| 339 | X |   |   |   | X | X |   | X |   | X | X |
| 340 | X | X |   |   | X | X |   | X |   | X | X |
| 341 | X | X |   |   | X | X |   | X |   | X | X |
| 342 | X | X |   |   | X | X |   | X |   | X | X |
| 343 | X | X |   |   | X | X |   | X |   | X | X |
| 344 | X | X |   |   | X | X |   | X |   | X | X |
| 345 | X | X |   |   | X | X |   | X |   | X | X |
| 346 | X | X |   |   | X | X |   | X |   | X | X |
| 347 | X | X |   |   | X | X |   | X |   | X | X |
| 348 | X | X |   |   | X | X |   | X |   | X | X |
| 349 | X | X |   |   | X | X |   | X |   | X | X |
| 350 | X | X |   |   | X | X |   | X |   | X | X |
| 351 | X | X |   |   | X | X |   | X |   | X | X |
| 352 | X | X |   |   | X | X |   | X |   | X | X |
| 353 | X | X |   |   | X | X |   | X |   | X | X |
| 354 | X | X |   |   | X | X |   | X |   | X | X |
| 355 | X | X |   |   | X | X |   | X |   |   | X |
| 356 | X | X |   |   | X |   |   | X |   | X | X |
| 357 | X | X |   |   |   | X |   |   |   | X | X |
| 358 | X | X |   |   | X | X |   |   |   | X | X |
| 359 | X | X |   |   | X | X |   |   |   |   | X |
| 360 |   | X |   |   | X | X |   | X |   |   | X |
| 361 |   | X |   |   | X | X |   | X |   | X | X |
| 362 |   | X |   | X | X | X |   | X |   | X | X |
| 363 |   |   |   |   | X | X |   |   | X |   |   |
| 364 | X | X | X |   | X | X |   | X | X | X | X |
| 365 | X | X | X | X | X | X |   | X | X | X | X |
| 366 | X | X | X | X | X | X |   | X | X | X | X |
| 367 | X | X | X | X | X | X |   | X | X | X | X |
| 368 | X | X | X | X | X | X |   | X | X | X | X |
| 369 | X | X | X | X | X | X |   | X | X | X | X |
| 370 | X | X | X | X | X | X |   | X | X | X | X |
| 371 | X | X | X | X | X | X |   | X | X | X | X |

TABLE 3-continued

| R2 | 1 | 2 | 3 | 4 | 8 | 12 | 11 | 7 | 6 | 5 | 10 |
|---|---|---|---|---|---|---|---|---|---|---|---|
| 372 | X | X | X | X | X | X | X | X | X | X | X |
| 373 | X | X | X | X | X | X | X | X | X | X | X |
| 374 | X | X | X | X | X | X | X | X | X | X | X |
| 375 | X | X | X | X | X | X | X | X | X | X | X |
| 376 | X | X | X | X | X | X | X | X | X | X | X |
| 377 | X |   |   | X | X | X | X | X |   | X | X |
| 378 | X | X | X | X | X | X | X | X | X | X | X |
| 379 | X | X | X | X | X | X | X | X | X | X | X |
| 380 | X | X | X | X | X | X | X | X | X | X | X |
| 381 | X | X | X | X | X | X | X | X | X | X | X |
| 382 | X | X | X | X | X | X | X | X | X | X | X |
| 383 | X | X | X | X | X | X | X | X | X | X | X |
| 384 | X | X | X | X | X | X | X | X | X | X | X |
| 385 | X | X | X | X | X | X | X | X | X | X | X |
| 386 | X | X | X | X | X | X | X | X | X | X | X |
| 387 | X | X | X | X | X | X | X | X | X | X | X |
| 388 | X | X | X | X | X | X | X | X | X | X | X |
| 389 | X | X | X | X | X | X | X | X | X | X | X |
| 390 | X | X | X | X | X | X | X | X | X | X | X |
| 391 | X | X | X | X | X | X | X | X | X | X | X |
| 392 | X |   | X | X | X | X | X |   | X | X | X |
| 393 | X | X |   | X | X | X | X |   |   | X |   |
| 394 | X |   |   | X | X |   | X |   |   | X | X |
| 395 | X |   | X | X | X | X | X | X |   | X | X |
| 396 | X | X |   | X | X |   | X | X | X |   |   |
| 397 | X | X |   | X | X | X |   | X |   | X | X |
| 398 | X |   | X | X | X | X |   | X | X | X |   |
| 399 | X | X | X | X | X | X | X | X | X | X |   |
| 400 | X | X |   | X | X | X | X | X | X | X |   |
| 401 | X | X |   | X | X | X | X | X | X | X |   |
| 402 | X | X | X | X | X | X | X | X | X | X |   |
| 403 | X | X | X | X | X | X | X | X |   |   |   |
| 404 | X | X | X | X | X |   | X | X | X | X | X |
| 405 | X | X |   | X | X |   | X | X | X | X |   |
| 406 | X | X |   | X | X | X | X | X | X | X |   |
| 407 | X |   | X | X | X | X | X | X | X | X | X |

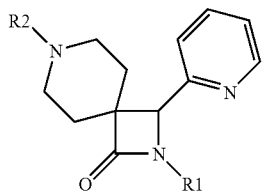

(ID)

wherein R$^1$ and R$^2$ are denoted using an "X" as set forth below in Table 4, and defined below in Tables 5 and 6, respectively.

TABLE 4

| R2 | 1 | 3 | 4 | 6 | 8 | 10 | 2 | 11 | 7 | 12 | 5 |
|---|---|---|---|---|---|---|---|---|---|---|---|
| 1 | X | X | X | X | X | X | X | X | X | X |   |
| 2 | X | X | X | X | X |   |   |   |   |   |   |
| 3 | X | X | X | X | X |   |   |   |   |   |   |
| 4 | X | X | X |   | X | X | X | X | X | X |   |
| 5 | X | X | X |   | X |   |   |   |   |   |   |
| 6 | X | X | X | X | X | X | X | X | X | X |   |
| 7 | X | X | X | X | X |   |   |   |   |   |   |
| 8 | X | X | X |   | X | X | X | X | X | X |   |
| 9 | X | X | X |   | X |   |   |   |   |   |   |
| 10 | X | X | X | X | X |   |   |   |   |   |   |
| 11 | X | X | X | X | X |   |   |   |   |   |   |
| 12 | X | X | X | X | X |   |   |   |   |   |   |
| 13 | X | X | X |   | X |   |   |   |   |   |   |

TABLE 4-continued

| R2 | 1 | 3 | 4 | 6 | 8 | 10 | 2 | 11 | 7 | 12 | 5 |
|---|---|---|---|---|---|---|---|---|---|---|---|
| 14 | X | X | X | X | X |   |   |   |   |   |   |
| 15 | X | X | X | X | X |   |   |   |   |   |   |
| 16 | X | X | X | X | X |   |   |   |   |   |   |
| 17 | X | X | X | X | X |   |   |   |   |   |   |
| 18 | X | X | X | X | X |   |   |   |   |   |   |
| 19 | X | X | X | X | X |   |   |   |   |   |   |
| 20 | X | X | X | X | X |   |   |   |   |   |   |
| 21 | X | X | X | X | X |   |   |   |   |   |   |
| 22 | X | X | X | X | X | X | X | X | X | X |   |
| 23 | X | X | X | X | X |   |   |   |   |   |   |
| 24 | X | X | X | X | X |   |   |   |   |   |   |
| 25 | X | X | X | X | X |   |   |   |   |   |   |
| 26 | X | X | X | X | X | X | X | X | X | X |   |
| 27 | X | X | X | X | X |   |   |   |   |   |   |
| 28 | X | X | X | X | X | X | X | X | X | X |   |
| 29 | X | X | X | X | X |   |   |   |   |   |   |
| 30 | X | X | X |   | X |   |   | X | X | X |   |
| 31 | X | X | X | X | X |   |   |   |   |   |   |
| 32 | X | X | X | X | X |   |   |   |   |   |   |
| 33 | X | X | X | X | X |   |   |   |   |   |   |
| 34 | X | X | X | X | X |   |   |   |   |   |   |
| 35 | X | X | X | X | X | X | X | X | X | X |   |
| 36 | X | X | X | X | X |   |   |   |   |   |   |
| 37 | X | X | X | X | X |   |   |   |   |   |   |
| 38 | X | X | X | X | X | X |   | X | X | X |   |
| 39 | X | X | X | X | X |   |   |   |   |   |   |
| 40 | X | X | X |   | X |   |   |   |   |   |   |
| 41 | X | X | X | X | X |   |   |   |   |   |   |
| 42 | X | X | X | X | X |   |   |   |   |   |   |
| 43 | X | X | X |   | X | X | X | X | X | X |   |
| 44 | X | X | X | X | X |   |   |   |   |   |   |
| 45 | X | X | X | X | X |   |   |   |   |   |   |
| 46 | X | X | X | X | X |   |   |   |   |   |   |
| 47 | X | X | X | X | X |   |   |   |   |   |   |
| 48 | X | X | X | X | X |   |   |   |   |   |   |
| 49 | X | X | X | X | X |   |   |   |   |   |   |
| 50 | X | X | X | X | X |   |   |   |   |   |   |
| 51 | X | X | X | X | X |   |   |   |   |   |   |
| 52 | X | X | X | X | X | X | X | X | X | X |   |
| 53 | X | X | X | X | X |   |   |   |   |   |   |
| 54 | X | X | X | X | X |   |   |   |   |   |   |
| 55 | X | X | X | X | X | X | X | X | X | X |   |
| 56 | X | X | X | X | X | X | X | X | X | X |   |
| 57 | X | X | X | X | X |   |   |   |   |   |   |
| 58 | X | X | X | X | X |   |   |   |   |   |   |
| 59 | X | X | X | X | X |   |   |   |   |   |   |
| 60 | X | X | X | X | X |   |   |   |   |   |   |
| 61 | X | X | X | X | X |   |   |   |   |   |   |
| 62 | X | X | X | X | X |   |   |   |   |   |   |
| 63 | X | X | X | X | X | X |   | X | X | X |   |
| 64 | X | X | X | X | X |   |   |   |   |   |   |
| 65 | X | X | X | X | X |   |   |   |   |   |   |
| 66 | X | X | X | X | X |   |   |   |   |   |   |
| 67 | X | X | X | X | X | X | X | X | X | X |   |
| 68 | X | X | X | X | X | X |   | X | X | X |   |
| 69 | X | X | X | X | X |   |   |   |   |   |   |
| 70 | X | X | X | X | X |   |   |   |   |   |   |
| 71 | X | X | X | X | X |   |   |   |   |   |   |
| 72 | X | X | X | X | X | X | X | X | X | X |   |
| 73 | X | X | X | X | X |   |   |   |   |   |   |
| 74 | X | X | X | X | X |   |   |   |   |   |   |
| 75 | X | X | X | X | X |   |   |   |   |   |   |
| 76 | X | X | X | X | X | X | X | X | X | X |   |
| 77 | X | X | X | X | X |   |   |   |   |   |   |
| 78 | X | X | X | X | X |   |   |   |   |   |   |
| 79 | X | X | X | X | X |   |   |   |   |   |   |
| 80 | X | X | X | X | X |   |   |   |   |   |   |
| 81 | X | X | X | X | X |   |   |   |   |   |   |
| 82 | X | X | X | X | X |   |   |   |   |   |   |
| 83 | X | X | X | X | X |   |   |   |   |   |   |
| 84 | X | X | X | X | X |   |   |   |   |   |   |
| 85 | X | X | X | X | X |   |   |   |   |   |   |
| 86 | X | X | X | X | X |   |   |   |   |   |   |
| 87 | X | X | X | X | X |   |   |   |   |   |   |
| 88 | X | X | X | X | X |   |   |   |   |   |   |

TABLE 4-continued

| R2 | 1 | 3 | 4 | 6 | 8 | 10 | 2 | 11 | 7 | 12 | 5 |
|---|---|---|---|---|---|---|---|---|---|---|---|
| 133 | X | X | X | X | X | X |   | X | X | X | X |
| 134 | X | X | X |   | X | X | X | X | X | X | X |
| 135 | X | X | X | X | X | X | X | X | X | X | X |
| 137 | X | X | X | X | X | X | X |   | X | X | X |
| 138 | X | X | X | X | X | X | X | X | X | X | X |
| 139 | X | X | X |   | X |   |   |   | X |   |   |
| 140 | X | X | X | X | X |   |   |   | X |   |   |
| 141 | X | X | X |   | X |   |   |   | X |   |   |
| 142 | X | X | X | X | X |   |   |   | X |   |   |
| 143 | X | X | X | X | X | X | X | X | X | X | X |
| 144 | X | X | X | X | X |   |   |   | X |   |   |
| 145 | X | X | X | X | X |   |   |   | X |   |   |
| 146 | X | X | X | X | X | X | X | X | X | X | X |
| 147 | X | X | X | X | X | X | X | X | X | X | X |
| 148 | X | X | X | X | X | X | X | X | X | X | X |
| 149 | X | X | X | X | X |   |   |   | X |   |   |
| 150 | X | X | X | X | X | X | X | X | X | X | X |
| 151 | X | X | X | X | X |   |   |   | X |   |   |
| 152 | X | X | X | X | X |   |   |   | X |   |   |
| 153 | X | X | X | X | X | X | X | X | X | X | X |
| 154 | X | X | X | X | X | X |   |   | X | X | X |
| 155 | X | X | X | X | X |   |   |   | X |   |   |
| 156 | X | X | X | X | X |   |   |   | X |   |   |
| 157 | X | X | X | X | X |   |   |   | X |   |   |
| 158 | X | X | X | X | X |   |   |   | X |   |   |
| 159 | X | X | X | X | X |   |   |   | X |   |   |
| 160 | X | X | X | X | X |   |   |   | X |   |   |
| 161 | X | X | X | X | X |   |   |   | X |   |   |
| 162 | X | X | X | X | X |   |   |   | X |   |   |
| 163 | X | X | X | X | X | X | X | X | X | X | X |
| 164 | X | X | X | X | X |   |   |   | X |   |   |
| 165 | X | X | X | X | X |   |   |   | X |   |   |
| 166 | X | X | X | X | X |   |   |   | X |   |   |
| 167 | X | X | X | X | X |   |   |   | X |   |   |
| 168 | X | X | X | X | X |   |   |   | X |   |   |
| 169 | X | X | X | X | X |   |   |   | X |   |   |
| 170 | X | X | X | X | X |   |   |   | X |   |   |
| 171 | X | X | X | X | X |   |   |   | X |   |   |
| 172 | X | X | X | X | X | X | X | X | X | X | X |
| 173 | X | X | X | X | X |   |   |   | X |   |   |
| 174 | X | X | X | X | X |   |   |   | X |   |   |
| 175 | X | X | X | X | X |   |   |   | X |   |   |
| 176 | X | X | X | X | X |   |   |   | X |   |   |
| 136 |   | X | X |   | X |   |   |   | X |   |   |
| 177 | X | X | X |   | X | X | X | X |   | X |   |
| 178 | X | X | X |   | X |   |   | X |   | X | X |
| 179 | X | X | X |   | X | X | X | X |   |   |   |
| 180 | X |   | X |   | X |   | X |   | X |   |   |
| 181 | X |   | X |   | X | X | X |   | X |   |   |
| 211 | X | X | X |   | X | X |   |   |   |   |   |
| 182 | X | X | X |   | X | X |   | X | X | X | X |
| 183 | X | X | X |   | X | X | X | X |   |   |   |
| 184 | X | X | X |   | X | X | X | X |   | X |   |
| 212 | X |   |   |   | X | X | X |   |   |   |   |
| 185 | X |   |   | X | X |   | X |   | X |   |   |
| 186 | X |   |   | X | X | X | X |   | X |   | X |
| 187 | X |   |   | X | X | X | X |   | X |   |   |
| 188 | X | X | X |   | X | X | X | X | X | X | X |
| 189 | X | X | X |   | X | X | X | X |   |   |   |
| 190 | X | X | X |   | X | X | X | X |   | X |   |
| 191 | X | X | X |   | X | X | X | X | X |   | X |
| 192 | X | X | X |   | X | X | X | X |   |   |   |
| 194 | X | X | X |   | X | X | X | X | X | X |   |
| 195 | X | X | X |   | X | X | X | X |   | X | X |
| 196 | X | X |   |   | X |   | X | X |   |   |   |
| 197 | X | X | X |   | X | X | X | X |   | X |   |
| 198 | X |   | X |   | X |   | X | X |   |   |   |
| 199 | X |   |   |   | X |   | X | X |   |   |   |
| 200 | X |   | X |   | X | X | X | X |   |   |   |
| 201 | X | X | X |   | X | X | X | X | X |   |   |
| 202 | X |   | X |   | X | X | X | X |   |   |   |
| 203 | X |   | X |   | X | X | X | X | X | X |   |
| 204 | X | X | X |   | X | X | X | X | X | X |   |
| 207 | X |   | X |   | X | X | X | X |   |   |   |
| 208 | X |   | X |   | X | X | X | X |   |   |   |
| 214 |   | X | X |   | X | X |   |   |   |   |   |
| 210 |   |   |   |   |   | X | X | X | X | X | X |
| 215 |   |   |   |   |   |   |   | X | X |   |   |
| 193 |   |   | X |   |   |   |   | X | X |   |   |
| 205 |   |   | X |   |   | X |   | X | X |   |   |
| 206 |   |   | X |   |   |   |   | X | X |   |   |
| 209 |   |   | X |   |   | X |   |   | X |   |   |
| 216 |   |   | X |   |   | X |   |   | X |   |   |
| 217 | X | X | X |   |   | X | X | X | X | X | X |
| 218 | X | X | X |   |   | X |   | X | X |   | X |
| 226 | X |   | X |   |   | X |   | X | X |   |   |
| 220 | X | X | X |   | X |   |   |   |   |   | X |
| 221 | X | X | X |   |   | X |   | X | X | X | X |
| 230 | X |   | X |   |   |   |   |   | X |   |   |
| 222 | X | X | X |   |   | X |   |   | X |   | X |
| 223 | X |   | X |   |   | X |   | X | X |   |   |
| 224 | X |   | X |   |   | X |   | X |   |   |   |
| 231 | X | X | X |   |   |   |   | X | X |   |   |
| 225 | X |   | X |   |   | X |   | X |   |   |   |
| 229 |   | X | X | X |   | X |   | X |   |   |   |
| 234 |   | X | X |   |   | X |   |   | X |   | X |
| 219 |   | X | X |   |   | X |   | X |   |   |   |
| 227 |   | X |   |   |   | X |   | X |   |   | X |
| 228 |   |   |   |   |   | X |   | X | X | X |   |
| 236 |   |   |   | X |   | X |   |   | X | X |   |
| 232 |   |   |   |   |   |   |   | X | X |   |   |
| 233 |   |   |   |   |   | X |   |   |   |   |   |
| 237 |   |   |   |   |   | X |   | X | X | X | X |
| 238 |   |   |   |   |   | X |   | X | X | X | X |
| 239 |   |   |   |   |   | X |   | X | X | X | X |
| 240 |   |   |   |   |   | X |   | X | X | X | X |
| 241 |   |   |   |   |   | X | X | X | X | X | X |
| 242 |   |   |   |   |   | X |   | X | X | X | X |
| 243 |   |   |   |   |   | X |   | X | X | X | X |
| 244 |   |   |   |   |   | X |   | X | X | X | X |
| 245 |   |   |   |   |   | X |   | X | X | X | X |
| 246 |   |   |   |   |   | X |   | X | X | X | X |
| 247 |   |   |   |   |   | X |   | X | X | X | X |
| 248 |   |   |   |   |   | X |   | X | X | X | X |
| 249 |   |   |   |   |   | X |   | X | X | X | X |
| 250 |   |   |   |   |   | X |   | X | X | X | X |
| 251 |   |   |   |   |   | X |   | X | X | X | X |
| 300 |   |   |   |   |   | X |   | X | X | X | X |
| 252 |   |   |   |   |   | X |   | X | X | X | X |
| 253 |   |   |   |   |   | X |   | X | X | X | X |
| 254 |   |   |   |   |   | X |   | X | X | X | X |
| 255 |   |   |   |   |   | X |   | X | X | X | X |
| 256 |   |   |   |   |   | X |   | X | X | X | X |
| 257 |   |   |   |   |   | X |   | X | X | X | X |
| 258 |   |   |   |   |   | X |   | X | X | X | X |
| 259 |   |   |   |   |   | X |   | X | X | X | X |
| 260 |   |   |   |   |   | X |   | X | X | X | X |
| 261 |   |   |   |   |   | X |   | X | X | X | X |
| 262 |   |   |   |   |   | X |   | X | X | X | X |
| 263 |   |   |   |   |   | X |   | X | X | X | X |
| 264 |   |   |   |   |   | X |   | X | X | X | X |
| 265 |   |   |   |   |   | X |   | X | X | X | X |
| 266 |   |   |   |   |   | X |   | X | X | X | X |
| 267 |   |   |   |   |   | X |   | X | X | X | X |
| 268 |   |   |   |   |   | X |   | X | X | X | X |
| 269 |   |   |   |   |   | X |   | X | X | X | X |
| 270 |   |   |   |   |   | X |   | X | X | X | X |
| 271 |   |   |   |   |   | X |   | X | X | X | X |
| 272 |   |   |   |   |   | X |   | X | X | X | X |
| 273 |   |   |   |   |   | X |   | X | X | X | X |
| 274 |   |   |   |   |   | X |   | X | X | X | X |
| 276 |   |   |   |   |   | X |   | X | X | X | X |
| 277 |   |   |   |   |   | X |   | X | X | X | X |
| 278 |   |   |   |   |   | X |   | X | X | X | X |
| 279 |   |   |   |   |   | X |   | X | X | X | X |
| 280 |   |   |   |   |   | X |   | X | X | X | X |
| 281 |   |   |   |   |   | X |   | X | X | X | X |
| 282 |   |   |   |   |   | X |   | X | X | X | X |
| 283 |   |   |   |   |   | X |   | X | X | X | X |
| 284 |   |   |   |   |   | X |   | X | X | X | X |

TABLE 4-continued

| R2 | 1 | 3 | 4 | 6 | 8 | 10 | 2 | 11 | 7 | 12 | 5 |
|---|---|---|---|---|---|---|---|---|---|---|---|
| 285 | | | | | | X | X | X | X | X | |
| 286 | | | | | | X | X | X | X | X | |
| 287 | | | | | | X | X | X | X | X | |
| 288 | | | | | | X | X | X | X | X | |
| 289 | | | | | | X | X | X | X | X | |
| 290 | | | | | | X | X | X | X | X | |
| 291 | | | | | | X | X | X | X | X | |
| 292 | | | | | | X | X | X | X | X | |
| 293 | | | | | | X | X | X | X | X | |
| 294 | | | | | | X | X | X | X | X | |
| 295 | | | | | | X | X | X | X | X | |
| 296 | | | | | | X | X | X | X | X | |
| 297 | | | | | | X | X | X | X | X | |
| 298 | | | | | | X | X | X | X | X | |
| 301 | | | | | | | X | X | X | X | |
| 299 | | | | | | | X | X | X | X | |
| 275 | | | | | | | X | X | X | X | |
| 302 | | | | | | | X | X | X | X | |
| 303 | | | | | | | X | X | X | X | |
| 304 | | | | | | | X | X | X | X | |
| 305 | | | | | | | X | X | X | | |
| 334 | | | | | | X | X | X | | X | X |
| 360 | | | | | | X | X | X | | X | X |
| 335 | | | | | | X | X | X | | X | X |
| 336 | | | | | | X | | X | | X | X |
| 337 | | | | | | X | | X | | | X |
| 338 | | | | | | X | X | X | | X | X |
| 339 | | | | | | X | | | | | X |
| 340 | | | | | | X | X | X | | X | X |
| 341 | | | | | | X | X | X | | X | X |
| 342 | | | | | | X | X | X | | X | X |
| 343 | | | | | | X | X | X | | X | X |
| 344 | | | | | | X | X | X | | X | X |
| 345 | | | | | | X | X | | | X | X |
| 346 | | | | | | X | X | X | | X | X |
| 347 | | | | | | X | X | X | | X | X |
| 348 | | | | | | X | X | X | | X | X |
| 361 | | | | | | X | | X | | | X |
| 349 | | | | | | X | X | X | | X | X |
| 350 | | | | | | X | X | X | | X | X |
| 351 | | | | | | X | X | X | | X | X |
| 352 | | | | | | X | X | X | | | X |
| 363 | | | | | | X | | | | | X |
| 353 | | | | | | X | X | X | | X | X |
| 354 | | | | | | X | X | X | | X | X |
| 355 | | | | | | X | X | X | | X | X |
| 356 | | | | | | X | X | X | | X | X |
| 362 | | | | | | X | | X | | X | X |
| 357 | | | | | | X | X | X | | X | X |
| 358 | | | | | | X | X | | | | X |
| 359 | | | | | | X | | | | | X |
| 364 | X | X | X | X | X | X | X | X | X | X | X |
| 365 | X | X | X | X | X | X | X | X | X | X | X |
| 366 | X | X | X | X | X | X | X | X | X | X | X |
| 367 | X | X | X | X | X | X | X | X | X | X | X |
| 368 | X | X | X | X | X | X | X | X | X | X | X |
| 369 | X | X | X | X | X | X | X | X | X | X | X |
| 370 | X | X | X | X | X | X | X | X | X | X | X |
| 371 | X | X | X | X | X | X | X | X | X | X | X |
| 372 | X | X | X | X | X | X | X | X | X | X | X |
| 373 | X | X | X | X | X | X | X | X | X | X | X |
| 374 | X | X | X | X | X | X | X | X | X | X | X |
| 375 | X | X | X | X | X | X | X | X | X | X | X |
| 376 | X | X | X | X | X | X | X | X | | X | X |
| 377 | X | X | X | X | X | | | X | | X | X |
| 378 | X | X | X | X | X | X | X | X | X | X | X |
| 379 | X | X | X | X | X | X | X | X | X | X | X |
| 380 | X | X | X | X | X | X | X | X | X | X | X |
| 381 | X | X | X | X | X | X | X | X | X | X | X |
| 382 | X | X | X | X | X | X | X | X | X | X | X |
| 383 | X | X | X | X | X | X | X | X | X | X | X |
| 384 | X | X | X | X | X | X | X | X | X | X | X |
| 385 | X | X | X | X | X | X | X | X | X | X | X |
| 386 | X | X | X | X | X | X | X | X | X | X | X |
| 387 | X | X | X | X | X | X | X | X | X | X | X |
| 388 | X | X | X | X | X | X | X | X | X | X | X |
| 389 | X | X | X | X | X | X | X | X | X | X | X |
| 390 | X | X | X | X | X | X | X | X | X | X | X |
| 391 | X | X | X | X | X | X | X | X | X | X | X |
| 392 | X | X | X | X | X | X | X | X | X | X | X |
| 393 | X | X | X | X | X | | X | X | X | X | X |
| 394 | X | X | X | X | X | X | X | X | X | X | X |
| 395 | X | X | X | X | X | X | X | X | | X | X |
| 396 | X | | X | | X | X | X | X | X | | X |
| 397 | X | X | X | X | X | X | X | X | X | | X |
| 398 | X | X | X | X | X | X | X | X | X | X | X |
| 399 | X | X | X | X | X | | X | X | X | X | X |
| 400 | X | X | X | X | X | | X | X | X | X | X |
| 401 | X | X | X | X | X | X | X | X | X | X | X |
| 402 | X | X | X | X | X | X | X | X | X | X | X |
| 403 | X | X | X | X | X | X | X | X | X | X | X |
| 404 | X | X | X | X | X | X | X | X | X | X | X |
| 405 | X | X | X | X | X | X | X | X | X | X | X |
| 406 | X | X | X | X | X | X | X | X | X | X | X |
| 407 | X | X | X | X | X | X | X | X | X | X | X |

R¹ in tables 1-4 is defined in Table 5 below:

TABLE 5

| R1 | # |
|---|---|
| Z-phenyl | 1 |
| Z-(4-fluorophenyl) | 2 |
| Z-(pyrimidin-5-yl) | 3 |
| Z-(4-biphenyl) | 4 |
| Z-H | 5 |
| Z-Me | 6 |
| Z-iPr (isopropyl) | 7 |
| Z-CH₂-(2-chlorophenyl) | 8 |
| Z-iBu (isobutyl) | 9 |

TABLE 5-continued
| R1 | # |
|---|---|
| 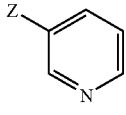 | 10 |
| 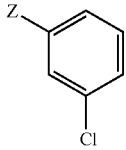 | 11 |
| 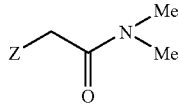 | 12 |
wherein Z represents the point of attachment of the R$^1$ group to the nitrogen atom to which it is attached; and
R$^2$ in Tables 1-4 is defined in Table 6 below:
TABLE 6
| R2 | # |
|---|---|
| 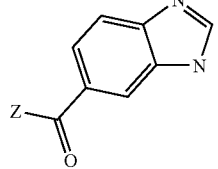 | 1 |
| 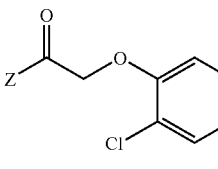 | 2 |
| 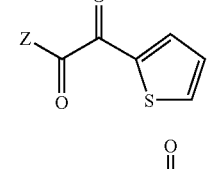 | 3 |
| 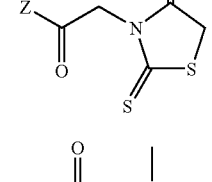 | 4 |
| 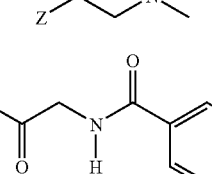 | 5 |
| 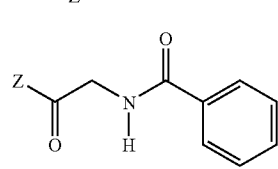 | 6 |
TABLE 6-continued
| R2 | # |
|---|---|
| 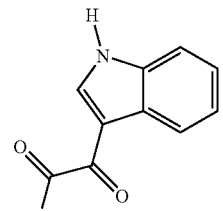 | 7 |
| 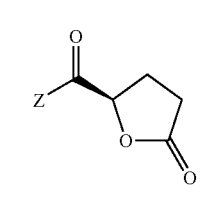 | 8 |
| 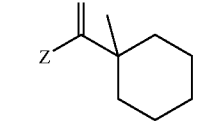 | 9 |
| 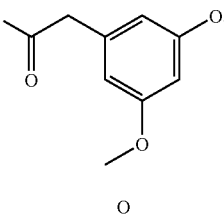 | 10 |
| 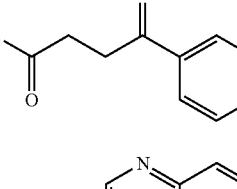 | 11 |
| 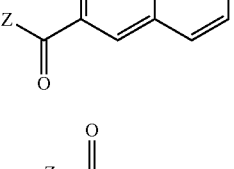 | 12 |
| 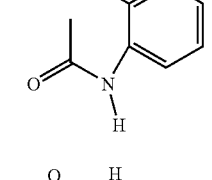 | 13 |
| 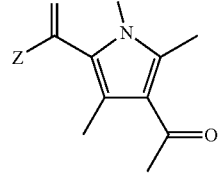 | 14 |

TABLE 6-continued

| R2 | # |
|---|---|
| (1-(4-chlorophenyl)cyclopropyl)carbonyl structure | 15 |
| 6-oxo-1,4,5,6-tetrahydropyridazine-3-carbonyl structure | 16 |
| 1H-1,2,3-thiadiazole-4-carbonyl structure | 17 |
| 1,2,3,4-tetrahydronaphthalene-2-carbonyl structure | 18 |
| 5-chlorothiophene-2-carbonyl structure | 19 |
| 2-(1H-pyrrol-1-yl)benzoyl structure | 20 |
| 3-(methoxycarbonyl)benzoyl structure | 21 |
| 2,4-dimethylthiazole-5-carbonyl structure | 22 |

TABLE 6-continued

| R2 | # |
|---|---|
| (S)-2-(dipropylamino)propanoyl structure | 23 |
| 3,6-dimethylpyrazolo-triazine carbonyl structure | 24 |
| 2,4,5-trifluorobenzoyl structure | 25 |
| tetrahydrofuran-3-carbonyl structure | 26 |
| 2,6-dimethoxynicotinoyl structure | 27 |
| 1-methyl-1H-pyrrole-2-carbonyl structure | 28 |
| (S)-5-ethoxy-3-methyl-5-oxopentanoyl structure | 29 |
| 1H-imidazole-5-carbonyl structure | 30 |
| 4-(trifluoromethyl)nicotinoyl structure | 31 |

TABLE 6-continued

| R2 | # |
|---|---|
| (structure) | 32 |
| (structure) | 33 |
| (structure) | 34 |
| (structure) | 35 |
| (structure) | 36 |
| (structure) | 37 |
| (structure) | 38 |
| (structure) | 39 |
| (structure) | 40 |
| (structure) | 41 |
| (structure) | 42 |
| (structure) | 43 |
| (structure) | 44 |
| (structure) | 45 |
| (structure) | 46 |
| (structure) | 47 |

TABLE 6-continued
| R2 | # |
|---|---|
| 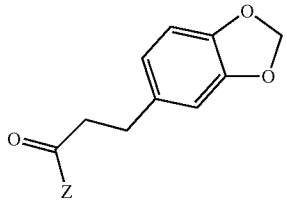 | 48 |
| 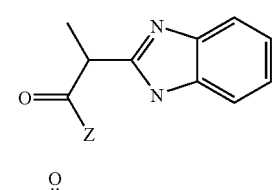 | 49 |
| 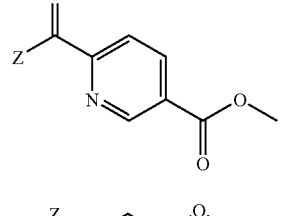 | 50 |
| 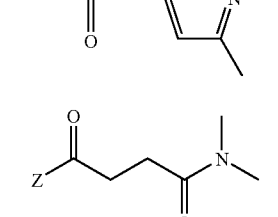 | 51 |
| 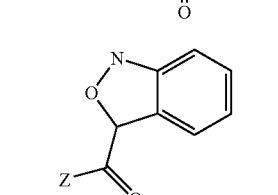 | 52 |
| 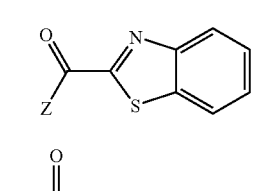 | 53 |
| 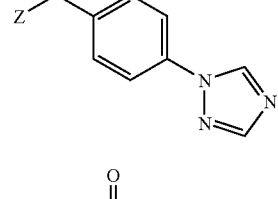 | 54 |
| 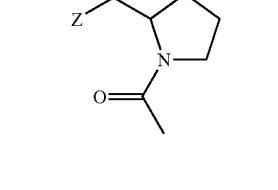 | 55 |
|  | 56 |
TABLE 6-continued
| R2 | # |
|---|---|
| 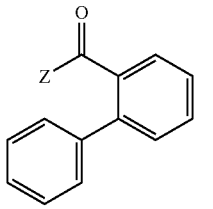 | 57 |
| 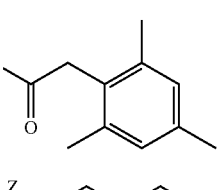 | 58 |
| 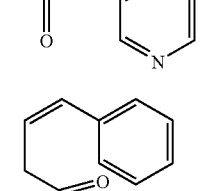 | 59 |
| 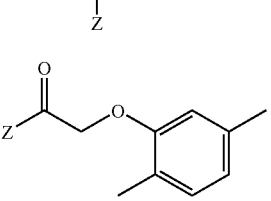 | 60 |
| 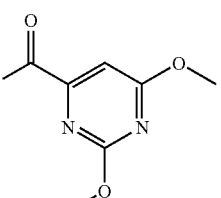 | 61 |
| 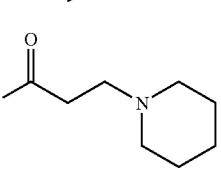 | 62 |
| 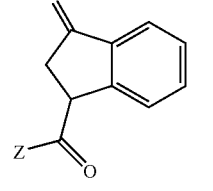 | 63 |
| 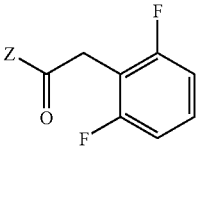 | 64 |
|  | 65 |

TABLE 6-continued
| R2 | # |
|---|---|
| 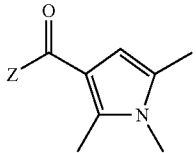 | 66 |
| 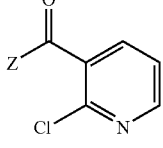 | 67 |
| 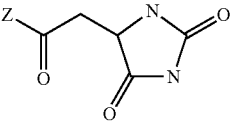 | 68 |
| 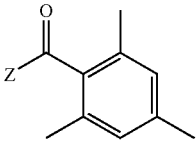 | 69 |
| 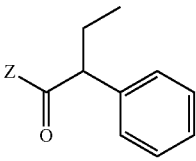 | 70 |
| 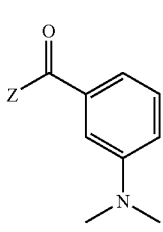 | 71 |
| 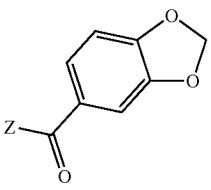 | 72 |
| 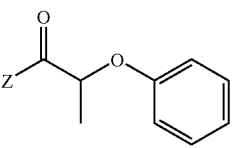 | 73 |
| 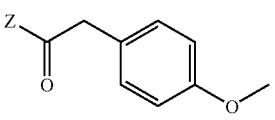 | 74 |
TABLE 6-continued
| R2 | # |
|---|---|
| 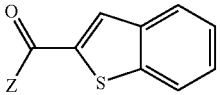 | 75 |
| 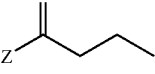 | 76 |
| 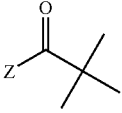 | 77 |
| 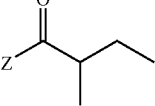 | 78 |
| 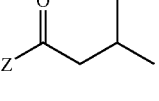 | 79 |
| 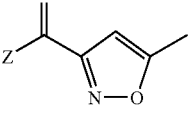 | 80 |
| 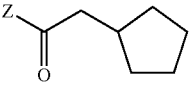 | 81 |
| 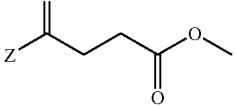 | 82 |
| 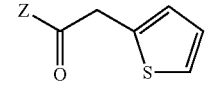 | 83 |
| 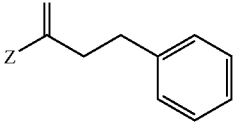 | 84 |
| 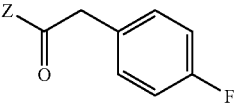 | 85 |
| 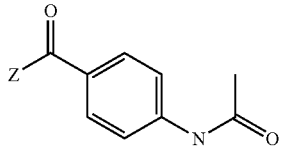 | 86 |

TABLE 6-continued
| R2 | # |
|---|---|
| 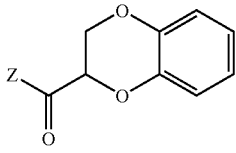 | 87 |
| 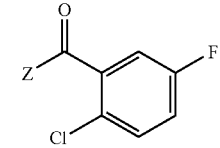 | 88 |
| 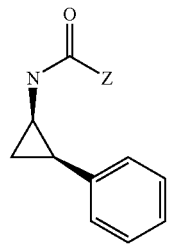 | 133 |
| 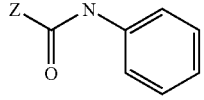 | 134 |
| 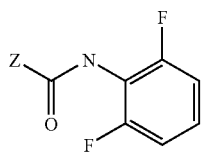 | 135 |
| 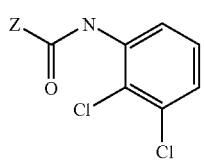 | 136 |
| 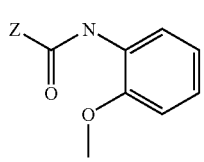 | 137 |
| 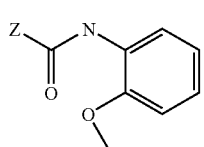 | 138 |
| 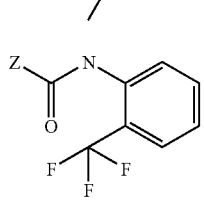 | 139 |
TABLE 6-continued
| R2 | # |
|---|---|
| 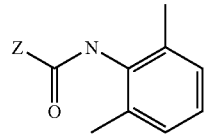 | 140 |
| 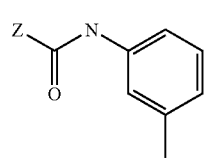 | 141 |
| 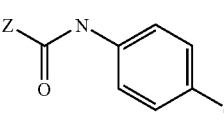 | 142 |
| 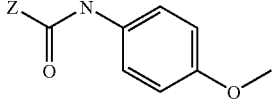 | 143 |
| 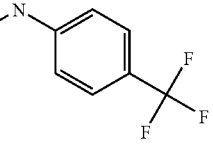 | 144 |
| 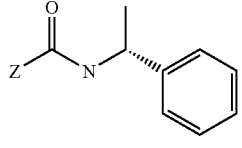 | 145 |
| 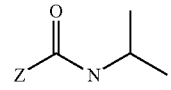 | 146 |
| 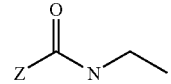 | 147 |
| 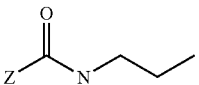 | 148 |
| 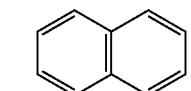 | 149 |
| 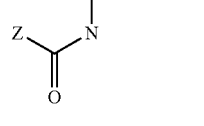 | 150 |

TABLE 6-continued
| R2 | # |
|---|---|
| 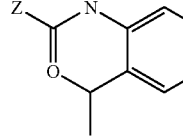 | 151 |
| 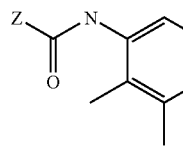 | 152 |
| 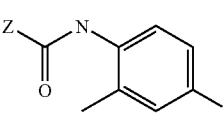 | 153 |
| 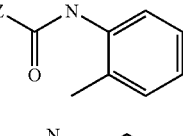 | 154 |
| 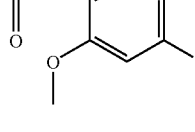 | 155 |
| 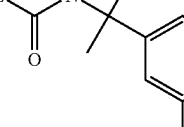 | 156 |
| 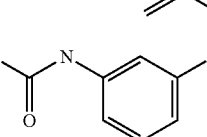 | 157 |
| 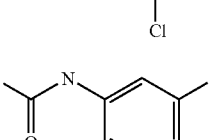 | 158 |
| 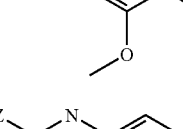 | 159 |
| 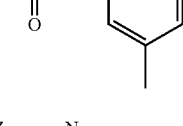 | 160 |
TABLE 6-continued
| R2 | # |
|---|---|
|  | 161 |
|  | 162 |
|  | 163 |
|  | 164 |
|  | 165 |
|  | 166 |
|  | 167 |
|  | 168 |
|  | 169 |
| 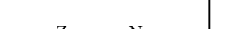 | 170 |

TABLE 6-continued
| R2 | # |
|---|---|
| 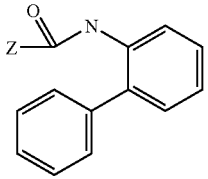 | 171 |
| 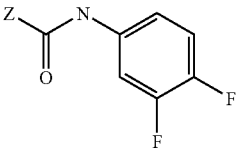 | 172 |
| 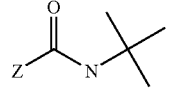 | 173 |
| 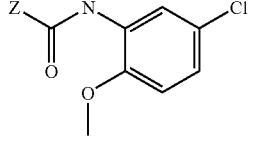 | 174 |
| 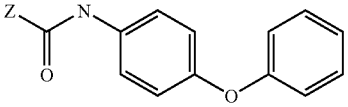 | 175 |
| 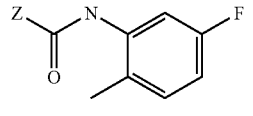 | 176 |
| 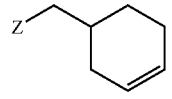 | 177 |
| 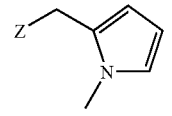 | 178 |
| 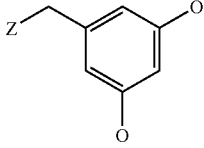 | 179 |
| 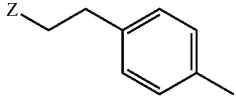 | 180 |
| 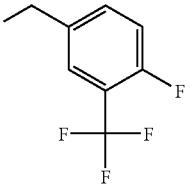 | 181 |
TABLE 6-continued
| R2 | # |
|---|---|
| 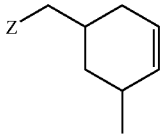 | 182 |
| 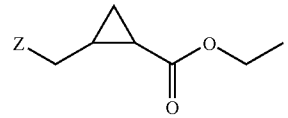 | 183 |
| 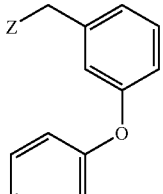 | 184 |
| 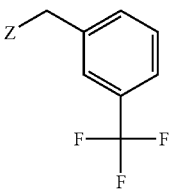 | 185 |
| 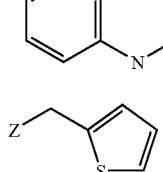 | 186 |
| 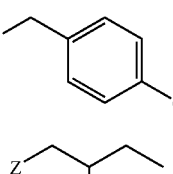 | 187 |
| 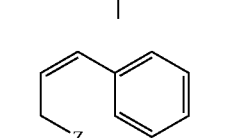 | 188 |
| 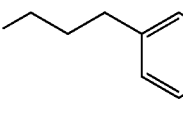 | 189 |
|  | 190 |
|  | 191 |
|  | 192 |

TABLE 6-continued
| R2 | # |
|---|---|
| 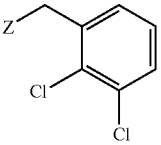 | 193 |
| 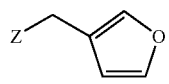 | 194 |
| 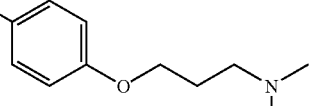 | 195 |
| 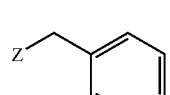 | 196 |
| 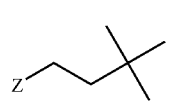 | 197 |
| 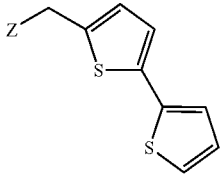 | 198 |
| 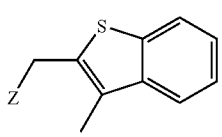 | 199 |
| 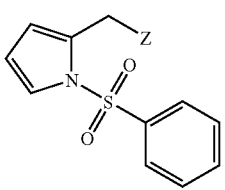 | 200 |
| 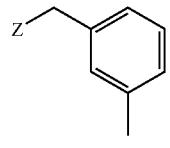 | 201 |
| 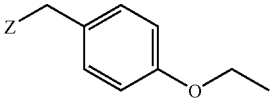 | 202 |
| 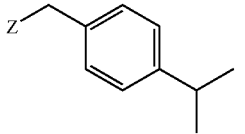 | 203 |
TABLE 6-continued
| R2 | # |
|---|---|
| 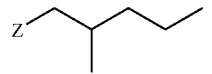 | 204 |
| 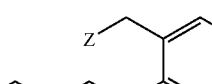 | 205 |
| 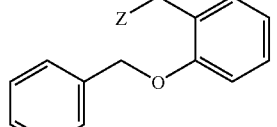 | 206 |
| 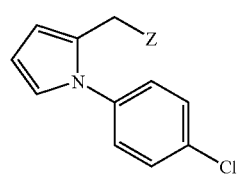 | 207 |
| 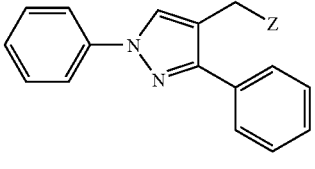 | 208 |
| 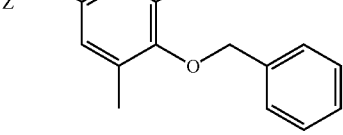 | 209 |
|  | 210 |
| 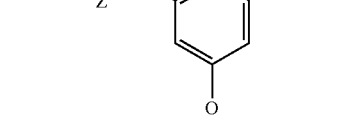 | 211 |
| 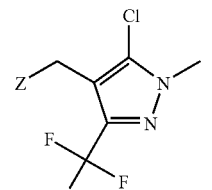 | 212 |

TABLE 6-continued
| R2 | # |
|---|---|
| 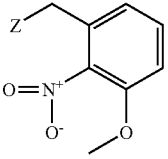 | 213 |
| 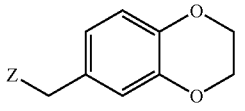 | 214 |
| 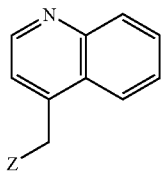 | 215 |
| 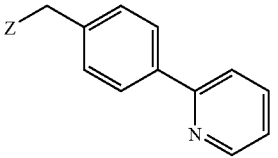 | 216 |
| 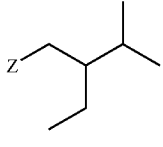 | 217 |
| 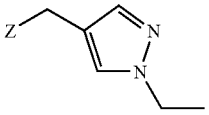 | 218 |
| 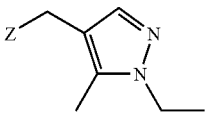 | 219 |
| 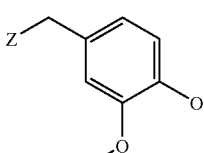 | 220 |
| 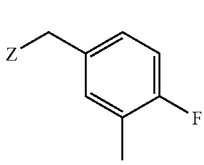 | 221 |
| 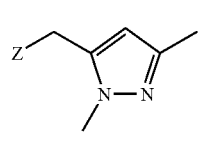 | 222 |
TABLE 6-continued
| R2 | # |
|---|---|
| 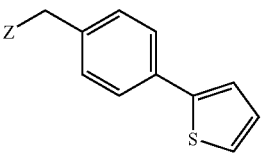 | 223 |
| 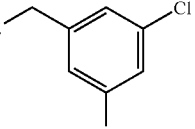 | 224 |
| 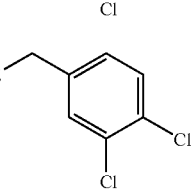 | 225 |
| 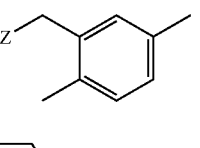 | 226 |
| 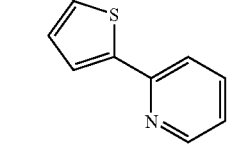 | 227 |
| 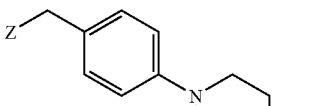 | 228 |
| 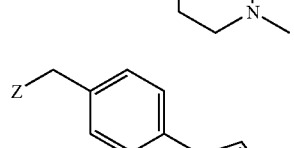 | 229 |
| 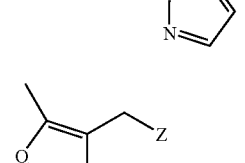 | 230 |
| 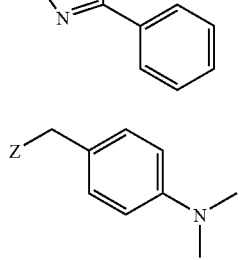 | 231 |

TABLE 6-continued
| R2 | # |
|---|---|
| 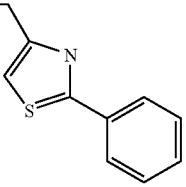 | 232 |
| 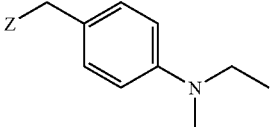 | 233 |
| 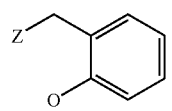 | 234 |
| 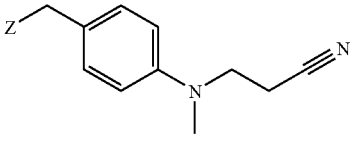 | 235 |
| 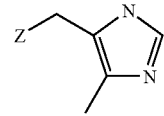 | 236 |
| 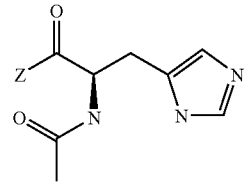 | 237 |
| 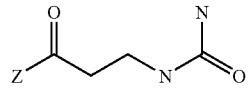 | 238 |
| 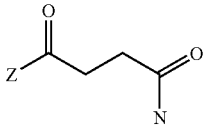 | 239 |
| 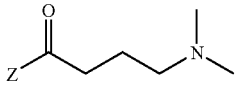 | 240 |
| 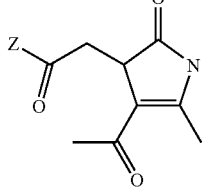 | 241 |
TABLE 6-continued
| R2 | # |
|---|---|
| 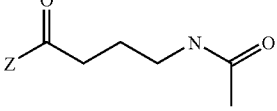 | 242 |
| 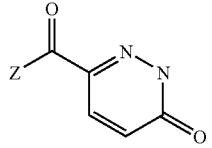 | 243 |
| 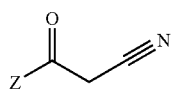 | 244 |
| 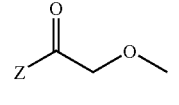 | 245 |
| 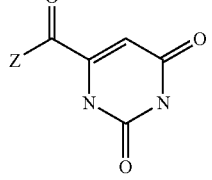 | 246 |
| 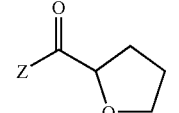 | 247 |
| 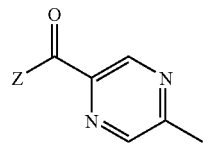 | 248 |
| 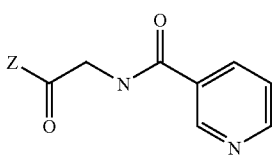 | 249 |
| 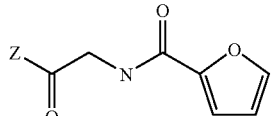 | 250 |
| 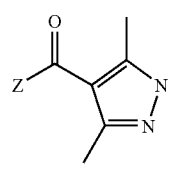 | 251 |

TABLE 6-continued

| R2 | # |
|---|---|
| (structure) | 252 |
| (structure) | 253 |
| (structure) | 254 |
| (structure) | 255 |
| (structure) | 256 |
| (structure) | 257 |
| (structure) | 258 |
| (structure) | 259 |
| (structure) | 260 |
| (structure) | 261 |
| (structure) | 262 |
| (structure) | 263 |
| (structure) | 264 |
| (structure) | 265 |
| (structure) | 266 |
| (structure) | 267 |
| (structure) | 268 |
| (structure) | 269 |
| (structure) | 270 |

TABLE 6-continued

| R2 | # |
|---|---|
| (2H-1,4-benzoxazin-3(4H)-one-N-CH2-C(O)-Z) | 271 |
| (3-pyridyl-CH2CH2-C(O)-Z) | 272 |
| (2,5-dimethylfuran-3-yl-C(O)-Z) | 273 |
| (CH3-S-CH2CH2-C(O)-Z) | 274 |
| (1H-indazol-3(2H)-one-4-yl-C(O)-Z) | 275 |
| (6-morpholinopyridin-3-yl-C(O)-Z) | 276 |
| (tBu-CH2-C(O)-Z) | 277 |
| (AcNH-CH(Ph)-C(O)-Z) | 278 |
| (2,5-dimethylthiazol-4-yl-CH2-C(O)-Z) | 279 |

TABLE 6-continued

| R2 | # |
|---|---|
| (PhCH2-C(O)-NH-CH2-C(O)-Z) | 280 |
| (6-oxo-1,6-dihydropyridin-2-yl-C(O)-Z) | 281 |
| (phthalimido-CH2-C(O)-Z) | 282 |
| (3-acetyl-2,2-dimethylcyclobutyl-CH2-C(O)-Z) | 283 |
| (4-methoxycyclohexyl-C(O)-Z) | 284 |
| (4-dimethylaminophenyl-C(O)-Z) | 285 |
| (1-ethyl-3-methyl-1H-pyrazol-5-yl-C(O)-Z) | 286 |
| (5-trifluoromethyl-2-oxo-1,2-dihydropyridin-1-yl-CH2CH2-C(O)-Z) | 287 |
| (4-acetylphenyl-C(O)-Z) | 288 |

TABLE 6-continued
| R2 | # |
|---|---|
| 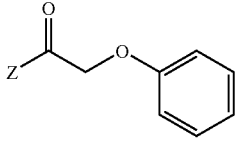 | 289 |
| 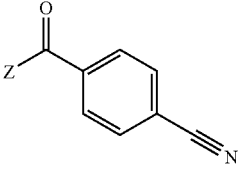 | 290 |
| 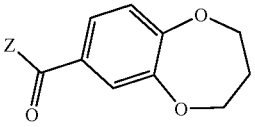 | 291 |
| 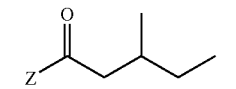 | 292 |
| 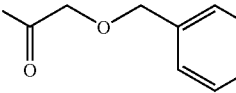 | 293 |
| 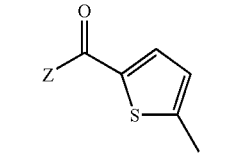 | 294 |
| 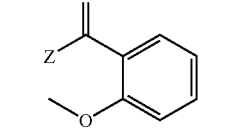 | 295 |
| 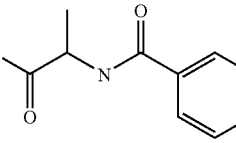 | 296 |
| 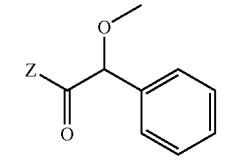 | 297 |
| 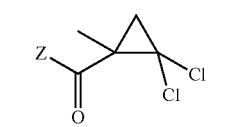 | 298 |
TABLE 6-continued
| R2 | # |
|---|---|
| 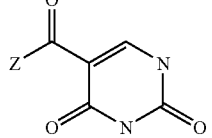 | 299 |
| 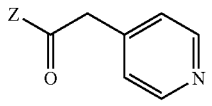 | 300 |
| 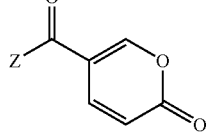 | 301 |
| 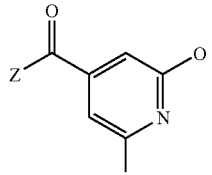 | 302 |
| 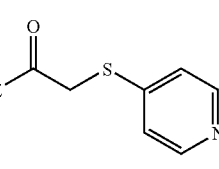 | 303 |
| 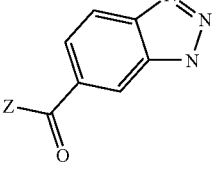 | 304 |
| 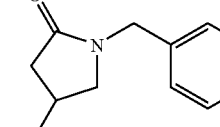 | 305 |
| 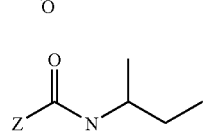 | 334 |
| 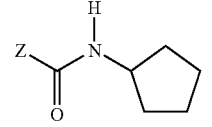 | 335 |

TABLE 6-continued
| R2 | # |
|---|---|
| 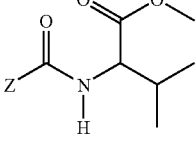 | 336 |
| 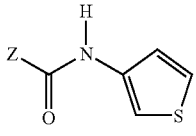 | 337 |
| 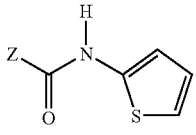 | 338 |
| 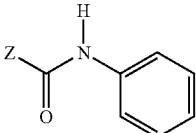 | 339 |
|  | 340 |
| 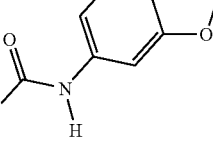 | 341 |
| 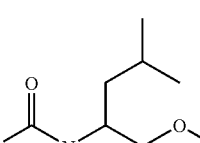 | 342 |
| 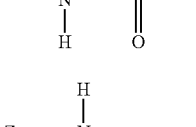 | 343 |
| 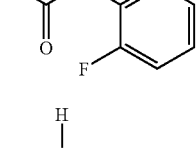 | 344 |
| 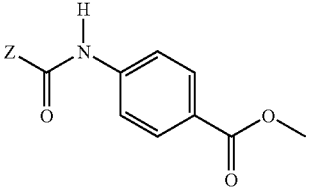 | 345 |
| 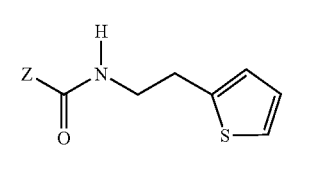 | 346 |
| 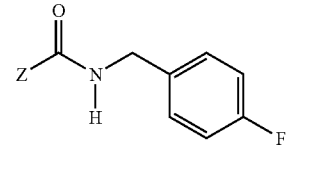 | 347 |
| 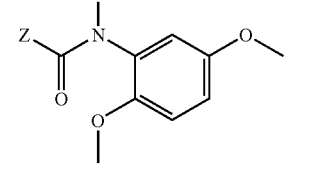 | 348 |
| 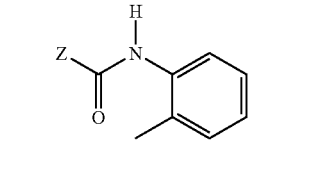 | 349 |
| 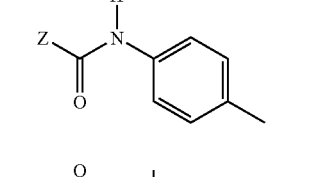 | 350 |
| 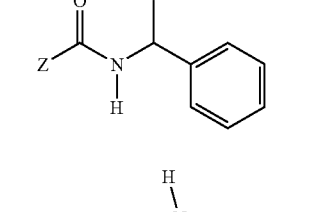 | 351 |
| 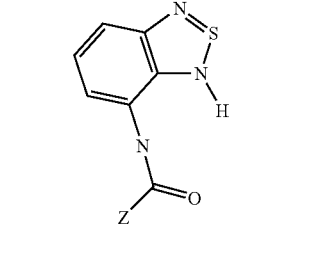 | 352 |

TABLE 6-continued
| R2 | # |
|---|---|
| 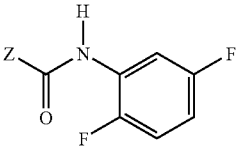 | 353 |
| 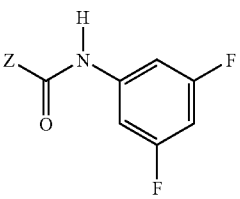 | 354 |
| 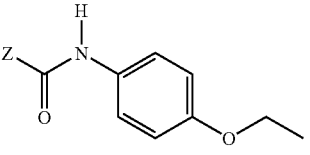 | 355 |
| 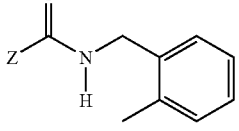 | 356 |
| 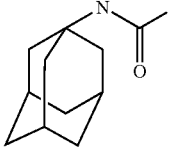 | 357 |
| 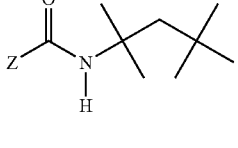 | 358 |
| 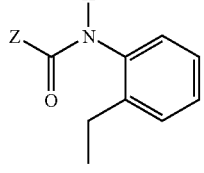 | 359 |
| 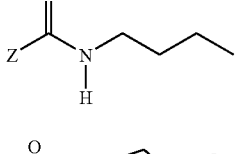 | 360 |
| 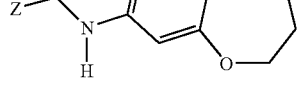 | 361 |
TABLE 6-continued
| R2 | # |
|---|---|
| 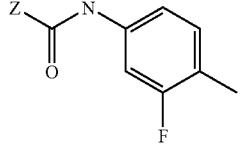 | 362 |
| 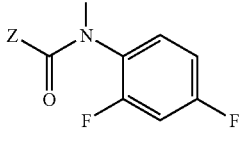 | 363 |
| 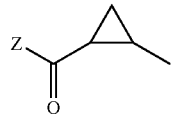 | 364 |
| 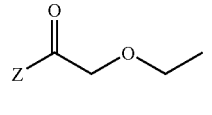 | 365 |
| 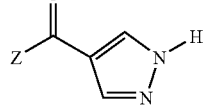 | 366 |
| 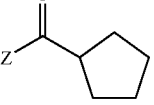 | 367 |
| 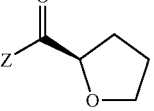 | 368 |
| 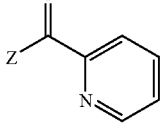 | 369 |
| 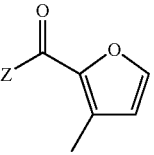 | 370 |
| 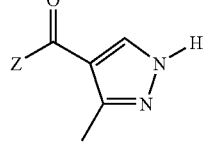 | 371 |

TABLE 6-continued

| R2 | # |
|---|---|
| (structure) | 372 |
| (structure) | 373 |
| (structure) | 374 |
| (structure) | 375 |
| (structure) | 376 |
| (structure) | 377 |
| (structure) | 378 |
| (structure) | 379 |
| (structure) | 380 |
| (structure) | 381 |
| (structure) | 382 |
| (structure) | 383 |
| (structure) | 384 |
| (structure) | 385 |
| (structure) | 386 |
| (structure) | 387 |
| (structure) | 388 |

TABLE 6-continued
| R2 | # |
|---|---|
| 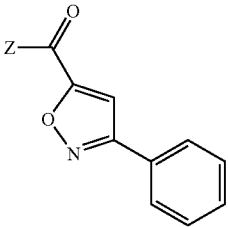 | 389 |
| 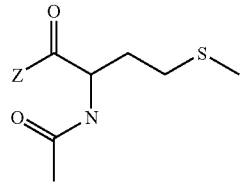 | 390 |
| 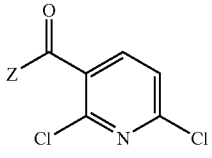 | 391 |
| 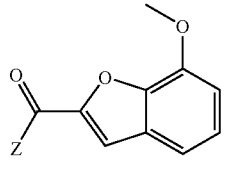 | 392 |
| 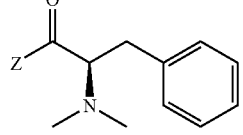 | 393 |
| 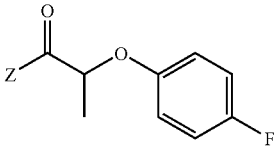 | 394 |
| 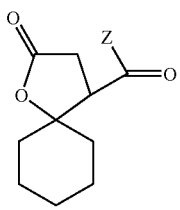 | 395 |
| 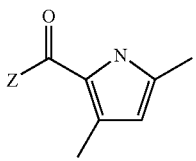 | 396 |
TABLE 6-continued
| R2 | # |
|---|---|
| 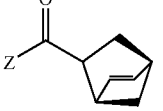 | 397 |
| 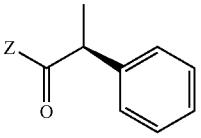 | 398 |
| 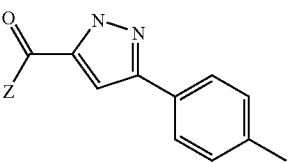 | 399 |
| 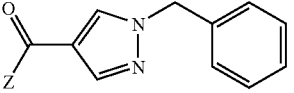 | 400 |
| 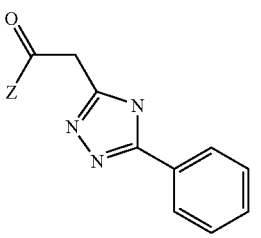 | 401 |
| 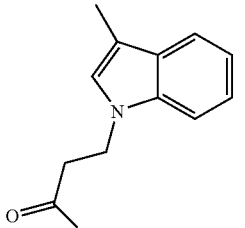 | 402 |
| 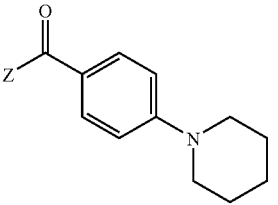 | 403 |
| 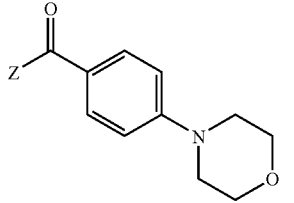 | 404 |

TABLE 6-continued

| R2 | # |
|---|---|
| 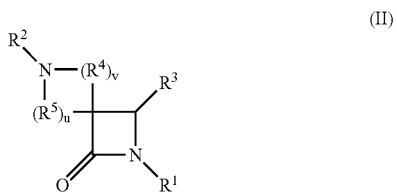 | 405 |
| | 406 |
| | 407 | wherein Z represents the point of attachment of the $R^2$ group to the nitrogen atom to which it is attached.

In another aspect, the invention provides azetidinone compounds of formula (II):

(II)

and pharmaceutically acceptable salts, solvates, esters, prodrugs and stereoisomers thereof, wherein:

$R^1$ is H, alkyl, aryl, arylalkyl, heteroaryl, heteroarylalkyl, cycloalkylalkyl, cycloalkyl, cycloalkenyl, heterocycloalkyl, heterocycloalkenyl, or -alkylene-C(O)N(alkyl)$_2$, wherein an alkyl or aryl group may be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —C(O)N(R$^6$)$_2$, —S(O)alkyl, —SO$_2$-alkyl, or —P(O)(O-alkyl)$_2$, an aryl group may further be optionally and independently substituted with one or more alkyl groups, and an alkyl group may further be optionally and independently substituted with one or more aryl groups;

$R^2$ is H, alkyl, cycloalkyl, aryl, arylalkyl, heteroarylalkyl, heterocycloalkyl, heterocycloalkylalkyl, $R^6$-A-, alkyl-O—C(O)—, (alkyl)$_2$-N-alkylene-C(O), CN-alkylene-C(O)—, alkyl-O-alkylene-C(O)—, alkyl-C(O)-alkylene-C(O)—, alkyl-NH—C(O)— or alkyl-O—C(O)-alkylene-C(O)—, wherein an alkyl or aryl group may be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$, and an aryl group may further be optionally and independently substituted with one or more alkyl groups;

$R^3$ is H, alkyl, aryl, arylalkyl, arylalkenyl, arylalkynyl, —NH-arylalkyl, arylalkoxy, cycloalkyl, heteroaryl, heteroarylalkyl, heteroarylalkenyl or heteroarylalkynyl, wherein an alkyl or aryl group can be optionally and independently substituted with one or more of the following groups: —(C=N—O-alkyl)CH$_3$, —NH—C(O)NH-alkyl, —O(O)NH$_2$, —CN, —C(O)NH-alkyl, —C(O)O-alkyl, —C(O)H, —C(O)OH, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_{31}$—OH, -halo, —CN, -alkoxy, —C(O)O-alkyl, —S(O)alkyl, —SO$_2$-alkyl, or —P(O)(O-alkyl)$_2$, an aryl group can be optionally and independently substituted with one or more alkyl groups, and a heteroaryl group can be optionally and independently substituted with one or more aryl or heteroaryl groups;

each occurrence of $R^4$ and $R^5$ is independently —C(R$^7$)$_2$—, wherein the ring carbon atom of one $R^4$ group and the ring carbon atom of one $R^5$ group may optionally be joined by a —CH$_2$—CH$_2$— group;

each occurrence of $R^6$ is independently alkyl, alkenyl, aryl, heteroaryl, cycloalkyl, cycloalkylalkyl, heterocycloalkyl, cycloalkenyl, heterocycloalkenyl, benzofused cycloalkyl, benzofused heterocycloalkyl or benzofused heterocycloalkenyl;

each occurrence of $R^7$ is independently H, alkyl, —CN, or —OH;

A is —C(O)—, —OC(O), —NHC(O), -alkylene-C(O)—, —O-alkylene-C(O)—, —C(O)-alkylene-C(O)—, —C(O)—CH$_2$—NHC(O)—, -alkylene-, -alkenylene-, -alkenylene-C(O)—,

or -alkylene-NHC(O)—, wherein an A group is joined to the nitrogen atom to which it is attached via a terminal C(O) group;

u is an integer ranging from 0 to 3; and v is an integer ranging from 0 to 3; such that the sum of u and v is from 3 to 5, such that the compound of formula (II) is not a compound of formula (IA), (IB), (IC) or (ID) as set forth in Tables 1-4 above.

In another aspect, the invention provides azetidinone compounds of formula (III):

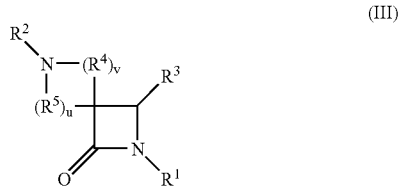

(III)

and pharmaceutically acceptable salts, solvates, esters, prodrugs and stereoisomers thereof, wherein:

$R^1$ is alkyl, aryl, cycloalkyl, —$CH_2$-cycloalkyl, —$CH_2$-aryl, —$CH(aryl)_2$, heteroaryl, wherein an aryl group may be optionally substituted with up to 3 substituents independently selected from alkyl, halo, —$NO_2$, —O-alkyl, —CN, —C(O)O-alkyl, —$CF_3$, —C(O)-alkyl or —$S(O)_2$-alkyl;

$R^2$ is H, —C(O)aryl, —C(O)NH-alkyl, —C(O)NH-alkylene-aryl, —C(O)NR$^6$-aryl, —C(O)NH-cycloalkyl, —C(O)NH—$CH_2$-aryl, —C(O)NH-heteroaryl, —C(O)NH-heterocycloalkyl, —C(O)NH-benzofused heterocycloalkyl, —C(O)O-alkyl or

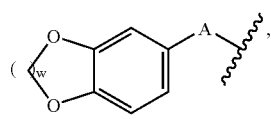

wherein an alkyl group may be optionally substituted with up to 2 substituents independently selected from —OH, —O-alkyl, —C(O)OR$^6$ or —C(O)N(R$^6$)$_2$; an aryl group may be optionally substituted with up to 3 substituents independently selected from alkyl, —O-alkyl, -halo, unsubstituted alkyl, —CN or —$CF_3$; and a cycloalkyl group may be may be optionally and independently substituted with up to 3 unsubstituted alkyl groups;

$R^3$ is H, aryl or heteroaryl, wherein an aryl group or may be optionally substituted with up to 2 substituents independently selected from alkyl, halo, —OH, or —O-benzyl;

each occurrence of $R^4$ and $R^5$ is independently —CH($R^7$)—, wherein the ring carbon atom of one $R^4$ group and the ring carbon atom of one $R^5$ group may optionally be joined by a —$CH_2$—$CH_2$— group;

each occurrence of $R^6$ is H or alkyl;

each occurrence of $R^7$ is independently H, alkyl, —CN, or —OH;

A is —$CH_2$— or —C(O)—;

u and v are each 2; and w is an integer ranging from 1 to 3, such that the compound of formula (III) is not a compound of formula (IA), (IB), (IC) or (ID) as set forth in Tables 1-4 above.

The compounds described by formulas (IA)-(ID) and defined by an "X" in Tables 1-4 have the $R^1$ and $R^2$ definitions as indicated by an "X" in the box formed by the intersection of the $R^2$ column and the $R^1$ row, and are not within the scope of the present invention. The numbers in the top row of Tables 1-4 represent the $R^1$ groups defined in Table 5. The numbers in the leftmost column in Tables 1-4 represent the $R^2$ groups defined in Table 6. The compounds described by formulas (IA)-(ID) and denoted using an "X" in tables 1-4 are specifically excluded from the scope of the present invention. The compounds represented by blank boxes in Tables 1-4 are not excluded from the scope of the present invention.

The compounds of formulas (I), (II) and (III) (the "Azetidinone Derivatives") are useful for treating or preventing a disorder of lipid metabolism, pain, diabetes, a vascular condition, demyelination or nonalcoholic fatty liver disease (each being a "Condition").

The present invention also relates to compositions comprising an Azetidinone Derivative and a pharmaceutically acceptable carrier. The compositions are useful for treating or preventing a Condition in a patient.

The present invention also relates to methods for treating or preventing a Condition in a patient, comprising administering to the patient an effective amount of an Azetidinone Derivative.

The present invention further relates to methods for treating or preventing a Condition in a patient, comprising administering to the patient an effective amount of an Azetidinone Derivative and an effective amount of another therapeutic agent.

It is further contemplated that the combination therapies of the present invention can be provided as a kit comprising in a single package at least one Azetidinone Derivative in a pharmaceutical composition, and at least one separate pharmaceutical composition comprising at least one additional therapeutic agent.

DETAILED DESCRIPTION OF THE INVENTION

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc. . . .

As used above, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"At least one" when referring to an Azetidinone Derivative, means from 1 to 4 different Azetidinone Derivatives. In one embodiment, the term "at least one" is used to designate a single Azetidinone Derivative. In another embodiment, the term "at least one" is used to designate two Azetidinone Derivatives. Similarly, when "at least one" is used in connection with the additional agents used in the combinations, from 1 to 4 additional agents are contemplated. In one embodiment, the term "at least one" is used to designate a single additional agent. In another embodiment, the term "at least one" is used to designate two additional agents.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. An aryl group may be unsubstituted or optionally and independently substituted with one or more groups selected from —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzothiadiazolyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like, "Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Benzofused cycloalkyl", "benzofused cycloalkenyl", "benzofused heterocycloalkyl", and "benzofused heterocycloalkenyl" mean cycloalkyl, cycloalkenyl, heterocycloalkyl or heterocycloalkenyl rings fused to a benzene ring at two adjacent carbon atoms of the non-aromatic rings, for example:

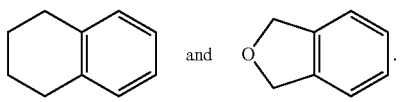

The Benzofused cycloalkyl", "benzofused cycloalkenyl", "benzofused heterocycloalkyl", and "benzofused heterocycloalkenyl rings are joined to the rest of the molecule by a bond to a carbon atom of their non-aromatic ring.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are —(CH$_2$)$_3$—, —(CH$_2$)$_4$—, —O—CH$_2$—O—, —O(CH$_2$)$_2$—O—, —O(CH$_2$)$_3$—O—, —NH—NH—NH—, —NH—S—NH—, —NH—O—NH—, or —NH—NH—C(O)—, and the like which form moieties such as, for example:

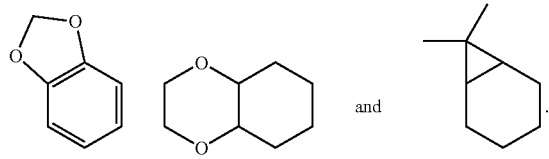

When R$^1$, R$^2$ and/or R$^3$ is an aryl or heteroaryl ring, the ring system substituent can also be a sugar, a polyol, a glucuronide or a sugar carbamate.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" or "heterocycloalkyl" may also be substituted by a moiety which simultaneously replaces two available hydrogens on the same carbon atom on a ring system (e.g., carbonyl). An example of such moiety is:

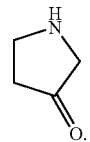

"Heterocyclylalkyl" or "heterocycloalkylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" or "heterocycloalkenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also be substituted by a moiety which simultaneously replaces two available hydrogens on the same carbon atom on a ring system (e.g., carbonyl). An example of such moiety is:

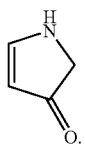

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

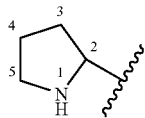

there is no —OH attached directly to carbons marked 2 and 5.

It should also be noted that tautomeric forms such as, for example, the moieties:

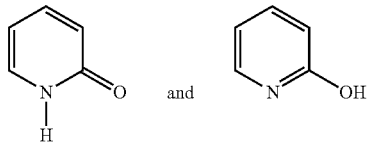

are considered equivalent in certain embodiments of this invention.

"Heteroaralkyl" or "heteroarylalkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described, Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Polyol" means a compound or residue having a plurality of —OH groups; in particular, polyols are alkyl groups in which a plurality of C—H bonds are replaced by C—OH bonds. Typical polyols include glycerol, erythritol, sorbitol, xylitol, mannitol, and inositol. Linear polyol residues generally have the empirical formula —C$_y$H$_{2y+1}$O$_y$, and cyclic polyol residues generally have the formula —C$_y$H$_{2y-1}$O$_y$—. Polyols wherein y is 3, 4, 5 or 6 are preferred. Cyclic polyols also include reduced sugars such as glucitol.

"Sugar" means a carbohydrate comprised of one or two saccharose groups. Monosaccharide sugars, also known as simple sugars, are composed of chains of 2-7 carbon atoms, wherein one of the carbons carries aldehydic or ketonic oxygen, which may be combined in acetal or ketal forms. The remaining carbons usually have hydrogen atoms and hydroxyl groups, or protecting groups for hydroxyl, such as acetate. Typical monosaccharides considered "sugars" in the present invention are arabinose, ribose, xylose, xylulose, deoxyribose, galactose, glucose, mannose, fructose, sorbose, tagatose, fucose, quinovose, rhamnose, manno-heptulose and sedoheptulose. Typical disaccharides are sucrose, lactose, maltose and cellobiose. Unless specifically modified, the term "sugar" refers to both D-sugars and L-sugars. The sugar may be protected. The sugar can be attached through an oxygen or a carbon.

Reduced C-attached sugars or C-glycosyl compounds are also encompassed by the invention. The reduced sugars (e.g., glucitol) can be classified as either polyols or sugars, and are also known as alditols. Alditols are polyols having the general formula HOCH$_2$[CH(OH)]$_x$CH$_2$OH.

"Glucuronide" means a glycoside of glucuronic acid.

"Sugar carbamate" means a mono-, di- or oligo-saccharide in which one or more hydroxyl groups are derivatized as carbamates, particularly as phenyl carbamates or substituted phenyl carbamates.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction, Suitable protecting groups will be recognized by those with ordinary skill in the art as well as by reference to standard textbooks such as, for example, T. W. Greene et al., *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of Azetidinone Derivatives are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to provide an Azetidinone Derivative or a pharmaceutically acceptable salt, solvate or prod rug thereof. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if an Azetidinone Derivative or a pharmaceutically acceptable salt, solvate or prodrug thereof, contains a carboxylic acid functional group, a prodrug can comprise an ester formed by the replacement of the hydrogen atom of the acid group with a group such as, for example, $(C_1$-$C_8)$alkyl, $(C_2$-$C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)-aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di$(C_1$-$C_2)$alkylcarbamoyl-$(C_1$-$C_2)$alkyl and piperidino-, pyrrolidino- or morpholino$(C_2$-$C_3)$alkyl, and the like.

Similarly, if an Azetidinone Derivative contains an alcohol functional group, a prodrug can be formed by the replacement of the hydrogen atom of the alcohol group with a group such as, for example, $(C_1$-$C_6)$alkanoyloxymethyl, 1-(($C_1$-$C_6)$alkanoyloxy)ethyl, 1-methyl-1-(($C_1$-$C_6)$alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate), and the like.

If an Azetidinone Derivative contains an amine functional group, a prodrug can be formed by the replacement of a hydrogen atom in the amine group with a group such as, for example, R-carbonyl, RO-carbonyl, NRR'-carbonyl where R and R' are each independently $(C_1$-$C_{10})$alkyl, $(C_3$-$C_7)$cycloalkyl, benzyl, or R-carbonyl is a natural α-aminoacyl or natural α-aminoacyl, —$C(OH)C(O)OY^1$ wherein $Y^1$ is H, $(C_1$-$C_6)$alkyl or benzyl, —$C(OY^2)Y^3$ wherein $Y^2$ is $(C_1$-$C_4)$ alkyl and $Y^3$ is $(C_1$-$C_6)$alkyl, carboxy$(C_1$-$C_6)$alkyl, amino$(C_1$-$C_4)$alkyl or mono-N— or di-N,N—$(C_1$-$C_6)$alkylaminoalkyl, —$C(Y^4)Y^5$ wherein $Y^4$ is H or methyl and $Y^5$ is mono-N— or di-N,N—$(C_1$-$C_6)$alkylamino morpholino, piperidin-1-yl or pyrrolidin-1-yl, and the like.

The Azetidinone Derivatives may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more of the Azetidinone Derivatives may optionally be converted to a solvate. Preparation of solvates is generally known. Thus, for example, M. Caira et al., *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al., *AAPS Pharm Sci Tech.*, 5(1), article 12 (2004), and A. L. Bingham et al., *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The Azetidinone Derivatives can form salts that are also within the scope of this invention. Reference to an Azetidinone Derivative herein is understood to include reference to salts thereof unless otherwise indicated. The term "salt(s)", as employed herein, denotes acidic salts formed with inorganic and/or organic acids, as well as basic salts formed with inorganic and/or organic bases. In addition, when an Azetidinone Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the Azetidinone Derivatives can be formed, for example, by reacting an Azetidinone Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al. Camille G. (eds.) *Handbook of Pharmaceutical Salts, Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be salts within the scope of the invention and all acid and base salts are considered equivalent to the free forms of the corresponding compounds for purposes of the invention.

Pharmaceutically acceptable esters of the Azetidinone Derivatives include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The Azetidinone Derivatives, and pharmaceutically acceptable salts, solvates, esters and prodrugs thereof, may exist in their tautomeric form (for example, as an amide or imino ether). All such tautomeric forms are contemplated herein as part of the present invention.

The Azetidinone Derivatives may contain asymmetric or chiral centers, and, therefore, exist in different stereoisomeric forms. It is intended that all stereoisomeric forms of the Azetidinone Derivatives as well as mixtures thereof, including racemic mixtures, form part of the present invention. In addition, the present invention embraces all geometric and positional isomers. For example, if an Azetidinone Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Azetidinone Derivatives may be atropisomers (e.g., substituted biaryls) and are considered as part of this invention. Enantiomers can also be separated by use of chiral HPLC column.

All stereoisomers (for example, geometric isomers, optical isomers and the like) of the present compounds (including those of the salts, solvates, esters, prod rugs and stereoisomers of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if an Azetidinone Derivative incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the Azetidinone Derivatives, for example, be substantially free of other isomers, or may be admixed, for example, as racemates or with all other, or other selected, stereoisomers. When one or more chiral centers is present in an Azetidinone Derivative, of the present invention, each chiral center can independently have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the Azetidinone Derivatives.

The Azetidinone Derivatives may contain asymmetric or chiral centers, and, therefore, exist in different stereoisomeric forms. It is intended that all stereoisomeric forms of the Azetidinone Derivatives as well as mixtures thereof, including racemic mixtures, form part of the present invention. In addition, the present invention embraces all geometric and positional isomers. For example, if an Azetidinone Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Azetidinone Derivatives may be atropisomers (e.g., substituted biaryls) and are considered as part of this invention. Enantiomers can also be separated by use of chiral HPLC column.

The straight line - as a bond generally indicates a mixture of, or either of, the possible isomers, non-limiting example(s) include, containing (R)— and (S)-stereochemistry. For example,

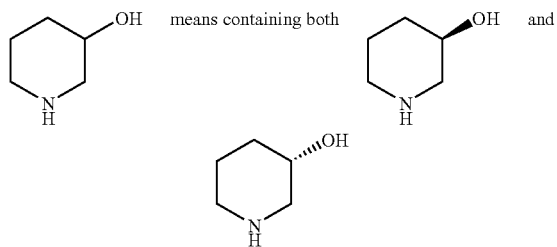

A dashed line (---)represents an optional bond.

Lines drawn into the ring systems, such as, for example:

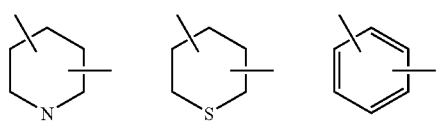

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

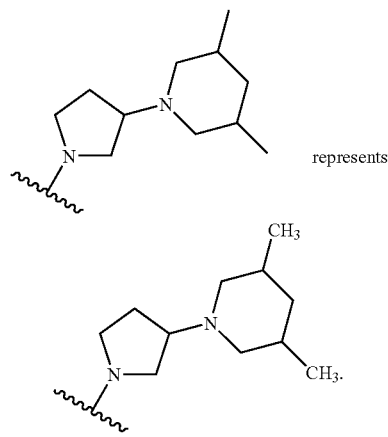

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if an Azetidinone Derivative incorporates a double bond or a fused ring, both the cis- and trans-forms, as well as mixtures, are embraced within the scope of the invention.

The present invention also embraces isotopically-labelled Azetidinone Derivatives which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Azetidinone Derivatives (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled Azetidinone Derivatives can generally be prepared by following procedures analogous to those disclosed in the Schemes and/or in the Examples herein below, by substituting an appropriate isotopically labelled reagent for a non-isotopically labelled reagent.

Polymorphic forms of the Azetidinone Derivatives, and of the salts, solvates, esters, prodrugs and stereoisomers thereof, are intended to be included in the present invention.

Those skilled in the art will appreciate that for some of the Azetidinone Derivatives, one isomer will show greater pharmacological activity than other isomers.

The following abbreviations are used herein and are defined as follows; BOC (tert-butoxycarbonyl); DCE (dichloroethane); DMSO (d$_6$ dimethylsulfoxide); Dioxane (1,4-dioxane); EtOAc (ethyl acetate); EtOH (ethanol); ether (diethyl ether); IPA (isopropyl alcohol); LCMS (liquid chromatography mass spectrometry); LDA (lithium diisopropylamide); Me (methyl); SiO$_2$ (silica gel for flash chromatography); TFA (trifluoroacetic acid); THF (tetrahydrofuran).

The Azetidinone Derivatives

The Azetidinone Derivatives of Formula (I)

The present invention provides Azetidinone Derivatives of Formula (I):

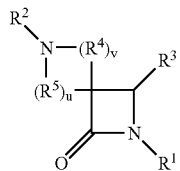

(I)

and pharmaceutically acceptable salts, solvates, prodrugs, esters and stereoisomers thereof, wherein $R^1$, $R^2$, $R^3$, $R^4$, $R^5$, u and v are as defined above for the Azetidinone Derivatives of formula (I).

In one embodiment, $R^1$ is —H, -alkyl, -aryl, -substituted aryl, -diphenylmethyl, -heteroaryl, -substituted heteroaryl, -arylalkyl, -cycloalkylalkyl or cycloalkyl.

In another embodiment, $R^1$ is —H diphenylmethyl, methyl, -isopropyl, —CH$_2$-cyclopropyl, -benzyl, 2-chlorobenzyl, -2-pyridyl, or -phenyl, wherein a phenyl may be optionally and independently substituted with up to 2 substituents selected from —Cl, —Br, —F, -methoxy, —C(O)CH$_3$, —NO$_2$, —CN, —S(O)$_2$CH$_3$, —C(O)OCH$_3$ and —CF$_3$.

In one embodiment, $R_1$ is —H.

In another embodiment, $R_1$ is -aryl.

In another embodiment, $R_1$ is -phenyl.

In one embodiment, $R_1$ is -phenyl, which is substituted with one or more -halo.

In another embodiment, $R_1$ is -phenyl, which is substituted with —CN.

In still another embodiment, $R_1$ is -phenyl, which is substituted with —CF$_3$.

In yet another embodiment, $R_1$ is -phenyl, which is substituted with —NO$_2$.

In another embodiment, $R_1$ is -phenyl, which is substituted with —OH.

In a further embodiment, $R_1$ is -phenyl, which is substituted with —C(O)O-alkyl.

In another embodiment, $R_1$ is -phenyl, which is substituted with —O-alkyl.

In another embodiment, $R_1$ is -phenyl, which is substituted with —O-methyl.

In one embodiment, $R_1$ is -arylalkyl.

In a specific embodiment, $R^1$ is -benzyl.

In another embodiment, $R^1$ is -benzyl which is substituted with -halo, pyridyl or pyrimidyl.

In one embodiment, $R_1$ is -alkyl.

In another embodiment, $R_1$ is -methyl.

In still another embodiment, $R_1$ is -isopropyl.

In yet another embodiment, $R_1$ is -t-butyl.

In another embodiment, $R_1$ is —CH(phenyl)$_2$.

In one embodiment, $R_1$ is -heteroaryl.

In another embodiment, $R_1$ is -pyridyl.

In still another embodiment, $R_1$ is -2-pyridyl.

In another embodiment, $R_1$ is -alkylene-C(O)N(alkyl)$_2$.

In one embodiment, $R^2$ is —H.

In one embodiment, $R^2$ is

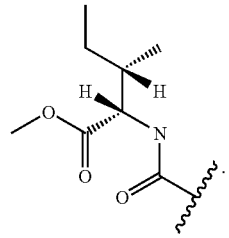

In one embodiment, $R^2$ is $R^6$-A- wherein A is —C(O)—NH—.

In another embodiment, $R^2$ is $R^6$-A- wherein A is —C(O)—.

In another embodiment, $R^2$ is $R^6$-A- wherein A is —C(O)-alkylene-.

In one embodiment, $R^2$ is $R^6$-A- wherein A is —C(O)—, C(O)NH— or —C(O)-alkylene- and $R^6$ is aryl, heteroaryl, cycloalkyl, cycloalkylalkyl, heterocycloalkyl, cycloalkenyl, heterocycloalkenyl, benzofused cycloalkyl, benzofused heterocycloalkyl, or benzofused heterocycloalkenyl.

In another embodiment, $R^2$ is $R^6$-A- wherein A is —C(O)—, C(O)NH— or —C(O)-alkylene- and $R^6$ is aryl.

In still another embodiment, $R^2$ is $R^6$-A- wherein A is —C(O)—, C(O)NH— or —C(O)-alkylene- and $R^6$ is heteroaryl.

In yet another embodiment, $R^2$ is $R^6$-A- wherein A is —C(O)—, C(O)NH— or —C(O)-alkylene- and $R^6$ is cycloalkyl.

In a further embodiment, $R^2$ is $R^6$-A- wherein A is —C(O)—, C(O)NH— or —C(O)-alkylene- and $R^6$ is phenyl.

In one embodiment, $R^2$ is $R^6$-A- wherein A is —C(O)—NH—, —C(O)— or —C(O)-alkylene-, and $R^6$ is cyclopentyl, cyclohexyl or cycloheptyl.

In yet another embodiment, $R^2$ is $R^6$-A- wherein A is —C(O)—, C(O)NH— or —C(O)-alkylene- and $R^6$ is phenyl, wherein the phenyl group is substituted with one or more of -halo, —CF$_3$, —CN, -alkoxy, —O-phenyl or —C(O)O-alkyl.

In one embodiment $R^2$ is $R^6$—C(O)—, and $R^6$ is -alkyl, -aryl, -heteroaryl, -cycloalkyl, -cycloalkylalkyl, -heterocycloalkyl, -cycloalkenyl, -heterocycloalkenyl, -benzofused cycloalkyl, -benzofused heterocycloalkyl, or -benzofused heterocycloalkenyl.

In another embodiment, $R^2$ is $R^6$—NH—C(O)—, and $R^6$ is -alkyl, -aryl, -heteroaryl, -cycloalkyl, -cycloalkylalkyl, -heterocycloalkyl, -cycloalkenyl, -heterocycloalkenyl, -benzofused cycloalkyl, -benzofused heterocycloalkyl, or -benzofused heterocycloalkyl.

In another embodiment, $R^2$ is $R^6$—O—C(O)—, and $R^6$ is -alkyl, -aryl, -heteroaryl, -cycloalkyl, -cycloalkylalkyl, -heterocycloalkyl, -cycloalkenyl, -heterocycloalkenyl, -benzofused cycloalkyl, -benzofused heterocycloalkyl, or -benzofused heterocycloalkyl.

In yet another embodiment, $R^2$ is $R^6$—C(O)—, and $R^3$ is -phenyl, -benzofused heterocycloalkyl, indolin-1-yl,

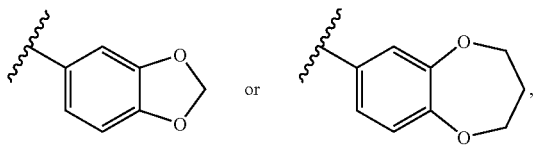

wherein a phenyl may be optionally and independently substituted with from 1-3 substitutents selected from -halo, -alkoxy or —$C_1$-$C_6$ alkyl.

In still another embodiment, $R^2$ is $R^6$—NH—C(O)—, and $R^6$ is -phenyl, -naphthyl, -benzyl, —$C_1$-$C_6$ alkyl, —CH(CH$_3$)-phenyl, -cyclopentyl, -cyclohexyl, -adamantyl, —CH(sec-butyl)-C(O)OCH$_3$, —CH(sec-butyl)-C(O)NH$_2$, —CH(CH$_2$CH$_3$)—CH$_2$OCH$_3$, —CH(isobutyl)-CH$_2$OH, —CH(isopropyl)-CH$_2$OH,

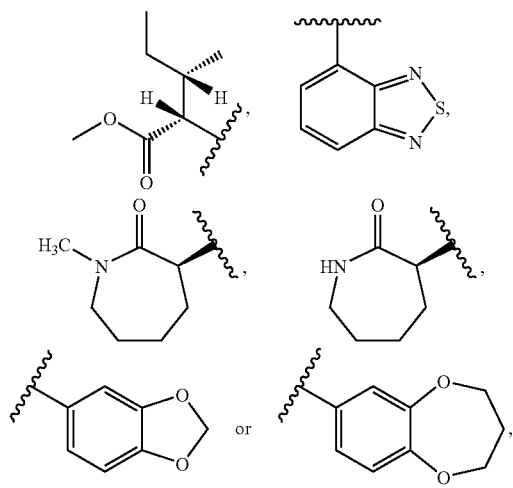

wherein a phenyl or benzyl may be optionally and independently substituted with from 1-3 substitutents selected from -halo, —CF$_3$, —CN, -alkoxy or —$C_1$-$C_6$ alkyl, and a cyclohexyl may be and independently substituted with a —$C_1$-$C_6$ alkyl group.

In a further embodiment, $R^2$ is $R^6$—NH—C(O)—, and $R^6$ is

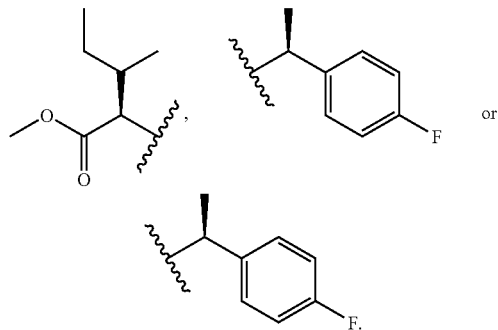

In another embodiment, $R^2$ is $R^6$—O—O(O)—, and $R^6$ is —$C_1$-$C_6$ alkyl.

In one embodiment, $R^2$ is —H, -alkyl, -cycloalkyl, -aryl, -arylalkyl, -heteroarylalkyl, -heterocycloalkyl, -heterocycloalkylalkyl, alkyl-O—C(O)—, (alkyl)$_2$N-alkylene-C(O)—, (alkyl)$_2$-N—C(O)-alkylene-C(O)—, CN-alkylene-C(O)—, alkyl-O-alkylene-C(O)—, alkyl-C(O)-alkylene-C(O)—, alkyl-C(O)—NH-alkylene-C(O)—, alkyl-NH—C(O)—, alkyl-O—C(O)-alkylene-C(O)—, alkyl-O—C(O)-cycloalkylene-alkylene-NH$_2$—C(O)—NH-alkylene-C(O)—, NH$_2$—C(O)-alkylene-C(O)—, alkyl-C(O)—NH-alkylene-S-alkylene-C(O)—, alkyl-O—C(O)-alkylene-C(O)—, alkyl-S-alkylene-C(O)—, alkyl-C(O)-cycloalkylene-alkylene-C(O)—, alkyl-S-alkylene-, (—NHC(O)alkyl)-C(O)—, alkyl(-C(O)Oalkyl)-NH—C(O)—, or —C(O)-alkylene-N(R$^6$)$_2$—; or alkyl-S-alkylene(-NHC(O)alkyl)-C(O)—, wherein an alkyl or aryl may be optionally and independently substituted with one or more of the following groups: —(C═N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$.

In another embodiment, $R^2$ is —H, -alkyl, -cycloalkyl, -aryl, -arylalkyl, -heteroarylalkyl, -heterocycloalkyl, -heterocycloalkylalkyl or

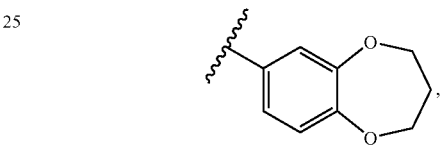

wherein an alkyl or aryl may be optionally and independently substituted with one or more of the following groups: —(C═N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$.

In still another embodiment, $R^3$ is —H, -aryl or -heteroaryl, wherein an aryl group may be optionally substituted with up to 2 substituents independently selected from -halo, —OH, or —O-benzyl.

In a further embodiment, $R^3$ is —H, -phenyl, 4-chlorophenyl, 4-fluorophenyl, 2-pyridyl, 4-hydroxyphenyl, 2,4-difluorophenyl, 4-bromophenyl or 4-(—O-benzyl)phenyl.

In one embodiment, $R_3$ is —H.
In another embodiment, $R_3$ is aryl.
In another embodiment, $R_3$ is phenyl.
In another embodiment, $R_3$ is phenyl substituted with one or more -halo.
In another embodiment, $R_3$ is phenyl substituted with —F.
In still another embodiment, $R_3$ is phenyl substituted with —Cl.
In a further embodiment, $R_3$ is phenyl substituted with —Br.
In yet another embodiment, $R_3$ is phenyl substituted with —OH.
In another embodiment, $R_3$ is heteroaryl.
In a further embodiment, $R_3$ is pyridyl.
In another embodiment, $R_3$ is 2-pyridyl.
In one embodiment, $R_4$ is —CH$_2$—.
In another embodiment, $R_5$ is —CH$_2$—.
In another embodiment, $R_4$ and $R_5$ are each —CH$_2$—.
In still another embodiment, u is 2.
In yet another embodiment, v is 2.
In a further embodiment, u and v are each 2.

In another embodiment, $R_4$ and $R_5$ are each —CH$_2$— and u and v are each 2.

In one embodiment, $R^1$ is alkyl, cycloalkyl or aryl; $R^2$ is aryl-NH—C(O)—, alkyl-NH—C(O)—, or alkyl-O—C(O)—; and $R^3$ is aryl.

In another embodiment, $R^1$ is -phenyl; $R^2$ is aryl-NH—C(O)—, alkyl-NH—C(O)—, or alkyl-O—C(O)—; and $R^3$ is phenyl.

In one embodiment, $R^1$ is alkyl and $R^2$ is —H, 3,5-di-chloro-phenyl-NH—C(O)—, 3,4-di-fluoro-phenyl-NH—C(O)—, 4-chloro-phenyl-NH—C(O)—, 3,5-di-fluoro-phenyl-NH—C(O)—, 4-fluoro-phenyl-NH—C(O)—, (CH$_3$)C—CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—,

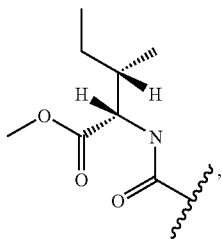

2-CF$_3$-phenyl-NHC(O)—, 2-chloro-6-methyl-phenyl-NHC(O)—, 2,6-di-chloro-phenyl-NHC(O)—, or t-Bu-phenyl-NHC(O)—; and $R^3$ is 4-chlorophenyl, phenyl, 2-pyridyl, 4-bromophenyl, or 4-benzyloxy-phenyl.

In another embodiment, $R^7$ is cycloalkyl; $R^2$ is —H, 3,5-di-chloro-phenyl-NH—C(O)—, 3,4-di-fluoro-phenyl-NH—C(O)—, 4-chloro-phenyl-NH—C(O)—, 3,5-di-fluoro-phenyl-NH—C(O)—, 4-fluoro-phenyl-NH—C(O)—, (CH$_3$)C—CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—,

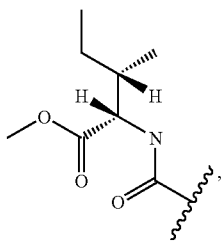

2-CF$_3$-phenyl-NHC(O)—, 2-chloro-6-methyl-phenyl-NHC(O)—, 2,6-di-chloro-phenyl-NHC(O)—, or t-Bu-phenyl-NHC(O)—.

In another embodiment, $R^1$ is phenyl and $R^2$ is —H, 3,5-di-chloro-phenyl-NH—C(O)—, 3,4-di-fluoro-phenyl-NH—C(O)—, 4-chloro-phenyl-NH—C(O)—, 3,5-di-fluoro-phenyl-NH—C(O)—, 4-fluoro-phenyl-NH—C(O)—, (CH$_3$)C—CH$_2$—C(CH$_3$)$_2$—NH—C(O)—, phenyl-NH—C(O)—, 2-methyl-phenyl-NH—C(O)—, 4-CH$_3$O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—,

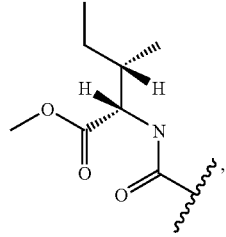

2-CF$_3$-phenyl-NHC(O)—, 2-chloro-6-methyl-phenyl-NHC(O)—, 2,6-di-chloro-phenyl-NHC(O)—, or t-Bu-phenyl-NHC(O)—; and $R^3$ is 4-chlorophenyl, phenyl, 2-pyridyl, 4-bromophenyl, or 4-benzyloxy-phenyl.

In one embodiment, $R^1$ is alkyl and $R^2$ is —H, 3,5-di-chloro-phenyl-NH-G(O)—, 3,4-di-fluoro-phenyl-NH—C(O)—, 4-chloro-phenyl-NH—C(O)—, 3,5-di-fluoro-phenyl-NH—C(O)—, 4-fluoro-phenyl-NH—C(O)—, (CH$_3$)C—CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)— t-Bu-O—C(O)—, 4-isopropyl-phenyl-NH—C(O)—,

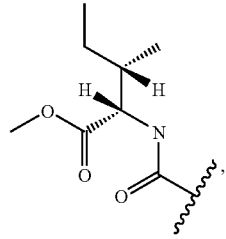

2-CF$_3$-phenyl-NHC(O)—, 2-chloro-6-methyl-phenyl-NHC(O)—, 2,6-di-chloro-phenyl-NHC(O)—, or t-Bu-phenyl-NHC(O)—; and $R^3$ is 4-chlorophenyl, phenyl, 2-pyridyl, 4-bromophenyl, or 4-benzyloxy-phenyl.

In another embodiment, $R^1$ is cycloalkyl; $R^2$ is —H, 3,5-di-chloro-phenyl-NH—C(O)—, 3,4-di-fluoro-phenyl-NH—C(O)—, 4-chloro-phenyl-NH—C(O)—, 3,5-di-fluoro-phenyl-NH—C(O)—, 4-fluoro-phenyl-NH—C(O)—, (CH$_3$)C—CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)-4-isopropyl-phenyl-NH—C(O)—,

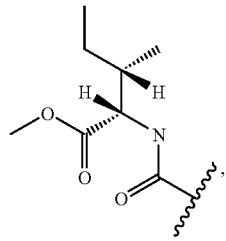

2-CF$_3$-phenyl-NHC(O)—, 2-chloro-6-methyl-phenyl-NHC(O)—, 2,6-di-chloro-phenyl-NHC(O), or t-Bu-phenyl-NHC(O)—; and R$^3$ is 4-chlorophenyl, phenyl, 2-pyridyl, 4-bromophenyl, or 4-benzyloxy-phenyl.

In another embodiment, R$^1$ is phenyl; R$^2$ is —H, 3,5-dichloro-phenyl-NH—C(O)—, 3,4-di-fluoro-phenyl-NH—C(O)—, 4-chloro-phenyl-NH—C(O)—, 3,5-di-fluoro-phenyl-NH—C(O)—, 4-fluoro-phenyl-NH—C(O)—, (CH$_3$)C=CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—,

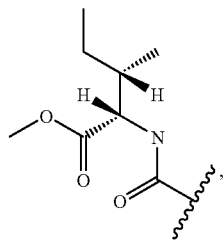

2-CF$_3$-phenyl-NHC(O)—, 2-chloro-6-methyl-phenyl-NHC(O)—, 2,6-di-chloro-phenyl-NHC(O)—, or t-Bu-phenyl-NHC(O)—; and R$^3$ is 4-chlorophenyl, phenyl, 2-pyridyl, 4-bromophenyl, or 4-benzyloxy-phenyl.

In still another embodiment, R$^1$ is alkyl, aryl or heteroaryl; R$^2$ is aryl-NH—C(O)—; and R$^3$ is aryl or heteroaryl.

In a further embodiment, R$^1$ is phenyl, pyrimidyl, isobutyl, biphenylyl, 2-pyridyl or 2-chlorobenzyl; R$^2$ is 4-CF$_3$-phenyl-NH—C(O)—, 4-isopropyl-phenyl-NH—C(O)—, naphthyl-NH—C(O)—, 4-phenoxy-phenyl-NH—C(O)—, 4-ethyl-phenyl-NH—C(O)—, or 2,5-di-chlorophenyl-NH—C(O)—; and R$^3$ is pyridyl, or phenyl, 4-chlorophenyl.

In one embodiment, R$^2$ is R$^6$—NH—C(O)— and R$^6$ is phenyl, naphthyl, benzyl, —C$_1$-C$_6$ alkyl, —CH(CH$_3$)-phenyl, cyclopentyl, cyclohexyl, cycloheptyl, adamantyl, —CH(sec-butyl)-C(O)OCH$_3$, —CH(isobutyl)-C(O)OCH$_3$, —C(isopropyl)-C(O)OCH$_3$, —CH(sec-butyl)-C(O)NH$_2$, —CH(CH$_2$CH$_3$)—CH$_2$OCH$_3$, —CH(CH$_2$CH$_3$)—CH$_2$OCH$_3$, —CH(isobutyl)-CH$_2$OH, —CH(isopropyl)-CH$_2$OH,

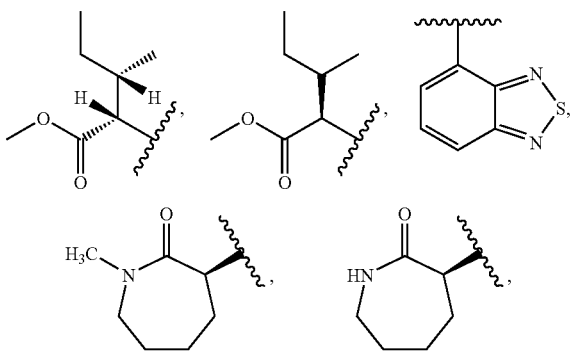

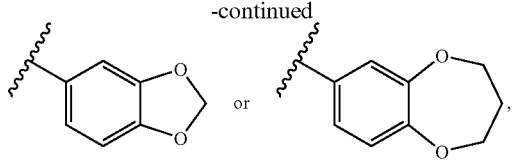

wherein a phenyl group or the phenyl moiety of a benzyl group may be optionally and independently substituted with from 1-3 substitutents selected from -halo, —CF$_3$, —CN, alkoxy or —C$_1$-C$_6$ alkyl, and wherein the methylene moiety of a benzyl group may be optionally substituted with a C$_1$-C$_6$ alkyl group, and wherein a cyclohexyl may be and independently substituted with a —C$_1$-C$_6$ alkyl group.

In another embodiment, R$^2$ is —C(O)NH—(C$_1$-C$_6$ alkyl), —C(O)NH-cyclopropyl, —C(O)NH-cycloheptyl, —C(O)NH-cyclopentyl, —C(O)NH-adamantyl or —C(O)NH-cyclohexyl, wherein a C$_1$-C$_6$ alkyl group may be optionally substituted with up to 2 substituents independently selected from —OH, —O-alkyl, phenyl, halo-substituted phenyl, —C(O)OR$^3$ or —C(O)N(R$^6$)$_2$, and a cycloalkyl group may be may be optionally and independently substituted with up to 3 unsubstituted alkyl groups.

In one embodiment, R$^1$ is H, alkyl, aryl, substituted aryl, diphenylmethyl, heteroaryl, substituted heteroaryl, arylalkyl, cycloalkylalkyl or cycloalkyl.

In another embodiment, R$^1$ is H, diphenylmethyl, methyl, isopropyl, —CH$_2$-cyclopropyl, benzyl, 2-chlorobenzyl, 2-pyridyl or phenyl, wherein a phenyl may be optionally and independently substituted with up to 2 substituents selected from Cl, Br, F, methoxy, —C(O)CH$_3$, —NO$_2$, —CN, —S(O)$_2$CH$_3$, —C(O)OCH$_3$ and —CF$_3$.

In another embodiment, R$^2$ is R$^6$—C(O)—, R$^6$—NH—C(O)— or R$^6$—O—C(O)—, and R$^6$ is alkyl, aryl, heteroaryl, cycloalkyl, cycloalkylalkyl, heterocycloalkyl, cycloalkenyl, heterocycloalkenyl, benzofused cycloalkyl, benzofused heterocycloalkyl, or benzofused heterocycloalkenyl.

In still another embodiment, R$^2$ is R$^6$—C(O)— and R$^6$ is phenyl, benzofused heterocycloalkyl, indolin-1-yl,

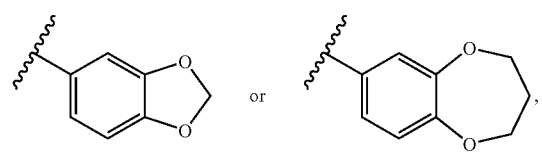

wherein a phenyl may be optionally and independently substituted with from 1-3 substitutents selected from halo, alkoxy or —C$_1$-C$_6$ alkyl.\

In another embodiment, R$^2$ is R$^6$—NH—C(O)— and R$^6$ is phenyl, naphthyl, benzyl, —C$_1$-C$_6$ alkyl, —CH(CH$_3$)-phenyl, cyclopentyl, cyclohexyl, cycloheptyl, adamantyl, —CH(sec-butyl)-C(O)OCH$_3$, —CH(isobutyl)-C(O)OCH$_3$, —C(isopropyl)-C(O)OCH$_3$, —CH(sec-butyl)-C(O)NH$_2$, —CH(CH$_2$CH$_3$)—CH$_2$OCH$_3$, —CH(CH$_2$CH$_3$)—CH$_2$OCH$_3$, —CH(isobutyl)-CH$_2$OH, —CH(isopropyl)-CH$_2$OH,

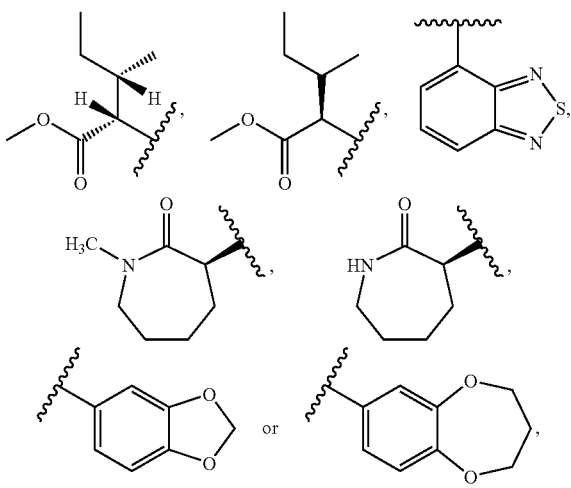

wherein a phenyl group or the phenyl moiety of a benzyl group may be optionally and independently substituted with from 1-3 substitutents selected from -halo, —CF$_3$, —CN, alkoxy or —C$_1$-C$_6$ alkyl, and wherein the methylene moiety of a benzyl group may be optionally substituted with a C$_1$-C$_6$ alkyl group, and wherein a cyclohexyl may be and independently substituted with a —C$_1$-C$_6$ alkyl group.

In a further embodiment, R$^2$ is H, alkyl, cycloalkyl, aryl, arylalkyl, heteroarylalkyl, heterocycloalkyl, heterocycloalkylalkyl, alkyl-O—C(O)—, (alkyl)$_2$N-alkylene-C(O)—, (alkyl)$_2$-N—C(O)-alkylene-C(O)—, CN-alkylene-C(O)—, alkyl-O-alkylene-C(O)—, alkyl-C(O)-alkylene-C(O)—, alkyl-C(O)—NH-alkylene-C(O)—, alkyl-NH—C(O)—, alkyl-O—C(O)-alkylene-C(O)—, alkyl-O—C(O)-cycloalkylene-alkylene-, NH$_2$—C(O)—NH-alkylene-C(O)—, NH$_2$—C(O)-alkylene-C(O)—, alkyl-C(O)—NH-alkylene-S-alkylene-C(O)—, alkyl-O—C(O)-alkylene-C(O)—, alkyl-S-alkylene-C(O)—, alkyl-C(O)-cycloalkylene-alkylene-C(O)—, alkyl-S-alkylene-, (—NHC(O)alkyl)-C(O)—, alkyl(-C(O)Oalkyl)-NH—C(O)—, or —C(O)-alkylene-N(R$^6$)$_2$—; or alkyl-S-alkylene(-NHC(O)alkyl)-C(O)—, wherein an alkyl or aryl may be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, halo, —CN, -alkoxy, —C(O)O-alkyl, —S(O)alkyl, —SO$_2$-alkyl, or —P(O)(O-alkyl)$_2$.

In another embodiment, R$^2$ is H, alkyl, cycloalkyl, aryl, arylalkyl, heteroarylalkyl, heterocycloalkyl, heterocycloalkylalkyl or

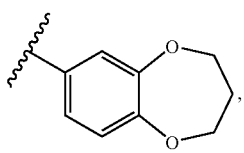

wherein an alkyl or aryl may be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$.

In one embodiment, u is 2, v is 2, each occurrence of R$^4$ is —CH$_2$— and each occurrence of R$^5$ is —CH$_2$—.

In another embodiment, R$^3$ is H, aryl or heteroaryl, wherein an aryl group may be optionally substituted with up to 2 substituents independently selected from halo, —OH, phenyl, pyridyl or —O-benzyl.

In another embodiment, R$^3$ is H, phenyl, 4-chlorophenyl, 4-fluorophenyl, 2-pyridyl, 4-hydroxyphenyl, 2,4-difluorophenyl, 4-bromophenyl, 4-(—O-benzyl)phenyl,

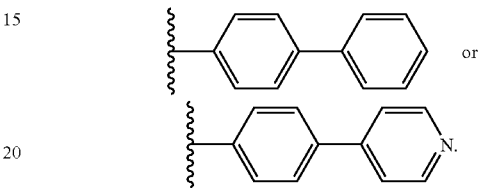

or

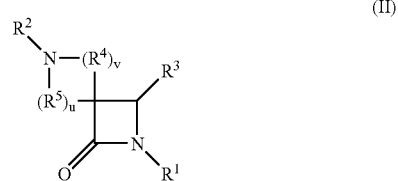

In one embodiment, the compounds of formula (I) are in purified form.

Non-limiting examples of compounds of formula (I) include those depicted in the Examples section below and include pharmaceutically acceptable salts, solvates, esters, prod rugs and stereo isomers thereof.

The Azetidinone Derivatives of Formula (II)

The present invention also provides Azetidinone Derivatives of Formula (II):

$$\text{(II)}$$

and pharmaceutically acceptable salts, solvates, prodrugs, esters and stereoisomers thereof, wherein R$^1$, R$^2$, R$^3$, R$^4$, R$^5$, u and v are as defined above for the Azetidinone Derivatives of formula (II).

In one embodiment, R$^1$ is —H, -alkyl, -aryl, -substituted aryl, -diphenylmethyl, heteroaryl, -substituted heteroaryl, -arylalkyl, -cycloalkylalkyl or -cycloalkyl.

In another embodiment, R$^1$ is —H, -diphenylmethyl, -methyl, -isopropyl, —CH$_2$-cyclopropyl, -benzyl, 2-chlorobenzyl, -2-pyridyl, -phenyl, wherein a phenyl may be optionally and independently substituted with up to 2 substituents selected from —Cl, —Br, —F, -methoxy, —C(O)CH$_3$, —NO$_2$, —CN, —S(O)$_2$CH$_3$, —C(O)OCH$_3$ and —CF$_3$.

In one embodiment, R$_1$ is —H.

In another embodiment, R$_1$ is -aryl.

In another embodiment, R$_1$ is -phenyl.

In one embodiment, R$_1$ is -phenyl, which is substituted with one or more -halo.

In another embodiment, R$_1$ is -phenyl, which is substituted with —CN.

In still another embodiment, R$_1$ is -phenyl, which is substituted with —CF$_3$.

In yet another embodiment, R₁ is -phenyl, which is substituted with —NO₂.

In another embodiment, R₁ is -phenyl, which is substituted with —OH.

In a further embodiment, R₁ is -phenyl, which is substituted with —C(O)O-alkyl.

In another embodiment, R₁ is -phenyl, which is substituted with —O-alkyl.

In another embodiment, R₁ is -phenyl, which is substituted with —O-methyl.

In one embodiment, R₁ is -arylalkyl.

In a specific embodiment, R¹ is -benzyl.

In another embodiment, R¹ is -benzyl which is substituted with -halo, pyridyl or pyrimidyl.

In one embodiment, R₁ is -alkyl.

In another embodiment, R₁ is -methyl.

In still another embodiment, R₁ is -isopropyl.

In yet another embodiment, R₁ is -t-butyl.

In another embodiment, R₁ is —CH(phenyl)₂.

In one embodiment, R₁ is -heteroaryl.

In another embodiment, R₁ is -pyridyl.

In still another embodiment, R₁ is -2-pyridyl.

In another embodiment, R₁ is -alkylene-C(O)N(alkyl)₂.

In one embodiment, R² is —H.

In one embodiment, R² is

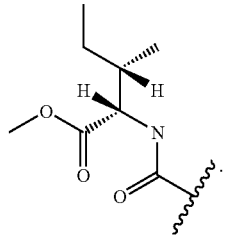

In one embodiment, R² is R⁶-A- wherein A is —C(O)—NH—.

In another embodiment, R² is R⁶-A- wherein A is —C(O)—.

In another embodiment, R² is R⁶-A- wherein A is —C(O)-alkylene-.

In one embodiment, R² is R⁶-A- wherein A is —C(O)—, C(O)NH— or —C(O)-alkylene- and R⁶ is aryl, heteroaryl, cycloalkyl, cycloalkylalkyl, heterocycloalkyl, cycloalkenyl, heterocycloalkenyl, benzofused cycloalkyl, benzofused heterocycloalkyl, or benzofused heterocycloalkenyl.

In another embodiment, R² is R⁶-A- wherein A is —C(O)—, C(O)NH— or —C(O)-alkylene- and R⁶ is aryl.

In still another embodiment, R² is R⁶-A- wherein A is —C(O)—, C(O)NH— or —C(O)-alkylene- and R⁶ is heteroaryl.

In yet another embodiment, R² is R⁶-A- wherein A is —C(O)—, C(O)NH— or —C(O)-alkylene- and R⁶ is cycloalkyl.

In a further embodiment, R² is R⁶-A- wherein A is —C(O)—, C(O)NH— or —C(O)-alkylene- and R⁶ is phenyl.

In one embodiment, R² is R⁶-A- wherein A is —C(O)—NH—, —C(O)— or —C(O)-alkylene-, and R⁶ is cyclopentyl, cyclohexyl or cycloheptyl.

In yet another embodiment, R² is R⁶-A- wherein A is —C(O)—, C(O)NH— or —C(O)-alkylene- and R⁶ is phenyl, wherein the phenyl group is substituted with one or more of -halo, —CF₃, —CN, -alkoxy, —O-phenyl or —C(O)O-alkyl.

In one embodiment R² is R⁶—C(O)—, and R⁶ is -alkyl, -aryl, -heteroaryl, -cycloalkyl, -cycloalkylalkyl, -heterocycloalkyl, -cycloalkenyl, -heterocycloalkenyl, -benzofused cycloalkyl, -benzofused heterocycloalkyl, or -benzofused heterocycloalkenyl.

In another embodiment, R² is R⁶—NH—C(O)—, and R⁶ is -alkyl, -aryl, -heteroaryl, -cycloalkyl, -cycloalkylalkyl, -heterocycloalkyl, -cycloalkenyl, -heterocycloalkenyl, -benzofused cycloalkyl, -benzofused heterocycloalkyl, or -benzofused heterocycloalkenyl.

In another embodiment, R² is R⁶—O—C(O)—, and R⁶ is -alkyl, -aryl, -heteroaryl, -cycloalkyl, -cycloalkylalkyl, -heterocycloalkyl, -cycloalkenyl, -heterocycloalkenyl, -benzofused cycloalkyl, -benzofused heterocycloalkyl, or -benzofused heterocycloalkenyl.

In yet another embodiment, R² is R⁶—C(O)—, and R⁶ is -phenyl, -benzofused heterocycloalkyl, indolin-1-yl,

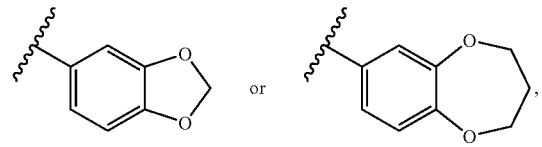

wherein a phenyl may be optionally and independently substituted with from 1-3 substitutents selected from -halo, -alkoxy or —C₁-C₆ alkyl.

In still another embodiment, R² is R⁶—NH—C(O)—, and R⁶ is -phenyl, -naphthyl, -benzyl, —C₁-C₆ alkyl, —CH(CH₃)-phenyl, -cyclopentyl, -cyclohexyl, -adamantyl, —CH(sec-butyl)-C(O)OCH₃, —CH(sec-butyl)-C(O)NH₂, —CH(CH₂CH₃)—CH₂OCH₃, —CH(isobutyl)-CH₂OH, —CH(isopropyl)-CH₂OH,

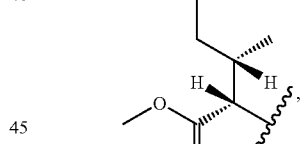

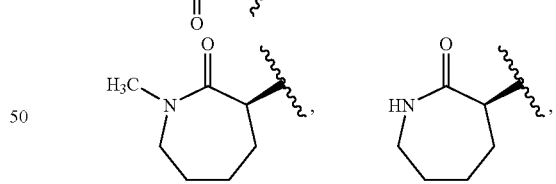

wherein a phenyl or benzyl may be optionally and independently substituted with from 1-3 substitutents selected from -halo, —CF₃, —CN, -alkoxy or —C₁-C₆ alkyl, and a cyclohexyl may be and independently substituted with a —C₁-C₆ alkyl group.

In a further embodiment, R² is R⁶—NH—C(O)—, and R⁶ is

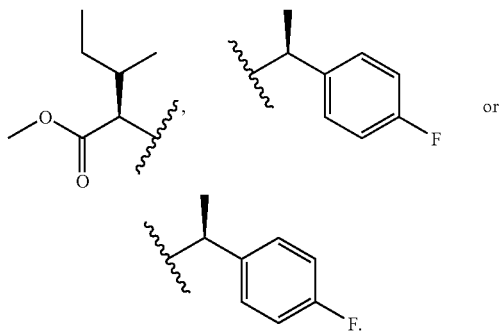

In another embodiment, $R^2$ is $R^6$—O—C(O)—, and $R^6$ is —$C_1$-$C_6$ alkyl.

In one embodiment, $R^2$ is —H, -alkyl, -cycloalkyl, -aryl, -arylalkyl, -heteroarylalkyl, -heterocycloalkyl, -heterocycloalkylalkyl, alkyl-O—C(O)—, (alkyl)$_2$N-alkylene-C(O)—, (alkyl)$_2$-N—C(O)-alkylene-C(O)—, CN-alkylene-C(O)—, alkyl-O-alkylene-C(O)—, alkyl-C(O)-alkylene-C(O)—, alkyl-C(O)—NH-alkylene-C(O)—, alkyl-NH—C(O)—, alkyl-O—C(O)-alkylene-C(O)—, alkyl-O—C(O)-cycloalkylene-alkylene-, NH$_2$—C(O)—NH-alkylene-C(O)—, NH$_2$—C(O)-alkylene-C(O)—, alkyl-C(O)—NH-alkylene-S-alkylene-C(O)—, alkyl-O—C(O)-alkylene-C(O)—, alkyl-S-alkylene-C(O)—, alkyl-C(O)-cycloalkylene-alkylene-C(O)—, alkyl-S-alkylene-, (—NHC(O)alkyl)-C(O)—, alkyl(-C(O)Oalkyl)-NH—C(O)—, or —C(O)-alkylene-N($R^6$)$_2$—; or alkyl-S-alkylene(-NHC(O)alkyl)-C(O)—, wherein an alkyl or aryl may be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$.

In another embodiment, $R^2$ is —H, -alkyl, -cycloalkyl, -aryl, -arylalkyl, -heteroarylalkyl, -heterocycloalkyl, -heterocycloalkylalkyl or

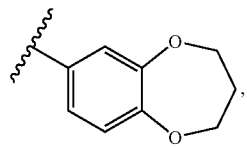

wherein an alkyl or aryl may be optionally and independently substituted with one or more of the following groups: —(C=N—O-alkyl)CH$_3$, —NC(O)NH$_2$, —NC(O)NH(alkyl), —NC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$.

In still another embodiment, $R^3$ is —H, -aryl or -heteroaryl, wherein an aryl group may be optionally substituted with up to 2 substituents independently selected from -halo, —OH, or —O-benzyl.

In a further embodiment, $R^3$ is —H, -phenyl, 4-chlorophenyl, 4-fluorophenyl, 2-pyridyl, 4-hydroxyphenyl, 2,4-difluorophenyl, 4-bromophenyl or 4-(—O-benzyl)phenyl.

In one embodiment, $R_3$ is —H.
In another embodiment, $R_3$ is aryl.
In another embodiment, $R_3$ is phenyl.
In another embodiment, $R_3$ is phenyl substituted with one or more -halo.
In another embodiment, $R_3$ is phenyl substituted with —F.
In still another embodiment, $R_3$ is phenyl substituted with —Cl.
In a further embodiment, $R_3$ is phenyl substituted with —Br.
In yet another embodiment, $R_3$ is phenyl substituted with —OH.
In another embodiment, $R_3$ is heteroaryl.
In a further embodiment, $R_3$ is pyridyl.
In another embodiment, $R_3$ is 2-pyridyl.
In one embodiment, $R_4$ is —CH$_2$—.
In another embodiment, $R_5$ is —CH$_2$—.
In another embodiment $R_4$ and $R_5$ are each —CH$_2$—.
In still another embodiment, u is 2.
In yet another embodiment, v is 2.
In a further embodiment, u and v are each 2.
In another embodiment, $R_4$ and $R_5$ are each —CH$_2$— and u and v are each 2.

In one embodiment, $R^2$ is $R^6$—NH—C(O)— and $R^6$ is phenyl, naphthyl, benzyl, —$C_1$-$C_6$ alkyl, —CH(CH$_3$)-phenyl, cyclopentyl, cyclohexyl, cycloheptyl, adamantyl, —CH(sec-butyl)-C(O)OCH$_3$, —CH(isobutyl)-C(O)OCH$_3$, —C(isopropyl)-C(O)OCH$_3$, —CH(sec-butyl)-C(O)NH$_2$, —CH(CH$_2$CH$_3$)—CH$_2$OCH$_3$, —CH(CH$_2$CH$_3$)—CH$_2$OCH$_3$, —CH(isobutyl)-CH$_2$OH, —CH(isopropyl)-CH$_2$OH,

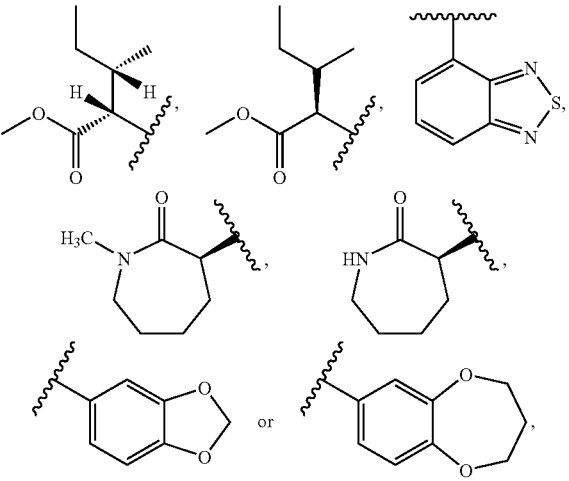

wherein a phenyl group or the phenyl moiety of a benzyl group may be optionally and independently substituted with from 1-3 substitutents selected from -halo, —CF$_3$, —CN, alkoxy or —$C_1$-$C_6$ alkyl, and wherein the methylene moiety of a benzyl group may be optionally substituted with a $C_1$-$C_6$ alkyl group, and wherein a cyclohexyl may be and independently substituted with a —$C_1$-$C_6$ alkyl group.

In another embodiment, $R^2$ is —C(O)NH—($C_1$-$C_6$ alkyl), —C(O)NH-cyclopropyl, —C(O)NH-cycloheptyl, —C(O)NH-cyclopentyl, —C(O)NH-adamantyl or —C(O)NH-cyclohexyl, wherein a $C_1$-$C_6$ alkyl group may be optionally substituted with up to 2 substituents independently selected from —OH, —O-alkyl, phenyl, halo-substituted phenyl, —C(O)OR$^6$ or —C(O)N(R$^6$)$_2$, and a cycloalkyl group may be may be optionally and independently substituted with up to 3 unsubstituted alkyl groups.

In one embodiment, the compounds of formula (II) are in purified form.

Non-limiting examples of compounds of formula (II) include those depicted in the Examples section below and include pharmaceutically acceptable salts, solvates, esters, prodrugs and stereoisomers thereof.

The Azetidinone Derivatives of Formula (III)

The present invention also provides Azetidinone Derivatives of Formula (III):

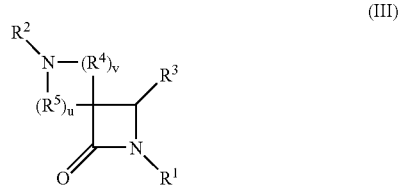

(III)

and pharmaceutically acceptable salts, solvates, prodrugs, esters and stereoisomers thereof, wherein R$^1$, R$^2$, R$^3$ and R$^5$ are as defined above for the Azetidinone Derivatives of formula (III).

In one embodiment, R$^1$ is —H, -diphenylmethyl, -methyl, -isopropyl, —CH$_2$-cyclopropyl, -benzyl, 2-chlorobenzyl, -2-pyridyl, -phenyl, wherein a phenyl may be optionally and independently substituted with up to 2 substituents selected from —Cl, —Br, —F, -methoxy, —C(O)CH$_3$, —NO$_2$, —CN, —S(O)$_2$CH$_3$, —C(O)OCH$_3$ and —CF$_3$.

In one embodiment, R$_1$ is —H.

In another embodiment, R$_1$ is -aryl.

In another embodiment, R$_1$ is -phenyl.

In one embodiment, R$_1$ is -phenyl, which is substituted with one or more -halo.

In another embodiment, R$_1$ is -phenyl, which is substituted with —CN.

In still another embodiment, R$_1$ is -phenyl, which is substituted with —CF$_3$.

In yet another embodiment, R$_1$ is -phenyl, which is substituted with —NO$_2$.

In another embodiment, R$_1$ is -phenyl, which is substituted with —OH.

In a further embodiment, R$_1$ is -phenyl, which is substituted with —C(O)O-alkyl.

In another embodiment, R$_1$ is -phenyl, which is substituted with —O-alkyl.

In another embodiment, R$_1$ is -phenyl, which is substituted with —O-methyl.

In one embodiment, R$_1$ is -arylalkyl.

In a specific embodiment, R$^1$ is -benzyl.

In another embodiment, R$^1$ is -benzyl which is substituted with -halo, pyridyl or pyrimidyl.

In one embodiment, R$_1$ is -alkyl.

In another embodiment, R$_1$ is -methyl.

In still another embodiment, R$_1$ is -isopropyl.

In yet another embodiment, R$_1$ is -t-butyl.

In another embodiment, R$_1$ is —CH(phenyl)$_2$.

In one embodiment, R$_1$ is -heteroaryl.

In another embodiment, R$_1$ is -pyridyl.

In still another embodiment, R$_1$ is -2-pyridyl.

In another embodiment, R$_1$ is -alkylene-C(O)N(alkyl)$_2$.

In one embodiment, R$_1$ is —H, -aryl, -substituted aryl, -alkylaryl, -cycloalkyl, -cycloalkylalkyl, or heteroaryl.

In one embodiment, R$^1$ is —H, -phenyl, 4-fluorophenyl, 3-fluorophenyl, 4-nitrophenyl, 4-cyanophenyl, 4-methoxyphenyl, 3-methoxyphenyl, 4-C(O)OCH$_3$-phenyl, 2-fluorophenyl, 3-trifluoromethylphenyl, 4-trifluoromethylphenyl, 3-C(O)CH$_3$-phenyl, 2-cyanophenyl, 4-SO$_2$CH$_3$-phenyl, 2-pyridyl, -methyl, ethyl, isopropyl, t-butyl, 2-chlorobenzyl, —CH(phenyl)$_2$, cyclopropyl, —CH$_2$-cyclopropyl, -cyclopentyl, -cyclohexyl or cycloheptyl.

In one embodiment, R$^1$ is -phenyl, 4-fluorophenyl, 3-fluorophenyl, 4-nitrophenyl, 4-cyanophenyl, 4-methoxyphenyl, 3-methoxyphenyl, 4-C(O)OCH$_3$-phenyl, 2-fluorophenyl, 3-trifluoromethylphenyl, 4-trifluoromethylphenyl, 3-C(O)CH$_3$-phenyl, 2-cyanophenyl, 4-SO$_2$CH$_3$-phenyl or 2-pyridyl.

In another embodiment, R$^1$ is -methyl, ethyl, isopropyl or t-butyl.

In another embodiment, R$^1$ is 2-chlorobenzyl, —CH(phenyl)$_2$.

In yet another embodiment, R$^1$ is cyclopropyl, —CH$_2$-cyclopropyl, -cyclopentyl, -cyclohexyl or cycloheptyl.

In one embodiment, R$^2$ is —H.

In one embodiment, R$^2$ is —H, —C(O)aryl, —C(O)NH-alkyl, —C(O)NH-alkylene-aryl, —C(O)NH-aryl, —C(O)NH-cycloalkyl, —C(O)NH—CH$_2$-aryl, —C(O)NH-heteroaryl, —C(O)NH-heterocycloalkyl, —C(O)NH-benzofused heterocycloalkyl, —C(O)O-alkyl or

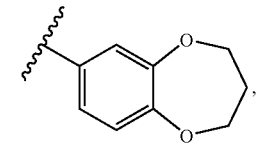

wherein an alkyl group may be optionally substituted with up to 2 substituents independently selected from —OH, —O-alkyl, —C(O)OR$^6$ or —C(O)N(R$^6$)$_2$; an aryl group may be optionally substituted with up to 3 substituents independently selected from —O-alkyl, -halo, unsubstituted alkyl, —CN or —CF$_3$; and a cycloalkyl group may be may be optionally and independently substituted with up to 3 unsubstituted alkyl groups;

In another embodiment, R$^2$ is —C(O)phenyl, —C(O)NH-alkylene-phenyl, —C(O)NH-phenyl, —C(O)NH—CH$_2$-phenyl, wherein a phenyl group may be optionally substituted with up to 3 substituents independently selected from —O-alkyl, -halo, unsubstituted alkyl, —CN or —CF$_3$.

In still another embodiment, R$^2$ is —C(O)NH—(C$_1$-C$_6$ alkyl), —C(O)NH-cyclopropyl, —C(O)NH-cyclopentyl, —C(O)NH-adamantyl or —C(O)NH-cyclohexyl, wherein a C$_1$-C$_6$ alkyl group may be optionally substituted with up to 2 substituents independently selected from —OH, —O-alkyl, —C(O)OR$^6$ or —C(O)N(R$^6$)$_2$, and a cycloalkyl group may be may be optionally and independently substituted with up to 3 unsubstituted alkyl groups.

In a further embodiment, R$^2$ is —C(O)NHCH(CH$_3$)-phenyl, —C(O)NHCH(sec-butyl)-C(O)OCH$_3$, —C(O)NHCH(sec-butyl)-C(O)NH$_2$, —C(O)NHCH(CH$_2$CH$_3$)—CH$_2$OCH$_3$, —C(O)NHCH(isobutyl)-CH$_2$OH, —C(O)NHCH(isopropyl)-CH$_2$OH or

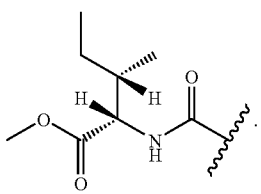

In one embodiment, $R^2$ is —C(O)NH-heteroaryl, —C(O)NH-heterocycloalkyl or —C(O)NH-benzofused heterocycloalkyl.

In another embodiment, $R^2$ is

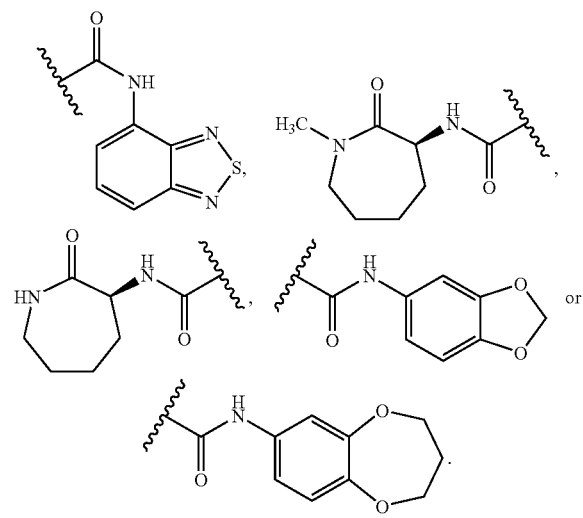

or

In one embodiment, $R^3$ is —H, -phenyl, 4-chlorophenyl, 4-fluorophenyl, 2-pyridyl, 4-hydroxyphenyl, 2,4-difluorophenyl, 4-bromophenyl or 4-(—O-benzyl)phenyl.

In another embodiment, $R_3$ is —H.

In another embodiment, $R_3$ is aryl.

In another embodiment, $R_3$ is phenyl.

In another embodiment, $R_3$ is phenyl substituted with one or more -halo.

In another embodiment, $R_3$ is phenyl substituted with —F.

In still another embodiment, $R_3$ is phenyl substituted with —Cl.

In a further embodiment, $R_3$ is phenyl substituted with —Br.

In yet another embodiment, $R_3$ is phenyl substituted with —OH.

In one embodiment, $R_3$ is -phenyl, -4-chlorophenyl, 4-fluorophenyl, 4-hydroxyphenyl or 2-pyridyl.

In another embodiment, $R_3$ is heteroaryl.

In a further embodiment, $R_3$ is pyridyl.

In another embodiment, $R_3$ is 2-pyridyl.

In one embodiment, $R_4$ is —CH$_2$—.

In another embodiment, $R_5$ is —CH$_2$—.

In another embodiment, $R_4$ and $R_5$ are each —CH$_2$—.

In one embodiment, $R^2$ is $R^6$—NH—C(O)— and $R^6$ is phenyl, naphthyl, benzyl, —C$_1$-C$_6$ alkyl, —CH(CH$_3$)-phenyl, cyclopentyl, cyclohexyl, cycloheptyl, adamantyl, —CH(sec-butyl)-C(O)OCH$_3$, —CH(isobutyl)-C(O)OCH$_3$, —C(isopropyl)-C(O)OCH$_3$, —CH(sec-butyl)-C(O)NH$_2$, —CH(CH$_2$CH$_3$)—CH$_2$OCH$_3$, —CH(CH$_2$CH$_3$)—CH$_2$OCH$_3$, —CH(isobutyl)-CH$_2$OH, —CH(isopropyl)-CH$_2$OH,

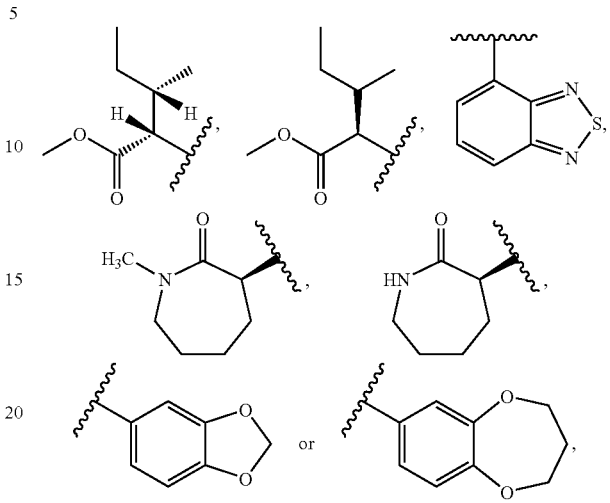

or wherein a phenyl group or the phenyl moiety of a benzyl group may be optionally and independently substituted with from 1-3 substitutents selected from -halo, —CF$_3$, —CN, alkoxy or —C$_1$-C$_6$ alkyl, and wherein the methylene moiety of a benzyl group may be optionally substituted with a C$_1$-C$_6$ alkyl group, and wherein a cyclohexyl may be and independently substituted with a —C$_1$-C$_6$ alkyl group.

In a further embodiment, $R^2$ is $R^6$—NH—C(O)—, and $R^6$ is

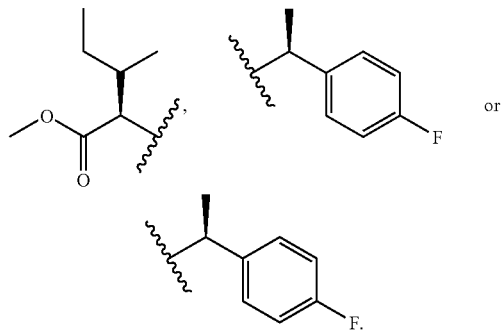

In another embodiment, $R^2$ is —C(O)NH—(C$_1$-C$_6$alkyl), —C(O)NH-cyclopropyl, —C(O)NH-cycloheptyl, —C(O)NH-cyclopentyl, —C(O)NH-adamantyl or —C(O)NH-cyclohexyl, wherein a C$_1$-C$_6$ alkyl group may be optionally substituted with up to 2 substituents independently selected from —OH, —O-alkyl, phenyl, halo-substituted phenyl, —C(O)OR$^6$ or —C(O)N(R$^6$)$_2$, and a cycloalkyl group may be may be optionally and independently substituted with up to 3 unsubstituted alkyl groups.

In one embodiment, $R^1$ is H, diphenylmethyl, methyl, isopropyl, isobutyl, cyclopropyl, —CH$_2$-cyclopropyl, benzyl, 2-chlorobenzyl, 2-pyridyl or phenyl, wherein a phenyl may be optionally and independently substituted with up to 2 substituents selected from Cl, Br, F, methoxy, —C(O)CH$_3$, —NO$_2$, —CN, —S(O)$_2$CH$_3$, —C(O)OCH$_3$ and —CF$_3$.

In another embodiment, $R^2$ is H, —C(O)aryl, —C(O)NH-alkyl, —C(O)NH-alkylene-aryl, —C(O)NH-aryl, —C(O)

NH-cycloalkyl, —C(O)NH—CH$_2$-aryl, —C(O)NH-heteroaryl, —C(O)NH-heterocycloalkyl, —C(O)NH-benzofused heterocycloalkyl, —C(O)O-alkyl or

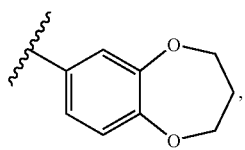

wherein an alkyl group may be optionally substituted with up to 2 substituents independently selected from —OH, —O-alkyl, —C(O)OR$^6$ or —C(O)N(R$^6$)$_2$; an aryl group may be optionally substituted with up to 3 substituents independently selected from —O-alkyl, halo, unsubstituted alkyl, —CN or —CF$_3$; and a cycloalkyl or heterocycloalkyl group may be may be optionally and independently substituted with up to 3 unsubstituted alkyl groups.

In another embodiment, R$^2$ is —C(O)phenyl, —C(O)NH-alkylene-phenyl, —C(O)NH-phenyl, —C(O)NH—CH$_2$-phenyl, wherein a phenyl group may be optionally substituted with up to 3 substituents independently selected from —O-alkyl, halo, unsubstituted alkyl, —CN or —CF$_3$.

In still another embodiment, R$^2$ is —C(O)NH—(C$_1$-C$_6$ alkyl), —C(O)NH-cyclopropyl, —C(O)NH-cycloheptyl, —C(O)NH-cyclopentyl, —C(O)NH-adamantyl or —C(O)NH-cyclohexyl, wherein a C$_1$-C$_6$ alkyl group may be optionally substituted with up to 2 substituents independently selected from —OH, —O-alkyl, phenyl, halo-substituted phenyl, —C(O)OR$^6$ or —C(O)N(R$^6$)$_2$, and a cycloalkyl group may be may be optionally and independently substituted with up to 3 unsubstituted alkyl groups.

In yet another embodiment, R$^2$ is —C(O)NHCH(CH$_3$)-phenyl, —C(O)NHCH(sec-butyl)-C(O)OCH$_3$, —C(O)NHCH(isopropyl)-C(O)OCH$_3$, —C(O)NHCH(sec-butyl)-C(O)NH$_2$, —C(O)NHCH(CH$_2$CH$_3$)—CH$_2$OCH$_3$, —C(O)NHCH(isobutyl)-CH$_2$OH, —C(O)NHCH(isopropyl)-CH$_2$OH or

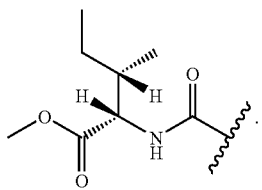

In one embodiment, R$^2$ is

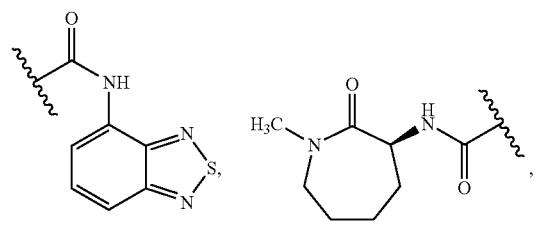

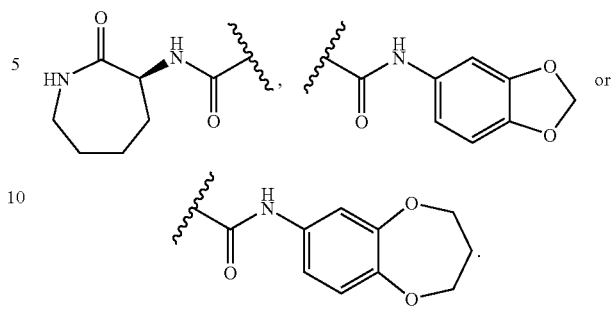

In another embodiment, R$^3$ is H, phenyl, 4-chlorophenyl, 4-fluorophenyl, 2-pyridyl, 4-hydroxyphenyl, 2,4-difluorophenyl, 4-bromophenyl or 4-(—O-benzyl)phenyl.

In one embodiment, the compounds of formula (III) are in purified form.

Non-limiting examples of compounds of formula (III) include those depicted in the Examples section below and include pharmaceutically acceptable salts, solvates, esters, prodrugs and stereoisomers thereof.

Additional non-limiting examples of the Azetidinone Derivatives include the following compounds:

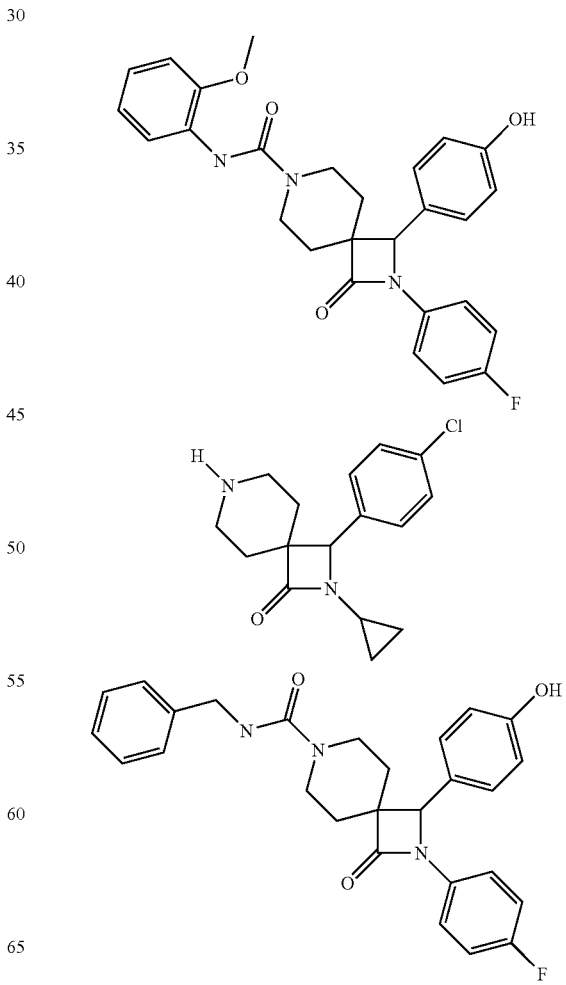

-continued
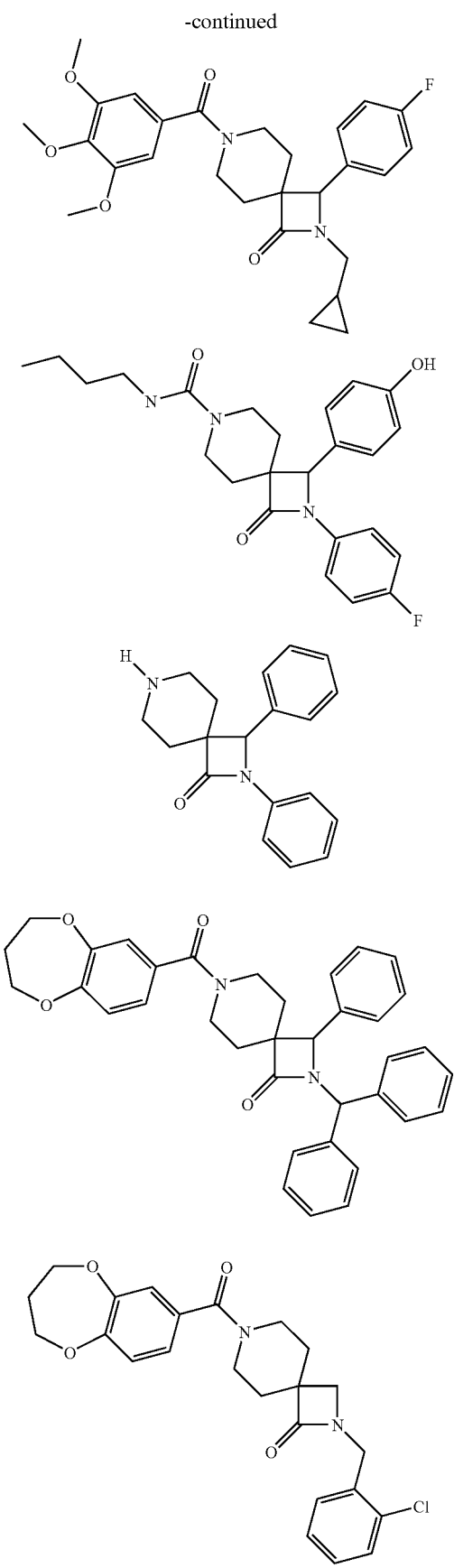
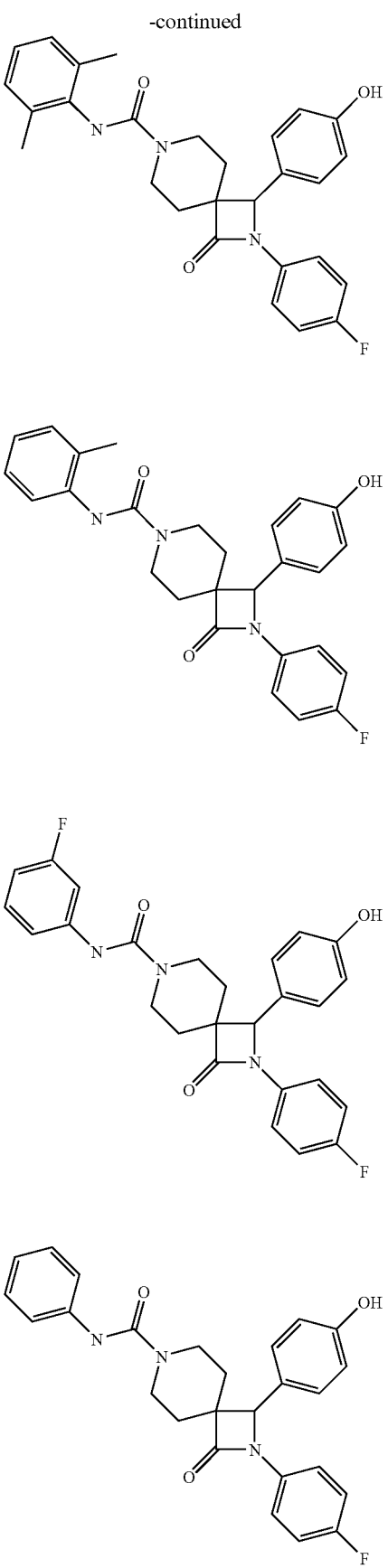

-continued
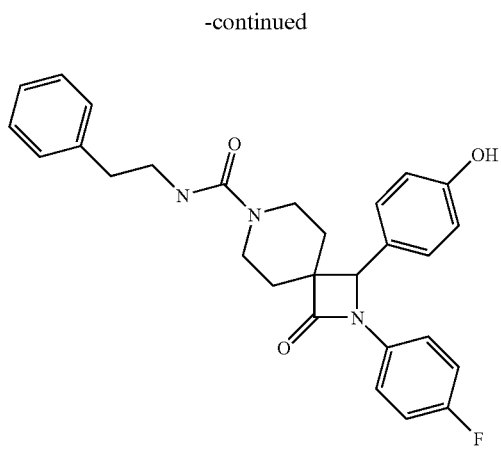
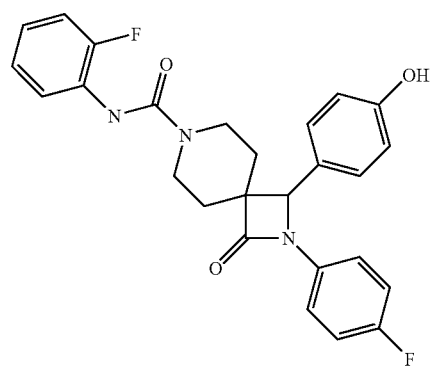
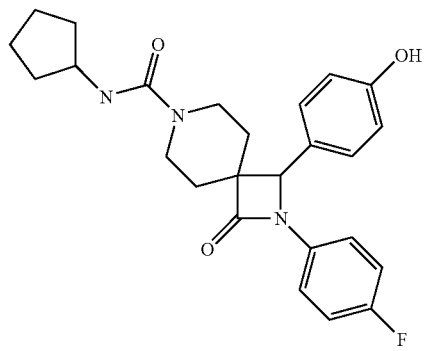
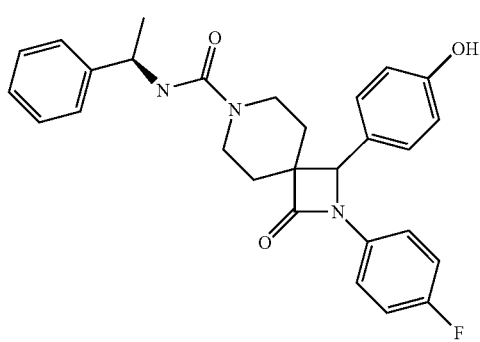
-continued
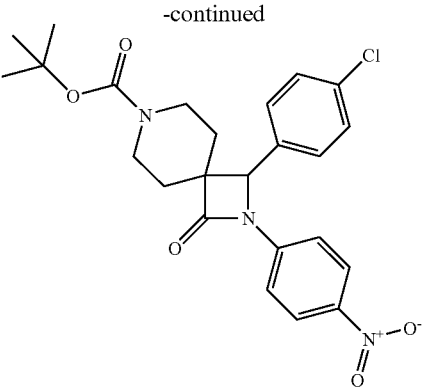
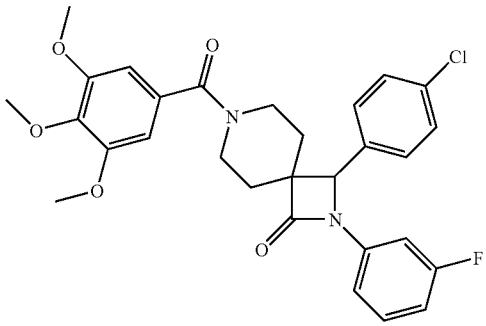
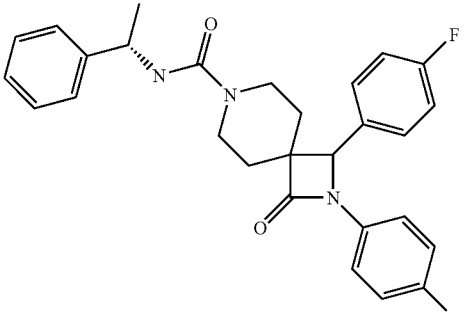
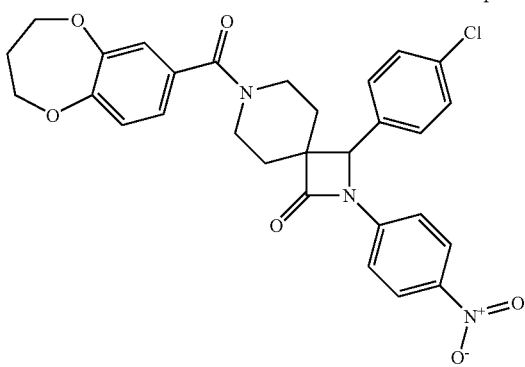
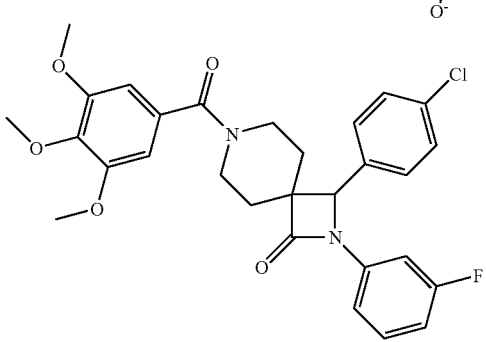

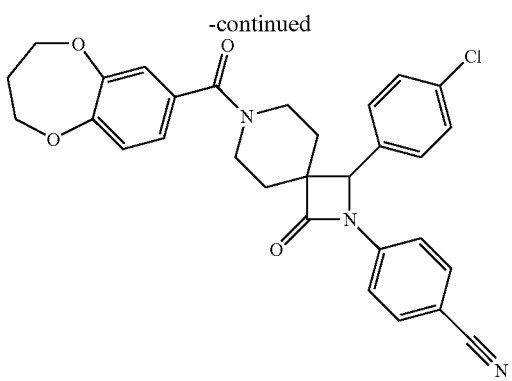
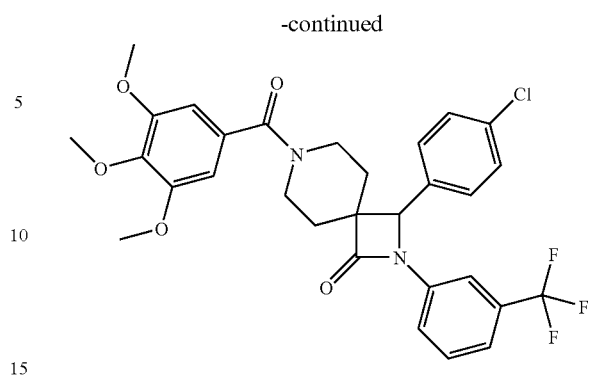
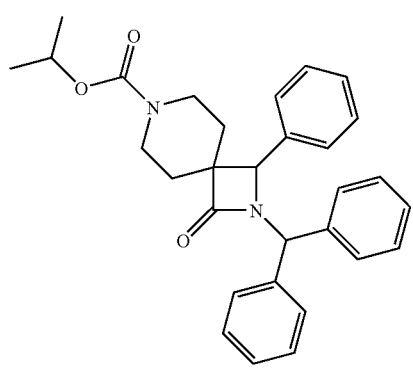
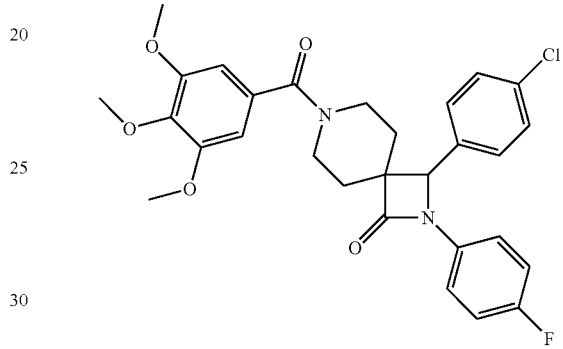
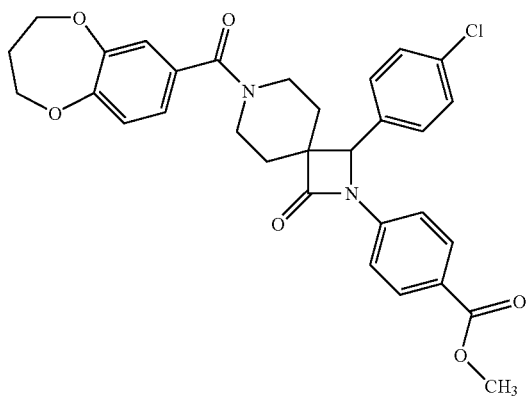
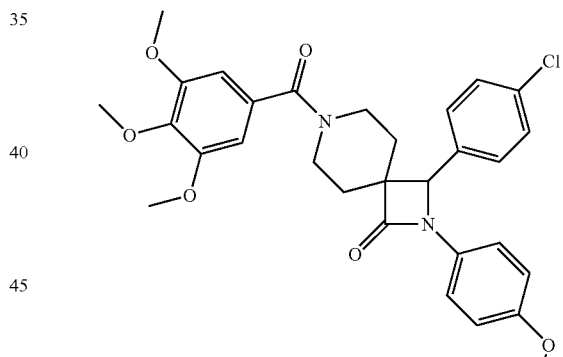
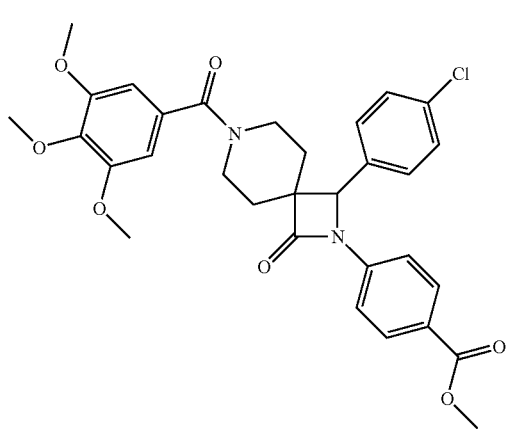
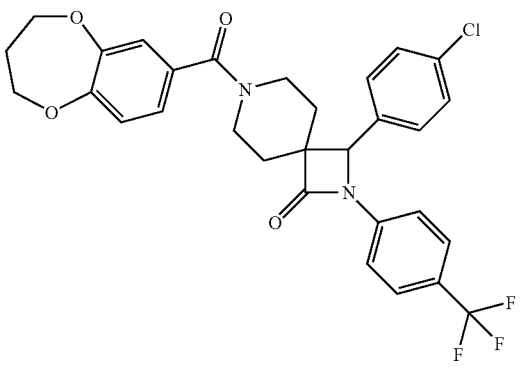

101
-continued
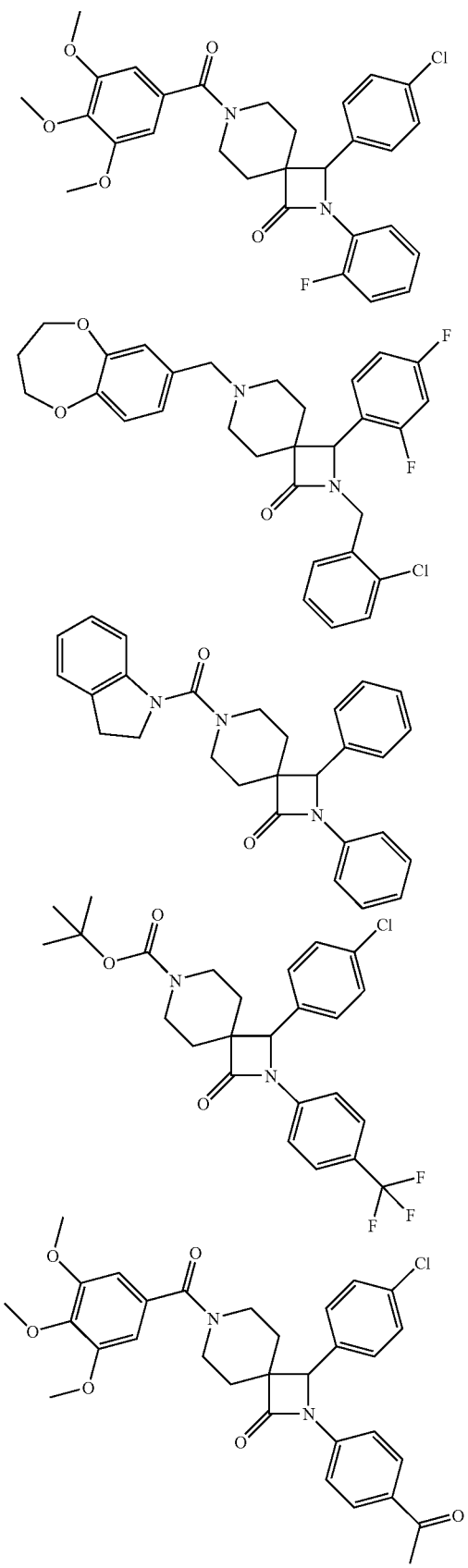
102
-continued
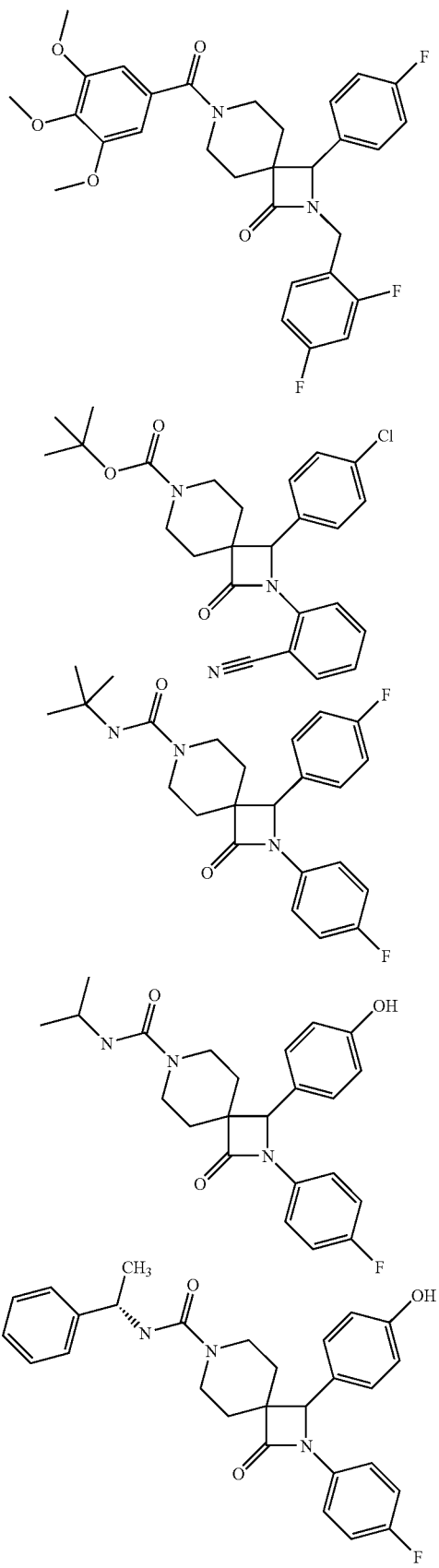

-continued
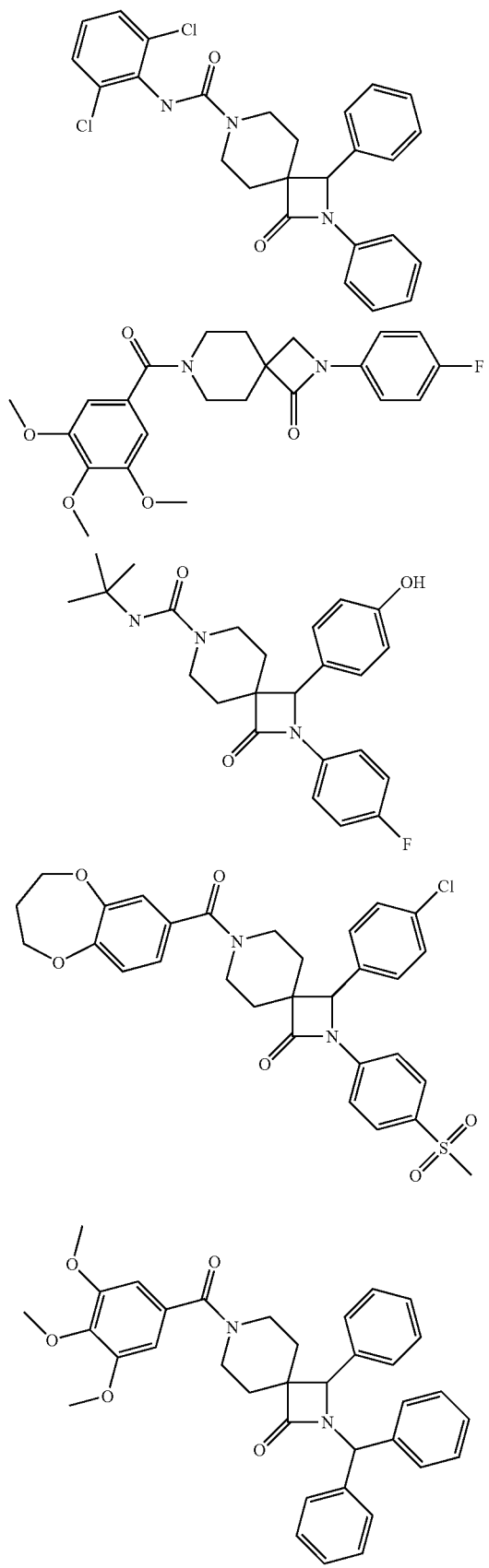
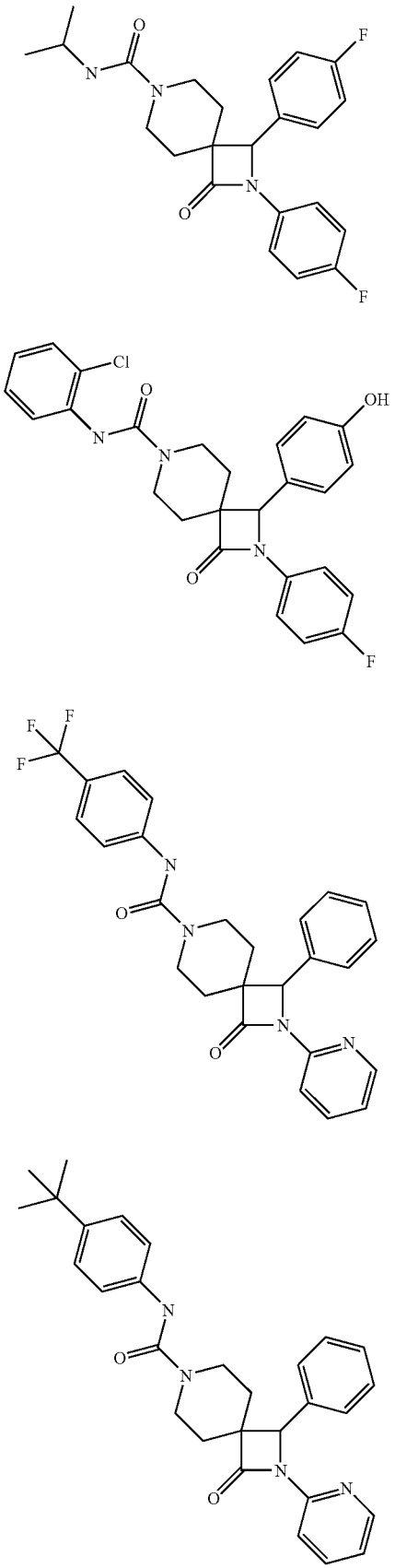

-continued
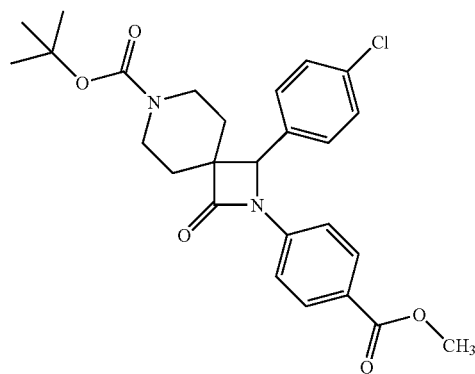
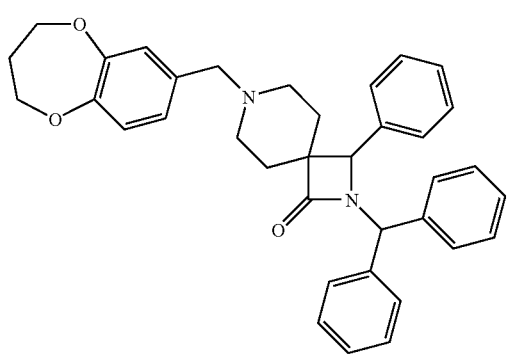
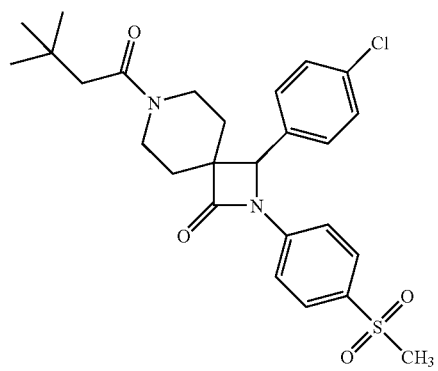
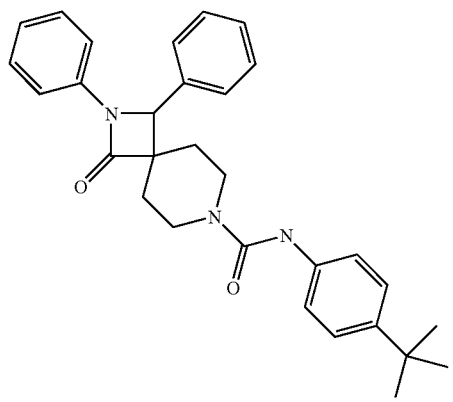
-continued
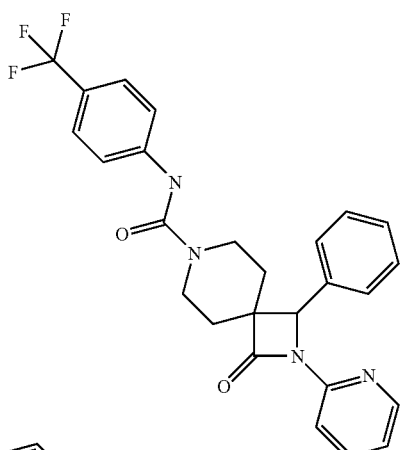
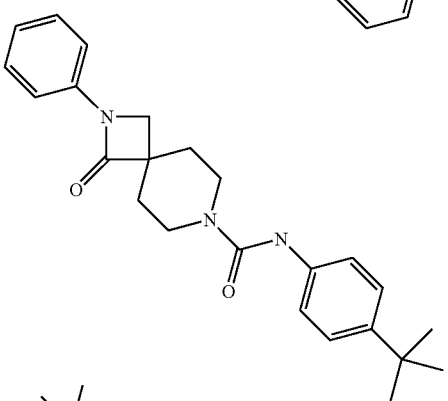
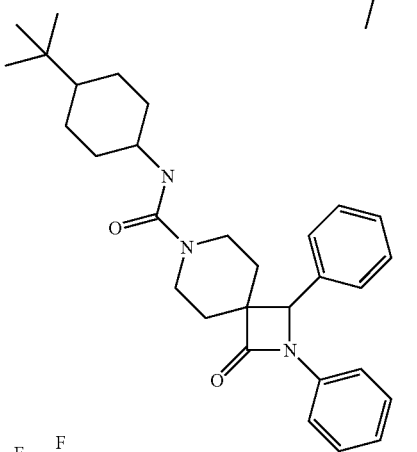
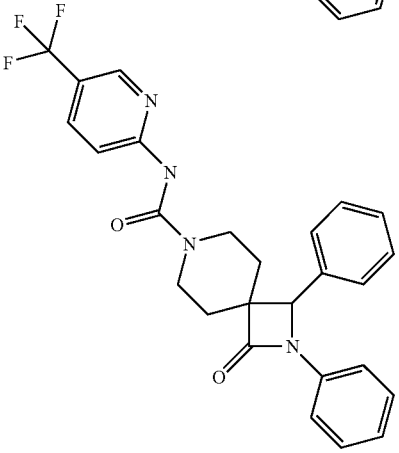

-continued
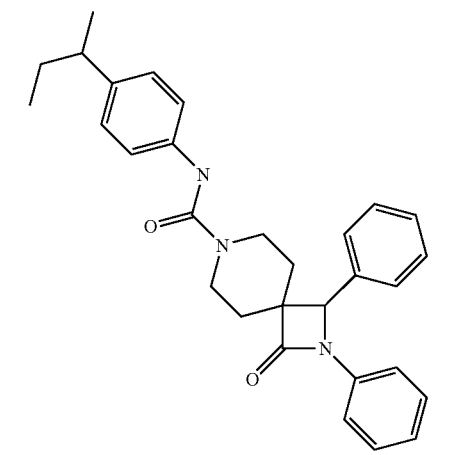
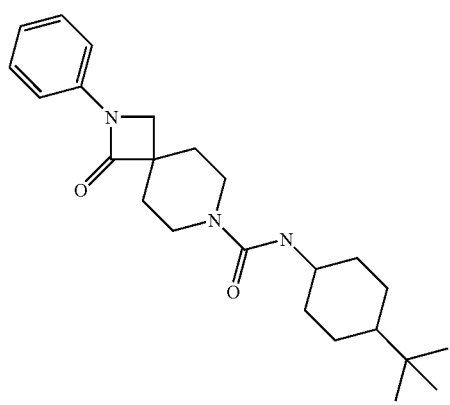
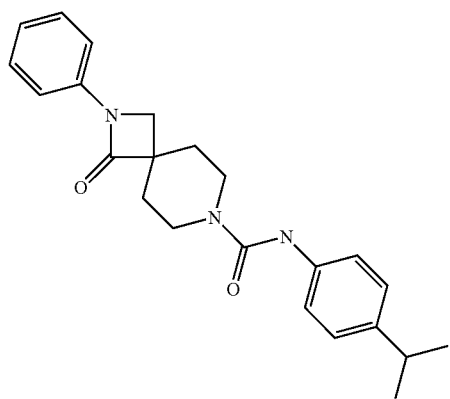
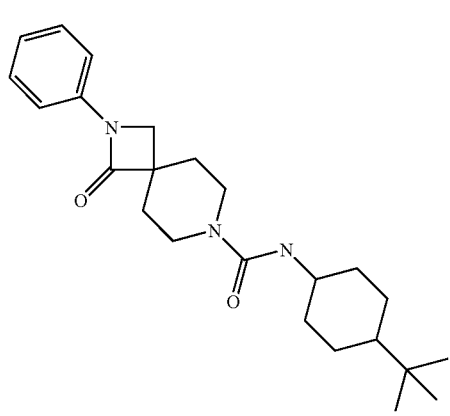
-continued
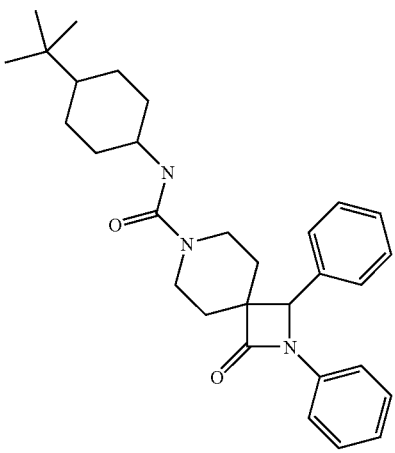
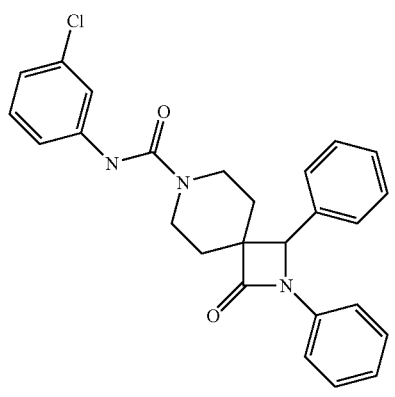
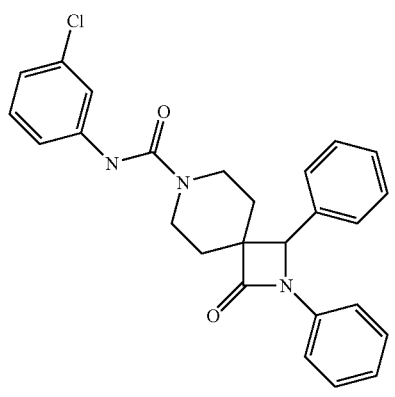
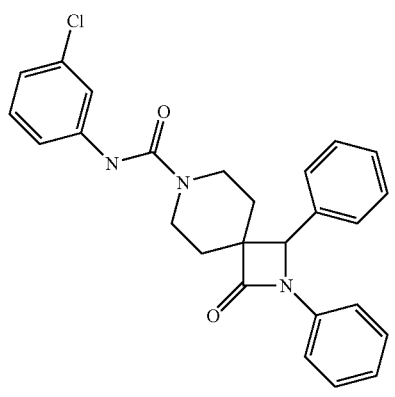

-continued
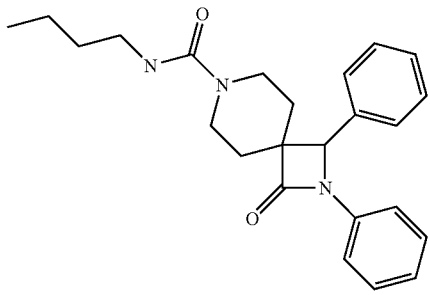
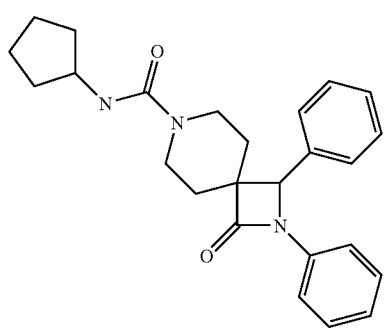
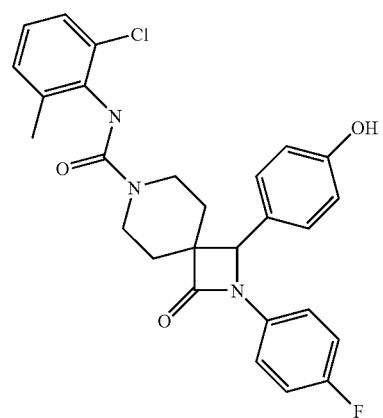
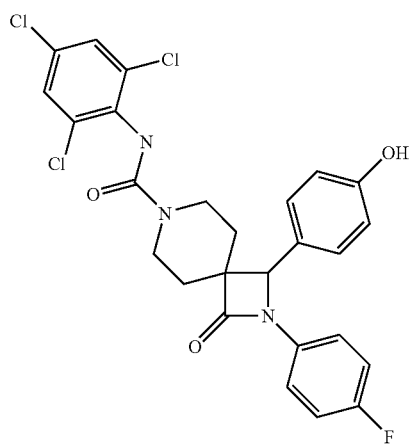
-continued
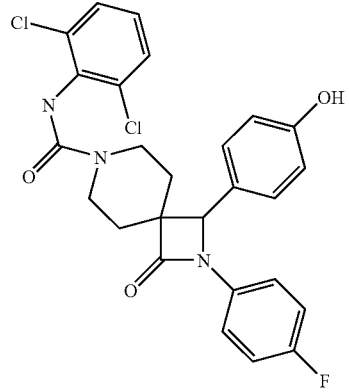
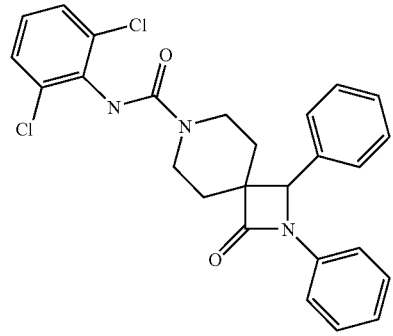
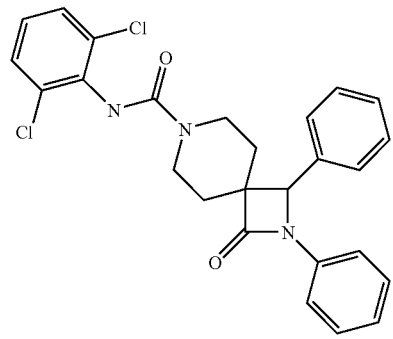
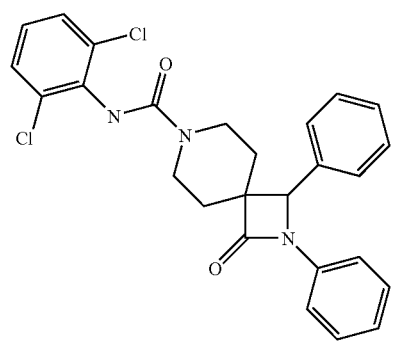

-continued
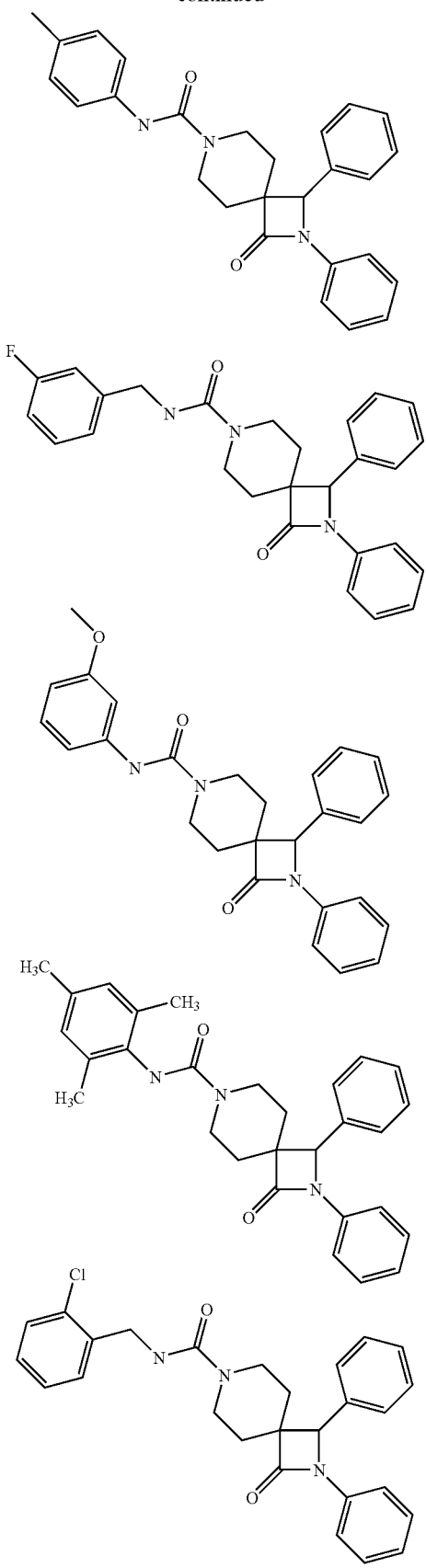
-continued
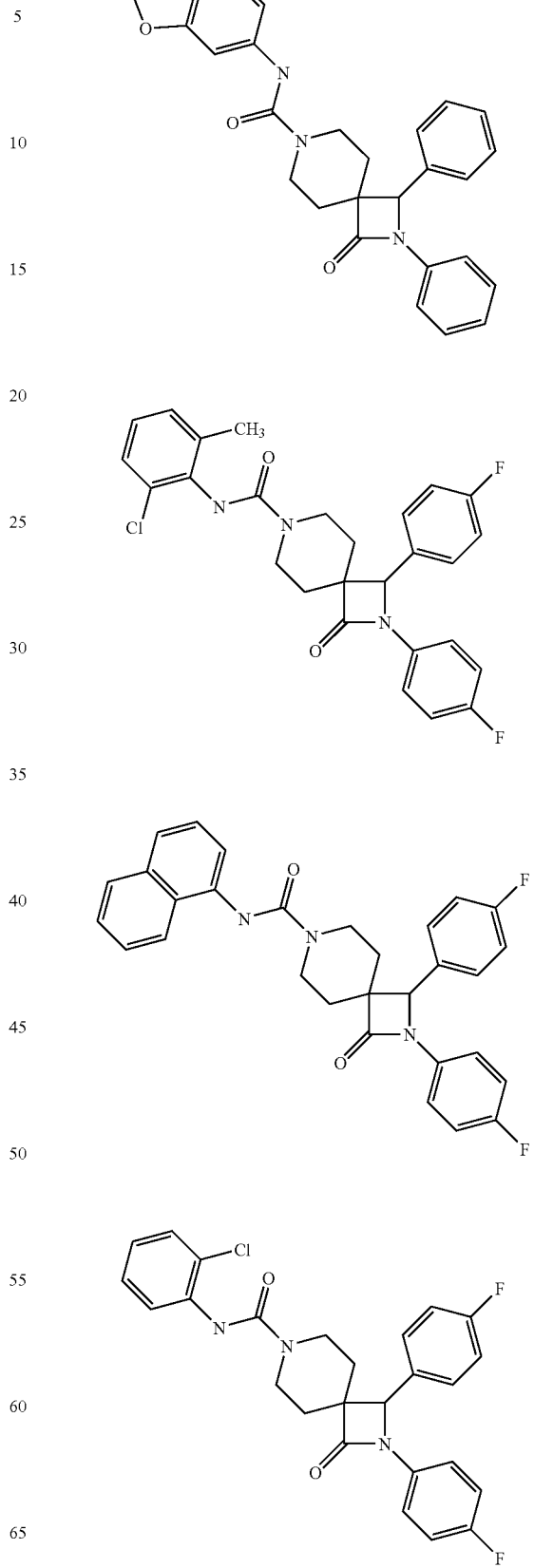

-continued
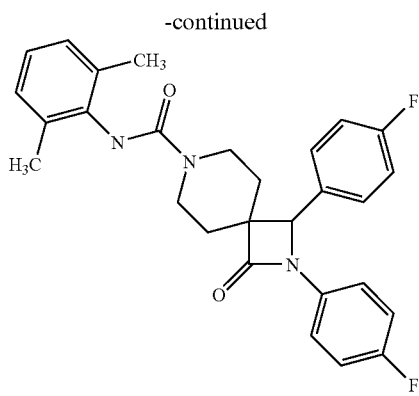
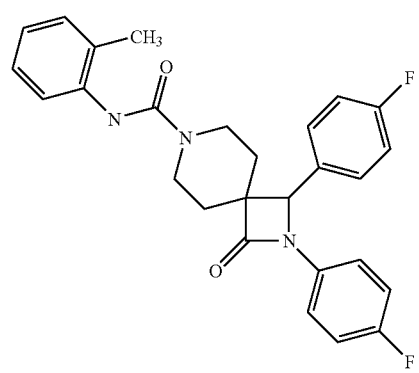
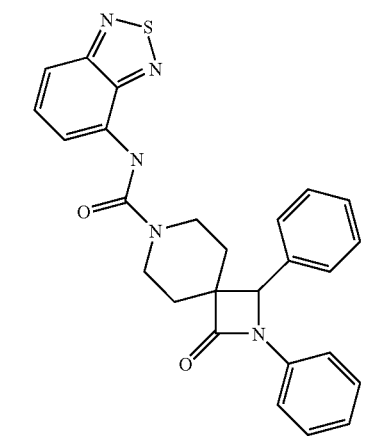
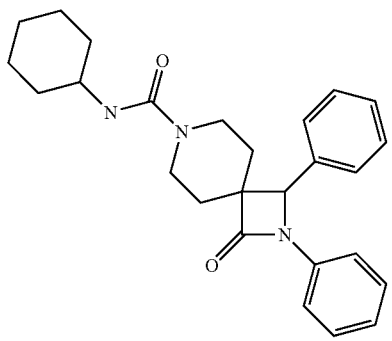
-continued
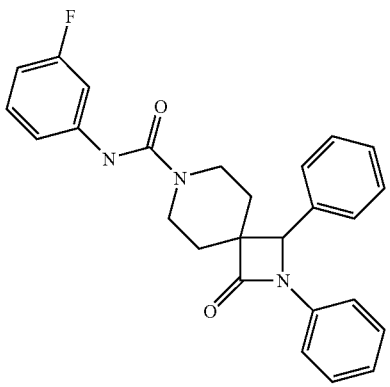
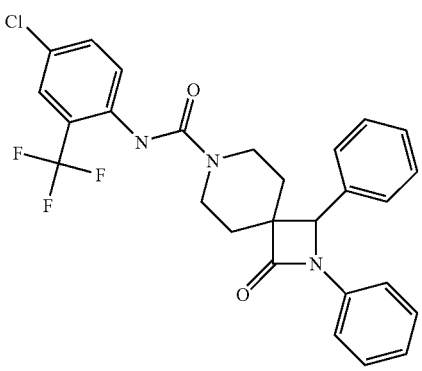
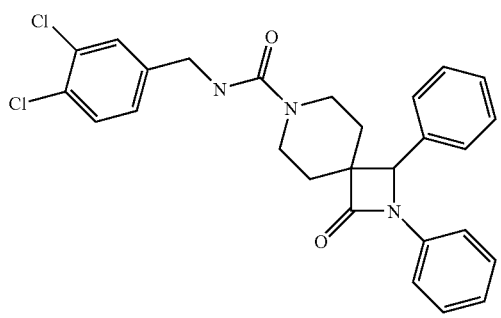
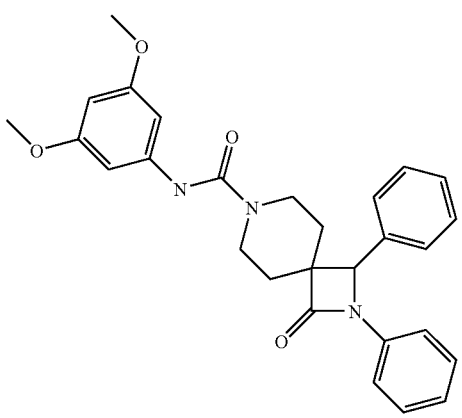

-continued
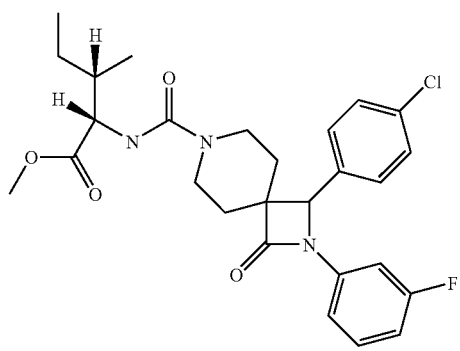
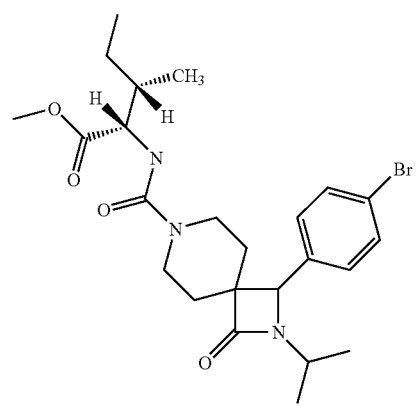
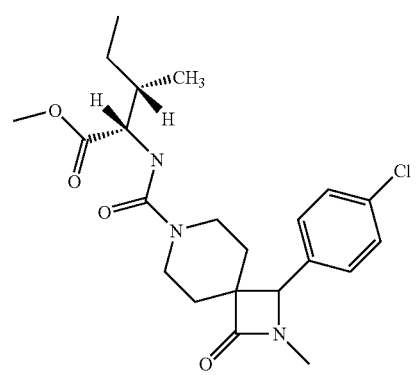
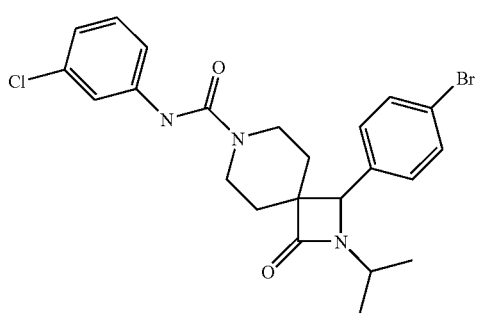
-continued
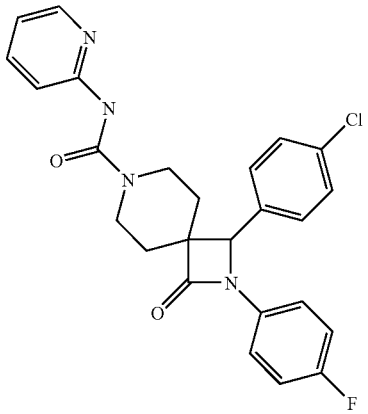
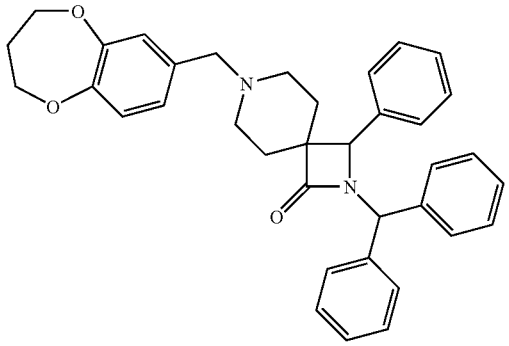
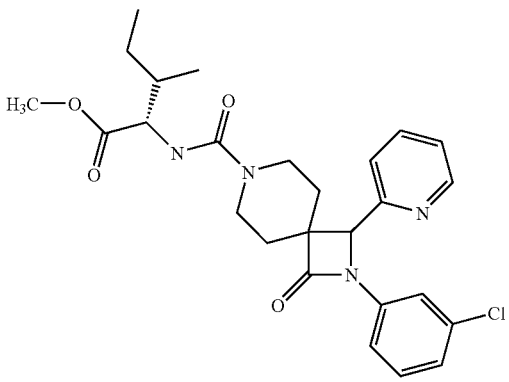
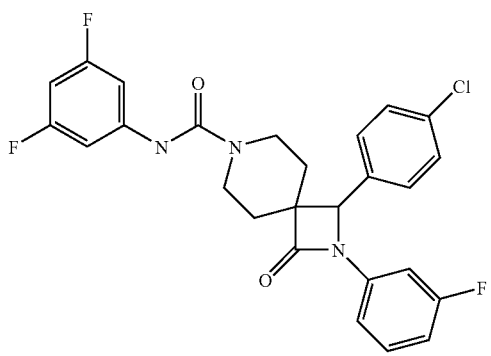

-continued
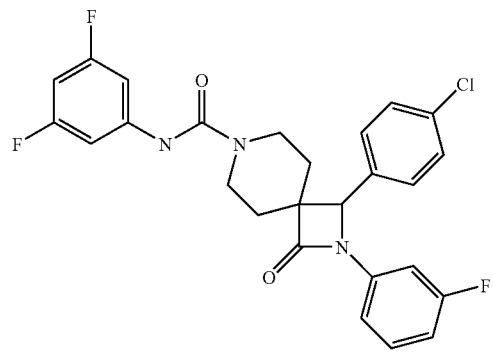
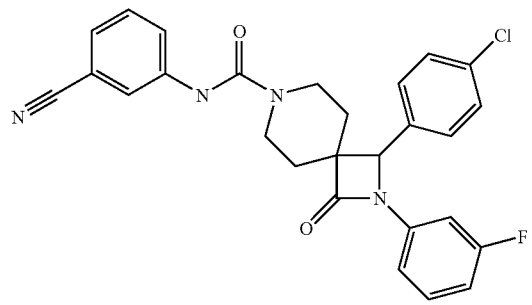
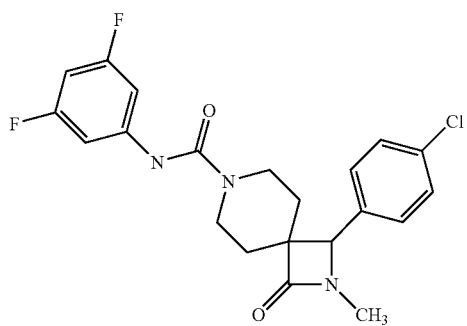
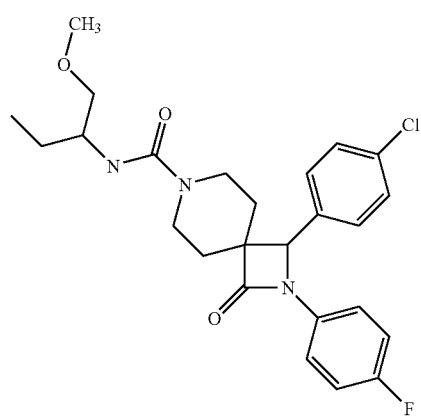
-continued
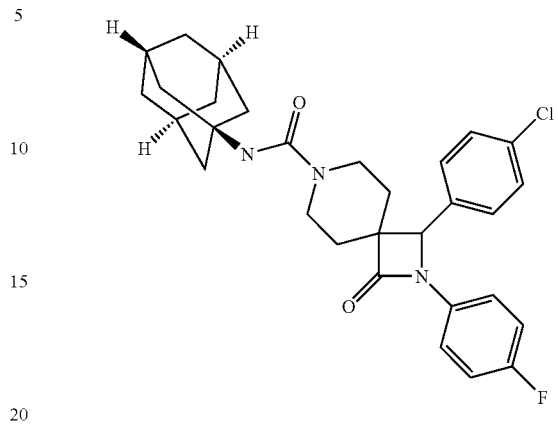
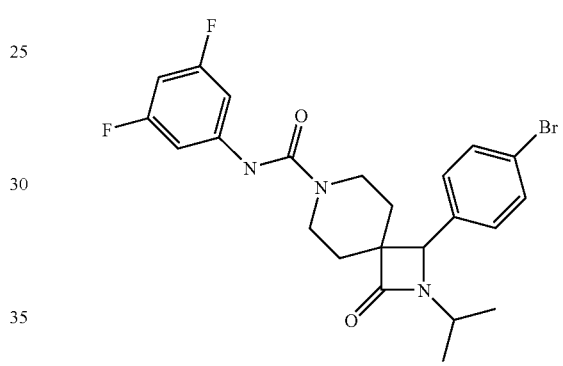
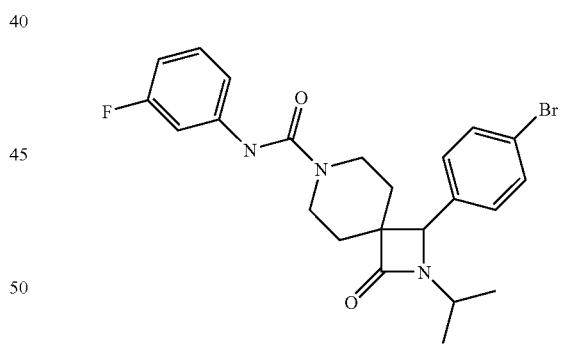
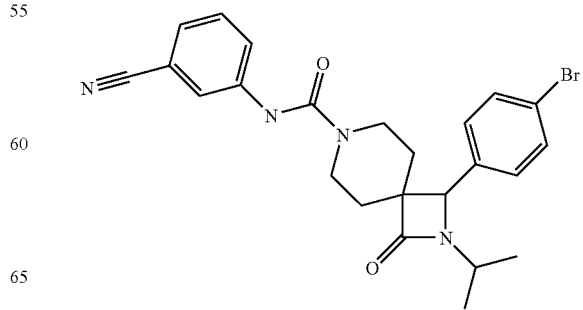

-continued
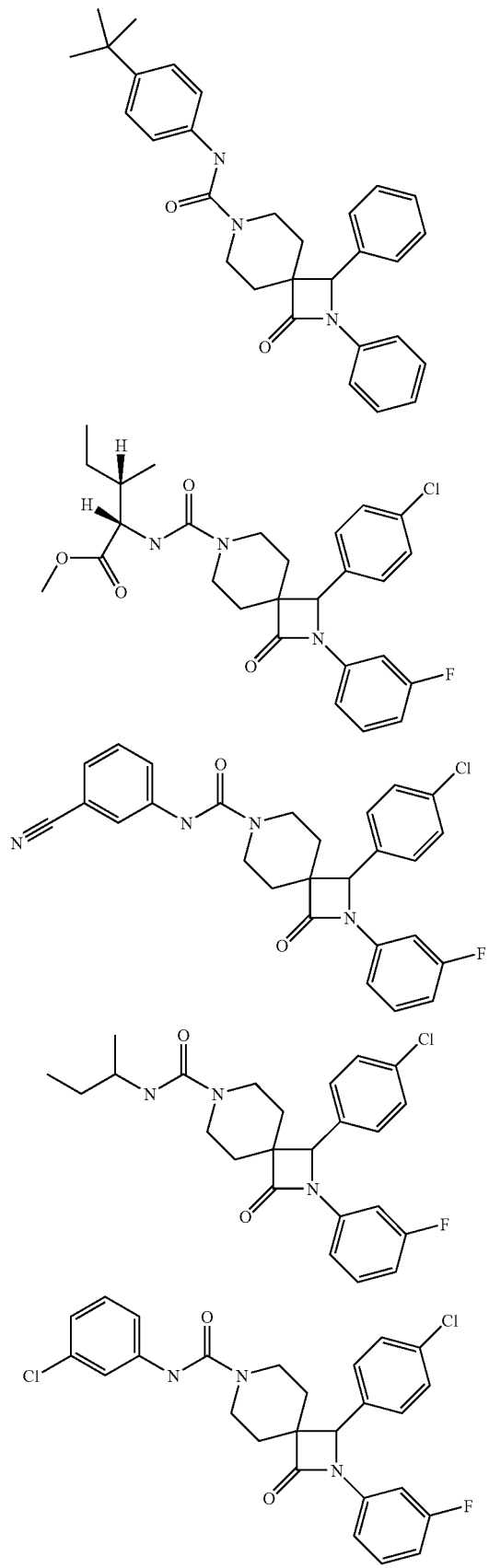
-continued
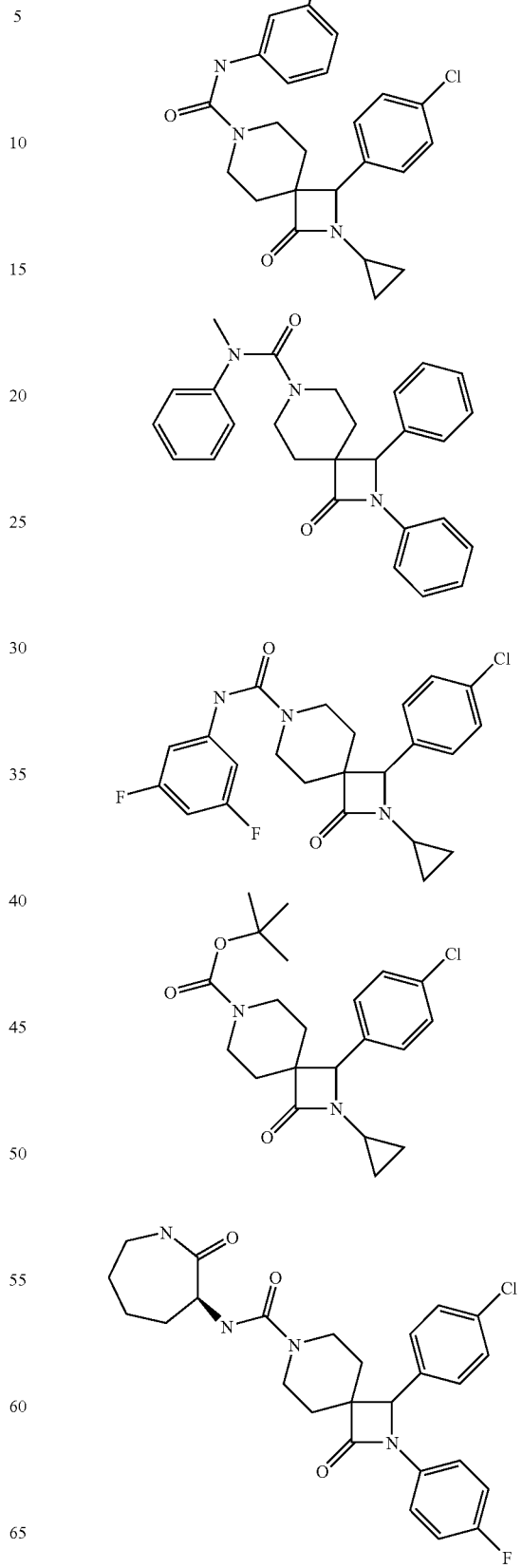

121 122
-continued -continued
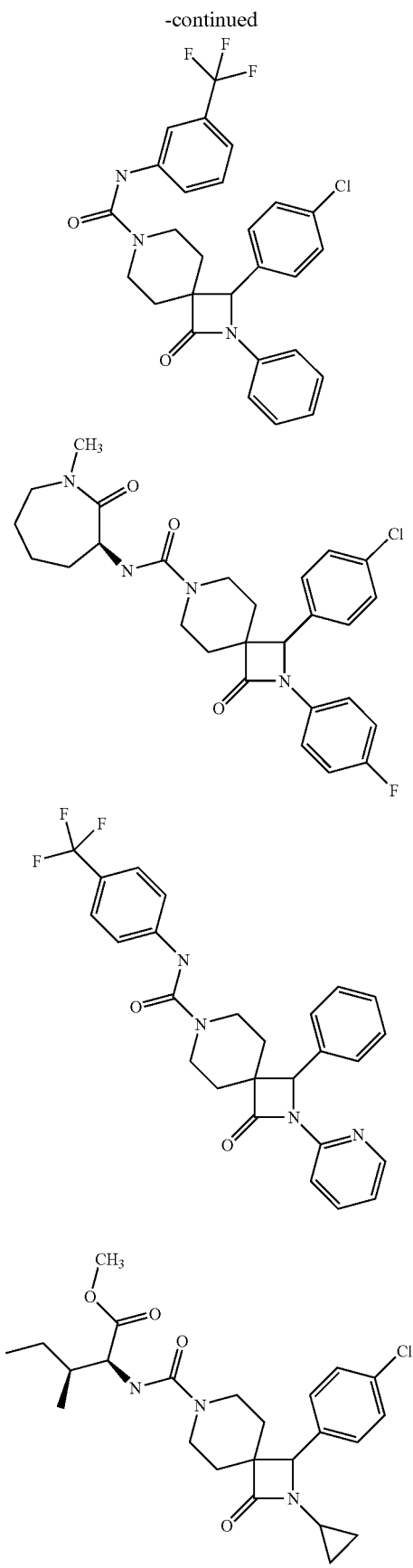
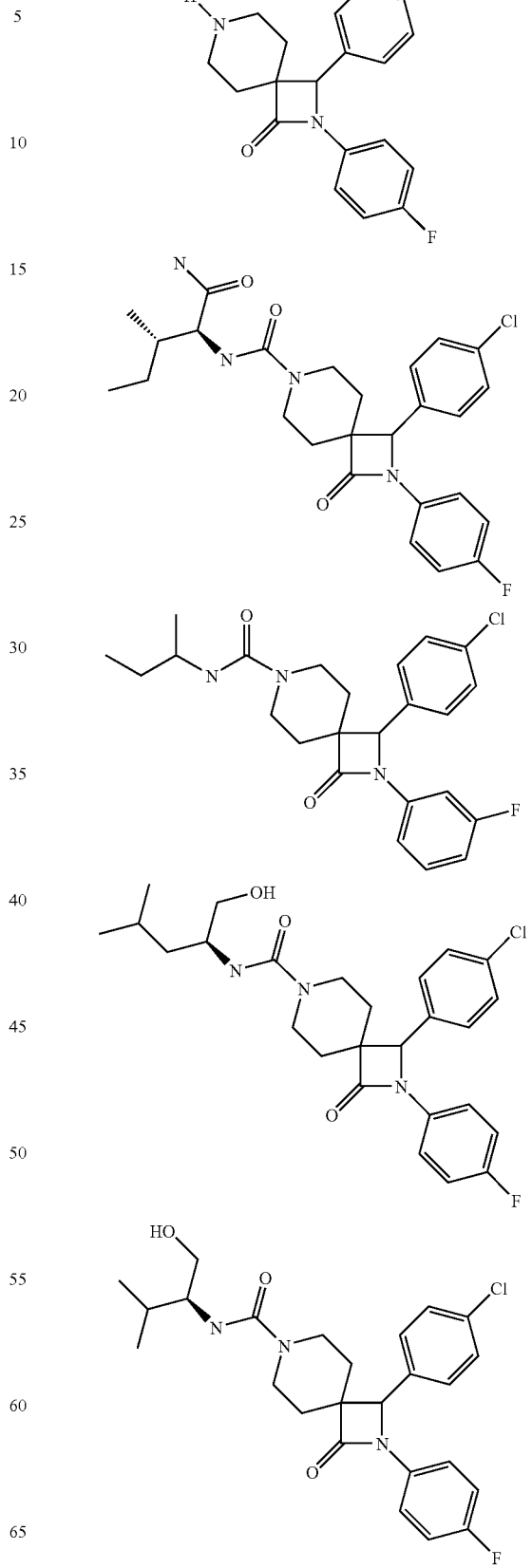

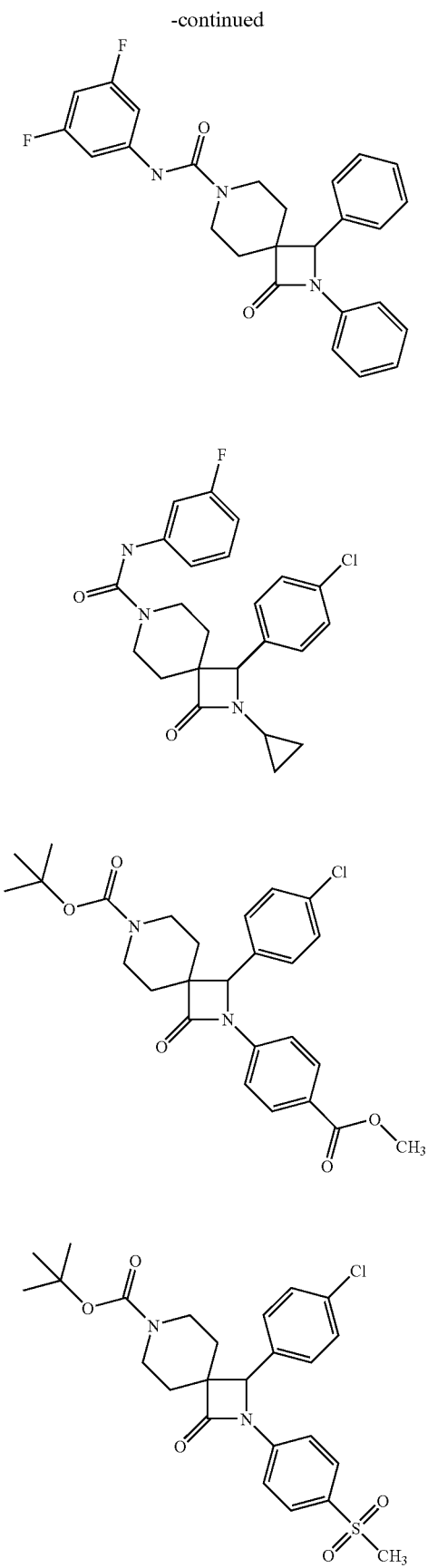

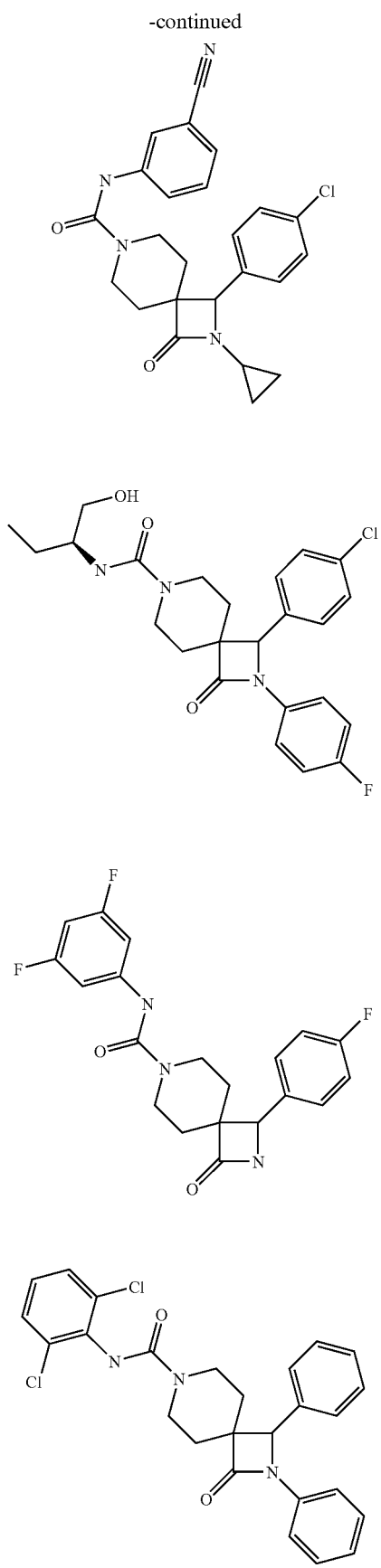

pharmaceutically acceptable salts, solvates, esters, prodrugs and stereoisomers thereof.

Methods For Making the Azetidinone Derivatives

Methods useful for making the Azetidinone Derivatives of formulas (I) are set forth below in Schemes 1-5

Scheme 1 illustrates a method for making the Azetidinone Derivatives of formula (I)-(III) wherein $R^1$, $R^2$, $R^3$, $R^4$, $R^5$, u and v are as defined above for the compounds of formulas (I)-(III).

-continued

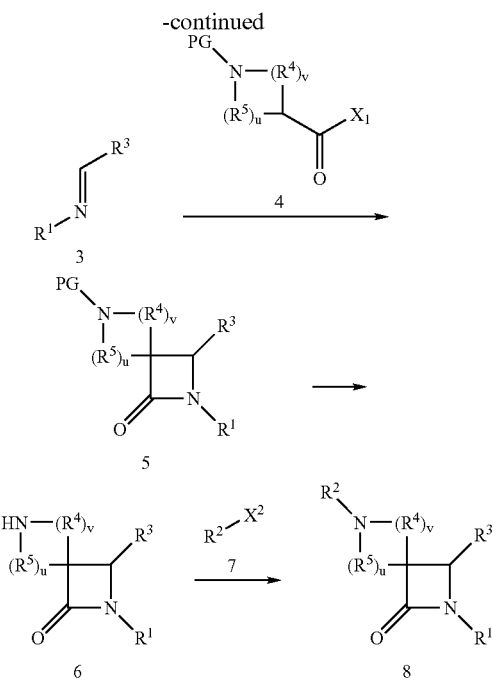

An aldehyde compound of formula 1 in a solvent such as toluene or isopropanol can be reacted with an amine compound of formula 2 to provide an imine compound of formula 3. A compound of formula 4 (where $X^1$ is a halogen or alkoxy group such as OEt) is then treated with a base such as LDA or LHMDS at $-78°$ C., and the resulting enolate is reacted with a compound of formula 3 to provide a spirocyclic compound of formula 5. The N-protecting group of a compound of formula 5 can then be removed to provide a piperidine compound of formula 6. A compound of formula 6 can then be reacted with a compound of formula 7 (which can be a carboxylic acid, an alkyl or aryl halide, or an isocyanate) in the presence of an appropriate base or coupling agent to provide the Azetidinone Derivatives of the invention, denoted by formula 8.

Scheme 2 illustrates an alternative method for making the Azetidinone Derivatives of formula (I)-(III) wherein $R^1$, $R^2$ and $R^3$ are as defined above for the compounds of formulas (I)-(III).

Scheme 2

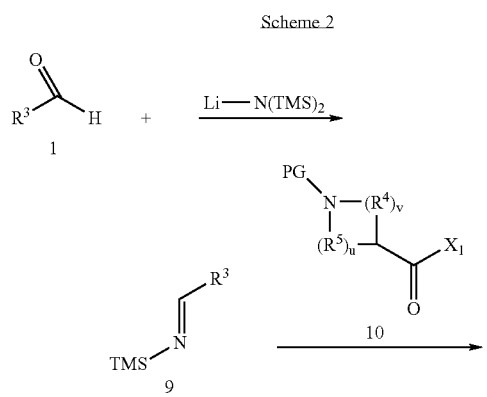

-continued

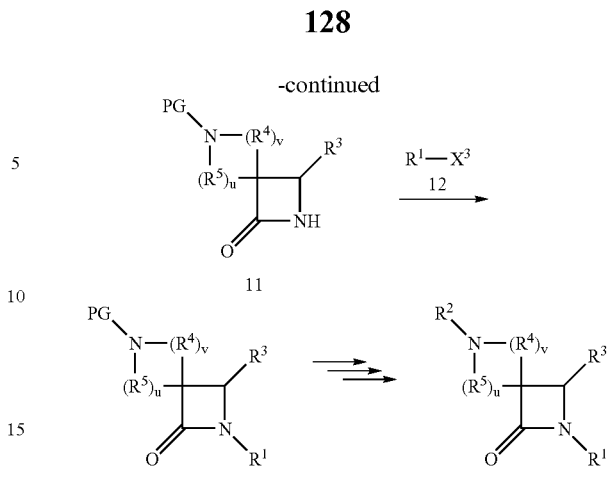

An aldehyde compound of formula 1 is reacted with lithium hexamethyldisilazide to provide a TMS-protected imine of formula 9. A compound of formula 10 (where $X^1$ is a halogen or alkoxy group such as OEt) is then treated with a base such as LDA or LHMDS at $-78°$ C., and the resulting enolate can be reacted with a compound of formula 9 to provide a spirocyclic compound of formula 11. A compound of formula 11 can then be reacted with a compound of formula 12 (wherein $X^3$ is a good leaving group, such as Cl, Br, I, O-triflyl, O-tosyl or O-mesyl), in the presence of a base, such as a NaH, to provide a intermediate compound of formula 5, which can subsequently be converted to the Azetidinone Derivatives of the invention (8) using the methods set forth above in Scheme 1.

Scheme 3 illustrates a general method useful for making the Azetidinone Derivatives of formulas (I)-(III), wherein the $R^2$ group forms a tertiary urea with the nitrogen atom to which it is attached.

Scheme 3

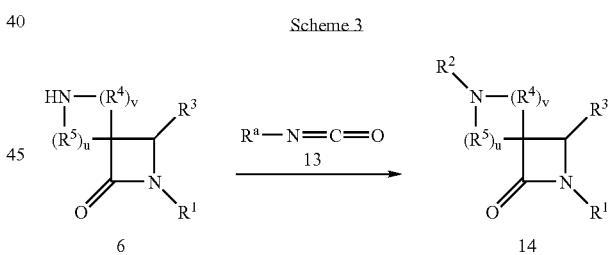

A spirocyclic intermediate of formula 6 is reacted with an isocyanate of formula 13 to provide an Azetidinone Derivative formula 14, wherein the $R^2$ group forms a tertiary urea with the nitrogen atom to which it is attached, and wherein $R^1$ and $R^3$ are as defined above herein for the compounds of formulas (I)-(III).

General Method for the Preparation of Ureas of Formula 14

To a solution of an intermediate compound of formula 6 (0.025 mmol) in DCE/MeOH (25:1 v/v, 1 mL) was added a 0.5 M solution of an isocyanate compound of formula 13 (0.075 mmol) in DCE. The reaction mixture was allowed to stir at room temperature for 20 hours, after which time dichloroethane (0.5 mL), polystyrene isocyanate resin (0.057 g, 0.087 mmol) and polystyrene trisamine resin (0.049 g, 0.207 mmol) were added. The resultant reaction was allowed to stir at room temperature for 16 hours. The reaction product was filtered and the resin was washed with acetonitrile (0.5 mL). The organic solvent was evaporated under reduced pressure to provide an Azetidinone Derivative of formula 14, wherein the $R_2$ group forms a tertiary urea with the nitrogen atom to which it is attached.

Scheme 4 illustrates a general method useful for making the Azetidinone Derivatives of formulas (I)-(III) wherein the $R^2$ group forms an amide with the nitrogen atom to which it is attached.

Scheme 4

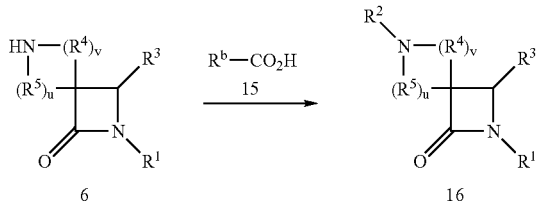

A spirocyclic intermediate of formula 6 is reacted with carboxylic acid of formula 15 to provide an Azetidinone Derivative of formula 16, wherein the $R_2$ group forms an amide with the nitrogen atom to which it is attached, wherein $R^b$ represents the amide substituents listed in Table 5, and wherein $R^1$ and $R^3$ are as defined above herein.

General Method for the Preparation of Amides of Formula 16

To a mixture of polystyrene EDC resin (0.106 g, 0.146 mmol) and a compound of formula 6 (0.025 mmol) in MeCN/THF (3:1 v/v, 1 mL) was added a 1 M solution of a carboxylic acid of formula 15 (0.038 mmol) in DMF. To the resultant mixture was added a solution of HOBT (0.5M, 0.038 mmol) in MeCN/THF (3:1 v/v, 0.20 mL). The reaction mixture was allowed to stir at room temperature for 20 hours, after which time acetonitrile (0.5 mL), polystyrene isocyanate resin (0.049 g, 0.075 mmol) and polystyrene trisamine resin (0.035 g, 0.148 mmol) were added. The resultant reaction mixture was allowed to stir at room temperature for 64 hours and the reaction product was filtered and the resin was washed with acetonitrile (0.5 mL). The organic solvent was concentrated in vacuo to provide an Azetidinone Derivative of formula 16, wherein the $R_2$ group forms an amide with the nitrogen atom to which it is attached.

Scheme 5 illustrates a general method useful for making the Azetidinone Derivatives of formulas (I)-(III), wherein the $R^2$ group is joined to the nitrogen atom to which it is attached via a —$CH_2$— linker.

Scheme 5

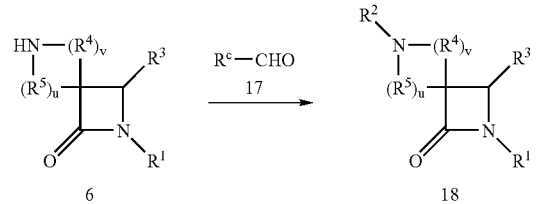

A spirocyclic intermediate of formula 6 is reacted with aldehyde of formula 17 to provide an Azetidinone Derivative of formula 18, wherein the $R^2$ group is selected from groups 177-236 as shown in Table 6. The variable $R^c$ of the compounds of formula 17 corresponds to $R^2$ groups 177-236 as set forth in Table 6 minus their terminal methylene group, and $R^1$ and $R^3$ are as defined above herein.

General Method for the Preparation of N-Methylene Compounds of Formula 18

To a solution of a compound of formula 6 (0.025 mmol) in DMF/THF (1:1 v/v, 1 mL) was added a solution of aldehyde 17 (0.075 mmol) in DCE, followed by addition of sodium triacetoxyborohydride (3 eq.). The reaction mixture was allowed to stir at room temperature for about 20 hours. MeOH (0.5 mL) was added to each reaction vessel, and shaken for 10 minutes or until gas evolution ceases. MP-TsOH resin (~100 mg) was added to the reaction vessel and the resultant mixture was shaken for about 2 hours. The solvent was then removed by filtration and the resin washed sequentially with DCE (3×), then methanol (3×), and the desired products were eluted off the resin by stirring with 2N ammonia in methanol (1.5-2 mL, for 1 hour) and filtration. The organic solvent was evaporated under reduced pressure to provide an Azetidinone Derivative of formula 18, wherein the $R^2$ group is joined to the nitrogen atom to which it is attached via a —$CH_2$— linker.

Uses of the Azetidinone Derivatives

The Azetidinone Derivatives are useful for treating or preventing a condition in a patient. Accordingly, in one embodiment, the invention provides methods for treating a condition in a patient comprising administering to the patient an effective amount of an Azetidinone Derivative. In another embodiment, the present methods for treating a Condition in a patient further comprise administering another therapeutic agent.

In one embodiment, the other therapeutic agent is selected from an agent useful for treating pain, an antidiabetic agent, a T-type calcium channel blocking agent, an antagonist of TRPV1, an agonist of TRPV1, an agonist of GPR119, an antagonist of NPC1L1, an inhibitor of HMG-CoA reductase, a nicotinic acid receptor agonist or an inhibitor of cholesterol ester transfer protein.

Pain

The Azetidinone Derivatives are useful for treating pain. Current chronic pain therapies provide only partial relief in responsive patients and are either not tolerated or ineffective in others. Chronic pain may arise as a consequence of tissue inflammation, viral infection (HIV, Herpes zoster) direct tissue injury or trauma, as a result of chemotherapy (e.g. taxol, vincristine), lesions of the central nervous system (e.g. stroke MS) or as a consequence of diabetes. When chronic pain is associated with somatic or visceral tissue injury, symptoms usually include severe sensory disturbances characterized by spontaneous pain (often described as stabbing, burning, electric-shock-like or throbbing), hyperalgesia (exaggerated responsiveness to painful stimuli) and allodynia (perception of non-noxious stimuli as painful). Prevalent symptoms in human patients include cold hyperalgesia, tactile allodynia and less commonly, heat hyperalgesia. Symptoms may present in isolation or in combination and there is often appreciable variation in the symptomatology associated with different disease states and typically between patients presenting with the same condition. In cases of somatic or visceral tissue injury/diseases, these distorted sensory perceptions have been linked to inappropriate activity (pathological hyperexcitability) in the peripheral nerves innervating the affected area. Neuronal hyperexcitability may arise as a result of altered ion channel function or activity.

Chronic pain is a true disease. It is believed to be a result, at least in part, of the plasticity at synapses in nociceptive processing centers, a phenomenon referred to as "central sensitization" which consists of increased excitability of spinal cord dorsal horn neurons. Maintenance of central sensitization is believed to require sustained peripheral neuronal activity (hyperexcitability) in sensory afferent nerves and such activity may be generated as a result of ectopic foci. Large T-type calcium currents can be found in sensory afferent neurons of the dorsal root ganglia (DRG). T-type calcium channels have been implicated as a causal factor in establishing such abnormal hyperexcitability, due to their known ability to function as neuronal pacemakers. Pharmacological and antisense oligonucleotide evidence supports a key role for DRG T-type calcium channels preclinical models of chronic pain.

T-type calcium channels are voltage-gated channels that can be opened with relatively small depolarizations from the resting potential of excitable cells. There are three distinct genes for T-type calcium currents that encode for $Ca_v3.1$, $Ca_v3.2$ and $Ca_v3.3$. The individual subtypes have unique patterns of distribution and are expressed in peripheral and central portions of pain pathways. T-type calcium channels are found in small and medium sized DRG neurons ($Ca_v3.2$) and regions of the CNS involved in pain processing including the dorsal horn of the spinal cord an the thalamus (Talley et al., *J Neurosci*, 1999, 19:1895-1911). T-type calcium currents have been shown to play a role in neuronal burst firing via low-threshold calcium spikes that permit rapid burst of neuronal action potentials (Suzuki and Rogwoski, *Proc Natl Acad Sci USA*, 1989, 86:7228-7232; White et al., *Proc Natl Acad Sci USA*, 1989, 86:6802-6806).

Inhibition of T-type calcium channel function in vivo through either the use of pharmacological blockers or antisense oligonucleotide mediated knockdown strongly implicate T-type channels in normal and pathological pain processing. Mibefradil and/or ethosuximide are selective for T-type calcium channel and have been shown to be effective in a number of preclinical pain models including: acute thermal and mechanical pain, phase I and II of the formalin model, the rat spinal nerve ligation model, capsaicin-induced mechanical hyperalgesia, rat tail flick, paclitaxil- and vincristine-induced chemoneuropathy (Barton et al., *Eur J Pharmacol*, 2005, 521:79-8; Dogrul et al., *Pain*, 2003, 105:159:168; Flatters and Bennett, *Pain*, 2004, 109:150-161; Todorovic et al., *Brain Res*, 2002, 951:336-340).

Pain relief in response to ethosuximide could be due to either central or peripheral actions. However efficacy in response to mibefradil can be attributed to peripheral effects for two reasons. First systemically administered mibefradil does not enter the brain. In addition intrathecal administration of mibefradil is ineffective (Dogrul et al., *Pain*, 2003, 105: 159:168). Further evidence supporting efficacy from block of peripheral T-type channels comes from studies with antisense oligonucleotide directed against on type of T-type channel, $Ca_v3.2$. Intrathecal injection of hCaV3.2 specific oligonucleotides decreased T-type calcium currents in DRG neurons and produced antinociceptive, anti-hyperalgesic and anti-allodynic effects. In these studies the uptake of oligonucleotide and the antisense mediated knockdown of T-type currents occurred in DRG neurons close to the site of injection but not in spinal cord (Bourinet et al., *EMBO J*, 2005 24:315-324).

The Azetidinone Derivatives of this invention are T-type calcium channel blockers. Accordingly, the present compounds are useful in the treatment or prevention of conditions that are treatable or preventable by administering T-type calcium channel blockers. Such conditions include, but are not limited to, the treatment or prevention of neuropathic pain.

The Azetidinone Derivatives of this invention are TRPV1 antagonists and are therefore useful in treating or preventing conditions that are treatable or preventable by administering a TRPV1 antagonist.

Conditions treated by TRPV1 antagonists include acute pain, chronic pain, neuropathic pain, postoperative pain, post rheumatoid arthritic pain, osteoarthritic pain, back pain, visceral pain, cancer pain, algesia, neuralgia, dental pain, headache, migraine, cluster headache, mixed-vascular and non-vascular syndromes, tension headache, neuropathies, carpal tunnel syndrome, diabetic neuropathy, HIV-related neuropathy, post-herpetic neuralgia, fibromyalgia, neuritis, sciatica, nerve injury, ischemia, neurodegeneration, stroke, post stroke pain, multiple sclerosis, respiratory diseases, asthma, cough, chronic obstructive pulmonary disease, bronchoconstriction, inflammatory disorders (such as general inflammation, inflammatory eye disorders, inflammatory bladder disorders, inflammatory skin disorders, chronic inflammatory conditions), inflammatory pain and associated hyperalgesia and allodynia, neuropathic pain and associated hyperalgesia and allodynia, oesophagitis, heart burn, Barrett's metaplasia, dysphagia, gastroesophageal reflux disorder, stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis, causalgia, sympathetically maintained pain, deafferentation syndromes, epithelial tissue damage or dysfunction, disturbances of visceral motility at respiratory, genitourinary, gastrointestinal or vascular regions, wounds, vitiligo, diarrhea, gastric lesions caused by necrotising agents and hair growth.

In one embodiment, the Azetidinone Derivatives of the present invention are used to treat inflammatory or neuropathic pain.

Additional agents useful in the present methods for treating inflammatory pain include corticosteroids, non-steroidal anti-inflammatory agents, COX-I and COX-II inhibitors, agents useful for treating inflammatory bowel disease and agents useful for treating rheumatoid arthritis. In one embodiment, additional agents for treating inflammatory pain are steroids and non-opioid analgesic agents.

Neuropathic pain as used herein refers to an abnormal state of pain sensation, in which a reduction of pain threshold and the like are continued, due to functional abnormalities accompanying damage or degeneration of a nerve, plexus or perineural soft tissue, which is caused by wound (e.g., lacerations, contusions, nerve avulsion injuries, amputation of a limb), compression (carpal tunnel syndrome, trigeminal neuralgia, tumor activity), infection, cancer, ischemia and the like, or metabolic disorders such as diabetes mellitus and the like. Neuropathic pain includes pain caused by either central or peripheral nerve damage. It also includes pain caused by either mononeuropathy or polyneuropathy. In some embodiments, the neuropathic pain is induced by diabetes.

Other examples of neuropathic pain treatable or preventable using the Azetidinone Derivatives include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, post-stroke pain, pain associated with Parkinson's disease, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, bursitis, pain associated with AIDS, pain associated with multiple sclerosis, pain due to spinal trauma and/or degeneration, burn pain, referred pain, enhanced memory of pain and neuronal mechanisms involved in coping with pain. Inflammatory pain may arise as a result of soft tissue injury including that involving the musculature (myositis) and viscera (colitis and inflammatory bowel disease, pancreatitis, cystitis, ileitis, Crohn's disease), nerves (neuritis, radiculopathies, radioculogangionitis), arthritic conditions (e.g. rheumatoid disease and related conditions such as ankylosing spondylitis), joint disease (including osteoarthritis). In specific embodiments, the Azetidinone Derivatives of the present invention are useful for treating or preventing allodynia or hyperalgesia.

Other additional agents useful in the present methods for treating neuropathic pain include non-opioid (also known as non-steroidal anti-inflammatories) analgesics such as acetylsalicylic acid, choline magnesium trisalicylate, acetaminophen, ibuprofen, fenoprofen, diflusinal, and naproxen; opioid analgesics such as morphine, hydromorphone, methadone, levorphanol, fentanyl, oxycodone, and oxymorphone; steroids such as prednisolone, fluticasone, triamcinolone, beclomethasone, mometasone, budisamide, betamethasone, dexamethasone, prednisone, flunisolide and cortisone; COX-I inhibitors such as aspirin and piroxicam; COX-II inhibitors such as rofecoxib, celecoxib, valdecoxib and etoricoxib; agents useful for treating inflammatory bowel disease such as IL-10, steroids, and azulfidine; agents useful for treating rheumatoid arthritis such as methotrexate, azathioprine, cyclophosphamide, steroids and mycophenolate mofetil; antimigraine agents, antiemetics, β-adrenergic blockers; anticonvulsants; antidepressants; other $Ca^{2+}$-channel blockers; sodium channel blockers; anticancer agents; agents for treating or preventing UI; agents for treating hypertension; agents for treating or preventing angina pectoris; agents for treating atrial fibrillation; agents for treating insomnia, agents for treating renal failure; agents for treating Alzheimer's disease; agents for treating or preventing IBS; agents for treating Parkinson's disease and parkinsonism; agents for treating anxiety; agents for treating epilepsy; agents for treating a stroke; agents for treating psychosis; agents for treating Huntington's chorea; agents for treating ALS; agents for treating vomiting; agents for treating dyskinesia; and agents for treating depression.

In one embodiment, the other agents for treating neuropathic pain are opioid and non-opioid analgesics. In another embodiment, the other agents for agents for treating neuropathic pain are selected from acetylsalicylic acid, choline magnesium trisalicylate, acetaminophen, ibuprofen, fenoprofen, diflusinal, naproxen, morphine, hydromorphone, methadone, levorphanol, fentanyl, oxycodone, and oxymorphone.

Disorders of Lipid Metabolism

The Azetidinone Derivatives are useful for treating disorders of lipid metabolism. The Azetidinone Derivatives of this invention are NPC1L1 antagonists. In one embodiment, the Azetidinone Derivatives are therefore useful for treating disorders of lipid metabolism, in particular for inhibiting absorption of cholesterol. It is to be understood that when the Azetidinone Derivatives are administered for inhibiting the absorption of cholesterol in a patient, the inhibition may be partial or complete. Accordingly, in one embodiment, the absorption of cholesterol in a patient is partially inhibited. In another embodiment, the absorption of cholesterol in a patient is completely inhibited.

Methods of treating disorders of lipid metabolism include treating hyperlipidemia, hypercholesterolemia, hypertriglyceridemia, sitosterolemia and arteriosclerotic symptoms; inhibiting absorption of cholesterol from the intestine; reducing blood plasma or serum concentrations of LDL cholesterol; reducing the concentrations of cholesterol and cholesterol ester in blood plasma or serum; reducing blood plasma or serum concentrations of C-reactive protein (CRP); reducing blood plasma or serum concentrations of triglycerides; reducing blood plasma or serum concentrations of apolipoprotein B; increasing blood plasma or serum concentrations of high density lipoprotein (HDL) cholesterol; increasing the fecal excretion of cholesterol; treating a clinical condition for which a cholesterol absorption inhibitor is indicated; reducing the incidence of cardiovascular disease-related events; reducing plasma or tissue concentration of at least one noncholesterol sterol or 5α-stanol; treating or preventing vascular inflammation; preventing, treating or ameliorating symptoms of Alzheimer's Disease; regulating the production or level of at least one amyloid β peptide in the bloodstream and/or brain of a patient; regulating the amount of ApoE isoform 4 in the bloodstream and/or brain; preventing and/or treating obesity; and preventing or decreasing the incidence of xanthomas.

Additional agents useful in the present methods for treating a disorder of lipid metabolism include inhibitors of cholesterol absorption (e.g., NPC1L1 antagonists such as ezetimibe); inhibitors of cholesterol biosynthesis; cholesterol ester transfer protein (CETP) inhibitors, such as torcetrapib; bile acid sequesterants; nicotinic acid or a derivative thereof; nicotinic acid receptor agonists, such as niacin or niaspan; peroxisome proliferator-activator receptor (PPAR) agonists or activators; acylcoenzyme A: cholesterol acyltransferase (ACAT) inhibitors; ideal bile acid transport ("IBAT") inhibitors (or apical sodium co-dependent bile acid transport ("ASBT") inhibitors; obesity control medications; hypoglycemic agents; antioxidants; acylCoA: cholesterol O-acyltransferase ("ACAT") inhibitors; cholesteryl ester transfer protein ("CETP") inhibitors; probucol or derivatives thereof; low-density lipoprotein ("LDL") receptor activators, omega 3 fatty acids ("3-PUFA"); natural water soluble fibers; plant sterols, plant stanols and/or fatty acid esters of plant stanols; and antihypertensive agents.

Non-limiting examples of suitable cholesterol biosynthesis inhibitors useful in the present methods include competitive inhibitors of HMG-CoA reductase, squalene synthase inhibitors, squalene epoxidase inhibitors and mixtures thereof. Non-limiting examples of suitable HMG-CoA reductase inhibitors useful in the present methods include statins such as lovastatin, pravastatin, fluvastatin, simvastatin, atorvastatin, cerivastatin, CI-981, resuvastatin, rivastatin and pitavastatin, rosuvastatin; HMG-CoA reductase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other sterol biosynthesis inhibitors such as DMP-565. In one embodiment, HMG-CoA reductase inhibitors include lovastatin, pravastatin and simvastatin. In another embodiment, the HMG-CoA reductase inhibitor is simvastatin.

Bile acid squestrants bind bile acids in the intestine, interrupting the enterohepatic circulation of bile acids and causing an increase in the faecal excretion of steroids.

Non-limiting examples of suitable bile acid sequestrants useful in the present methods include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

The activators or agonists of PPAR act as agonists for the peroxisome proliferator-activated receptors. Three subtypes of PPAR have been identified, and these are designated as peroxisome proliferator-activated receptor alpha (PPARα), peroxisome proliferator-activated receptor gamma (PPARγ) and peroxisome proliferator-activated receptor delta (PPARδ). It should be noted that PPARδ is also referred to in the literature as PPARβ and as NUC1, and each of these names refers to the same receptor. The term "PPAR activator" as used herein, refers to activators of any PPAR receptor subtype.

PPARα regulates the metabolism of lipids. PPARα is activated by fibrates and a number of medium and long-chain fatty acids, and it is involved in stimulating β-oxidation of fatty acids. The PPARγ receptor subtypes are involved in activating the program of adipocyte differentiation and are not involved in stimulating peroxisome proliferation in the liver. PPARδ has been identified as being useful in increasing high density lipoprotein (HDL) levels in humans, See, e.g., WO 97/28149.

PPARα activator compounds are useful for, among other things, lowering triglycerides, moderately lowering LDL levels and increasing HDL levels. Useful examples of PPARα activators include fibrates.

Non-limiting examples of suitable fibric acid derivatives ("fibrates") useful in the present methods include clofibrate; gemfibrozil; ciprofibrate; bezafibrate; clinofibrate; binifibrate; lifibrol; fenofibrate and mixtures thereof. These compounds can be used in a variety of forms, including but not limited to acid form, salt form, racemates, enantiomers, zwitterions and tautomers.

Non-limiting examples of additional PPARα activators useful in the present methods include suitable fluorophenyl compounds as disclosed in U.S. Pat. No. 6,028,109 which is incorporated herein by reference; certain substituted phenylpropionic compounds as disclosed in WO 00/75103 which is incorporated herein by reference; PPARα activator compounds as disclosed in WO 98/43081 which is incorporated herein by reference.

Other examples of suitable PPARγ activators useful in the present methods include derivatives of glitazones or thiazolidinediones, such as, troglitazone; rosiglitazone and pioglitazone. Other useful thiazolidinediones include ciglitazone, englitazone, darglitazone and BRL 49653 as disclosed in WO 98/05331 which is incorporated herein by reference; PPARγ activator compounds disclosed in WO 00/76488 which is incorporated herein by reference; PPARγ activator compounds disclosed in U.S. Pat. No. 5,994,554 which is incorporated herein by reference; acetylphenols as disclosed in U.S. Pat. No. 5,859,051 which is incorporated herein by reference; quinoline phenyl compounds as disclosed in WO 99/20275 which is incorporated herein by reference; aryl compounds as disclosed in WO 99/38845 which is incorporated herein by reference; 1,4-disubstituted phenyl compounds as disclosed in WO 00/63161; aryl compounds as disclosed in WO 01/00579 which is incorporated herein by reference; benzoic acid compounds as disclosed in WO 01/12612 & WO 01/12187 which are incorporated herein by reference; and substituted 4-hydroxy-phenylalconic acid compounds as disclosed in WO 97/31907 which is incorporated herein by reference.

PPARδ compounds are useful for, among other things, lowering triglyceride levels or raising HDL levels. Non-limiting examples of PPARδ activators useful in the present methods include suitable thiazole and oxazole derivatives, such as C.A.S. Registry No. 317318-32-4, as disclosed in WO 01/00603 which is incorporated herein by reference); fluoro, chloro or thio phenoxy phenylacetic acids as disclosed in WO 97/28149 which is incorporated herein by reference; non-β-oxidizable fatty acid analogues as disclosed in U.S. Pat. No. 5,093,365 which is incorporated herein by reference; and PPARδ compounds as disclosed in WO 99/04815 which is incorporated herein by reference.

Moreover, compounds that have multiple functionality for activating various combinations of PPARα, PPARγ and PPARδ are also useful in the present methods. Non-limiting examples include substituted aryl compounds as disclosed in U.S. Pat. No. 6,248,781; WO 00/23416; WO 00/23415; WO 00/23425; WO 00/23445; WO 00/23451; and WO 00/63153, all of which are incorporated herein by reference, are described as being useful PPARα and/or PPARγ activator compounds. Other non-limiting examples of useful PPARα and/or PPARγ activator compounds include activator compounds as disclosed in WO 97/25042 which is incorporated herein by reference; activator compounds as disclosed in WO 00/63190 which is incorporated herein by reference; activator compounds as disclosed in WO 01/21181 which is incorporated herein by reference; biaryl-oxa(thia)zole compounds as disclosed in WO 01/16120 which is incorporated herein by reference; compounds as disclosed in WO 00/63196 and WO 00/63209 which are incorporated herein by reference; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G which are incorporated herein by reference; GW2331 or (2-(4-[difluorophenyl]-1heptylureido)ethyl]phenoxy)-2-methylbutyric compounds as disclosed in WO 98/05331 which is incorporated herein by reference; aryl compounds as disclosed in U.S. Pat. No. 6,166,049 which is incorporated herein by reference; oxazole compounds as disclosed in WO 01/17994 which is incorporated herein by reference; and dithiolane compounds as disclosed in WO 01/25225 and WO 01/25226 which are incorporated herein by reference.

Other useful PPAR activator compounds useful in the present methods include substituted benzylthiazolidine-2,4-dione compounds as disclosed in WO 01/14349, WO 01/14350 and WO/01/04351 which are incorporated herein by reference; mercaptocarboxylic compounds as disclosed in WO 00/50392 which is incorporated herein by reference, ascofuranone compounds as disclosed in WO 00/53563 which is incorporated herein by reference; carboxylic compounds as disclosed in WO 99/46232 which is incorporated herein by reference; compounds as disclosed in WO 99/12534 which is incorporated herein by reference; benzene compounds as disclosed in WO 99/15520 which is incorporated herein by reference; o-anisamide compounds as disclosed in WO 01/21578 which is incorporated herein by reference; and PPAR activator compounds as disclosed in WO 01/40192 which is incorporated herein by reference.

Probucol derivatives useful in the present methods include AGI-1067 and others disclosed in U.S. Pat. Nos. 6,121,319 and 6,147,250, which can reduce LDL and HDL levels, as cholesterol lowering agents.

IBAT inhibitors can inhibit bile acid transport to reduce LDL cholesterol levels. Non-limiting examples of suitable IBAT inhibitors useful in the present methods include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference.

As used herein, "nicotinic acid receptor agonist" means any compound comprising that will act as an agonist to the nicotinic acid receptor. Nicotinic acid receptor agonists useful in the present methods include those having a pyridine-3-carboxylate structure or a pyrazine-2-carboxylate structure, including acid forms, salts, esters, zwitterions and tautomers, where available. Examples of nicotinic acid receptor agonists useful in the present methods include niceritrol, nicofuranose and acipimox. Nicotinic acid and NAR agonists inhibit hepatic production of VLDL and its metabolite LDL and increases HDL and apo A-1 levels. An example of a suitable nicotinic acid product is NIASPAN® (niacin extended-release tablets) which are available from Kos Pharmaceuticals, Inc. (Cranbury, N.J.).

The present methods for treating a disorder of lipid metabolism can further comprise administering one or more ACAT inhibitors as lipid lowering agents. ACAT inhibitors reduce LDL and VLDL levels. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors useful in the present methods include avasimibe, HL-004, lecimibide and CL-277082 (N-(2,4-difluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 July; 60(1); 55-93, which is incorporated by reference herein.

The present methods for treating a disorder of lipid metabolism can further comprise administering one or more Cholesteryl Ester Transfer Protein ("CETP") Inhibitors coadministered with or in combination with one or more Azetidinone Derivatives. CETP is responsible for the exchange or transfer of cholesteryl ester carrying HDL and triglycerides in VLDL.

Non-limiting examples of suitable CETP inhibitors useful in the present methods are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be co-administered with or in combination with the fibric acid derivative(s) and sterol absorption inhibitor(s) discussed above.

In another embodiment, the present methods for treating a disorder of lipid metabolism can further comprise administering one or more low-density lipoprotein (LDL) receptor activators, as lipid lowering agents. Non-limiting examples of suitable LDL-receptor activators useful in the present methods include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioscler. Thromb.* 1993; 13-1005-12.

In one embodiment, the present methods for treating a disorder of lipid metabolism can further comprise administering fish oil, which contains Omega 3 fatty acids (3-PUFA), which can reduce VLDL and triglyceride levels, as a lipid lowering agent.

In another embodiment, the present methods for treating a disorder of lipid metabolism can further comprise administering natural water-soluble fibers, such as psyllium, guar, oat and pectin, which can reduce cholesterol levels.

In still another embodiment, the present methods for treating a disorder of lipid metabolism can further comprise administering plant sterols, plant stanols and/or fatty acid esters of plant stanols, such as sitostanol ester used in BENECOL® margarine, which can reduce cholesterol levels.

Demyelination

The Azetidinone Derivatives are useful for treating demyelination. Demyelination in the central nervous system (brain and spinal cord) occurs in several primary demyelinating diseases, such as multiple sclerosis, acute disseminated encephalomyelitis, adrenoleukodystrophy, adrenomyeloneuropathy, Leber's hereditary optic atrophy and HTLV-associated myelopathy.

Diabetes

The Azetidinone Derivatives are useful for treating diabetes mellitus. Diabetes mellitus, commonly called diabetes, refers to a disease process derived from multiple causative factors and characterized by elevated levels of plasma glucose, referred to as hyperglycemia. Premature development of atherosclerosis and increased rate of cardiovascular and peripheral vascular diseases are characteristic features of patients with diabetes. There are two major forms of diabetes. Type I diabetes (also referred to as insulin-dependent diabetes or IDDM) and Type II diabetes (also referred to as noninsulin dependent diabetes or NIDDM). In one embodiment, the Azetidinone Derivatives are useful for treating Type II diabetes.

Type I diabetes is the result of an absolute deficiency of insulin, the hormone that regulates glucose utilization. This insulin deficiency is usually characterized by $\beta$ cell destruction in the pancreas, which usually leads to absolute insulin deficiency. Type I diabetes has two forms: Immune-Mediated Diabetes Mellitus, which results from a cellular mediated autoimmune destruction of the $\beta$ cells of the pancreas; and Idiopathic Diabetes Mellitus, which refers to forms of the disease that have no known etiologies.

Type II diabetes is a disease characterized by insulin resistance accompanied by relative, rather than absolute, insulin deficiency. Type II diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals the body secretes abnormally high amounts of insulin to compensate for this defect. When inadequate amounts of insulin are present to compensate for insulin resistance and adequately control glucose, a state of impaired glucose tolerance develops. Insulin secretion may further decline over time.

Type II diabetes can be due to a resistance to insulin stimulating regulatory effects on glucose and lipid metabolism in the main insulin-sensitive tissues, such as muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type II diabetes, free fatty acid levels are often elevated in obese and some non-obese patients and lipid oxidation is increased.

The Azetidinone Derivatives of this invention are GPR119 agonists. In one embodiment, the Azetidinone Derivatives are therefore useful for treating diabetes. In particular, Type II diabetes can be treated by administration of an Azetidinone Derivative, alone or in combination with one or more additional agents for treating diabetes.

Examples of other agents useful in the present methods for treating Type II diabetes include sulfonylureas, insulin sensitizers (such as PPAR agonists, DPPIV inhibitors, PTP-1B inhibitors and glucokinase activators), α-glucosidase inhibitors, insulin secretagogues, hepatic glucose output lowering compounds, and insulin.

Non-limiting examples of sulfonylurea drugs include glipizide, tolbutamide, glyburide, glimepiride, chlorpropamide, acetohexamide, gliamilide, gliclazide, glibenclamide and tolazamide. Insulin sensitizers include PPAR-γ agonists described in detail above, preferably troglitazone, rosiglitazone, pioglitazone and englitazone; biguanidines such as metformin and phenformin; DPPIV inhibitors such as sitagliptin, saxagliptin, denagliptin and vildagliptin; PTP-1B inhibitors; and glucokinase activators. α-Glucosidase inhibitors that can be useful in treating type II diabetes include miglitol, acarbose, and voglibose. Hepatic glucose output lowering drugs include Glucophage and Glucophage XR. Insulin secretagogues include sulfonylurea and non-sulfonylurea drugs such as GLP-1, exendin, GIP, secretin, glipizide, chlorpropamide, nateglinide, meglitinide, glibenclamide, repaglinide and glimepiride. Insulin includes all formulations of insulin, including long acting and short acting forms of insulin.

The Azetidinone Derivatives of the invention may be administered in combination with anti-obesity agents for the treatment of diabetes. Examples of anti-obesity agents useful in the present methods include CB1 antagonists or inverse agonists such as rimonabant, neuropeptide Y antagonists, MCR4 agonists, MCH receptor antagonists, histamine H3 receptor antagonists or inverse agonists, leptin, appetite suppressants such as sibutramine, and lipase inhibitors such as xenical.

For treating diabetes, compounds of the invention may also be administered in combination with antihypertensive agents, for example β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

Certain meglitinide drugs lower blood glucose levels by stimulating the release of insulin from the pancreas. This action is dependent upon functioning β cells in the pancreatic islets. Insulin release is glucose-dependent and diminishes at low glucose concentrations. The meglitinide drugs close ATP-dependent potassium channels in the β cell membrane by binding at characterizable sites. This potassium channel blockade depolarizes the β cell, which leads to an opening of calcium channels. The resulting increased calcium influx induces insulin secretion. Non-limiting examples of suitable meglitinide drugs useful in the present methods include repaglinide and nateglinide.

Non-limiting examples of suitable antidiabetic agents that sensitize the body to the insulin that is already present include certain biguanides and certain glitazones or thiazolidinediones. Certain suitable biguanides lower blood sugar by decreasing hepatic glucose production, decreasing intestinal absorption of glucose and improving insulin sensitivity (increasing peripheral glucose uptake and utilization). A non-limiting example of a suitable biguanide is metformin. Non-limiting examples of metformin include metformin hydrochloride (N,N-dimethylimidodicarbonimidic diamide hydrochloride, such as GLUCOPHAGE® Tablets from Bristol-Myers Squibb); metformin hydrochloride with glyburide, such as GLUCOVANCE™ Tablets from Bristol-Myers Squibb); buformin.

Non-limiting examples of antidiabetic agents that slow or block the breakdown of starches and certain sugars and are suitable for use in the compositions of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of additional antidiabetic agents include orally administrable insulin. Non-limiting examples of suitable orally administrable insulin or insulin containing compositions include AL-401 from AutoImmune, and certain compositions as disclosed in U.S. Pat. Nos. 4,579,730; 4,849, 405; 4,963,526; 5,642,868; 5,763,396; 5,824,638; 5,843,866; 6,153,632; 6,191,105; and International Publication No. WO 85/05029 (each of which is incorporated herein by reference).

Vascular Conditions

The Azetidinone Derivatives are useful for treating a vascular condition. Vascular conditions include atherosclerosis, hyperlipidaemia (including but not limited to sitosterolemia), hypertension, vascular inflammation, angina, cardiac arrhythmias and stroke, as well as vascular conditions in subjects such as post-menopausal women and women needing hormone replacement therapy. Drugs known as "blood modifiers" are useful in combination with Azetidinone Derivatives for treating vascular conditions. "Blood modifiers" as used herein refer to those agents capable of altering the number of platelets per a given volume of blood, inhibiting platelet function, including but not limited to platelet adhesion, aggregation or factor release, or reducing platelet count in patients with abnormally high levels in certain hematological malignancies to levels approximating normal levels capable of impacting negatively upon the formation of blood clots, and decreasing blood viscosity. Blood modifiers useful in the present invention include but are not limited to anti-coagulants, antithrombotic agents, fibrinogen receptor antagonists, platelet inhibitors, platelet aggregation inhibitors, lipoprotein-associated coagulation inhibitor, hemorrheologic agents, Factor VIIa inhibitors, Factor Xa inhibitors, and combinations thereof and are meant to exclude HMG CoA reductase inhibitors. For treating vascular conditions in subjects such as post-menopausal women and women needing hormone replacement therapy, an Azetidinone Derivative can be administered in combination with hormone replacement therapy, including administration of androgens, estrogens, progestins, or their pharmaceutically acceptable salts and derivatives.

"Anti-coagulant agents" are agents which inhibit the coagulation pathway by impacting negatively upon the production, deposition, cleavage and/or activation of factors essential in the formation of a blood clot. Useful anti-coagulant agents include but are not limited to argatroban; bivalirudin; dalteparin sodium (heparin); desirudin; dicumarol; lyapolate sodium; nafamostate mesylate; dimethanesulfonate; tinzaparin sodium; warfarin sodium.

"Anti-thrombotic" agents are agents which prevent the formation of a blood thrombus. A thrombus is an aggregation of blood factors, primarily platelets and fibrin with entrapment of cellular elements, frequently causing vascular obstruction at the point of its formation. Suitable examples of anti-thrombotic agents include, but are not limited to, anagrelide hydrochloride; Tinzaparin sodium as described above; cilostazol; Dalteparin sodium (as described above), danaparoid sodium; Abciximab is the (Fab fragment of the chimeric human-murine monoclonal antibody 7E3 binds to the glycoprotein (GP) IIb/IIIa ((alpha)$_{IIb}$(beta)$_3$) receptor of human platelets and inhibits platelet aggregation. Abciximab also binds to the vitronectin ((alpha)$_v$(beta)$_3$) receptor found on platelets and vessel wall endothelial and smooth muscle cells; Bivalirudin as described above; Cilostazol as described above; efegatran sulfate; dazoxiben hydrochloride; danaparoid sodium (a low molecular weight heparinoid, a mixture of the sodium salts of heparan sulfate (approximately 84%), dermatan sulfate (approximately 12%), and chondroitin sulfate (approximately 4%). It is derived from hog intestinal mucosa); lotrafiban hydrochloride; ifetroban sodium; lamifiban; fluretofen; enoxaparin sodium; napsagatran; roxifiban acetate; sibrafiban; zolimomab aritox; trifenagrel.

"Fibrinogen receptor antagonists" are those agents which inhibit the common pathway of platelet aggregation. Suitable fibrinogen receptor antagonists include but are not limited toroxifiban acetate as described above; lotrafiban hydrochloride as described above, sibrafiban as described above, monoclonal antibody 7E3 (Fab fragment of the chimeric human-murine monoclonal antibody 7E3. binds to the glycoprotein (GP) IIb/IIIa ((alpha)$_{IIb}$(beta)$_3$) receptor of human platelets and inhibits platelet aggregation); orbofiban; xemilofiban; fradafiban; tirofiban.

"Platelet inhibitors" are those agents that impair the ability of mature platelets to perform their normal physiological roles (i.e., their normal function). Platelets are normally involved in a number of physiological processes such as adhesion, for example, to cellular and non-cellular entities, aggregation, for example, for the purpose of forming a blood clot, and release of factors such as growth factors (e.g. platelet-derived growth factor (PDGF)) and platelet granular components. Suitable platelet inhibitors include, but are not limited to clopidogrel bisulfate, indomethacin; mefenamate; Ticlopidine hydrochloride; epoprostenol sodium; aspirin, Benzoic acid; epoprostenol, naproxen; buprofen; droxicam; diclofenac; sulfinpyrazone; piroxicam; dipyridamole; lexipafant; apafant Morpholine.

The term "Platelet aggregation inhibitors" as used herein refer to those compounds which reduce or halt the ability of platelets to associate physically with themselves or with other cellular and non-cellular components, thereby precluding the ability of a platelet to form a thrombus. Suitable platelet aggregation inhibitors include but are not limited to beraprost; acadesine; beraprost sodium; ciprostene calcium; itazigrel; lifarizine; oxagrelate.

The term "Hemorrheologic agent" as used herein describes those compounds which improve the flow properties of blood by decreasing its viscosity. A suitable hemorrheologic agent of the present invention is pentoxifylline.

Pentoxifylline and its metabolites (which can be useful in the present invention) improve the flow properties of blood by decreasing its viscosity. In patients with chronic peripheral arterial disease, this increases blood flow to the affected microcirculation and enhances tissue oxygenation. The precise mode of action of pentoxifylline and the sequence of events leading to clinical improvement are still to be defined. Pentoxifylline administration has been shown to produce dose-related hemorrheologic effects, lowering blood viscosity, and improving erythrocyte flexibility. Leukocyte properties of hemorrheologic importance have been modified in animal and in vitro human studies. Pentoxifylline has been shown to increase leukocyte deformability and to inhibit neutrophil adhesion and activation. Tissue oxygen levels have been shown to be significantly increased by therapeutic doses of pentoxifylline in patients with peripheral arterial disease.

Lipoprotein-associated coagulation inhibitor (LACI) is a serum glycoprotein with a molecular weight of 38,000 Kd useful as a blood modifier of the present invention It is also known as tissue factor inhibitor because it is a natural inhibitor of thromboplastin (tissue factor) induced coagulation (U.S. Pat. Nos. 5,110,730 and 5,106,833 described tissue factor and are hereby incorporated by reference their entireties). LACI is a protease inhibitor and has 3 Kunitz domains, two of which are known to interact with factors VII and Xa respectively, while the function of the third domain is unknown. Many of the structural features of LACI can be deduced because of its homology with other well studies proteases. LACI is not an enzyme, so it probably inhibits its protease target in a stoichiometric manner, namely, one of the domains of LACI inhibits one protease molecule (see U.S. Pat. No. 6,063,74 herein incorporated by reference).

The term "Factor VIIa Inhibitors" as used herein are those agents which inhibit activated Factor VIIa from acting to contribute to the formation of a fibrin clot. Suitable Factor VIIa Inhibitors include but are not limited to, 4H-31-benzoxazin-4-ones, 4H-3,1-benzoxazin-4-thiones, quinazolin-4-thiones, benzothiazin-4-ones described in U.S. Pat. No. 6,180,625, imidazolyl-boronic acid-derived peptide analogues as described in U.S. Pat. No. 5,639,739, TFPI-derived peptides described in U.S. Pat. No. 6,180,625.

Additional suitable Factor VIIa Inhibitors include but are not limited to Naphthalene-2-sulfonic acid {1-[3-(aminoiminomethyl)-benzyl]-2-oxo-pyrrolidin-3-(S)-yl}amide trifluoroacetate, dibenzofuran-2-sulfonic acid {1-[3-(aminomethyl)-benzyl]-5-oxo-pyrrolidin-3-yl}-amide, toluene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate or combinations thereof.

The term "Factor Xa inhibitors" as used herein are those agents which inhibit activated Factor X from acting to contribute to the formation of a fibrin clot. Suitable agents for use in the present invention as Factor Xa inhibitors include but are not limited to disubstituted pyrazolines, disubstituted triazolines as described in U.S. Pat. No. 6,191,159, lipoprotein-associated coagulation inhibitor (LACI) (as described above), low molecular weight heparins described as below, heparinoids described as below, benzimidazolines, benzoxazolinones, bensopiperazinones, indanones, as described in U.S. Pat. No. 6,207,697, dibasic (amidinoaryl)propanoic acid derivatives as described in *J. Med. Chem.* 37:1200-1207 (1994); bis-arlysulfonylaminobenzamide derivatives as described in U.S. Pat. No. 5,612,378; amidinophenyl-pyrrolidines, amidinophenyl-pyrrolidines, amidinophenyl-isoxazolidines as described in U.S. Pat. No. 6,057,342; amidinoindoles, amidinoazoles as described in U.S. Pat. No. 6,043,257; peptidic Factor Xa inhibitors as described below; substituted n-[(aminoiminomethyl)phenyl]propylamides, substituted n-[(aminomethyl)phenyl]propylamides as described in U.S. Pat. No. 6,080,767; or combinations thereof.

Peptidic factor Xa inhibitors such as the leech-derived, 119-amino acid protein antistasin and the soft tick derived protein TAP (tick anticoagulant peptide) accelerate clot lysis and prevented reocclusion when given as adjuncts to thrombolysis (Mellott et al. *Circulation Research* 70:1152-1160 (1992); Sitko et al., *Circulation* 85:805-815 (1992)). U.S. Pat. No. 5,385,885 issued Jan. 31, 1995 discloses smooth muscle cell proliferation inhibitory activity of both tick anticoagulant peptide and antistasin. The peptide ecotin is another selective, reversible, tight-binding inhibitor of factor Xa that exhibits protein anticoagulant activity (Seymour et al., *Biochemistry* 33:3949-3959 (1994); PCT Published Application WO 94/20535, Sep. 14, 1994). Ixodidae, argasin and ancylostomatin are other representative peptidic factor Xa inhibitors isolated from animals that feed on blood (Markwardt, *Thrombosis and Hemostasis* 72: 477-479 (1994).

These non-limiting examples of peptidic Factor Xa inhibitors that may be used in the present invention are listed below with their CAS registry Number. These include Proteinase inhibitor, antistasin. CAS Registry Number 110119-38-5; tick anticoagulant peptide, (Proteinase inhibitor, TAP) CAS Registry Number 129737-17-3; ecotin, (Proteinase inhibitor, ecotin) CAS Registry Number 87928-05; argasin, CAS Registry Number 53092-89-0; ancylostomatin, CAS Registry Number 11011-09-9; Ixodidae (as described in Markwardt, 1994).

The term "Low molecular weight heparins" as used herein refer to agents derived from heparins which reduces the incidence of bleeding when compared with standard heparin. Heparins are glycosaminoglycans whose MW ranges from 2000-10000. They may be produced from porcine intestinal mucosa and except for nadroparan, are all sodium salts. A suitable heparinoid of the present invention includes but is not limited to enoxaparin, nardroparin, dalteparin, certroparin, parnaparin, reviparin, tinzaparin and combinations thereof.

The term "Heparinoid" as used herein refers to a modified form of heparin that reduces the incidence of bleeding when compared with standard heparin. A suitable heparinoid of the present invention includes but is not limited to Danaparoid CAS Registry Number 308068-55-5, (for example, Orgaran Injection Organon)

Examples of useful estrogens and estrogen combinations include:

(a) a mixture comprising the following synthetic estrogenic substances: sodium estrone sulfate, sodium equilin sulfate, sodium 17 α-dihydroequilin sulfate, sodium 17 α-estradiol sulfate, sodium 17 β-dihydroequilin sulfate, sodium 17 α-dihydroequilenin sulfate, sodium 17 β-dihydroequilenin sulfate, sodium equilenin sulfate and sodium 17 β-estradiol sulfate;

(b) ethinyl estradiol;
(c) esterified estrogen combinations such as sodium estrone sulfate and sodium equilin sulfate;
(d) estropipate; and
(e) conjugated estrogens (17 α-dihydroequilin, 17 α-estradiol, and 17 β-dihydroequilin); available from Wyeth-Ayerst Pharmaceuticals, Philadelphia, Pa., under the tradename PREMARIN.

Progestins and estrogens may also be administered with a variety of dosages, generally from about 0.05 to about 2.0 mg progestin and about 0.001 mg to about 2 mg estrogen. In one embodiment, the dosage is from about 0.1 mg to about 1 mg progestin and about 0.01 mg to about 0.5 mg estrogen. Examples of progestin and estrogen combinations that may vary in dosage and regimen include:

(a) the combination of estradiol and norethindrone, which is available from Pharmacia & Upjohn, Peapack, N.J., under the tradename ACTIVELLA;

(b) the combination of levonorgestrel and ethinyl estradial; available for example from Wyeth-Ayerst under the tradename ALESSE;

(c) the combination of ethynodiol diacetate and ethinyl estradiol; available from G.D. Searle & Co., Chicago, Ill., under the tradename DEMULEN;

(d) the combination of desogestrel and ethinyl estradiol; available from Organon under the tradenames DESOGEN and MIRCETTE;

(e) the combination of norethindrone and ethinyl estradiol; available from Parke-Davis, Morris Plains, N.J., under the tradenames ESTROSTEP and Femhrt;

(f) the combination of norgestrel and ethinyl estradiol; available from Wyeth-Ayerst under the tradenames OVRAL and LO/OVRAL;

(g) the combination of norethindrone, ethinyl estradiol, and mestranol, available from Watson under the tradenames BREVICON and NORINYL;

(h) the combination of 17 β-estradiol and micronized norgestimate, available from Ortho-McNeil under the tradename ORTHO-PREFEST;

(i) the combination of norgestimate and ethinyl estradiol; available from Ortho-McNeil under the tradenames ORTHO CYCLEN and ORTHO TRI-CYCLEN; and (j) the combination of conjugated estrogens (sodium estrone sulfate and sodium equilin sulfate) and medroxyprogesterone acetate, available from Wyeth-Ayerst under the tradenames PREMPHASE and PREMPRO.

In general, a dosage of progestins may vary from about 0.05 mg to about 10 mg or up to about 200 mg if microsized progesterone is administered. Examples of progestins include norethindrone; norgestrel; micronized progesterone; and medroxyprogesterone acetate.

Non-limiting examples of suitable estrogen receptor modulators or antiestrogens include raloxifene hydrochloride, tamoxifen citrate and toremifene citrate.

Nonalcoholic Fatty Liver Disease

The Azetidinone Derivatives are useful for treating nonalcoholic fatty liver disease (NAFLD). NAFLD describes a spectrum of liver diseases ranging from simple fatty liver (steatosis) to nonalcoholic steatohepatitis (NASH) with progressive fibrosis and liver failure. Hyperglycemia with or without evidence of hyperlipidemia is commonly associated with NAFLD. The disease exhibits the histological features of alcohol-induced liver disease in patients who do not consume significant amounts of alcohol. All of the stages of NAFLD have in common the accumulation of fat in the liver cells.

Farrell and Larter in *Hepatology*, 243:S99-S112 (2006) describe NASH as "the lynchpin" between hepatic steatosis and cirrhosis in the spectrum of NAFLD. See also, Palekar, et al., *Liver Int.*, 26(2):151-6 (2006). In NASH, the fat accumulation of associated with varying degrees of inflammation and fibrosis. Conditions most commonly associated with NAFLD are obesity, type II diabetes and metabolic syndrome.

US Publication No. 2004/29805 describes a method for preventing or treating NAFLD by administering an agent that antagonizes the receptor to glucose-dependent insulinotropic polypeptide. Treatments for NASH include diet and exercise and/or administering probucol, clofribrate, gemfibrozil, betaine, vitamins E and/or C, metformin, toglitaxone, rosiglitazone or plogitazone and vitamin E. M. Charlton, *Clinical Gastroenterology and Hepatology*, 2(12), 1048-56 (2004); P. Portincaso et al., *Clinical Biochemistry*, 38, 203-17 (2005). US Publication No. 2004/105870A1 describes a treatment for NASH which comprises administering a formulation comprising dietary lecithin supplement, vitamin B complex or an antioxidant. US Publication Nos. 2005/0032823A1 and 2004/0102466A1 describe pyrimidine derivatives, which are selective COX-2 inhibitors, as useful in treating NASH. Other compounds for the treatment of fatty liver disease are described in US Publication No. 2005/0004115A1. The prevention or amelioration of the development of cirrhosis and heptacellular carcinoma in a mammal by administering an effective amount of a therapeutic combination comprising at least one Azetidinone Derivative or an HMG-CoA reductase inhibitor and/or at least one $H_3$ receptor antagonist/inverse agonist to said mammal.

U.S. Provisional Application 60/752,710, filed Dec. 20, 2005, and U.S. Provisional Application 60/77048, filed Mar. 29, 2006, disclose the use of cholesterol absorption inhibitors, alone or in combination with an $H_3$ receptor antagonists/inverse agonist for treating NAFLD or NASH.

The present methods for treating NAFLD, include combination therapy comprising the administration of an Azetidinone Derivative and at least one $H_3$ receptor antagonist/inverse agonist. $H_3$ receptor antagonists/inverse agonists are well-known in the art. $H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation. $H_3$ receptor antagonists/inverse agonists are known to treat: allergy, allergy-induced airway (e.g., upper airway) responses, congestion (e.g., nasal congestion), hypotension, cardiovascular disease, diseases of the GI tract, hyper and hypo motility and acidic secretion of the gastrointestinal tract, obesity, sleeping disorders (e.g., hypersomnia, somnolence, and narcolepsy), disturbances of the central nervous system, attention deficit hyperactivity disorder (ADHD), hypo and hyperactivity of the central nervous system (for example, agitation and depression), and/or other CNS disorders (such as Alzheimer's, schizophrenia, and migraine) in a patient such as a mammal. These compounds are particularly useful for treating allergy, allergy-induced airway responses and/or congestion.

$H_3$ receptor antagonist/inverse agonists useful in the combination therapies of the present invention include, but are not limited to, imidazole type, such as those described in International Publication Nos. WO 95/14007 and WO 99/24405; non-imidazole $H_3$ receptor antagonists described in U.S. Pat. No. 6,720,328; indole derivatives described in U.S. Publication No. US 2004/0019099; benzimidazole derivatives described in U.S. Publication No. US 2004/0048843A1 and U.S. Publication No. US 2004/0097483A1; and piperidine compounds described in U.S. Pat. No. 6,849,621. The above-listed patents and applications relating to $H_3$ antagonists/inverse agonists are incorporated herein by reference.

Compositions and Administration

The present invention provides pharmaceutical compositions comprising an effective amount of an Azetidinone Derivative and a pharmaceutically acceptable carrier. For preparing pharmaceutical compositions from the compounds described for use in the methods of this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The Azetidinone Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the Azetidinone Derivatives are administered orally.

In another embodiment, the Azetidinone Derivatives are administered intravenously.

In one embodiment, a pharmaceutical preparation comprising one or more Azetidinone Derivatives is in unit dosage form. In such form, the preparation is subdivided into unit doses containing appropriate quantities of the active component, e.g., an effective amount to achieve the desired purpose.

The quantity of Azetidinone Derivative in a unit dose of preparation may be varied or adjusted from about 0.1 mg to about 1000 mg. In one embodiment, the quantity is from about 1 mg to about 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the Azetidinone Derivatives will be regulated according to the judgment of the attending clinician considering such factors as age, condition and size of the patient as well as severity of the symptoms being treated. A typical recommended dosage regimen for Azetidinone Derivatives for oral administration is from about 10 mg/day to about 2000 mg/day. In one embodiment, the dosage is from about 10 mg/day to about 1000 mg/day, in two to four divided doses to provide relief from the diseases or conditions listed above.

The doses and dosage regimen of the other agents used in the combination therapies of the present invention for the treatment or prevention of a Condition can be determined by the attending clinician in view of the approved doses and dosage regimen in the package insert, taking into consideration the age, sex and condition of the patient and the severity of the disease. When administered in combination, the Azetidinone Derivative(s) and the other agent(s) for treating diseases or conditions listed above can be administered simultaneously or sequentially. This is particularly useful when the components of the combination are preferably given on different dosing schedules, e.g., one component is administered once daily and another every six hours, or when the preferred pharmaceutical compositions are different, e.g. one is preferably a tablet and one is a capsule. A kit comprising the separate dosage forms is therefore advantageous.

Non-limiting dosage ranges for other therapeutic agents useful in the present methods are set forth below. The exact dose, however, is determined by the attending clinician and is dependent on such factors as the potency of the compound administered, the age, weight, condition and response of the patient.

Generally, a total daily dosage of cholesterol biosynthesis inhibitor(s) can range from about 0.1 to about 160 mg per day. In one embodiment, the dosage is from about 0.2 to about 80 mg/day, administered in a single dose or in 2-3 divided doses.

Generally, a total daily dosage of peroxisome proliferator-activated receptor(s) activator(s) can range from about 50 to about 3000 mg per day. In one embodiment, the daily dose is from about 50 to about 2000 mg per day, administered in a single dose or in 2-4 divided doses.

Generally, a total daily dosage of IBAT inhibitor(s) can range from about 0.01 to about 1000 mg/day. In one embodiment, the dosage is from about 0.1 to about 50 mg/day, administered in a single dose or in 2-4 divided doses.

Generally, a total daily dosage of nicotinic acid can range from about 500 to about 10,000 mg/day. In one embodiment, the dosage is from about 1000 to about 8000 mg/day. In another embodiment, the dosage is from about 3000 to about 6000 mg/day, administered in a single dose or in divided doses. Generally, the total daily dosage of a NAR agonist can range from about 1 to about 100 mg/day.

Generally, a total daily dosage of ACAT inhibitor(s) can range from about 0.1 to about 1000 mg/day, administered in a single dose or in 2-4 divided doses.

Generally, a total daily dosage of CETP inhibitor(s) can range from about 0.01 to about 1000 mg/day, and preferably about 0.5 to about 20 mg/kg/day, administered in a single dose or in 2 or more divided doses.

Generally, a total daily dosage of probucol or derivatives thereof can range from about 10 to about 2000 mg/day. In one embodiment, the dosage is from about 500 to about 1500 mg/day, administered in a single dose or in 2-4 divided doses.

Generally, a total daily dosage of LDL receptor activator(s) can range from about 1 to about 1000 mg/day, administered in a single dose or in 2-4 divided doses.

Generally, a total daily dosage of fish oil or Omega 3 fatty acids can range from about 1 to about 30 grams per day, administered in a single dose or in 2-4 divided doses.

Generally, a total daily dosage of natural water soluble fibers can range from about 0.1 to about 10 grams per day, administered in a single dose or in 2-4 divided doses.

Generally, a total daily dosage of plant sterols, plant stanols and/or fatty acid esters of plant stanols can range from about 0.5 to about 20 grams per day, administered in a single dose or in 2-4 divided doses.

Generally, the total daily dosage of antidiabetic agents can range from about 1 to about 3000 mg per day. In one embodiment, the total daily dose ranges from about 50 to about 2000 mg per day, administered in a single dose or in 2-4 divided doses.

Generally, a total dosage of blood modifier agents or medications can range from 1 to 3,000 mg/day, desirably from about 1 to 1,000 mg/day and more desirably from about 1 to 200 mg/day in single or 2-4 divided doses. Treatments can be administered in a therapeutically effective amount of blood modifier to treat the specified condition, for example in a daily dose preferably ranging from about 1 to about 1000 mg per day, and more preferably about 5 to about 200 mg per day, given in a single dose or 2-4 divided doses. The exact dose, however, is determined by the attending clinician and is dependent on such factors as the potency of the compound administered, the age, weight, condition and response of the patient.

The dosage of androgen and estrogen for use in the combinations with Azetidinone Derivatives vary, and are typically from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone.

Estrogens and estrogen combinations may vary in dosage from about 0.01 mg up to 8 mg. In one embodiment, the dosage is from about 0.3 mg to about 3.0 mg.

EXAMPLES

General Methods

All solvents and reagents were used as received. Proton NMR spectra were obtained using a Varian XL-400 (400 MHz) instrument and were reported as parts per million (ppm) downfield from $Me_4Si$. LCMS analysis was performed using an Applied Biosystems API-100 mass spectrometer equipped with a Shimadzu SCL-10A LC column: Altech platinum C18, 3 um, 33 mm×7 mm ID; gradient flow: 0 minutes, 10% $CH_3CN$; 5 minutes, 95% $CH_3CN$; 7 minutes, 95% $CH_3CN$; 7.5 minutes, 10% $CH_3CN$; 9 minutes, stop. Flash column chromatography was performed using Selecto Scientiic flash silica gel, 32-63 mesh. Analytical and preparative TLC was performed using Analtech Silica gel GE plates.

Example 1

Preparation of Compound A

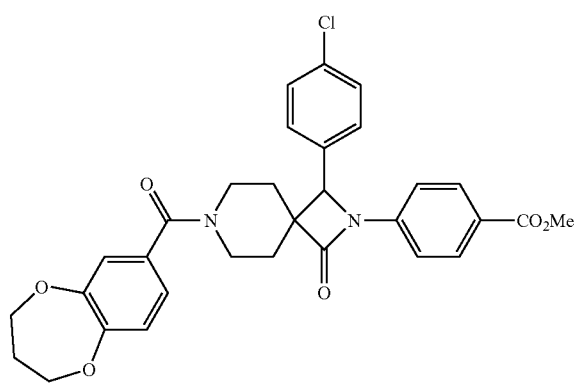

Step 1: Synthesis of Compound A-1

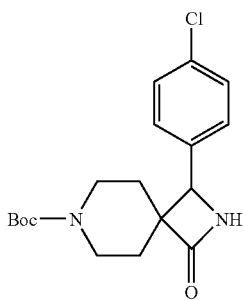

A solution of piperidine-1,4-dicarboxylic acid 1-tert-butyl ester 4-ethyl ester (9.3 g, 36 mmol) in THF (10 mL) was cooled to −78° C. and to the resulting solution was added lithium bis(trimethylsilyl)amide (1M solution in THF, 44 mL). The reaction was allowed to stir under a nitrogen atmosphere for 1 hour at −78° C. to provide Solution A.

A solution of 4-chlorobenzaldehyde (6.5 g, 46 mmol) in THF (20 mL) was cooled to −78° C. and to the resulting solution was added lithium bis(trimethylsilyl)amide (1M in THF, 50 mL). The reaction was allowed to stir under a nitrogen atmosphere for 1 hour at −78° C. to provide Solution B.

Solution B (at −78° C.) was added to solution A (at −78° C.) and the resulting reaction was allowed to stir for 1 hour at −78° C., then warmed to room temperature and allowed to stir at this temperature for about 15 hours. The reaction was then quenched using saturated aqueous NH$_4$Cl (50 mL). The resulting solution was extracted with ethyl acetate and the ethyl acetate dried over MgSO$_4$, filtered, and concentrated in vacuo to provide an amber foam, which was recrystallized from EtOAc/hexanes to provide compound A-1 as an off-white solid (7.5 g).

Step 2: Synthesis of Compound A-2

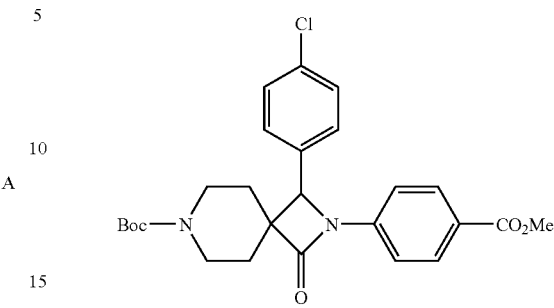

To a solution of Compound A-1 (0.60 g, 1.71 mmol) and 1,4-dioxane (4 mL) in a sealed tube, was sequentially added methyl 4-iodobenzoate (0.54 g, 2.1 mmol), copper(1) iodide (0.17 g, 0.090 mmol), N,N'-dimethylethylenediamine (0.018 mL, 0.17 mmol) and K$_3$PO$_4$ (0.55 g, 2.6 mmol). The tube was sealed and the reaction was heated to 60° C. and allowed to stir at this temperature for 24 hours. The reaction was cooled to room temperature, filtered through a pad of celite and concentrated in vacuo to provide a crude residue. The crude residue was purified using preparative TLC (eluent—20% ethyl acetate in hexanes) to provide Compound A-2 as a white solid (0.82 g).

Step 3: Synthesis of Compound A-3

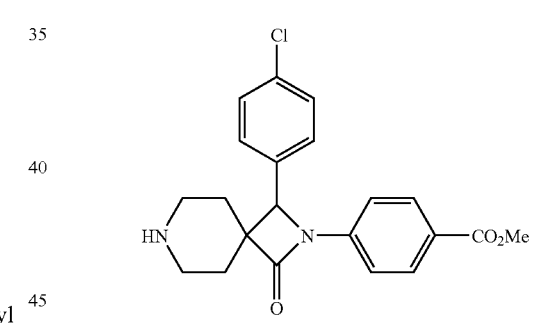

To a solution of Compound A-2 (0.13 g, 0.27 mmol), and CH$_2$Cl$_2$ (5 mL), was added TFA (0.10 mL, 1.3 mmol). The resulting reaction was allowed to stir at room temperature for 3 hours and was then concentrated in vacuo to provide Compound A-3 as a TFA salt (0.10 g).

Step 4: Synthesis of Compound A

To a solution of Compound A-3 (0.10 g, 0.26 mmol) in CH$_2$Cl$_2$ (3 mL), was added Et$_3$N (0.055 mL, 39 mmol), followed by 3,4-dihydro-2H-benzo[b][1,4]dioxepine-7-carbonyl chloride (0.66 g, 0.31 mmol). The resulting reaction was allowed to stir at room temperature for 1 hour. The reaction mixture was directly purified using preparative TLC (eluent—5% CH$_3$OH in CH$_2$Cl$_2$) to provide Compound A as a white solid (0.13 g).

Using the methods described above in Example 1, steps 1-4, employing the appropriate aryl iodides or aryl bromides in Step 27 and employing the appropriate acid chlorides in step 41 the following illustrative compounds of the present invention were made:

Chiral HPLC was performed using a Varian PrepStar system equipped with a Chiralpak OD column (Chiral Technologies).

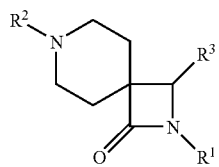
| R₁ | R₂ | R₃ | LCMS (M + H)⁺ |
|---|---|---|---|
| 4-CO₂Me-phenyl | 3,4-dihydro-2H-1,5-benzodioxepin-7-yl carbonyl | 4-Cl-phenyl | 561.3 |
| 4-CN-phenyl | 3,4-dihydro-2H-1,5-benzodioxepin-7-yl carbonyl | 4-Cl-phenyl | 528.3 |
| 4-CO₂Me-phenyl | 3,4,5-trimethoxybenzoyl | 4-Cl-phenyl | 579.3 |
| 4-F-phenyl | 4-(dimethylamino)benzoyl | 4-Cl-phenyl | 491.2 |
| 4-F-phenyl | 3,4-dihydro-2H-1,5-benzodioxepin-7-yl carbonyl | 4-Cl-phenyl | 520.2 |
| 2-F-phenyl | 3,4,5-trimethoxybenzoyl | 4-Cl-phenyl |  |

Example 2

Preparation of Compound B

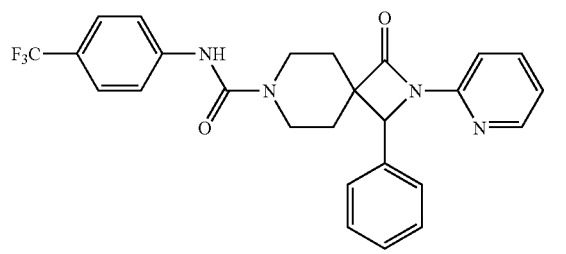
B (racemic)

Step 2: Synthesis of Compound B-1

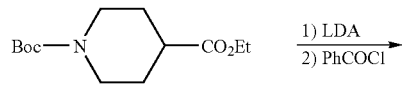

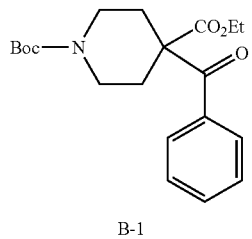
B-1

To a solution of N-Boc-piperidine ethylester (10.0 g, 38.9 mmol) in anhydrous THF (300 mL) at −10° C. was added dropwise LDA (1.5M in THF/cyclohexane, 38.9 mL, 58.35 mmol) and the mixture was allowed to stir for 1 hour. The solution was cooled to −78° C. and benzoyl chloride (11.3 mL, 97.25 mmol) was added dropwise. The reaction was allowed to stir at −78° C. for 1 hour, then was allowed to warm up to room temperature overnight. The reaction was quenched using saturated aqueous $NH_4Cl$ and extractive workup in ethyl acetate afforded a crude residue, which was purified using flash column chromatography on a silica gel (eluent—5-30% EtOAc/Hexane) to provide Compound B-1 (11.2 g, 80%).

Step 2: Synthesis of Compound B-2

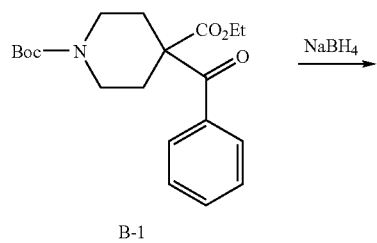

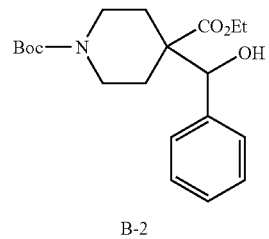
B-2

To a solution of Compound B-1 (3.61 g, 10 mmol) in EtOH (100 mL) was added $NaBH_4$ (400 mg, 10 mmol) and the reaction was allowed to stir at room temperature for 1 hour. Saturated aqueous $NH_4Cl$ was added carefully, followed by in vacuo removal of EtOH from the resulting solution. The concentrated mixture was extracted using EtOAc (3×50 mL). The ethyl acetate extractions were combined, dried over $MgSO_4$, and concentrated in vacuo to provide a crude residue which was purified using flash column chromatography on silica gel (eluent-10-30% EtOAc/Hexane) to provide Compound B-2 (2.89 g, 79%).

Step 3: Synthesis of Compound B-3

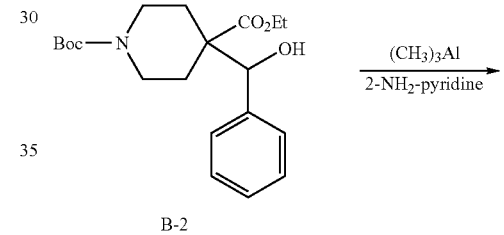
B-2

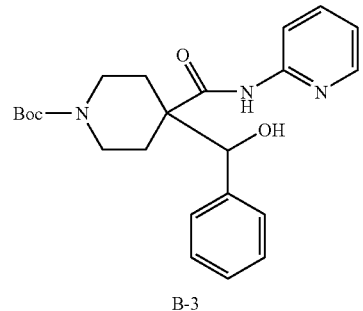
B-3

To a solution of 2-aminopyridine (3.35 g, 35 mmol) in $CH_2Cl_2$ (35 mL) was added $(CH_3)_3Al$ (2.0M in toluene, 17.8 mL, 35 mmol) dropwise and the mixture was stirred for 30 minutes. A solution of Compound B-2 (3.2 g, 8.8 mmol) in toluene (80 mL) was then added to the $(CH_3)_3Al$ solution and the mixture was heated to 60° C. and allowed to stir at this temperature for 48 hours. The reaction was then cooled to room temperature and was poured into 1N HCl (50 mL). The resulting solution was extracted using EtOAc (4×100 mL). The combined organic layers were dried over $MgSO_4$, concentrated in vacuo, and the resulting residue was purified using silica gel column to provide Compound B-3 (2.4 g, 66%).

Step 4: Synthesis of Compound B-4

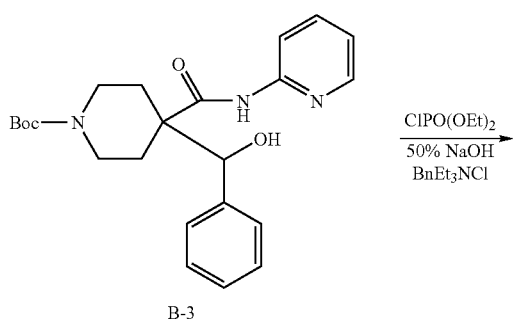

To a solution of Compound B-3 (433 mg, 1.05 mmol) in CH$_2$Cl$_2$ (10 mL) was sequentially added BnEt$_3$NCl (44 mg, 0.3 mmol), 50% aqueous NaOH (1.7 mL) and ClPO(OEt)$_2$ (168 μL, 1.26 mmol) and the resulting reaction was allowed to stir at room temperature for 16 hours. Additional 50% NaOH (1.7 mL) and ClPO(OEt)$_2$ (168 μL, 1.26 mmol) was added and the reaction was stirred for an additional 20 hours. The reaction mixture was then diluted with CH$_2$Cl$_2$ (20 mL) and washed with brine (5 mL). The organic phase was collected, dried over MgSO$_4$, and concentrated in vacuo to provide a crude residue which was purified using flash column chromatography on silica gel (eluent—10%-30% EtOAc/Hexane) to provide Compound B-4 (220 mg, 53%).

Step 5: Synthesis of Compound B

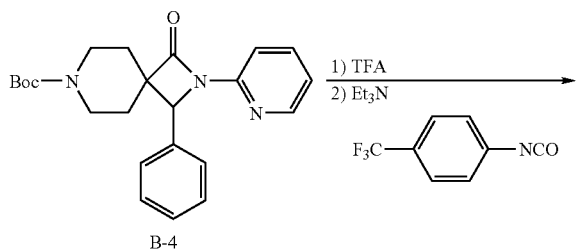

To a solution of Compound B-4 (300 mg, 0.76 mmol) in CH$_2$Cl$_2$ (4 mL) was added TFA (4 mL) and the mixture was allowed to stir at room temperature for 2 hours. The reaction mixture was then concentrated in vacuo to provide a crude residue. The crude residue was diluted with CH$_2$Cl$_2$ (4 mL), and to the resulting solution was added Et$_3$N (1 mL) followed by 1-isocyanato-4-trifluoromethyl benzene (150 μL, 0.8 mmol), and the reaction was allowed to stir at room temperature for about 15 hours. The reaction was concentrated in vacuo and the resulting residue was purified using flash column chromatography on silica gel (eluent—0-40% EtOAc/Hexane) to provide Compound B (255 mg, 70%). LCMS: ((M+1)) 481.2

Example 3

Preparation of Compound C

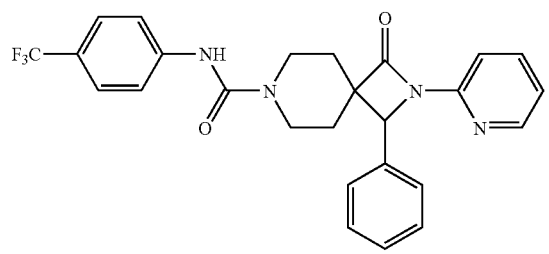

C (enantiomer A of Compound B-4)

Step 1: Chiral separation of Intermediate Compound B-4

Compound B-4 (300 mg, prepared as described above in Example 2, Step 4) was dissolved in a mixture of IPA (2 mL) and CHCl$_3$ (0.5 mL), and the resulting solution was injected into a Chiralcel OD column. The separation was performed using a flow rate of 40 mL/min with a mobile phase of 3:1 hexane/IPA. Enantiomer A was collected between 35 to 52 minutes with a peak elution at 36.5 minutes. Enantiomer B was collected between 68 to 90 minutes with a peak elution at 72 minutes. Enantiomer A was used in the next step.

Step 2: Synthesis of Compound C

Using the method described in Example 2, Step 5, and substituting Enantiomer A of Compound B-4 for the racemic Compound B-4, Compound C was prepared. LCMS: ((M+1)) 481.2

Example 4

Preparation of Compound D

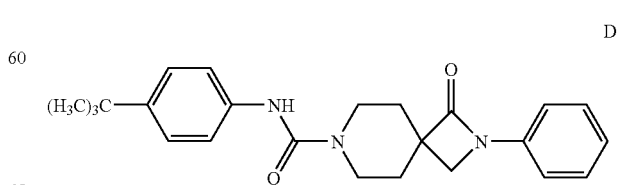

Step 1: Synthesis of Compound D-1

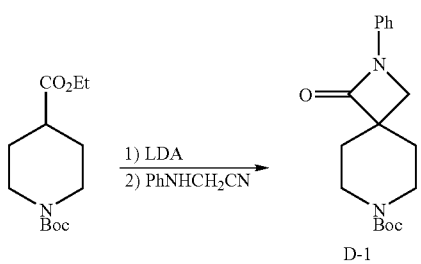

To Boc-piperidine ester (5.14 g, 0.02 mol) in THF at −20° C. was added LDA (16.7 m, 0.025 mol, 1.5 M in THF/cyclohexane) and the mixture was stirred for 1 hour. A solution of PhNHCH$_2$CN (1.32 g, 0.01 mol) in THF (5 mL) was then added dropwise. The solution was allowed to warm to 23° C. and stirred overnight. The reaction was quenched with water (50 mL) and extractive workup afforded a crude product which was purified on silica with 20-40% EtOAc/hexane (1.04 g, 34%).

Step 2: Synthesis of Compound D

Using the method described in Example 21 Step 5, and substituting Compound D-1 for Compound B-4, Compound D was prepared. LCMS: ((M+1)) 392.1

Using the methods described in Examples 2, 3 and 4, the following illustrative compounds of the present invention were prepared:

| Structure | LCMS: ((M + 1)) |
|---|---|
| racemic | 468.1 |
| racemic | 481.1 |
| 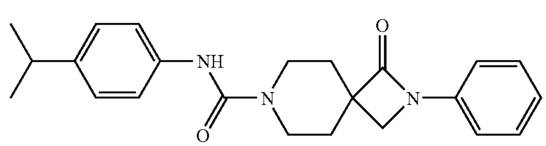 | 378.1 |
| enantiomer B | 468.1 |

-continued
| Structure | LCMS: ((M + 1)) |
|---|---|
| 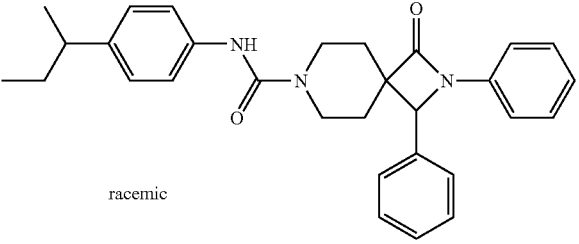 racemic | 468.1 |
| 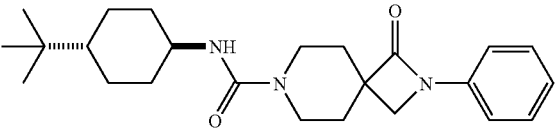 | 398.1 |
| 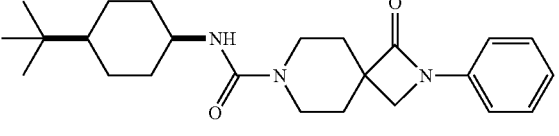 | 398.1 |
| 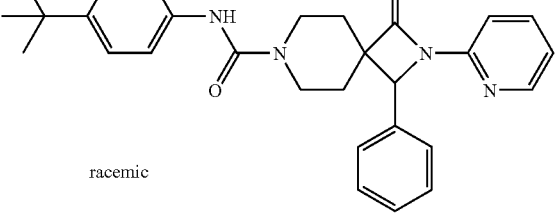 racemic | 469.1 |
| 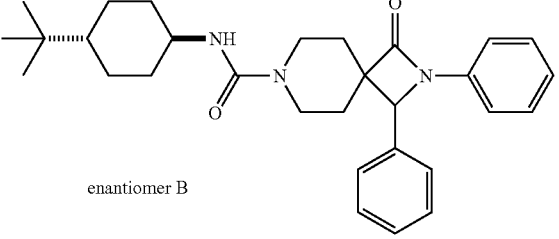 enantiomer B | 474.1 |
| 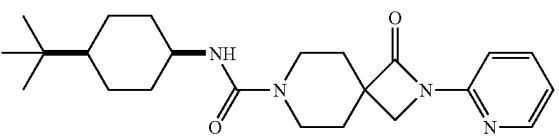 racemic | 474.1 |
| 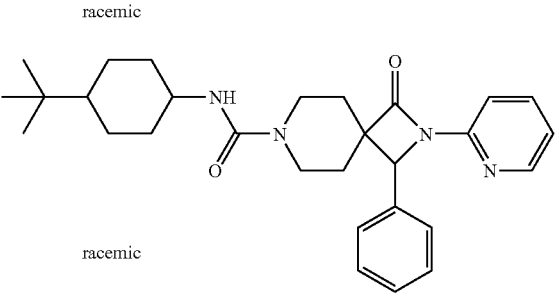 racemic | 475.1 |

-continued

| Structure | LCMS: ((M + 1)) |
|---|---|
| 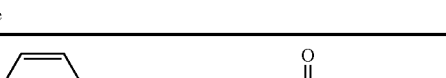 enantiomer B | 481.2 |

Example 5

Preparation of Compound E

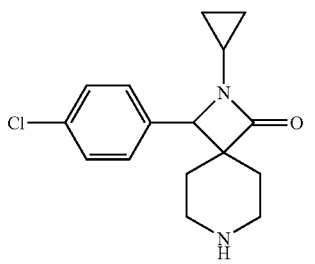

Step 1: Synthesis of Compound E-1

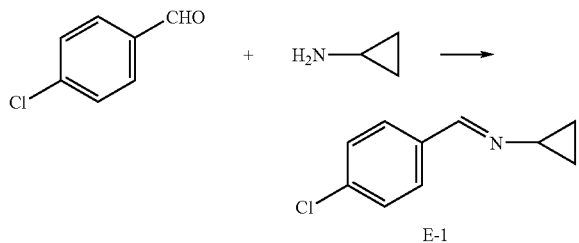

To a solution of 4-chlorobenzaldehyde (14.0 g) and cyclopropylamine (5.7 g) in anhydrous toluene (50 mL), was added molecular sieves. The resulting reaction was allowed to stir at room temperature for 48 hours. The reaction mixture was then filtered, and the filtrate concentrated in vacuo at 60° C. to provide Compound E-1 as a crystalline solid (15.98 g).

Step 2: Synthesis of Compound E-2

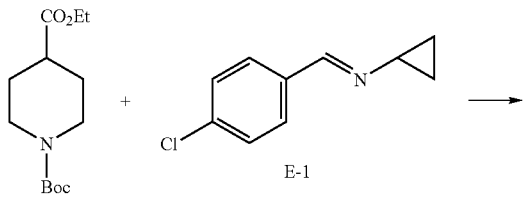

-continued

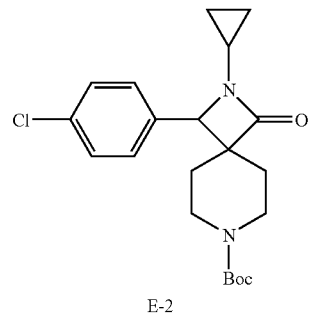

E-2

A solution of diisopropylamine (6.0 mL) in THF (10 mL) was cooled to −10° C. and n-butyllithium (2.5 M, 16.6 mL) was added dropwise. The resulting reaction was allowed to stir at −10° C. for 1 hour, then the reaction mixture was further cooled to −78° C. To the resulting solution was added dropwise a solution of ethyl 1-tert-butoxycarbonylpiperidine-4-carboxylate (10 g) in anhydrous THF (20 mL), and the resulting reaction was allowed to stir at −78° C. for 1.5 hours, after which time a solution of Compound E-1 (6.69 g) in THF (40 mL) was added and the reaction was allowed stir for 1 hour at −78° C. The reaction mixture was then warmed to room temperature and allowed to stir at this temperature for about 15 hours. The reaction was then quenched saturated aqueous NH₄Cl and the resulting mixture was extracted with EtOAc. The EtOAc solution was partitioned with 1N HCl, then brine. The EtOAc was then collected, dried over MgSO₄, filtered, and concentrated in vacuo to provide an amber oil (13.83 g). The amber oil was absorbed on Purasil 60A 230-400 mesh (~30 mL), and the Purasil was then placed in a syringe cartridge and eluted onto a Redi Sep Normal Phase Disposable Column (330 g, ISCO). The column was then eluted with hexane (one column volume), followed by a hexane/EtOAc gradient (0% to 55% EtOAc) at a flow rate of 65 mL/min. The desired fractions were combined and concentrated in vacuo to provide Compound E-2 (3.49 g).

Step 3: Synthesis of Compound E

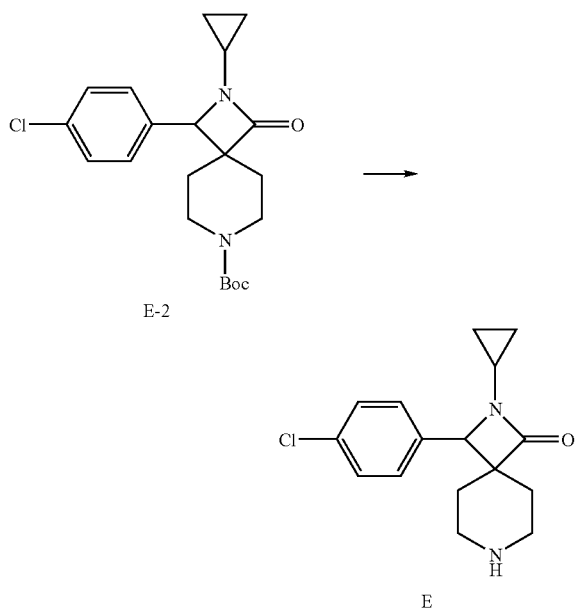

To a solution of compound E-2 (0.58 g) in dichloromethane (2 mL) was added TFA (2 mL) and resulting reaction was allowed to stir at room temperature for 1 hour. The reaction mixture was then concentrated in vacuo, the resulting residue was dissolved in dichloromethane (15 mL) and the resulting solution was concentrated in vacuo. This solution formation/concentration process using dichloromethane was repeated two more time to provide a white residue. This white residue was partitioned between dichloromethane and aqueous K₂CO₃ solution (2.5 N). The organic layer was collected, dried over MgSO4 and concentrated in vacuo to provide compound E as a white foam (0.48 g). LCMS: (M+1) 277 at 1.52 minutes.

Using the method described in Example 5 and employing the appropriate starting materials and reagents, the following illustrative compounds of the present invention were made:

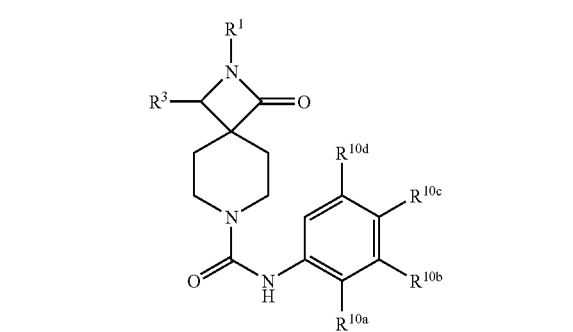

| $R^3$ | $R^1$ | $R^{10a}$ | $R^{10b}$ | $R^{10c}$ | $R^{10d}$ | LCMS ((M+1)) |
|---|---|---|---|---|---|---|
| 4-ClC₆H₄ | CH₃ | H | F | F | H | 420 |
| 4-ClC₆H₄ | CH₃ | H | F | H | F | 420 |
| 4-ClC₆H₄ | c-Pr | H | F | H | H | 428 |
| 4-ClC₆H₄ | c-Pr | H | CN | H | H | 435 |
| 4-ClC₆H₄ | c-Pr | H | Cl | H | H | 444 |

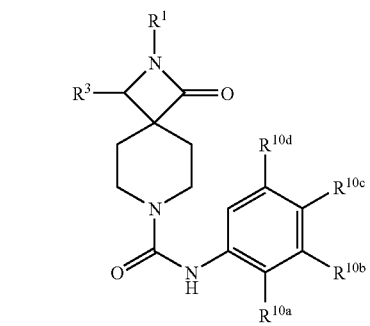

| $R^3$ | $R^1$ | $R^{10a}$ | $R^{10b}$ | $R^{10c}$ | $R^{10d}$ | LCMS ((M+1)) |
|---|---|---|---|---|---|---|
| 4-ClC₆H₄ | c-Pr | H | F | H | F | 446 |
| 4-ClC₆H₄ | 4-FC₆H₄ | H | F | F | H | 499 |
| 4-ClC₆H₄ | 4-FC₆H₄ | H | F | H | F | 499 |
| 4-ClC₆H₄ | 4-FC₆H₄ | H | H | F | H | 481 |
| 4-ClC₆H₄ | 4-FC₆H₄ | H | H | CO₂CH₃ | H | 521 |
| 4-ClC₆H₄ | C₆H₅ | H | CH₃ | H | H | 460 |
| 4-ClC₆H₄ | C₆H₅ | H | H | i-Pr | H | 488 |
| 4-ClC₆H₄ | C₆H₅ | H | CF₃ | H | H | 514 |

(A)

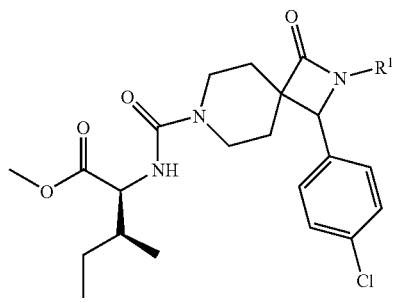

(B)

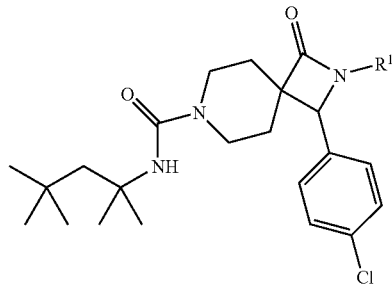

| Structure | $R^1$ | LCMS ((M+1)) |
|---|---|---|
| A | CH₃ | 436 |
| A | cyclopropyl | 461 |
| B | 4-FC₆H₄ | 501 |

Using the method described in Example 5 and employing the appropriate starting materials and reagents, the following additional illustrative compounds of the present invention were made:
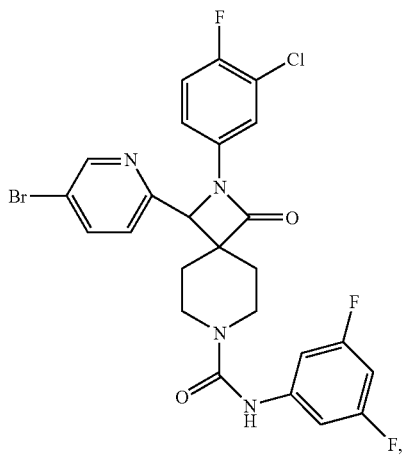
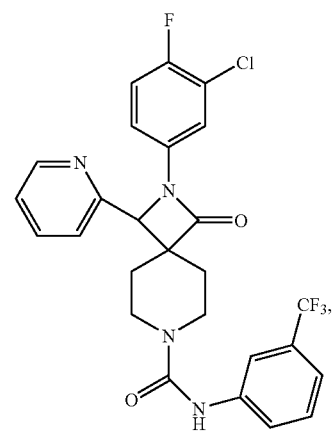
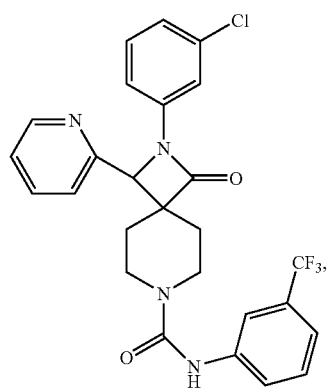
-continued
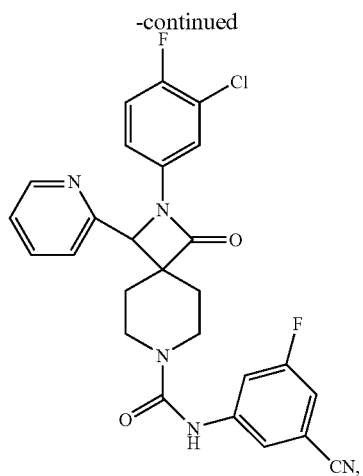
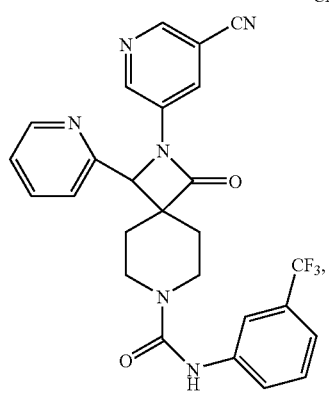
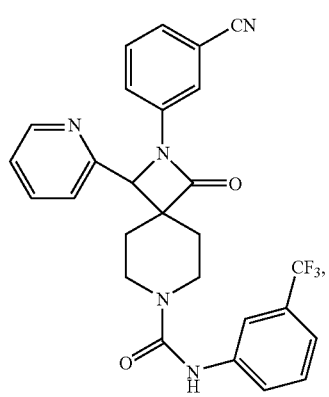
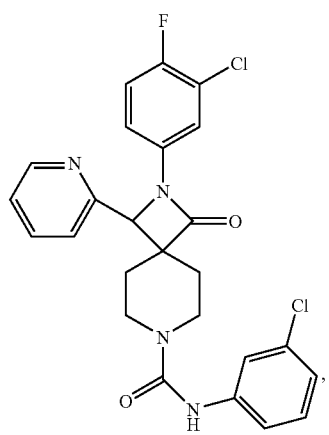

167 -continued
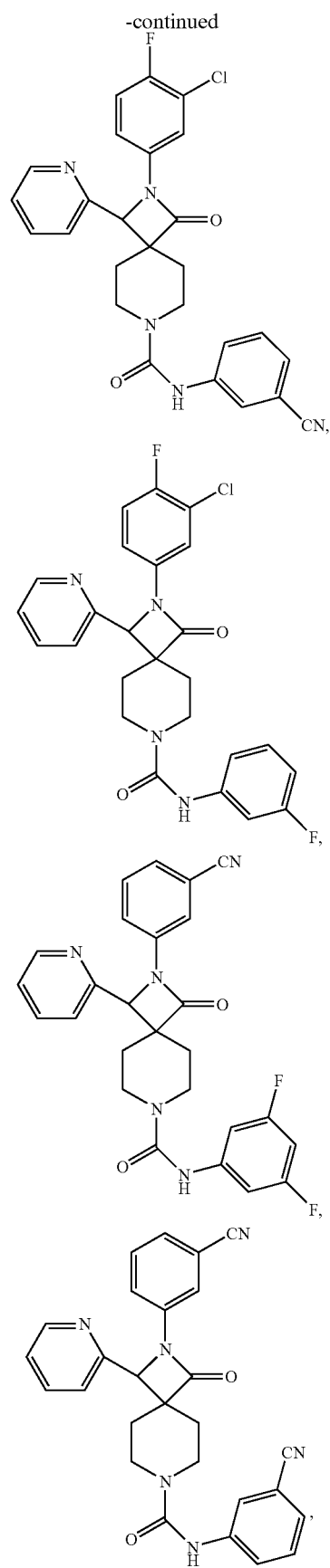
168 -continued
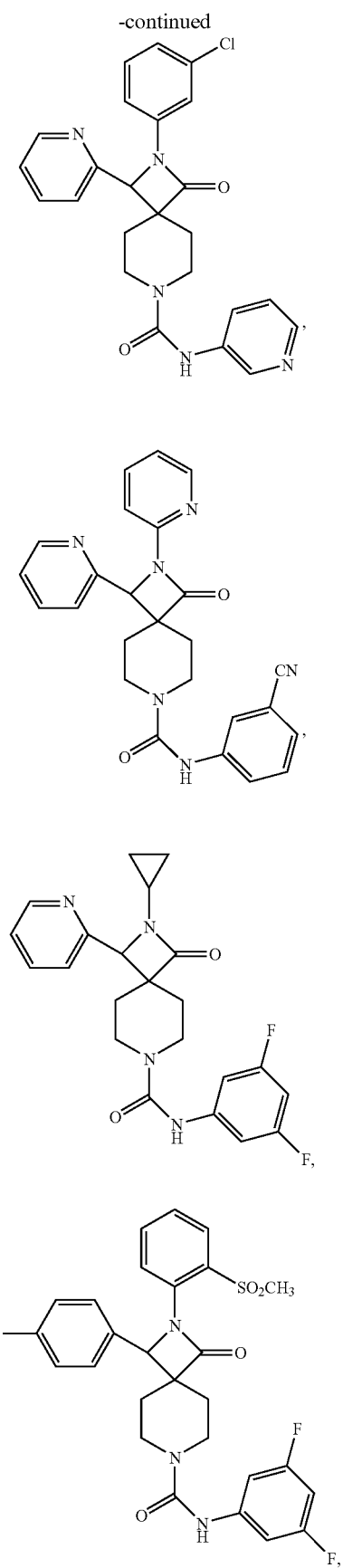

-continued

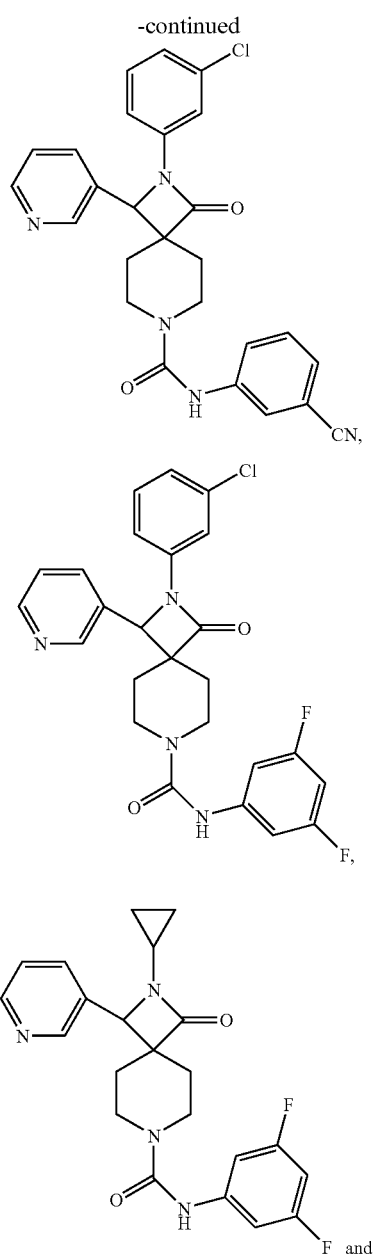

Example 6

Preparation of Compound F

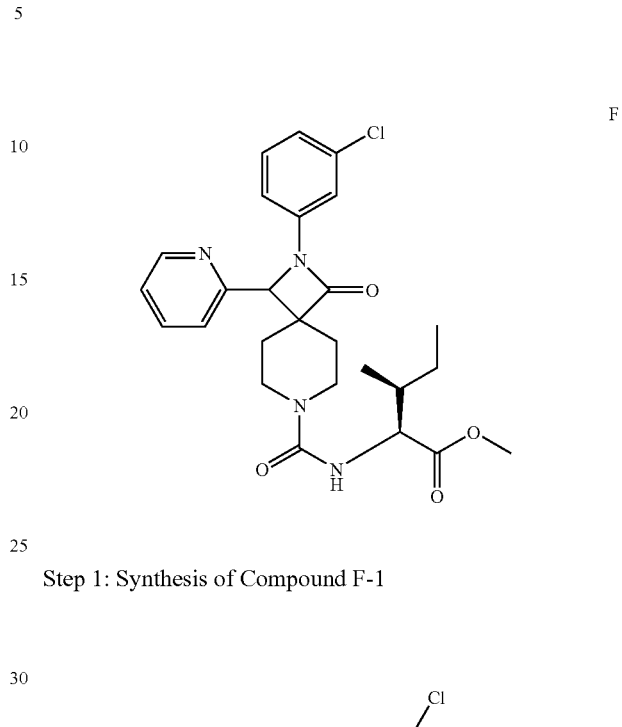

Step 1: Synthesis of Compound F-1

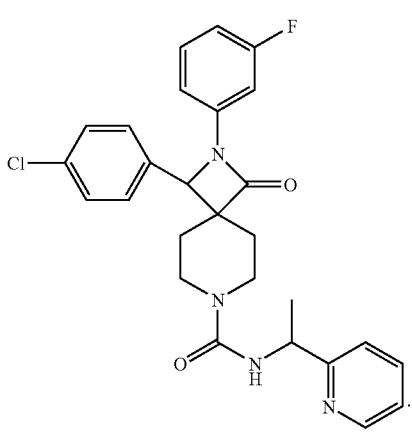

To a solution of 2-pyridinecarboxaldehyde (5.35 g) in isopropanol (75 mL), was added 3-chloroaniline (6.37 g) and the resulting reaction was heated to 30° C. and allowed to stir at this temperature for 44 hours. The reaction mixture was concentrated in vacuo to provide Compound F-1 as a yellow oil (10.73 g). NMR (CDCl$_3$): 7.14, d, 1H; 7.28, m, 2H; 7.33, t, 1H; 7.38, m, 1H; 7.82, t, 1H; 8.17, d, 1H; 8.56, s, 1H; 8.72, d, 1H.

Step 2: Synthesis of Compound F-2

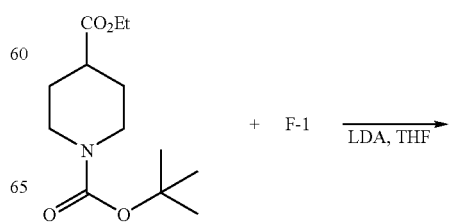

-continued

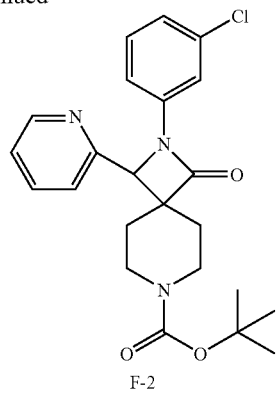

F-2

A solution of diisopropylamine (6 mL) in dry THF (10 mL) was cooled to −10° C. and n-butyllithium (2.5 M, 16.6 mL) was added dropwise. After 1 hour, the reaction mixture was cooled to −78° C., and a solution of ethyl 1-tert-butoxycarbonylpiperidine-4-carboxylate (10.0 g) in dry THF (20 mL) was added. The resulting reaction was allowed to stir for 1.5 hours at −78° C., then a solution of Compound F-1 (8.01 g) in THF (40 mL) was added. After stirring for 1 hour at −78° C., the reaction was warmed to room temperature and allowed to stir at this temperature for 20 hours. The reaction mixture was then quenches using saturated aqueous NH₄Cl and the resulting solution was extracted using EtOAc. The EtOAc solution was then back-extracted with brine and the EtOAc was then dried (MgSO₄) and concentrated in vacuo to provide an amber oil (10.87 g). The amber oil was absorbed on Purasil 60A, 230-400 mesh (30 mL) and placed in a cartridge. The cartridge was elute onto a Redi Sep Normal Phase Disposable Flash column (ISCO, 330 g) with hexane, followed by hexane:EtOAc 95:5; followed by hexane:EtOAc 60:40 to provide Compound F-2 as an off white foam (9.43 g), LCMS, (M+1) 428. NMR (DMSO-$d_6$): 1.40, m, 1H; 1.34, s, 9H; 1.47, m, 1H; 2.00, m, 2H; 2.88, m, 1H; 3.40, m, 1H; 3.53, m, 2H; 5.23, s, 1H; 7.01, d, 1H; 7.10, d, 1H; 7.28, d, 2H; 7.35, m, 1H; 7.45, t, 1H; 8.57, d, 1H.

Step 3: Synthesis of Compound F-3

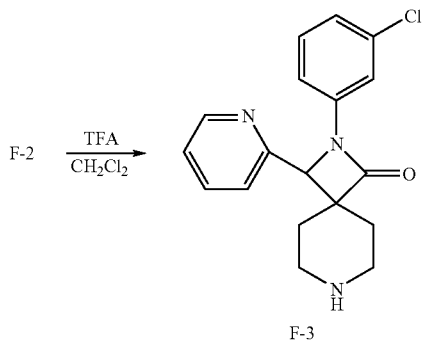

A solution of Compound F-3 (0.50 g) in dry CH₂Cl₂ (3 mL) was treated with TFA (3 mL) and the resulting reaction was allowed to stir at room temperature for 45 minutes under a nitrogen atmosphere. The reaction was concentrated in vacuo to provide a crude residue which was diluted with CH₂Cl₂ (40 mL) and concentrated in vacuo. This CH₂Cl₂ dilution/concentration procedure was repeated two more times to provide a viscous oil (5.76 g). The viscous oil was then partitioned between CH₂Cl₂ and 1N NaOH and the organic phase was collected, dried over MgSO₄, and concentrated in vacuo to provide Compound F-3 (0.41 g) as a viscous oil, LCMS (M+1) 328. NMR (DMSO-$d_6$): 1.33, m, 1H; 1.72, m, 1H; 2.23, m, 1H; 2.32, m, 1H; 2.67, m, 1H; 2.99, m, 1H; 3.25, t, 2H; 5.31, s, 1H; 7.01, d, 1H; 7.13, d, 1H; 7.28, m, 1H; 7.32, t, 1H; 7.38, dd, 1H; 7.85, t, 1H; 8.46, m, 1H; 8.59, d, 1H.

Step 4: Synthesis of Compound F

To a solution of Compound F-3 (0.043 g) in CH₃CN (2 mL), was added (2S,3S)-2-isocyanato-3-methylvaleric acid, methyl ester (65 μl), and the resulting reaction was allowed to stir at room temperature for 66 hours. PS-Trisamine (3.11 mmol/g, Argonaut) (250 mg) and CH₃ON (2 mL) were then added to the reaction and the resulting mixture was shaken for 3 hours. The reaction mixture was filtered, the resin washed with CH₂Cl₂ (2 mL), and the filtrates combined. The combined filtrates were then concentrated in vacuo and the crude residue provided was purified using preparative TLC (eluent—CH₂Cl₂:MeOH (95:5)) to provide Compound F as a white residue (0.0621 g), LCMS (M+1) 499. NMR (DMSO-$d_6$): 0.77, m, 6H; 1.12, m, 2H; 1.43, m, 2H; 1.73, m, 1H; 1.93, m, 2H; 2.90, m, 1H; 3.40, m, 1H; 3.55, m, 2H; 3.56, s, 3H; 3.89, q, 1H; 5.23, s, 1H; 6.51, d, 1H; 7.01, d, 1H; 7.10, d, 1H; 7.29, d, 2H; 7.33, m, 1H; 7.82, t, 1H; 8.58, s, 1H.

Using the method described in Example 6 and employing the appropriate starting materials and reagents, the following illustrative compounds of the present invention were made:

| $R^3$ | $R^1$ | $R^{10a}$ | $R^{10b}$ | $R^{10c}$ | $R^{10d}$ | LCMS ((M + 1)) |
|---|---|---|---|---|---|---|
| 4-ClC₆H₄ | CH₃ | H | F | F | H | 420 |
| 4-ClC₆H₄ | CH₃ | H | F | H | F | 420 |
| 4-ClC₆H₄ | c-Pr | H | F | H | H | 428 |
| 4-ClC₆H₄ | c-Pr | H | CN | H | H | 435 |
| 4-ClC₆H₄ | c-Pr | H | Cl | H | H | 444 |
| 4-ClC₆H₄ | c-Pr | H | F | H | F | 446 |
| 4-ClC₆H₄ | 4-FC₆H₄ | H | F | F | H | 499 |
| 4-ClC₆H₄ | 4-FC₆H₄ | H | F | H | F | 499 |
| 4-ClC₆H₄ | 4-FC₆H₄ | H | H | F | H | 481 |
| 4-ClC₆H₄ | 4-FC₆H₄ | H | H | CO₂CH₃ | H | 521 |
| 4-ClC₆H₄ | C₆H₅ | H | CH₃ | H | H | 460 |
| 4-ClC₆H₄ | C₆H₅ | H | H | i-Pr | H | 488 |
| 4-ClC₆H₄ | C₆H₅ | H | CF₃ | H | H | 514 |

Using the method described in Example 6 and employing the appropriate starting materials and reagents, the following additional illustrative compounds of the present invention were made.

173
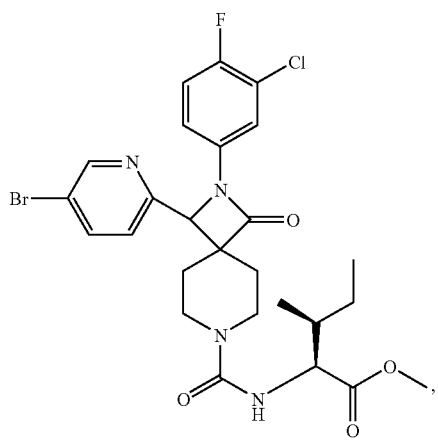
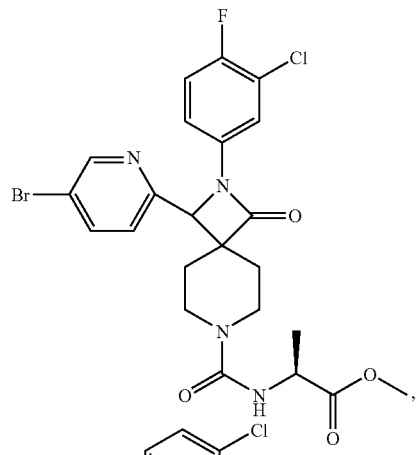
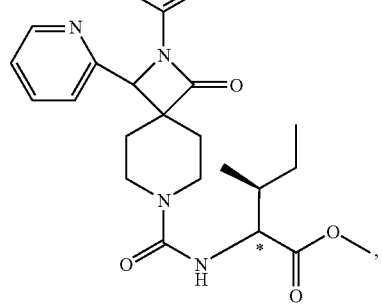
isomer 1
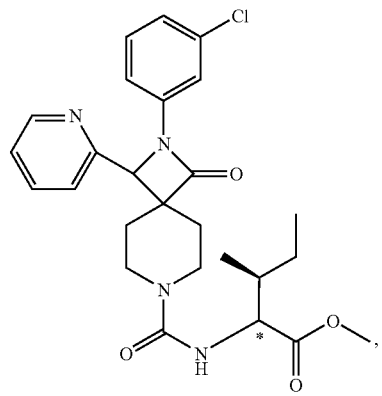
isomer 2
174
-continued
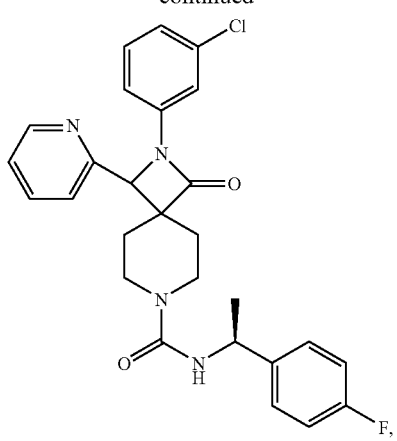
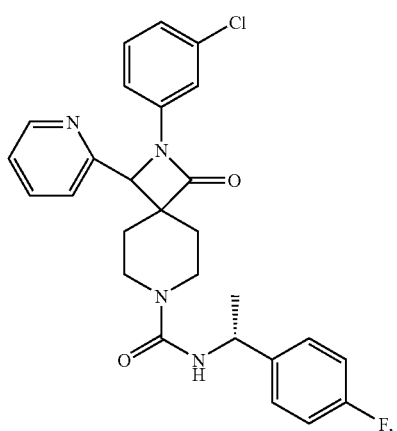
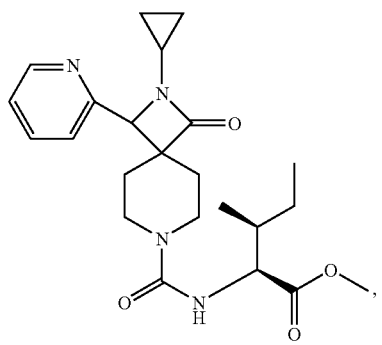
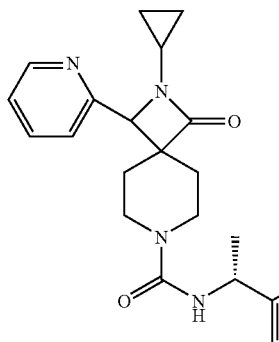

-continued
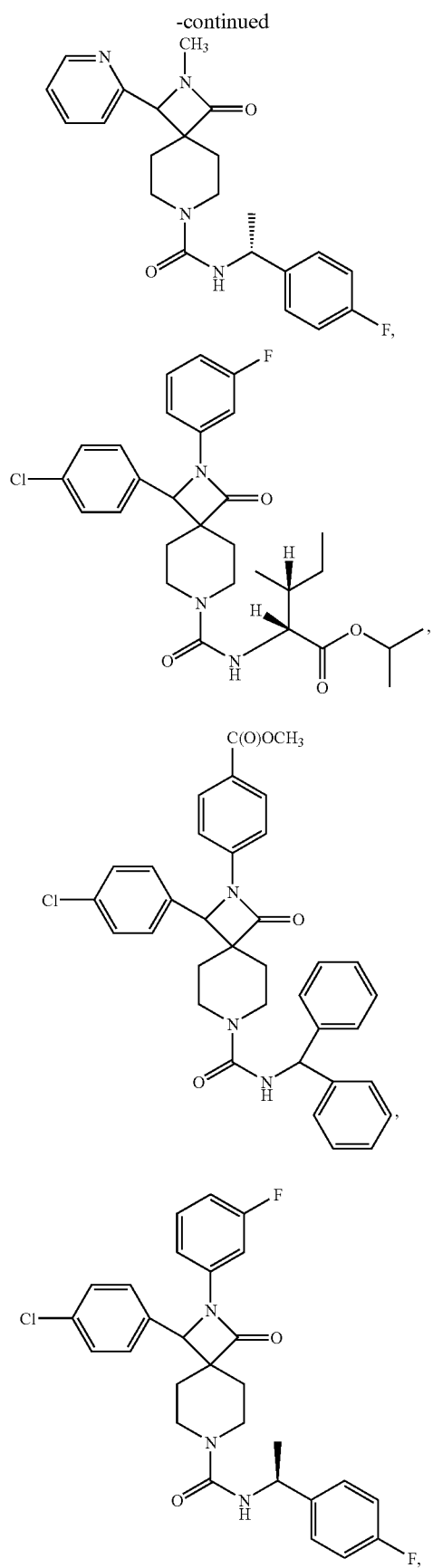
-continued
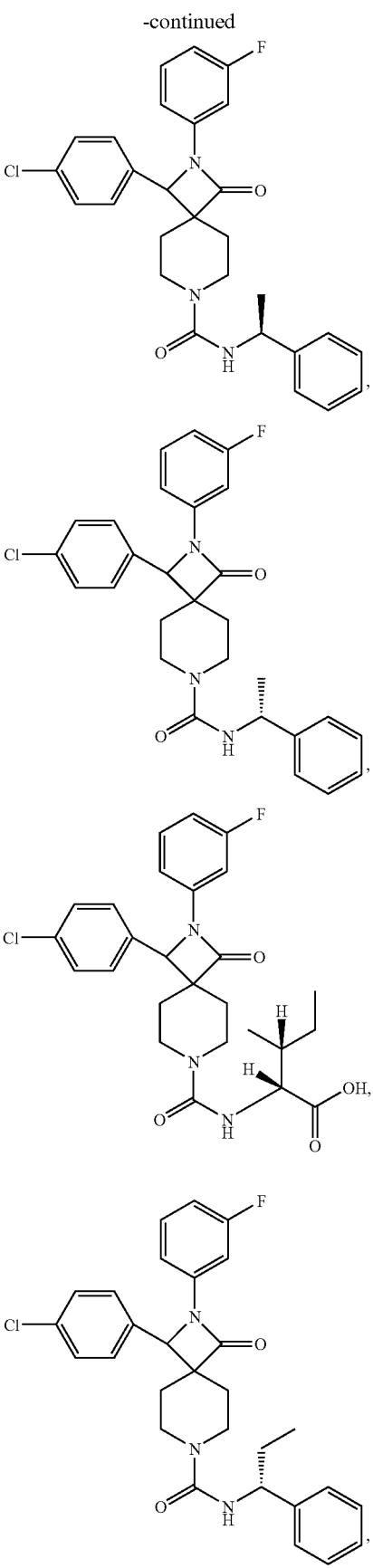

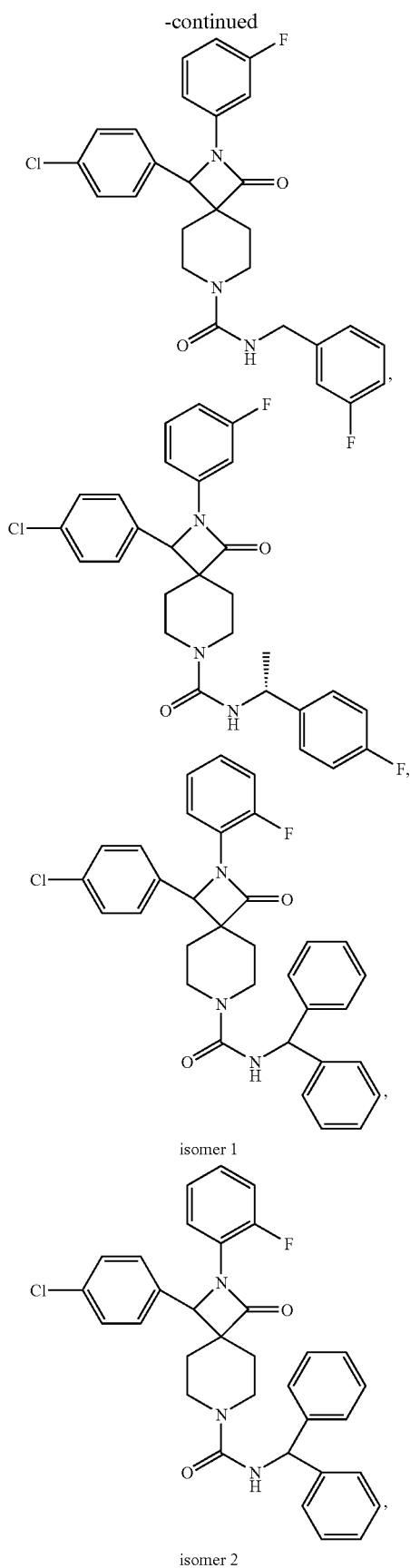
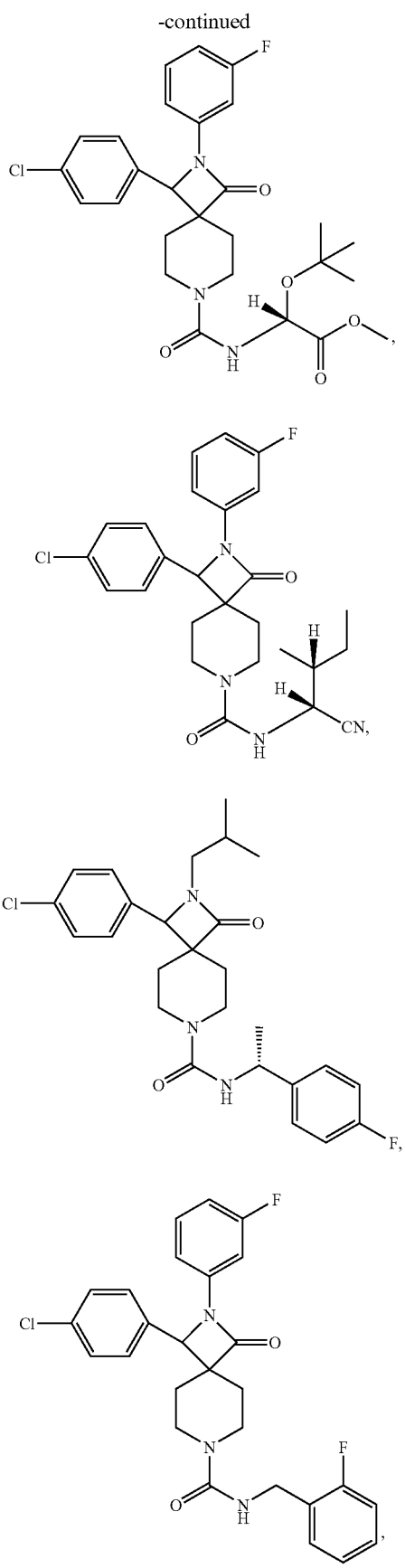

-continued
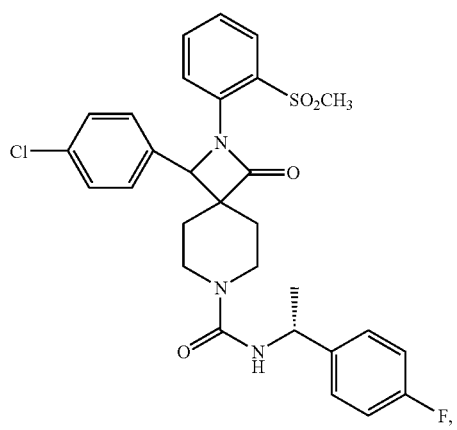
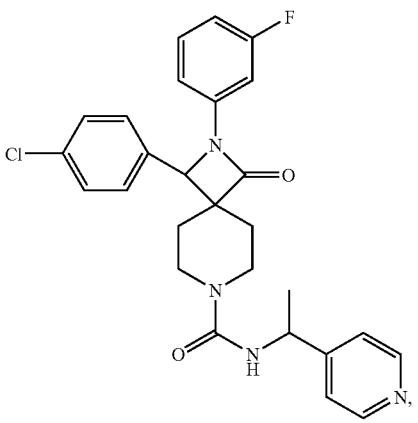
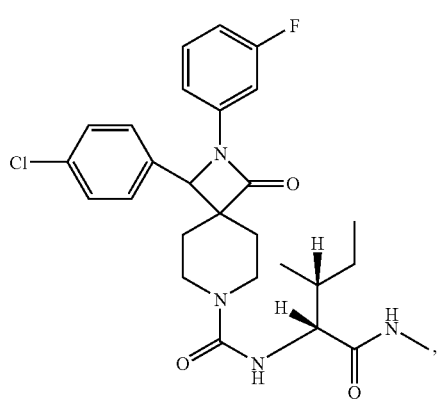
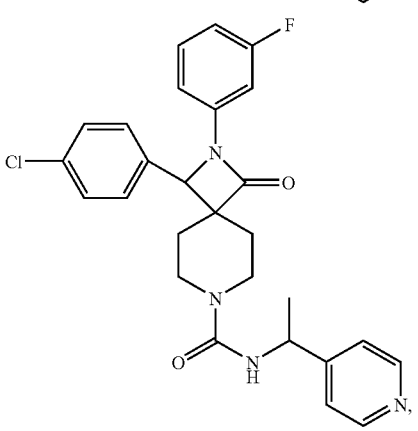
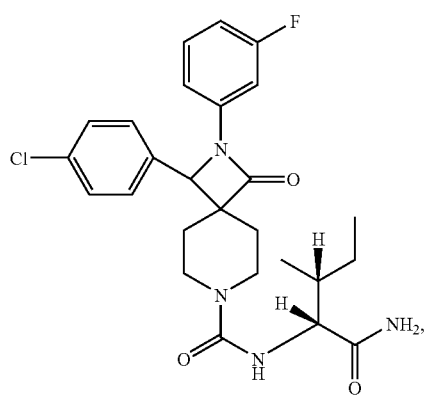
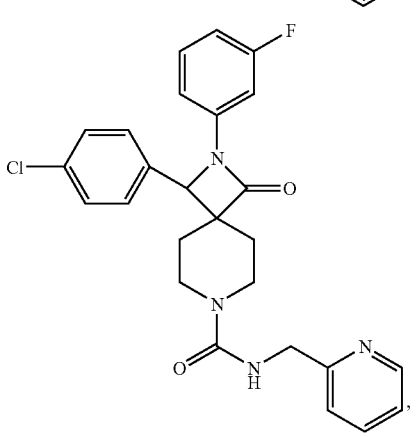
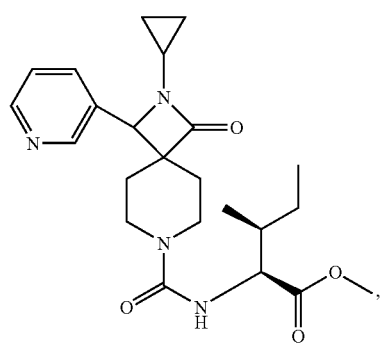
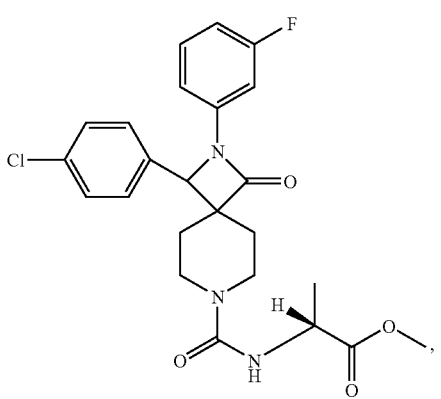

-continued
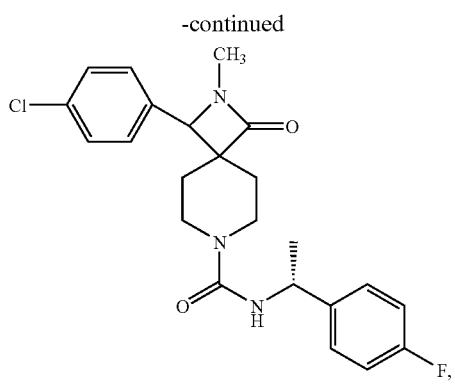
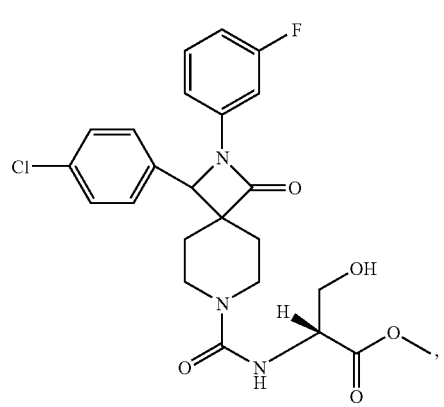
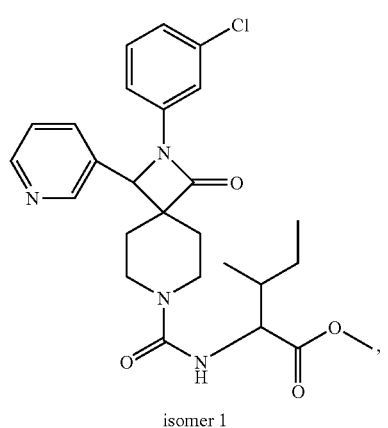
isomer 1
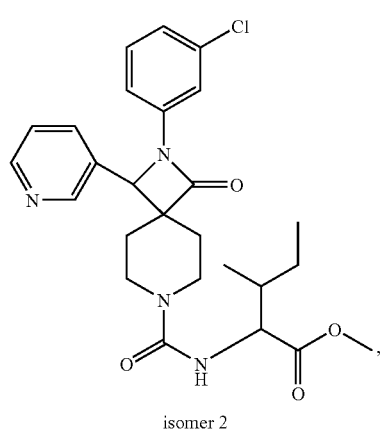
isomer 2
-continued
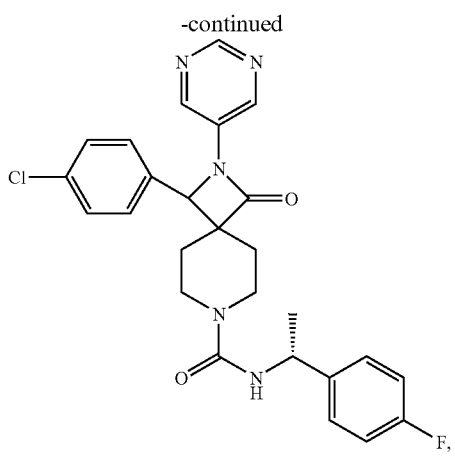
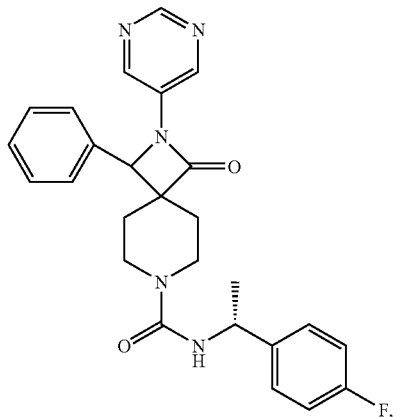
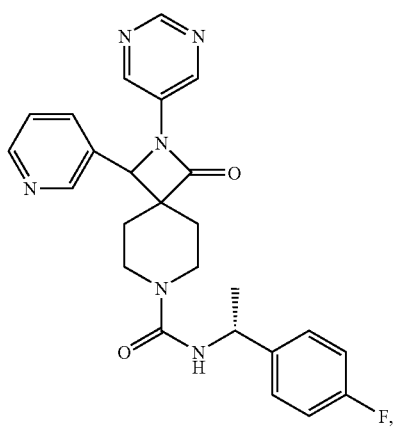
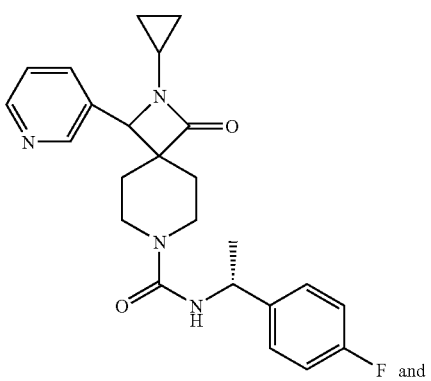
and -continued

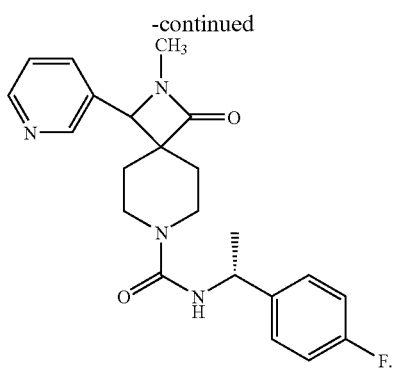

Example 7

Preparation of Compound G

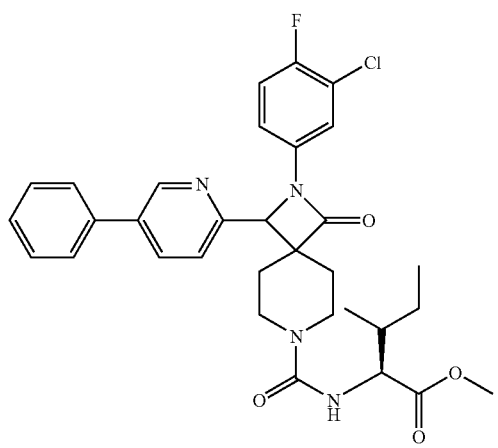

G

Step 1: Synthesis of Compound G-2

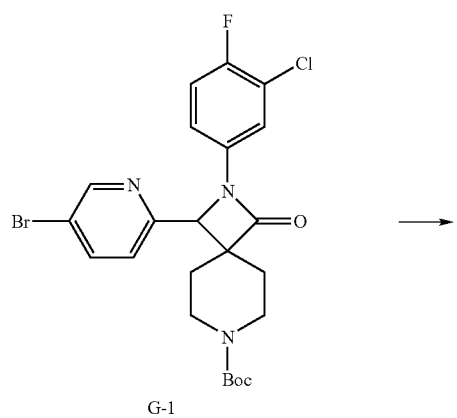

G-1

-continued

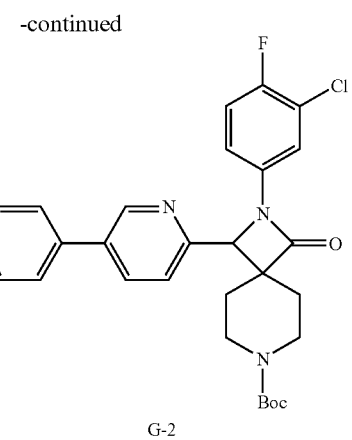

G-2

In each of 8 microwave tubes was placed compound G-1 (110 mg in each tube, prepared in a similar manner as that described in Example 6, Step 1 and 2), phenyl boronic acid (60 mg), absolute ethanol (4 mL), tetrakis(triphenylphosphine)palladium(0) (60 mg) and 1N $K_2CO_3$ (0.9 mL), and the tubes were then sealed. The tubes were sealed and the reactions were each microwaved for 12 minutes, during which time the reaction temperature reached 150° C. Each of the resulting reaction mixtures were then separately purified using sixteen Si Carbonate columns (2 g) and eluting each column with dichloromethane (12 mL). The column outputs were collected, combined, and concentrated in vacuo to provide a yellow residue which was purified using preparative TLC on 20 separate silica gel plates (2000 μm, each plate was eluted twice with 100% dichloromethane) to provide compound G-2 as a light yellow solid (0.56 g), LCMS: (M+1) 522 at 5.40 minutes.

Step 2: Synthesis of Compound G-3

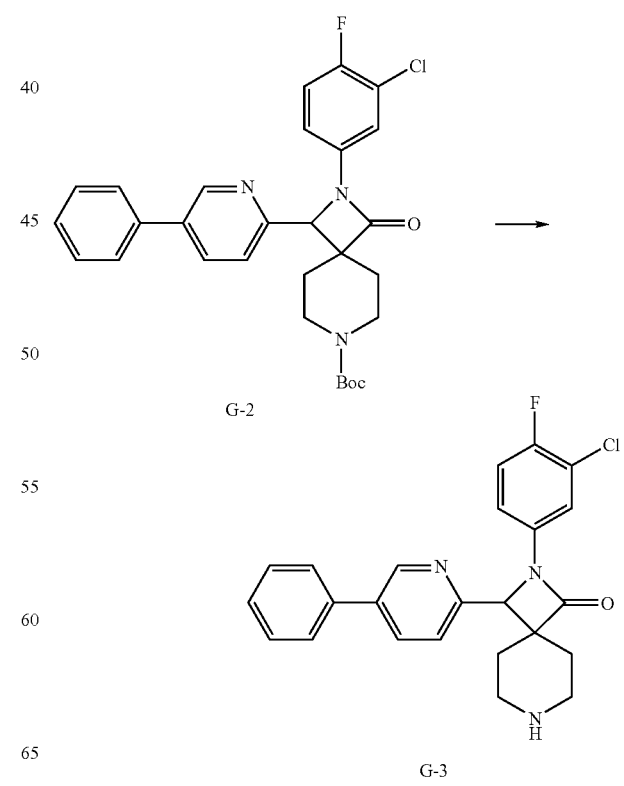

To a solution of compound G-2 (0.25 g) in dichloromethane (3 mL) was added TFA (3 mL) and the resulting reaction was allowed to stir at room temperature for 2 hours. The reaction mixture was then concentrated in vacuo and the residue obtained was partitioned between dichloromethane and aqueous $K_2CO_3$ solution (2.5 N). The organic layer was collected, dried over $MgSO_4$, and concentrated in vacuo to provide a light tan foam. This light tan foam was purified using preparative TLC on four silica gel plates (1000 μm, eluted with dichloromethane/methanol 4:1) to provide compound G-3 as a white foam (0.105 g), LCMS: (M+1) 422 at 3.49 minutes.

Step 3: Synthesis of Compound G

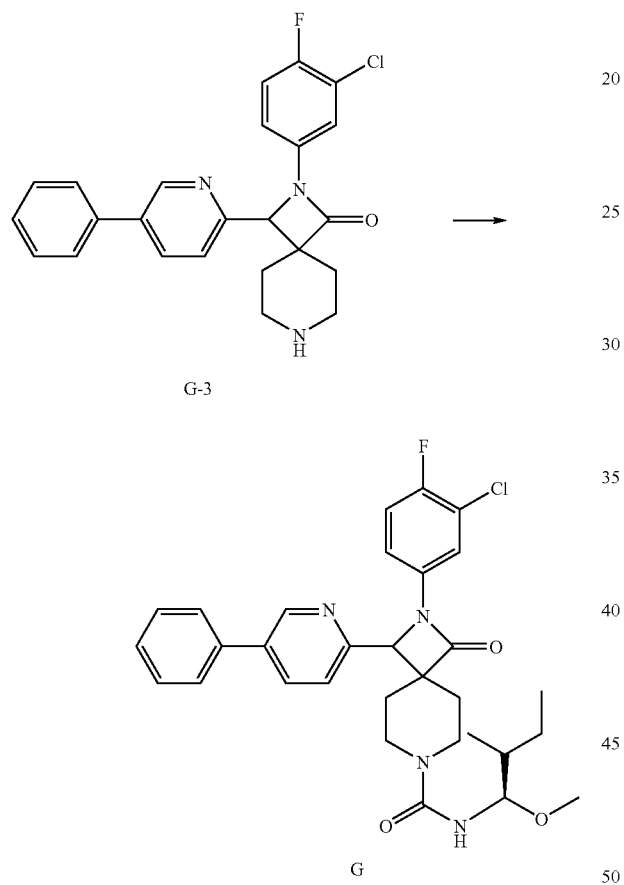

A solution of G-3 (43 mg) and (2S,3S)-2-isocyanato-3-methylvaleric acid, methyl ester (30 mg) in acetonitrile (2 mL) was allowed to stir at room temperature for 20 hours. The reaction mixture was then directly purified using preparative TLC on two silica gel plates (1000 μm plates; dichloromethane:methanol 19:1 as eluent) to provide a white foam residue (51 mg). The residue was purified using preparative LC using a C18 column and the following solvent gradient at 30 mL/minute: solvent A: water/0.1% formic acid and solvent B: acetonitrile/0.1% formic acid (0-1 min 10% B; 1-11 min 10% B to 100% B; 11-17 min 100% B; and 17-23 min 10% B) to provide compound G as a white foam (27 mg), LCMS: (M+1) 593 at 4.97 minutes.

Using the method described in Example 7 and employing the appropriate starting materials and reagents, the following additional illustrative compounds of the present invention were made:

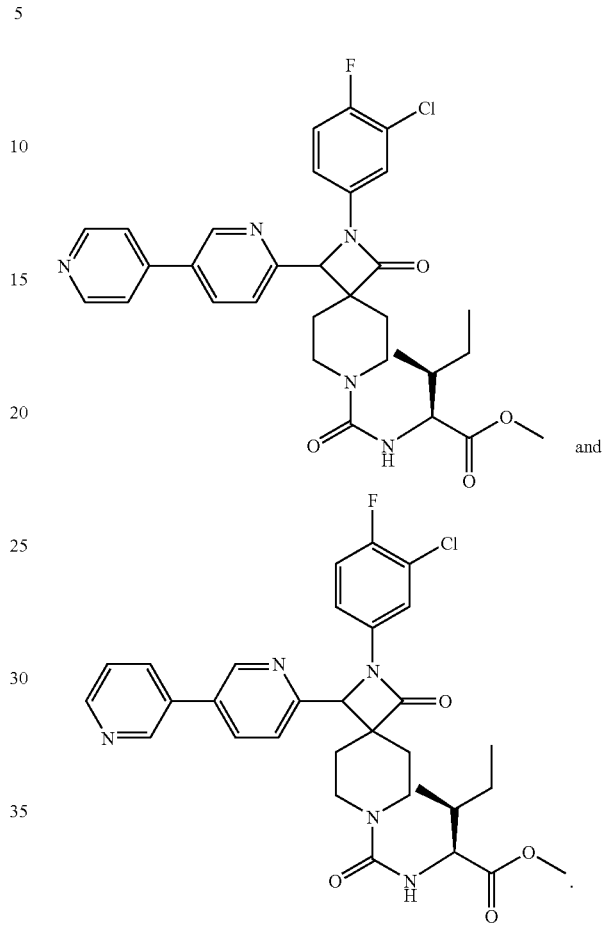

Example 8

Preparation of Compound H

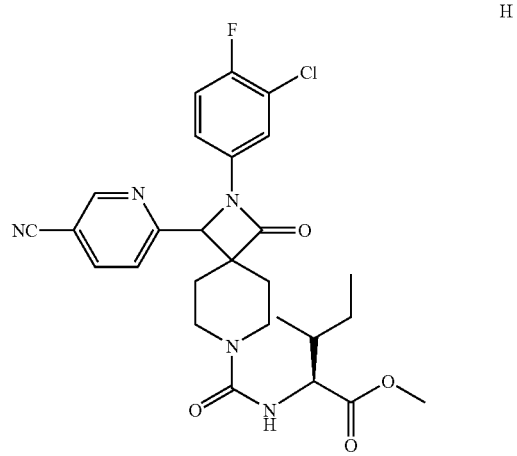

Step 1: Synthesis of Compound H-2

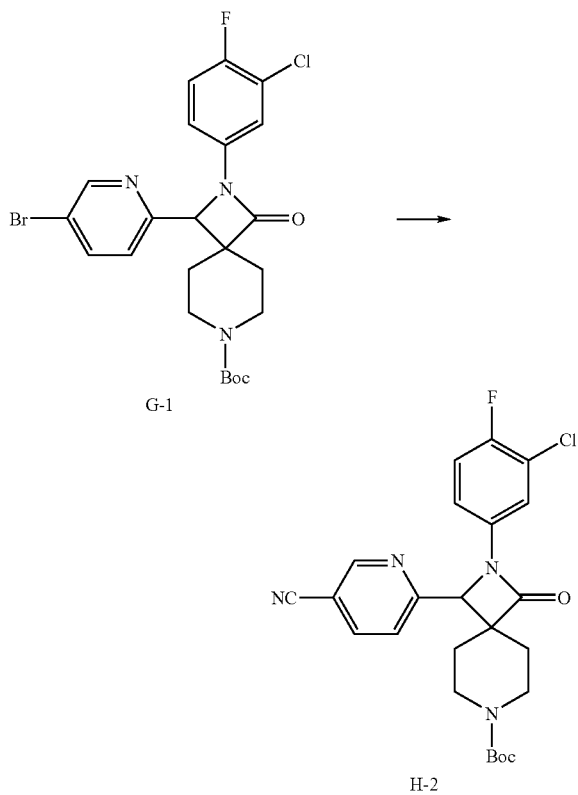

In each of 6 microwave tubes was placed a solution comprising compound G-1 (115 mg, prepared in a similar manner as described in Example 6, Step 1 and 2) (115 mg), zinc cyanide (30 mg) and tetrakis(triphenylphosphine)palladium (0) (45 mg) and DMAF (3 mL). The tubes were sealed and the reactions were each microwaved for 12 minutes, during which time the reaction temperature reached 150° C. The reaction mixtures were then combined, diluted with water and the resulting solution was extracted with dichloromethane. The dichloromethane was dried over MgSO$_4$, filtered and concentrated in vacuo to provide a crude brown oil. The crude brown oil was purified using ten preparative TLC plates (1000 μm, eluted with EtOAc/hexane 1:4) to provide compound H-2 as an off white foam (0.54 g), LCMS: (M+1) 417 at 4.86 minutes.

Step 2: Synthesis of Compound H-3

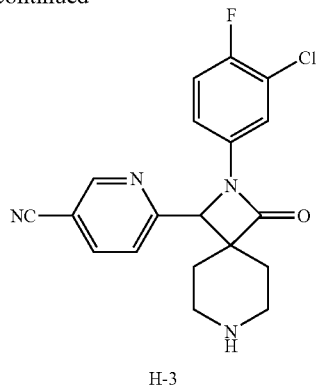

To a solution of H-2 (0.53 g) in dichloromethane (6 mL) was added TFA (3 mL) and the resulting reaction was allowed to stir at room temperature for 1 hour. The reaction mixture was concentrated in vacuo and the residue obtained was partitioned between dichloromethane and aqueous K$_2$CO$_3$ solution (2.5 N). The organic layer was dried over MgSO$_4$, filtered and concentrated in vacuo to provide an off-white solid residue, which was purified using preparative TLC on 4 plates (1000 μm, eluted with dichloromethane/methanol 4:1) to provide compound H-3 as a white foam (0.44 g), LCMS: (M+1) 542 at 4.45 minutes.

Step 3: Synthesis of Compound H

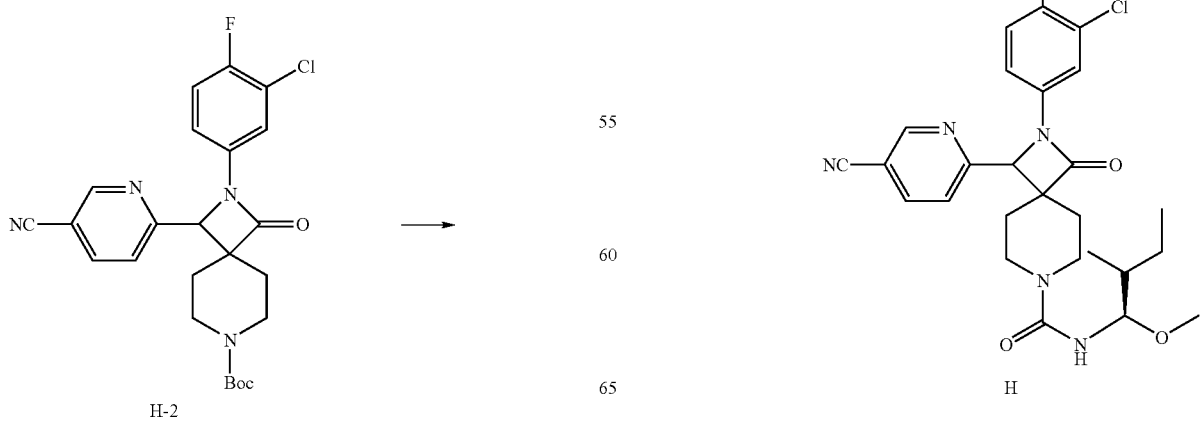

A solution of compound H-3 (54 mg) and (2S,3S)-2-isocyanato-3-methylvaleric acid, methyl ester (33 mg) in acetonitrile (2 mL) was allowed to stir for 20 hours. The reaction mixture was then directly purified using preparative TLC on two silica gel plates (1000 μm, dichloromethane:methanol 97:3 as eluent) to provide a white foam residue (58.8 mg). This residue was purified using preparative LC A: water/0.1% formic acid and B: acetonitrile/0.1% formic acid with gradient (0-1 min 10% B; 1-11 min 10% 8 to 100% B; 11-17 min 100% B; and 17-23 min 10% B) to provide compound H as a white foam (40.8 mg). LCMS: (M+1) 593 at 4.97 minutes.

Example 9

Preparation of Compound J

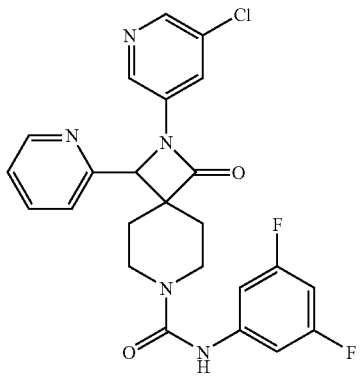

Step 1: Synthesis of Compound J-1

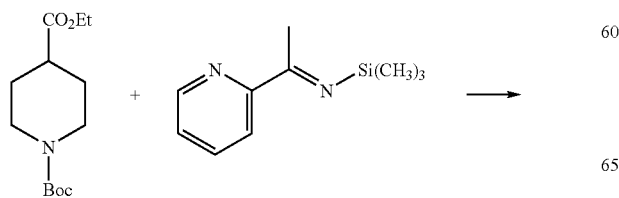

To a solution of 2-pyridinecarboxaldehyde (4.42 mL) in THF (10 mL) was added dry molecular sieves (5 Å). The resulting solution was cooled to −30° C. and lithium bis(trimethylsilyl)amide in THF (1 N, 47 mL) was added dropwise, while maintaining the reaction temperature between 14 and −25° C. The reaction mixture was then brought to 0° C. and allowed to stir at this temperature for 30 minutes. The reaction mixture, which contains compound J-1, was then warmed to −30° C. and used directly in Step 2.

Step 2: Synthesis of Compound J-2

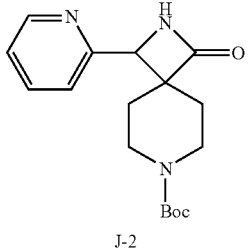

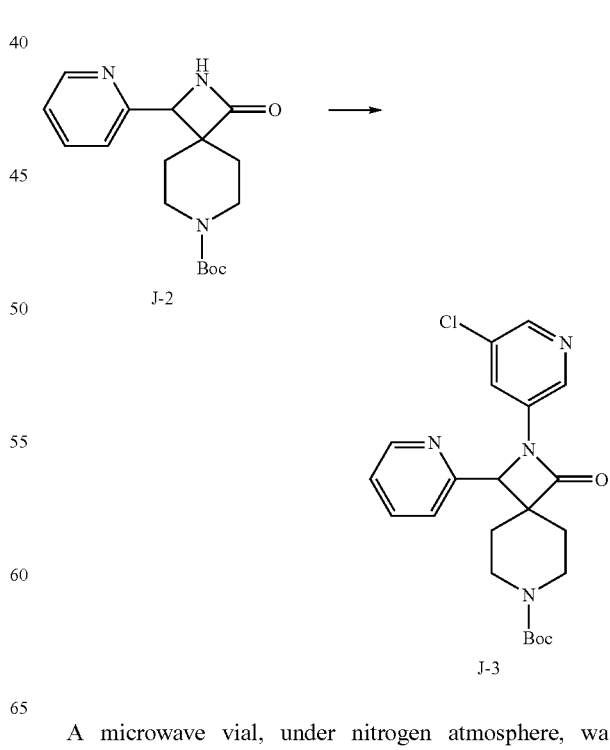

A solution of diisopropylethylamine (6.1 mL) in dry THF (10 mL) was cooled to 0° C., placed under nitrogen atmosphere, and n-butyllithium in hexane (2.5 M, 17.4 mL) was then added and the resulting reaction was further cooled to −65° C. and allowed to stir at this temperature for 30 minutes A solution of ethyl 1-tert-butoxycarbonylpiperazine-4-carboxylate (9.5 g) in dry THF (10 mL) was added to the reaction mixture and the resulting mixture was cooled to −70° C. and allowed to stir at this temperature for 90 minutes. The reaction mixture containing compound J-1 (about 46 mL, as prepared in Step 1) was then added to the reaction mixture and the resulting reaction was allowed to warm to room temperature on its own and stir at room temperature for 17 hours. The reaction was then quenched by adding saturated aqueous ammonium chloride solution (100 mL) and the resulting solution was extracted with EtOAc (2×200 mL). The combined organic layers were washed with brine, dried (MgSO₄), then filtered through a silica gel plug and concentrated in vacuo to provide a crude amber film. The crude film was diluted with EtOAc (10 mL), triturated with hexane (10 mL) and allowed to crystallize to provide compound J-2 as a yellow solid (9.08 g). LCMS: (M+1) 318 at 2.28 minutes.

Step 3: Synthesis of Compound J-3

A microwave vial, under nitrogen atmosphere, was charged with compound J-2 (163 mg), a solution of 3-bromo- 5-chloropyridine (200 mg) in dioxane (4 mL), N,N-dimethylethylenediamine (88 µL), copper iodide (36 mg), and ground K₂CO₃ (260 mg). The vial was sealed and microwaved for 8 hours, during which time the reaction temperature reached 120° C. The reaction mixture was then directly purified using preparative TLC on two silica gel plates (1000 µm, eluted with dichloromethane:methanol 19:1) to provide compound J-3 (128 mg). LCMS: (M+1) 429 at 4.12 minutes.

Step 4: Synthesis of Compound J-4

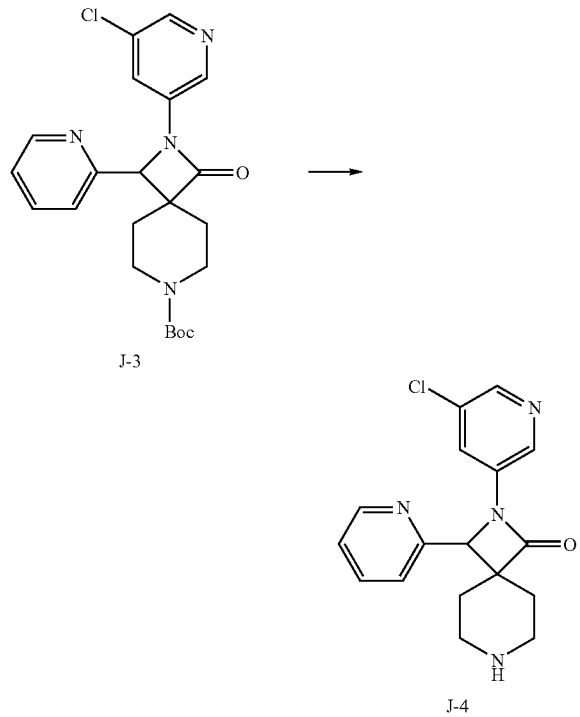

To a solution of compound J-3 (0.123 g) in dichloromethane (1.2 mL) was added TFA (1 mL) and the resulting reaction was allowed to stir for 1 hour. The reaction mixture was concentrated in vacuo and the resulting residue was partitioned between dichloromethane and aqueous K₂CO₃ solution (2.5 N). The organic layer was dried over MgSO₄, filtered and concentrated in vacuo to provide compound J-4 as a white foam (0.076 g) which was used without further purification. LCMS: (M+1) 329 at 2.05, 0.76 minutes.

Step 5: Synthesis of Compound J

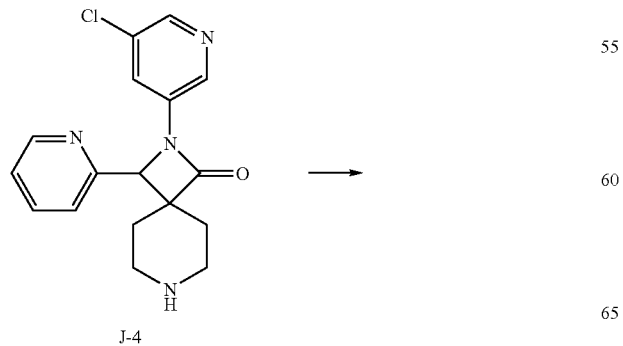

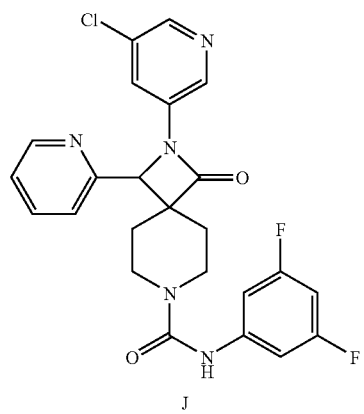

A solution of compound J-4 (23 mg) and 3,5-difluorophenylisocyanate (12 µL) in acetonitrile (1.5 mL) was allowed to stir at room temperature for 17 hours. The reaction mixture was then directly purified using preparative TLC on two silica gel plates (1000 µm, eluted with dichloromethane:methanol 9:1) to provide to provide compound J as a white foam (27 mg), LCMS: (M+1) 484 at 3.82 minutes.

Using the method described in Example 9 and employing the appropriate starting materials and reagents, the following additional illustrative compounds of the present invention were made:

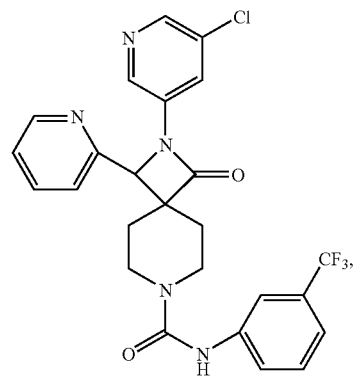

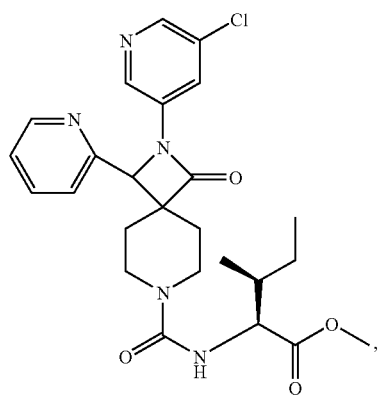

-continued
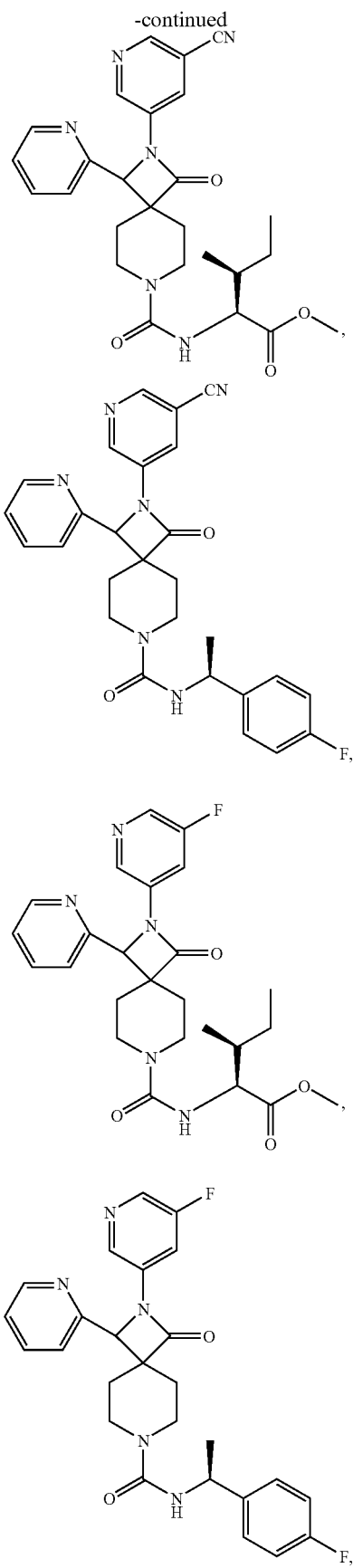
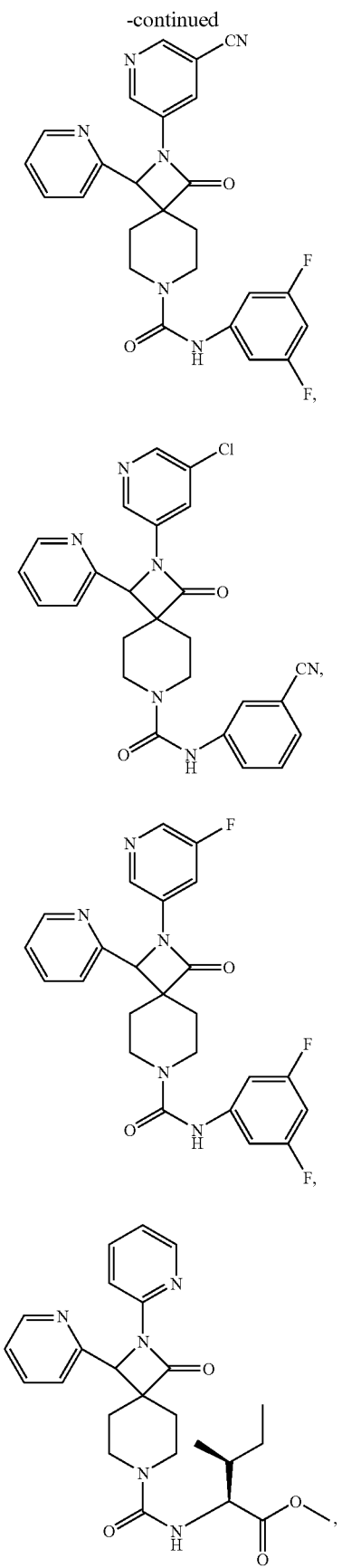

-continued
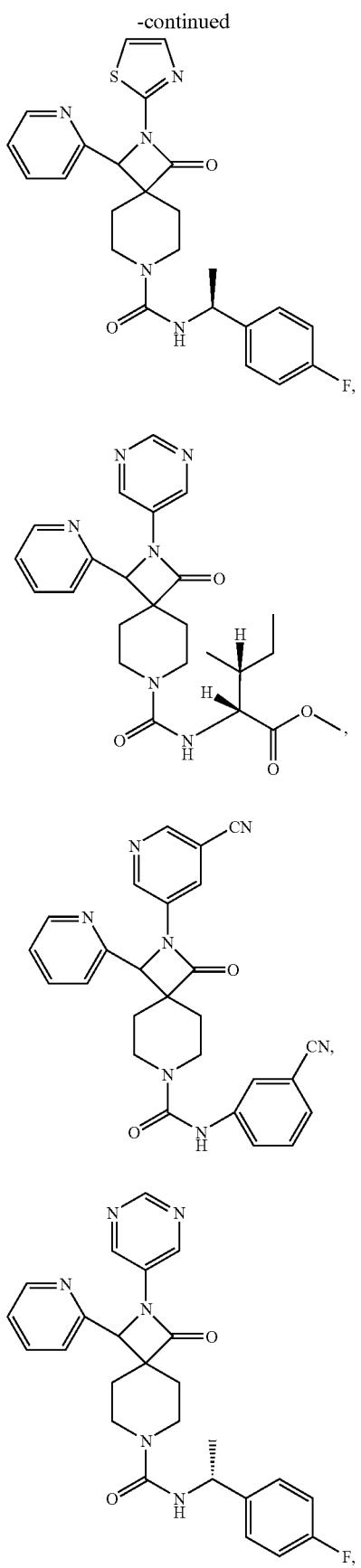
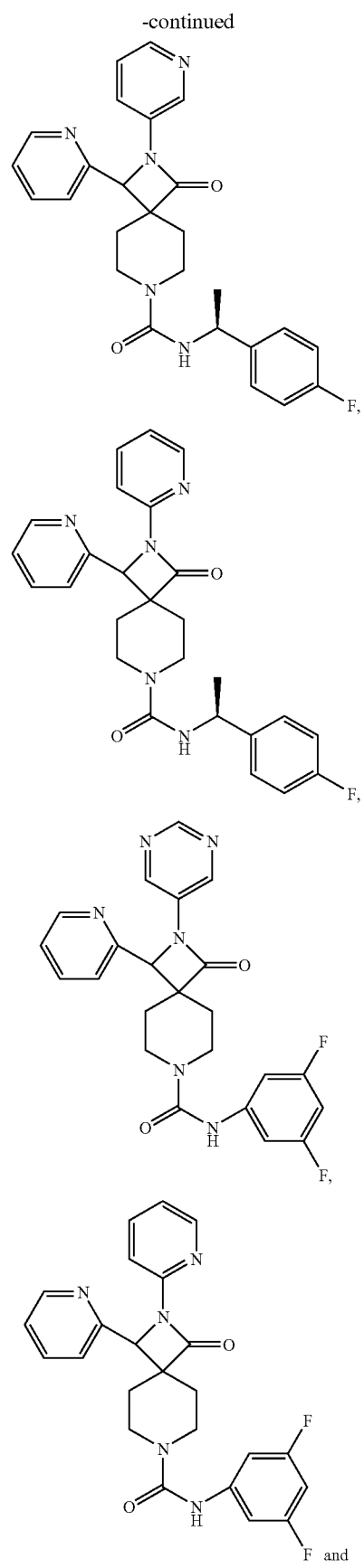

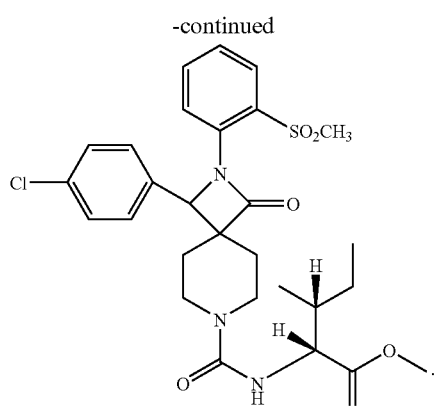

Example 10

Preparation of Compound K

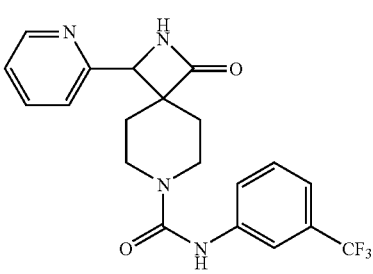

K

Step 1: Synthesis of Compound K-1

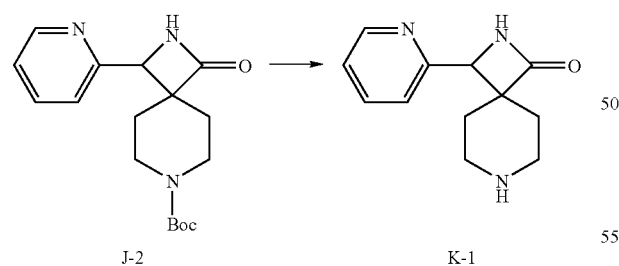

To a solution of compound J-2 (500 mg) in dichloromethane (3 mL) was added TFA (1.5 mL) and the resulting reaction was allowed to stir for 2.5 hours. The reaction mixture was concentrated in vacuo and the resulting residue was partitioned between dichloromethane and aqueous $K_2CO_3$ solution (2.5 N). The dried ($K_2CO_3$) solution was concentrated in vacuo to provide compound K-1 as an amber film (0.065 g), LCMS: (M+1) 218 at 0.73 minutes.

Step 2: Synthesis of Compound K

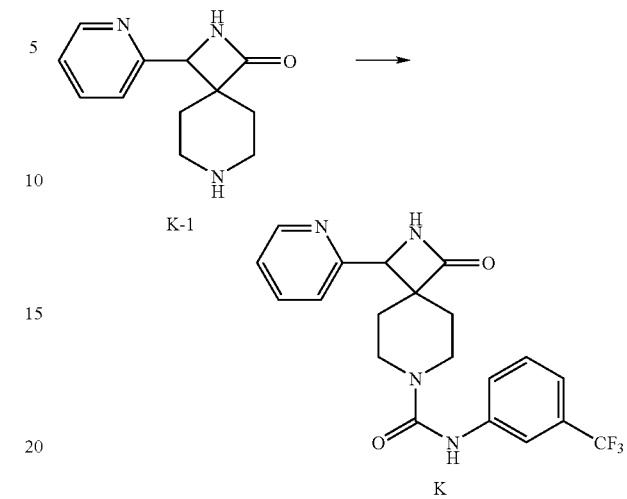

Stir compound K-1 (250 mg) and 3,5-difluorophenylisocyanate (63 µL) in acetonitrile (1 mL) for 17 hours. The reaction mixture was then directly purified using preparative TLC on two silica gel plates (1000 µm, eluted with EtOAc: methanol 9:1) to provide compound K as a white solid (45.6 mg), LCMS: (M+1) 405 at 2.73 minutes.

Using the method described in Example 10 and employing the appropriate starting materials and reagents, the following additional illustrative compound of the present invention was made:

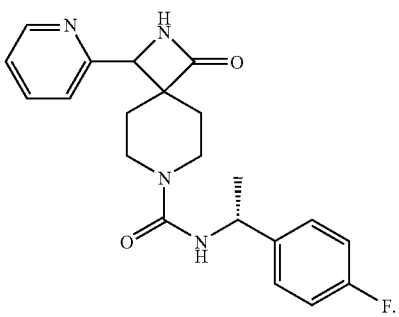

Example 11

Preparation of Compound L

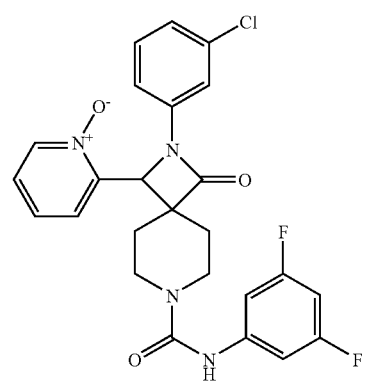

Step 1: Synthesis of Compound L

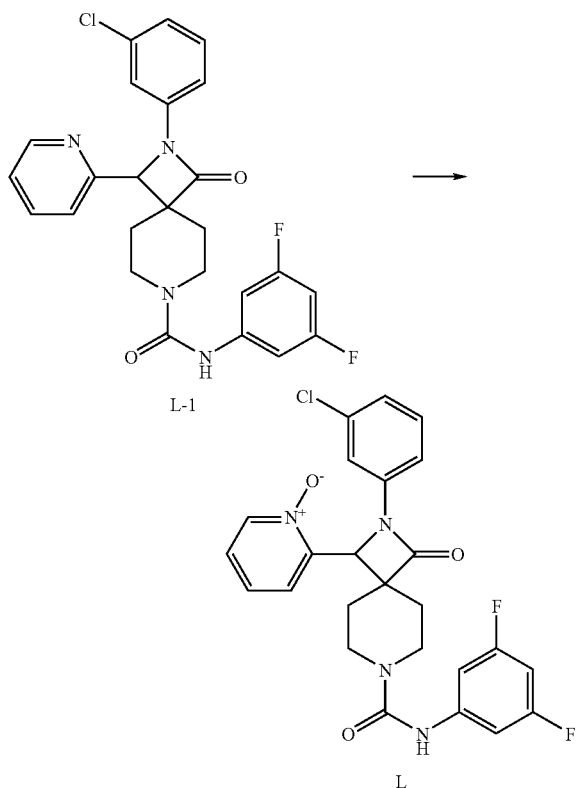

To a solution of L-1 (55 mg) (prepared by steps described in Example 5) in dichloromethane (10 mL) was added m-chloroperbenzoic acid (35 mg) After 1 hour, additional m-chloroperbenzoic acid (20 mg) was added. After 2 additional hours, the reaction mixture was partitioned between aqueous $K_2CO_3$ solution (2.5 N) and $CH_2Cl_2$. The organic layer was dried over $MgSO_4$, filtered and concentrated in vacuo to provide a crude amber foam (46.6 mg). This amber foam was purified using preparative TLC on to silica gel plates (1000 μm eluted with $CH_2Cl_2$:MeOH 19:1); to provide compound L as a tan foam (24.8 mg). LCMS: (M+1) 499 at 4.09 minutes.

Example 12

Preparation of Compound M

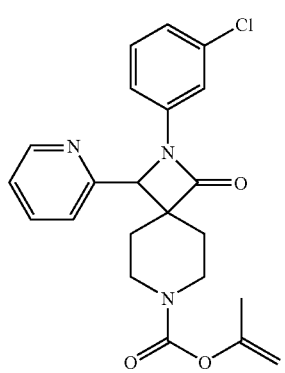

Step 1: Synthesis of Compound M

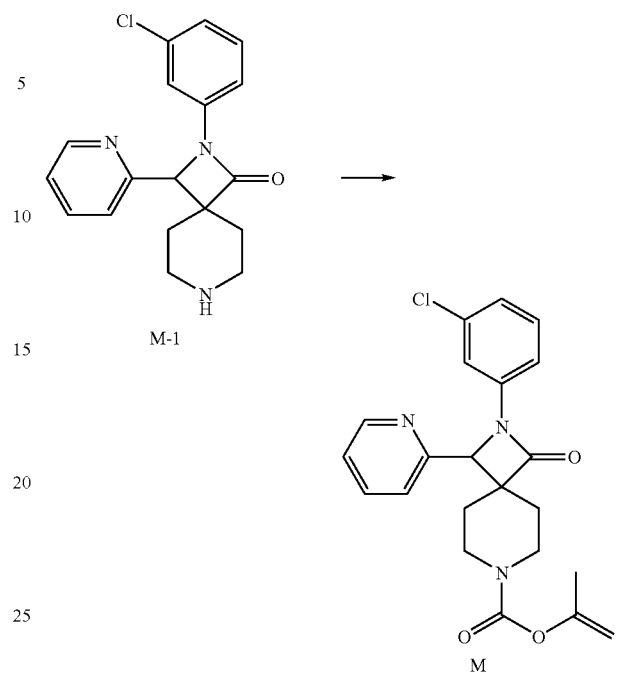

Sodium hydroxide (37 mg) was place in a vial, and the vial was placed in a 0° C. ice bath. Water (50 μL) was added to the vial and 15 minutes later, EtOAc (500 μL) was added to the vial. 5 minutes after the EtOAc addition, a solution of compound M-1 (200 mg) in EtOAc (500 μL) was added and the resulting reaction was allowed to stir at 0° C. for 20 minutes. Isopropenyl chloroformate (93.6 mL) was then added to the reaction mixture and the resulting reaction was allowed to stir at 0° C. for 1.5 hours. Additional isopropenyl chloroformate (20 μL) was then added to the reaction mixture, which was then allowed to stir for an additional 2 hours, then cold EtOAc (20 mL) was added. Brine was added to the reaction mixture and the resulting solution was extracted with EtOAc. The organic layer was dried ($MgSO_4$), filtered, then concentrated in vacuo to provide compound M as a film (241 mg). LCMS: (M+1) 412 at 4.34 minutes.

Example 13

Preparation of Compound N

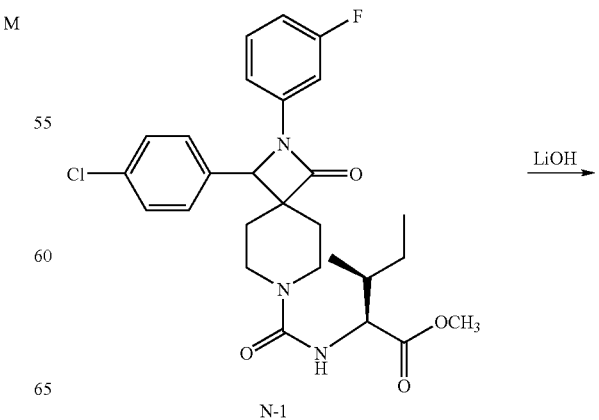

-continued

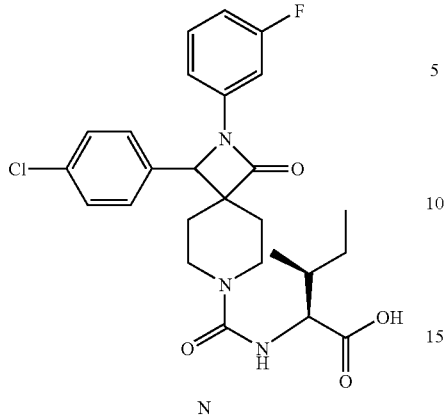

N

To a solution of compound N-1 (1.2 g) in tetrahydrofuran (20 mL) was added a solution of LiOH (0.5 M in H₂O, 30 mL) and the resulting reaction mixture was stirred at 0° C. for 5 hours. Then, the reaction mixture was diluted with EtOAc (50 mL) and HCl solution (1N, 150 mL). The layers were separated and the aqueous layer was extracted with EtOAc (2×50 mL). All the organic layers were combined and the resulting solution was dried over $Na_2SO_4$, filtered, and concentrated. The crude product was purified by flash column chromatography using a mixture of $MeOH:CH_2Cl_2:AcOH$ (5:95:1) as eluent to provide Compound N as a white foam (0.73 g), LCMS, M+1 is 502. H NMR (DMSO-$d_6$): 0.82, m, 6H; 1.12, m, 2H; 1.42, m, 2H; 1.74, m, 1H; 1.90, m, 1H; 1.93, m, 2H; 2.02, m, 1H; 3.05, m, 1H; 3.20, m, 1H; 3.51, m, 1H; 3.60, m, 1H; 3.91, t, 1H; 5.20, s, 1H; 6.32, d, 1H; 6.92, m, 3H; 7.10, dt, 1H; 7.35, m, 3H; 7.46, d, 2H; 12.17, br s, 1H.

Example 14

Preparation of Compound O

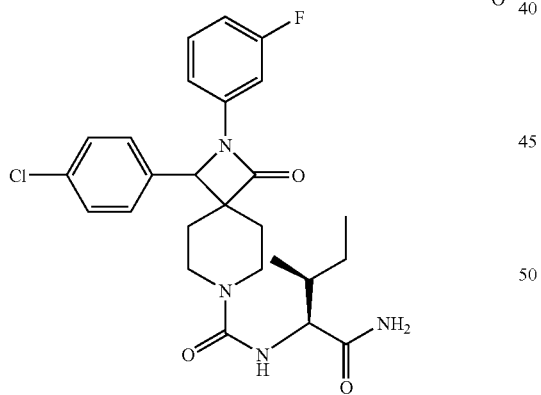

O

To a solution of compound N (0.17 g) in tetrahydrofuran (5 mL) was added N-(3-dimethylaminopropyl)-N'-ethylcarbodiimide hydrochloride (0.085 g), 1-hydroxybenzotriazole hydrate (catalytic amount) and triethylamine (0.14 mL). The resulting reaction mixture was stirred at 0° C. for 45 minutes. Then, the reaction mixture was treated with ammonium hydroxide (~14.8 N, 0.23 mL) at 0° C. The reaction mixture was stirred at RT for 20 hours. The reaction mixture was diluted with EtOAc (50 mL) and washed with sat. $NaHCO_{3(aq)}$ (2×100 mL), half sat. $NaHCO_{3(aq)}$ (1×50 mL), dried over $Na_2SO_4$, filtered, and concentrated. The crude product was purified by flash column chromatography using a mixture of $MeOH:CH_2Cl_2$ (10:90) as eluent to provide Compound O as white solid (0.13 g), LCMS, M is 501. H NMR (DMSO-$d_6$): 0.80, m, 6H; 1.06, m, 2H; 1.42, m, 2H; 1.68, m, 1H; 1.96, m, 3H; 3.07, m, 1H; 3.19, m, 1H; 3.51, m, 1H; 3.60, m, 1H; 3.89, t, 1H; 5.20, s, 1H; 6.11, d, 1H; 6.93, m, 3H; 7.08, d, 1H; 7.26, s, 1H; 7.35, m, 3H; 7.46, d, 2H.

Example 15

Preparation of Compound P

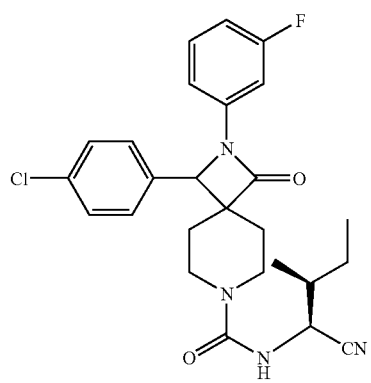

P

To a solution of compound O (0.063 g) in $CH_2Cl_2$ (5 mL) was added trifluoroacetic anhydride (0.142 mL) and triethylamine (0.036 mL) at 0° C. The resulting reaction mixture was stirred at 0° C. for 10 minutes and at RT thereafter. After 23 hours of stirring, the reaction mixture was quenched with H₂O (5 mL). Then, the reaction mixture was diluted with EtOAc (50 mL) and sat. $NaHCO_3$ (50 mL). The layers were separated and the organic layer was washed with brine (1×100 mL), dried over $Na_2SO_4$, filtered, and concentrated. The crude product was purified by preparatory thin layer chromatography using a mixture of EtOAc:Hexane (30:70) as eluent to provide Compound P as a white foam (0.030 g), LCMS, M is 483. H NMR (DMSO-$d_6$): 0.81, t, 3H; 0.96, d, 3H; 0.96, m, 2H; 1.42, m, 2H; 1.75, m, 1H; 1.97, m, 2H; 3.07, m, 1H; 3.19, m, 1H; 3.47, m, 1H; 3.62, m, 1H; 4.44, t, 1H; 5.18, s, 1H; 6.93, m, 2H; 7.08, m, 2H; 7.34, m, 2H; 7.44, d, 2H.

Example 16

Preparation of Compound Q

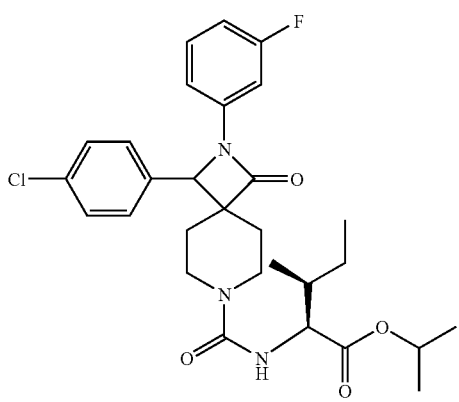

Q

To a solution of compound N (0.054 g) in DMF (2 mL) was added N-(3-dimethylaminopropyl)-N'-ethylcarbodiimide hydrochloride (0.031 g), 1-hydroxybenzotriazole hydrate (catalytic amount) and triethylamine (0.030 mL). Then, the reaction mixture was treated with i-PrOH (0.083 mL). After 19 hours of stirring at RT, the reaction mixture was treated with additional i-PrOH (10 mL), and kept stirred at RT for additional 18 hours. The reaction mixture was diluted with EtOAc (30 mL) and washed with H₂O (3×50 mL), dried over Na₂SO₄, filtered, and concentrated. The crude product was purified by preparatory thin layer chromatography using a mixture of EtOAc:Hexane (35:65) as eluent to provide Compound Q as a white foam (0.016 g), LCMS, M is 544. H NMR (CDCl₃): 0.90, m, 6H; 1.23, m, 7H; 1.41, m, 1H; 1.62, m, 2H; 1.85, m, 1H; 1.99, m, 1H; 2.19, m, 1H; 3.34, m, 2H; 3.63, m, 1H; 3.76, m, 1H; 4.41, m, 1H; 4.77, s, 1H; 5.00, m, 2H; 6.77, m, 1H; 6.94, d, 1H; 7.07, d, 1H; 7.18, m, 4H; 7.35, m, 2H.

Example 17

Preparation of Compound R

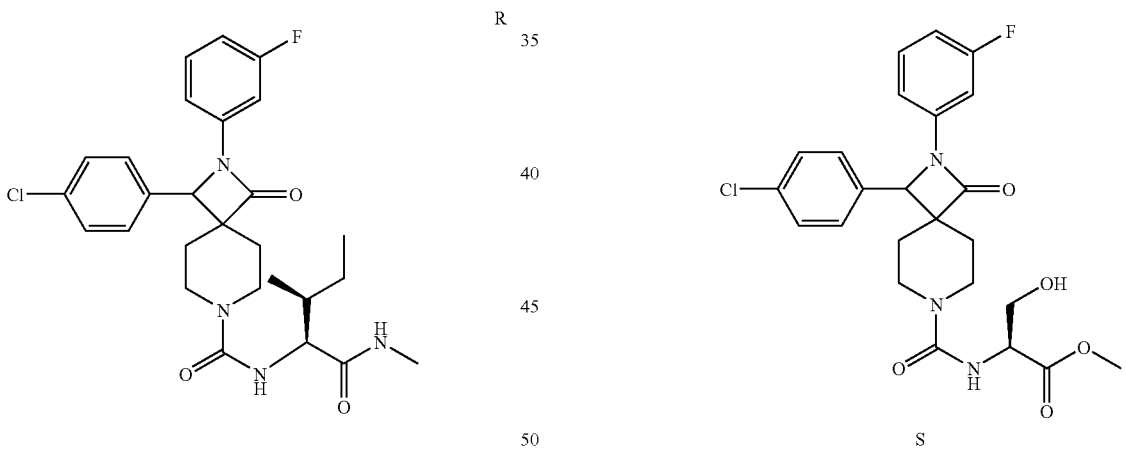

To a solution of compound N (0.054 g) in DMF (2 mL) was added N-(3-dimethylaminopropyl)-N'-ethylcarbodiimide hydrochloride (0.031 g), 1-hydroxybenzotriazole hydrate (catalytic amount) and triethylamine (0.030 mL). Then, the reaction mixture was treated with methylamine hydrochloride (0.015 g). After 19 hours of stirring at RT, the reaction mixture was diluted with EtOAc (30 mL) and washed with H₂O (2×50 mL), brine (1×50 mL), dried over Na₂SO₄, filtered, and concentrated. The crude product was purified by preparatory thin layer chromatography using a mixture of MeOH:CH₂Cl₂ (3:97) as eluent to provide Compound R as white solid (0.033 g), LCMS, M is 515. H NMR (CDCl₃): 0.88, m, 6H; 1.17, m, 3H; 1.52, m, 2H; 1.76, m, 1H; 1.97, m, 2H; 2.18, m, 1H; 2.75, d, 2H; 3.66, m, 2H; 4.06, t, 1H; 4.76, s, 1H; 5.22, d, 1H; 6.51, m, 1H; 6.77, m, 1H; 6.93, d, 1H; 7.06, d, 1H; 7.19, m, 3H; 7.35, m, 2H.

Example 18

Preparation of Compound S

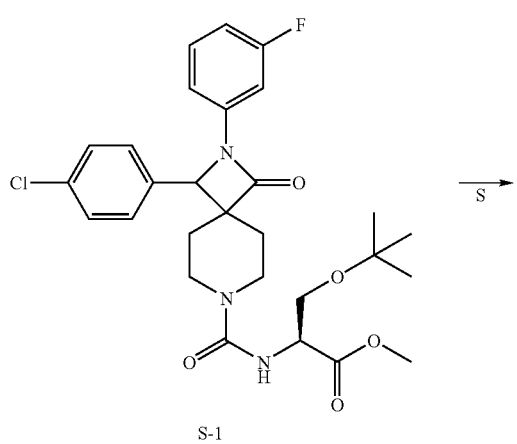

To a solution of compound S-1 (0.051 g) in CH₂Cl₂ (5 mL) was added trifluoroacetic acid (0.1 mL). After 22 hours of stirring at RT, the reaction mixture was treated with additional trifluoroacetic acid (0.5 mL). After additional 22 hours of stirring, the reaction mixture was concentrated by rotary evaporator. The crude product was purified by preparatory thin layer chromatography using a mixture of CH₃CN:CH₂Cl₂ (30:70) as eluent to provide Compound S as white solid (0.033 g), LCMS, M is 490. H NMR (CDCl₃): 1.13, m, 2H; 1.53, m, 1H; 1.94, m, 1H; 2.12, d, 1H; 3.33, m, 2H; 3.56, m, 1H; 3.69, m, 4H; 3.83, m, 2H; 4.46, br s, 1H; 4.71, s, 1H; 5.39, d, 1H; 6.71, m, 1H; 6.87, m, 1H; 7.01, d, 1H; 7.14, m, 3H; 7.29, m, 2H.

Example 19

Preparation of Compound T

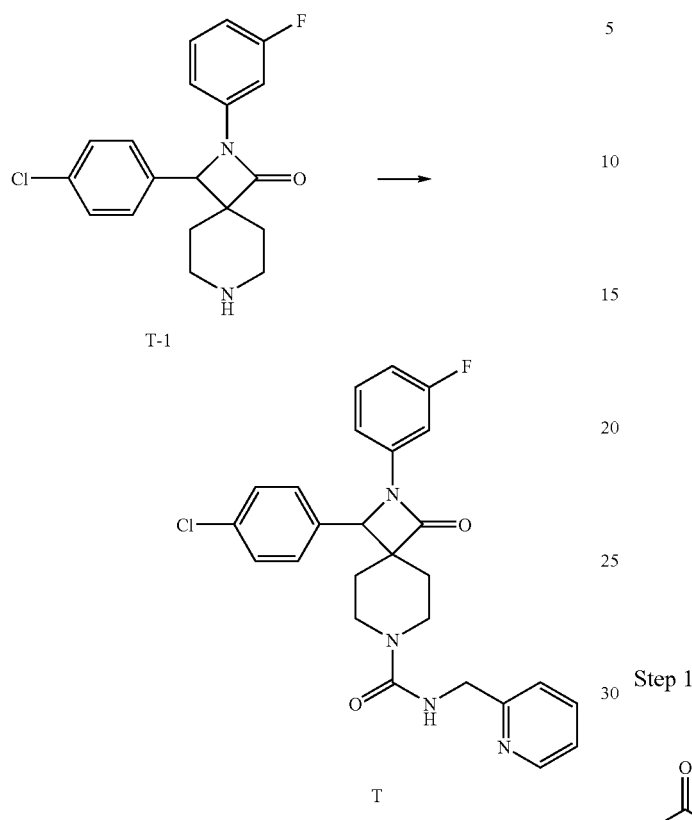

To a solution of carbodiimidazole (0.092 g) in CH$_2$Cl$_2$ (2 mL) at 0° C. was added a solution of Compound T-1 (0.178, prepared according to steps 1-3 in Example 5 using metafluoroaniline and p-chlorobenzaldehyde) in CH$_2$Cl$_2$ (1 mL) dropwise. The reaction mixture was stirred at RT under N$_2$ for 3 hours. Then, the reaction mixture was diluted with CH$_2$Cl$_2$ (50 mL) and the resulting solution was washed with H$_2$O (1×50 mL). The aqueous layer was extracted with CH$_2$Cl$_2$ (1×50 mL). The organic layers were combined, dried over Na$_2$SO$_4$, filtered, and concentrated. The crude product obtained was dissolved in CH$_2$Cl$_2$ (5 mL) and treated with iodomethane (0.128 mL) at RT. The reaction mixture was stirred at RT under N$_2$ for 16 hours. Then, the reaction mixture was concentrated by rotary evaporator and further dried in vacuo. The crude product was then dissolved in CH$_2$CO$_2$ (6 mL) and divided into 3 equal parts. To one part of the solution was added triethylamine (0.027 mL) and 2-aminomethylpyridine (0.020 mL). The reaction mixture was stirred at RT under N$_2$ for 9 hours. Then, the reaction mixture was treated with additional 2-aminomethylpyridine (0.040 mL) and the reaction mixture was stirred at RT under N$_2$ for 6 hours. The reaction mixture was concentrated down by rotary evaporator. The crude product was purified by preparatory thin layer chromatography using a mixture of i-PrOH:CH$_2$Cl$_2$ (5:90) as eluent to provide Compound T as a white foam (0.017 g), LCMS, M is 479. H NMR (CDCl$_3$): 1.21, m, 2H; 1.60, m, 1H; 2.02, m, 1H; 2.20, m, 1H; 3.40, m, 2H; 3.65, m, 1H; 3.81, m, 1H; 4.49, d, 2H; 4.77, s, 1H; 5.89, m, 1H; 6.75, m, 1H; 6.94, m, 1H; 7.07, m, 1H; 7.18, m, 6H; 7.35, d, 2H.

Example 20

Preparation of Compound U

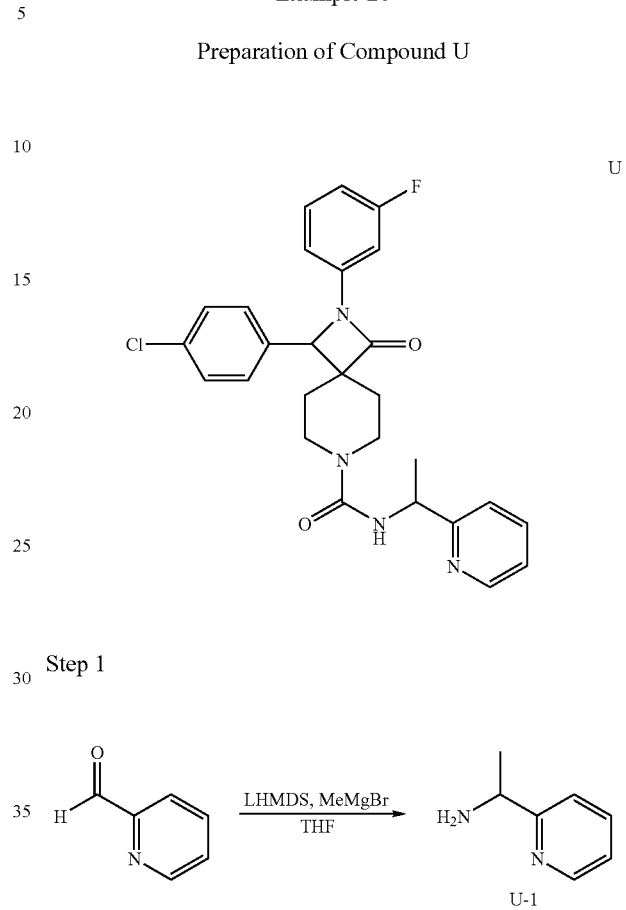

Step 1

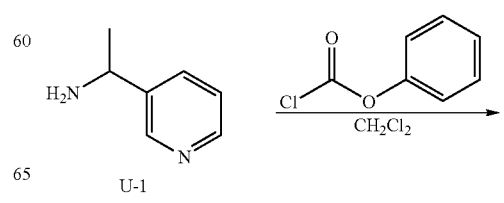

To a solution of 2-pyridinecarboxaldehyde (0.965 mL) in THF (4 mL) at 0° C. was added lithium bis(trimethylsilyl)amide (10M in THF, 12 mL). The reaction mixture was stirred at 0° C. under N$_2$ for 25 minutes. Then, the reaction mixture was treated with methylmagnesium bromide (3.0 M in Et$_2$O, 7.3 mL) at 0° C. The reaction mixture was stirred at 0° C. for 5 minutes and at RT for 30 minutes thereafter. The reaction mixture was quenched by slow addition of sat NH$_4$Cl(aq) (10 mL) at 0° C. The reaction mixture was then diluted with 1 N NaOH(aq) (100 mL) and extracted with EtOAc (6×100 mL). All the organic layers were combined, dried over Na$_2$SO$_4$, filtered, and concentrated to provide Compound U-1 as brown oil (0.970 g), LCMS, M+1 is 123.

Step 2

-continued

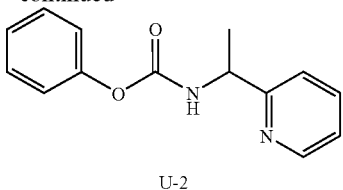

U-2

To a solution of Compound U-1 (0.97 g) in CH$_2$Cl$_2$ (40 mL) at 0° C. was added phenyl chloroformate (1.13 mL) dropwise. The reaction mixture was stirred at RT under N$_2$ for 15 hours. Then, the reaction mixture was diluted with sat NaHCO$_{3(aq)}$ (100 mL) and extracted with EtOAc (3×100 mL). All the organic layers were combined, washed with sat. NaHCO$_{3(aq)}$ (1×100 mL), brine (1×100 mL), dried over Na$_2$SO$_4$, filtered, and concentrated. The crude product was purified by silica gel flash column chromatography using a mixture of EtOAc:Hexanes (40:60) as an eluent to provide Compound U-2 (0-66 g) as slightly yellowish solids. LCMS M+1 is 243.

Step 3

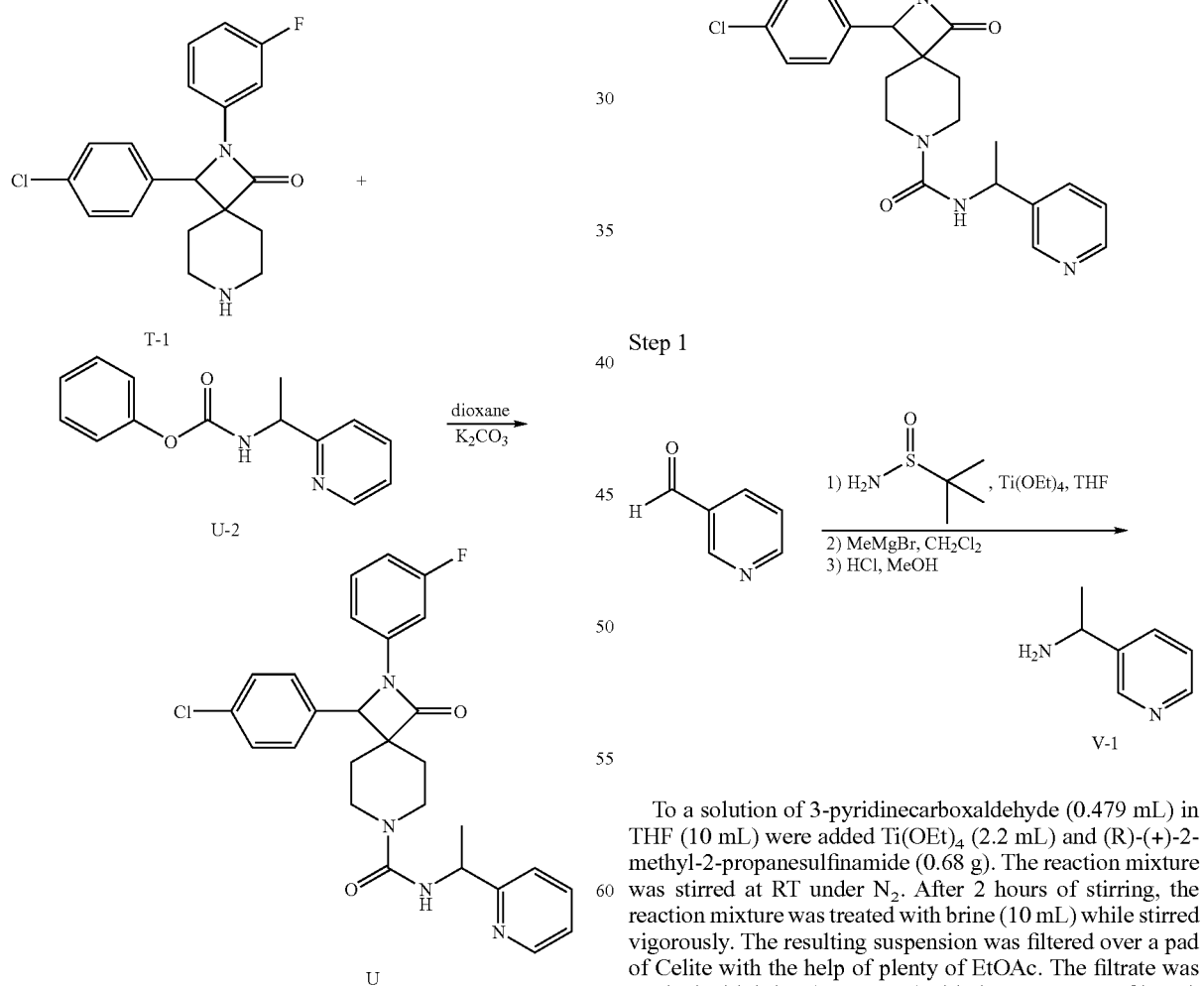

To a solution of Compound T-1 (0.035 g, which can be prepared using methods described in the Examples above herein and substituting the appropriate reactants) in dioxane (1 mL) were added the Compound 8-2 (0.029 g) and K$_2$CO$_3$ (0.1 g). The reaction mixture was heated at 100° C. for 15 minutes by microwave. The reaction mixture was filtered and the filtrates were concentrated by rotary evaporator. The crude product was purified by preparatory thin layer chromatography using a mixture of MeOH:CH$_2$Cl$_2$ (5:95) as an eluent to provide Compound U (0.034 g) as a white foam. LCMS M is 493. H NMR (DMSO-d$_6$) 1.07, m, 1H; 1.34, m, 3H; 1.45, m, 1H, 1.98, m, 2H; 3.13, m, 1H; 3.22, m, 1H; 3.51, m, 1H; 3.64, m, 1H; 4.81, m, 1H; 5.20, m, 1H; 6.79, m, 1H; 6.93, m, 2H; 7.08, m, 1H; 7.21, m, 1H; 7.31, m, 2H; 7.37, m, 2H; 7.46, m, 2H; 7.71, m, 1H; 8.46, m, 1H.

Example 21

Preparation of Compound V

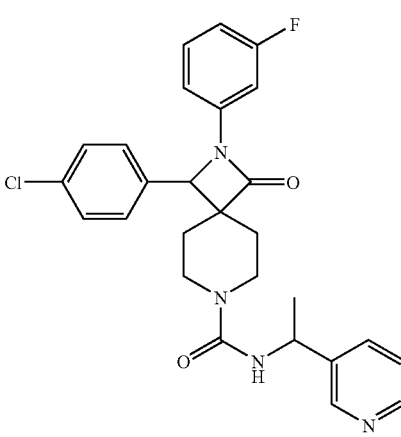

Step 1

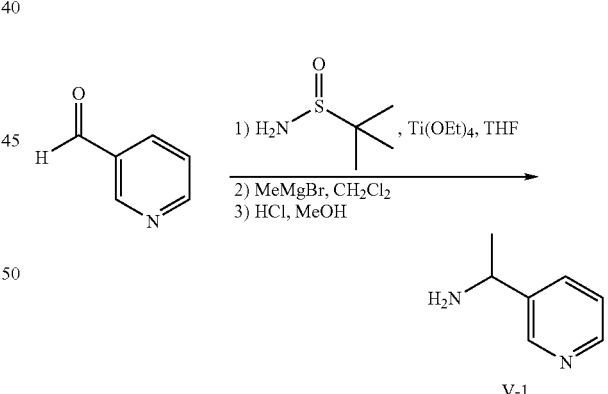

To a solution of 3-pyridinecarboxaldehyde (0.479 mL) in THF (10 mL) were added Ti(OEt)$_4$ (2.2 mL) and (R)-(+)-2-methyl-2-propanesulfinamide (0.68 g). The reaction mixture was stirred at RT under N$_2$. After 2 hours of stirring, the reaction mixture was treated with brine (10 mL) while stirred vigorously. The resulting suspension was filtered over a pad of Celite with the help of plenty of EtOAc. The filtrate was washed with brine (1×100 mL), dried over Na$_2$SO$_4$, filtered, and concentrated by rotary evaporator. The crude product obtained was purified by silica gel flash chromatography using a mixture of EtOAc:Hexanes (60:40) as an eluent to provide clear oil as product (0.71 g). This clear oil was dissolved in $CH_2Cl_2$ (17 mL) and cooled to −48° C. Then, the reaction mixture was treated with methylmagnesium bromide (3.0M in $Et_2O$, 2.3 mL). The reaction mixture was stirred at −48° C. under $N_2$ for 3 hours and at RT thereafter for 15 hours. The reaction mixture was treated with sat. $NH_4Cl_{(aq)}$ (40 mL) and diluted with EtOAc (50 mL). The layers were separated and the organic layers were washed with brine (1×50 mL), dried over $Na_2SO_4$, filtered, and concentrated. The crude product was purified by preparatory thin layer chromatography using a mixture of $MeOH:CH_2Cl_2$ (3:97) as an eluent to provide clear oil as product. (550 mg). The oil obtained was dissolved in MeOH (6 mL) and the solution was treated with HCl (4.0 M in dioxane, 3 mL). The reaction mixture was stirred at RT for 3 hours. The reaction mixture was concentrated down by rotary evaporator and the crude product obtained was recrystallized from minimum amount of MeOH and $Et_2O$ to provide Compound V-1 as white solid, hydrogen chloride salt (0.415 g). LCMS M+1 is 123.

Compound V was made using the methods described in Example 20, Steps 2 and 3, and substituting compound V-1 for compound U-1 in Step 2. LCMS M is 493.

Example 22

Preparation of Compound W

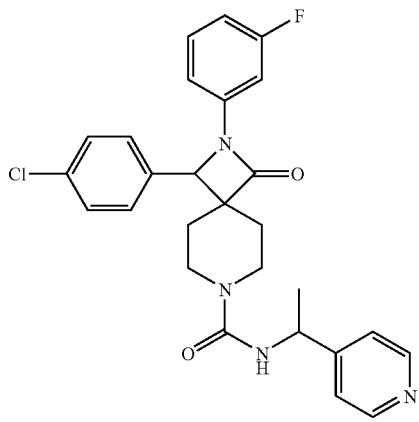

Compound W was made using the methods described in Example 20, Steps 1-3, and substituting 4-pyridinecarboxaldehyde for 2-pyridinecarboxaldehyde in Step 1. LCMS M is 493.

Example 23

Evaluation of Functional Effects of the Azetidinone Derivatives on Ion Channels

Functional evaluation of voltage-gated ion channels can be used to determine potency and/or single concentration efficacy of the Azetidinone Derivatives of the present invention. Two different methodologies can be used to measure ion currents: the IonWorks HT (Molecular Devices, Sunnyvale, Calif.) a moderate throughput voltage clamp screening platform that utilizes 96-well compound plates and conventional whole cell patch clamp for lower throughput, higher fidelity determinations.

Cell Lines

HEK cells are transiently transfected and then selected for stable heterologous expression of different channel proteins of interest. Calcium channel cell lines expressed a resting potassium current, human $K_{ir}2.1$, and the pore forming α-subunit of voltage-gated calcium channels. In the case of $Ca_V2.1$ cells the auxiliary subunit, $β_2a$, is also expressed. Calcium channel lines that are used to generate the data will express either human $Ca_V3.2$, rat $Ca_V3.2$ or human $Ca_V2.1$. The human heart sodium channel, $hNa_V1.5$, are stably expressed in CHO cells.

Cell lines can be grown at 37° C. in humidified incubators, equilibrated with 95% air/5% $CO_2$. CHO cells can be grown in Ham's F-12 medium. HEK cells can be grown in DMEM. All media are supplemented with 10% heat-inactivated fetal bovine serum, penicillin, streptomycin and appropriate selection antibiotics (zeocin, geneticin and/or hygromycin). Cells are passaged when 80% confluent or less.

IonWorks Screen for hCaV3.2

The extracellular buffer for experiments using this instrument contained the following (mM) (NaCl 125, HEPES 10, KCl 5.4, $CaCl_2$ 1.8, $MgCl_2$ 1.8, 0.2 $BaCl_2$ pH 7.35). The IonWorks uses amphotericin to gain electrical access to the cell interior. The internal solution contained (mM concentrations): 130 K-gluconate, 20 KCl, 5 HEPES-KOH (pH 7.25), 2 $CaCl_2$, 1 $MgCl_2$. Amphotericin added at 5 mg in 65 mL when present (in 650 µL DMSO). All internal and external solutions for this experiment contain 1% DMSO. Cells were acutely trypsinized from a T-75 flask and resuspended in extracellular buffer at a density of $2×10^5$ cells/mL.

Experiments were performed at room temperature. Transmembrane potential was held at −100 mV for 5 seconds prior to running the voltage protocol. During this time leak currents were measured during a step to −110 mV (200 milliseconds). T-type calcium currents were activated with a 250 millisecond step to −20 mV. This depolarization step was repeated for a total of 10 pulses with an interpulse interval of 1 second. Data were excluded if the following acceptance criteria were not met: total resistance for the pre-compound scan >65 MΩ, pre-compound current >250 pA, post compound total resistance >50 MΩ.

T-type currents were measured as the peak inward current minus the current at the end of the 250 msec step to −20 mV. After the recoding configuration was established there was a pre-compound measurement of current amplitude. Compound was added as a 3× solution containing 1% DMSO. After incubation with compound for 10 minutes currents were measured again. The current amplitude after compound addition was divided by the pre-compound current for pulse 10 to determine the fraction of current remaining after compound addition. For each compound, 8-point concentration-effect relationships were measured with ½ log serial dilutions. These data were then transferred into GraphPad Prism (v 4) and non-linear regression analysis was used to estimate the $IC_{50}$ for each test compound.

Using this method, the following data were obtained for the depicted Azetidinone Derivatives of the present invention:

| isomer A | isomer B | Structure | IW hCav3.2 IC50 nM |
|---|---|---|---|
| X | | 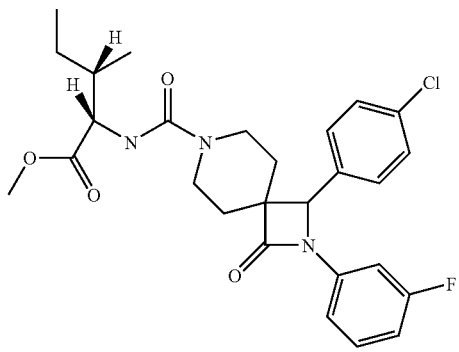 | 57 |
| X | | 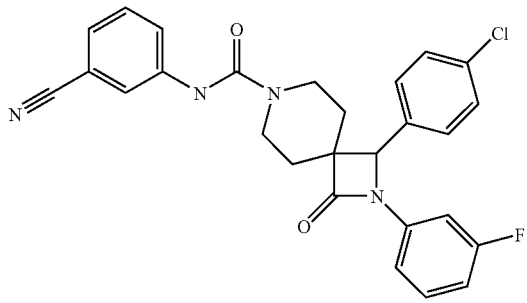 | 183 |
| | | 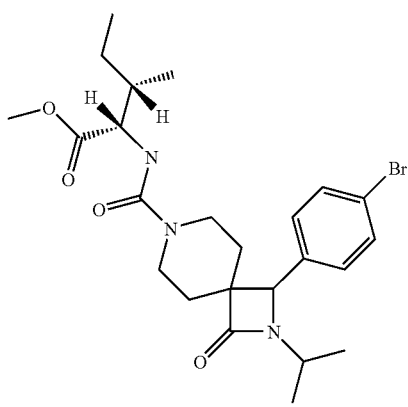 | 277 |
| X | | 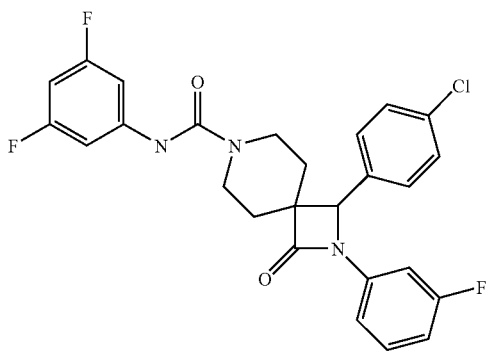 | 390 |

-continued
| isomer A | isomer B | Structure | IW hCav3 2 IC50 nM |
|---|---|---|---|
| | | 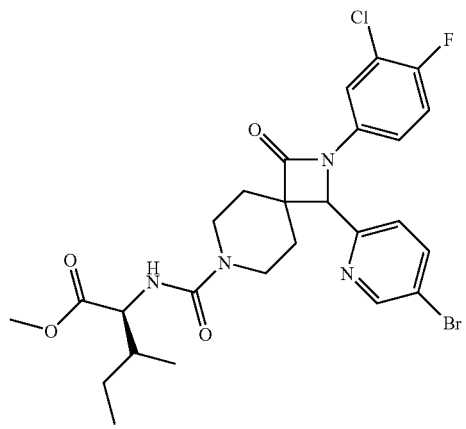 | 100 |
| | | 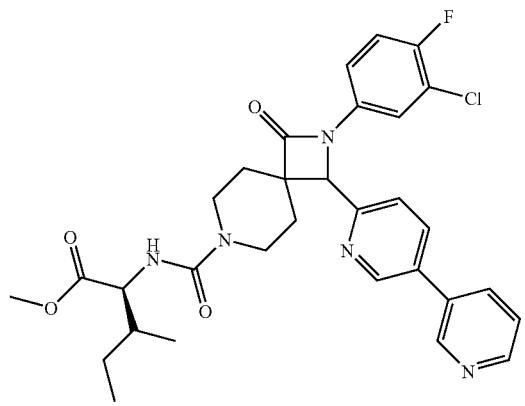 | 577 |
| | | 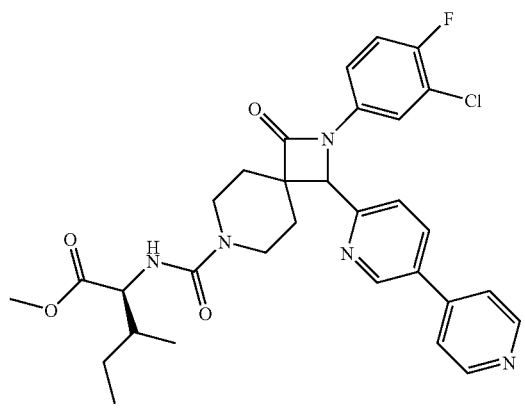 | 634 |

| isomer A | isomer B | Structure | IW hCav3 2 IC50 nM |
|---|---|---|---|
| | | 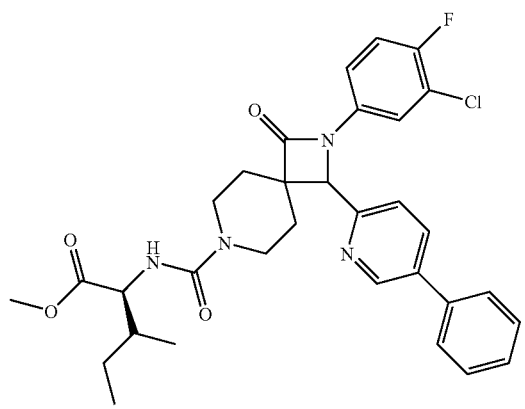 | 84 |
| | | | 136 |
| | | 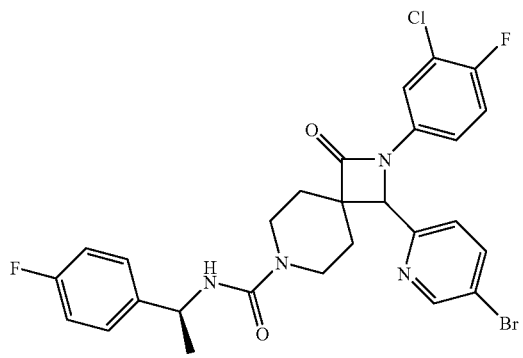 | 52.5 |
| | | 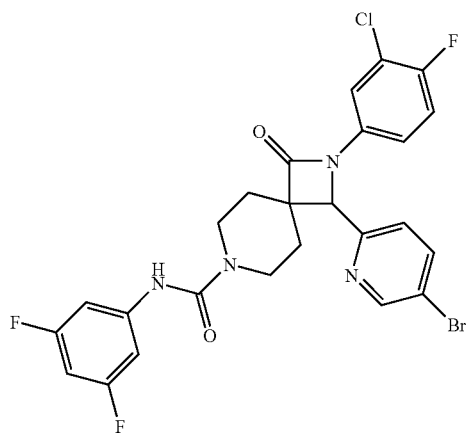 | |

| isomer A | isomer B | Structure | IW hCav3 2 IC50 nM |
|---|---|---|---|
| | | 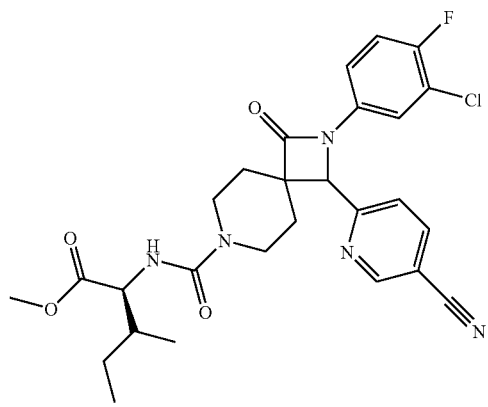 | 260 |
| | | 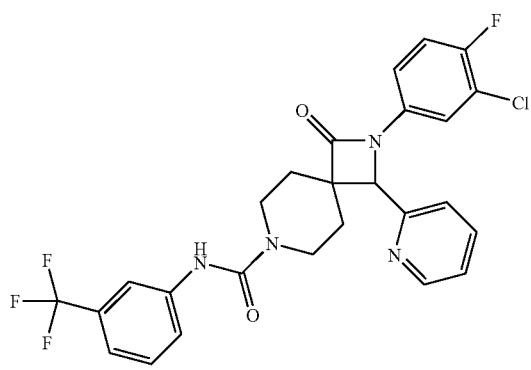 | 4.33 |
| | | 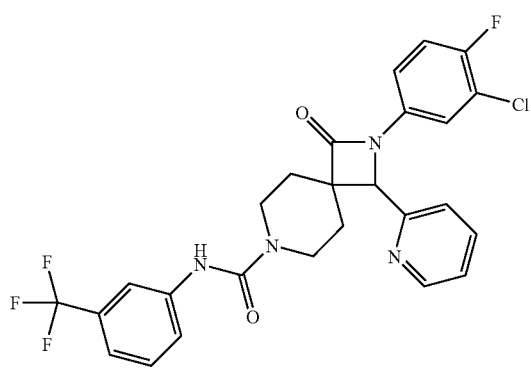 | 83 |
| | | 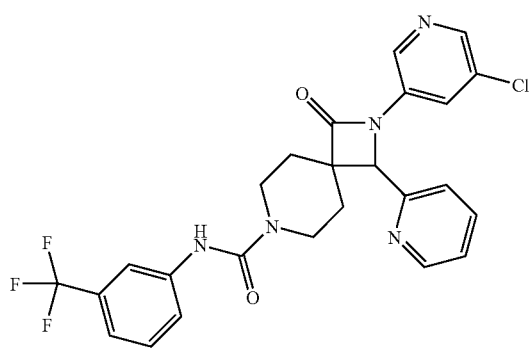 | 155 |

| isomer A | isomer B | Structure | IW hCav3 2 IC50 nM |
|---|---|---|---|
| | | 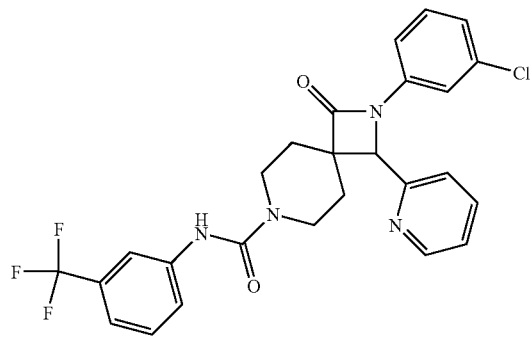 | 95.5 |
| | | 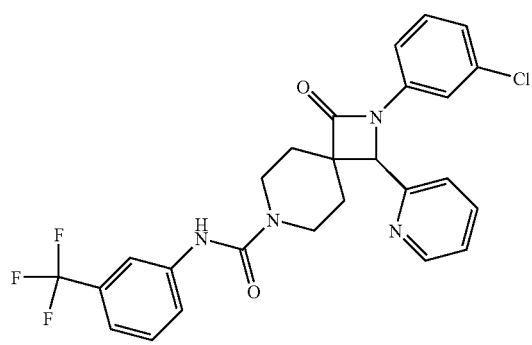 | 19.5 |
| | | 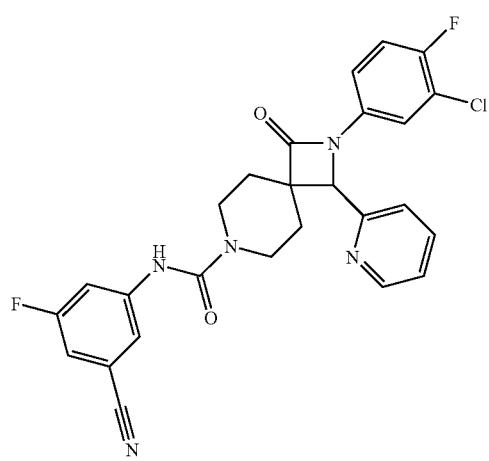 | 17.5 |
| | | 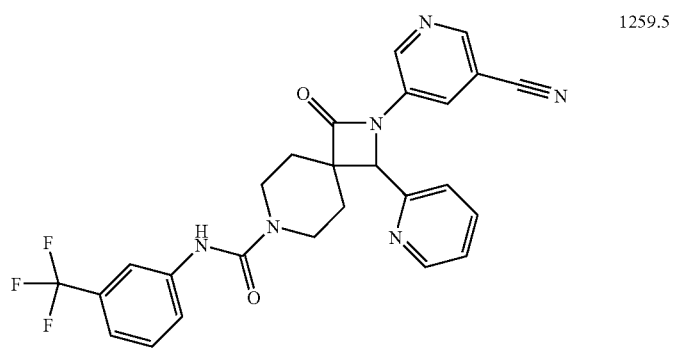 | 1259.5 |

-continued
| isomer A | isomer B | Structure | IW hCav3.2 IC50 nM |
|---|---|---|---|
| | | 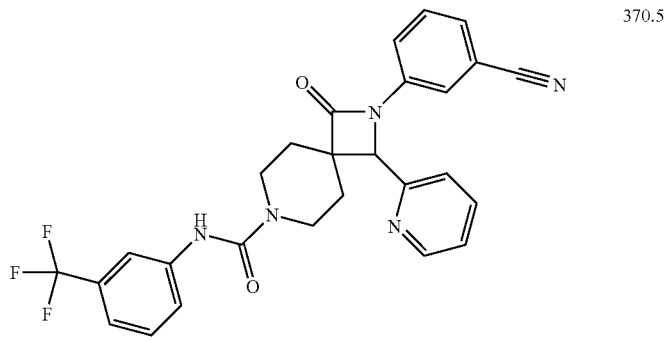 | 370.5 |
| | | 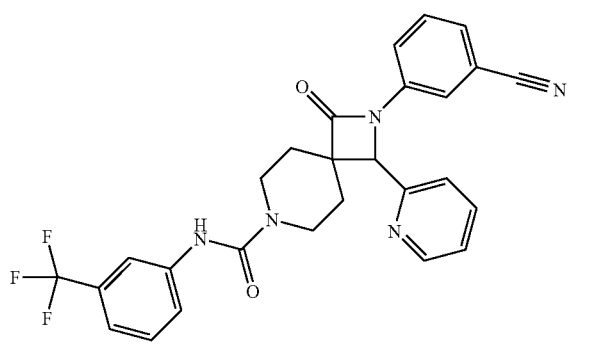 | 51 |
| | | 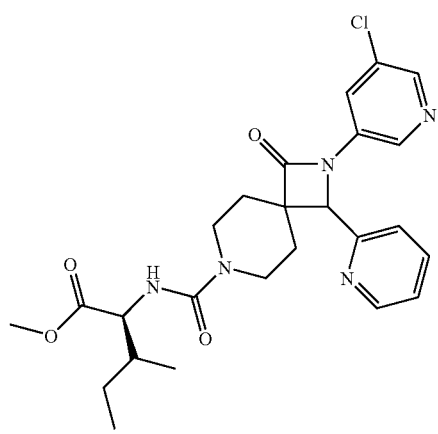 | |
| | | 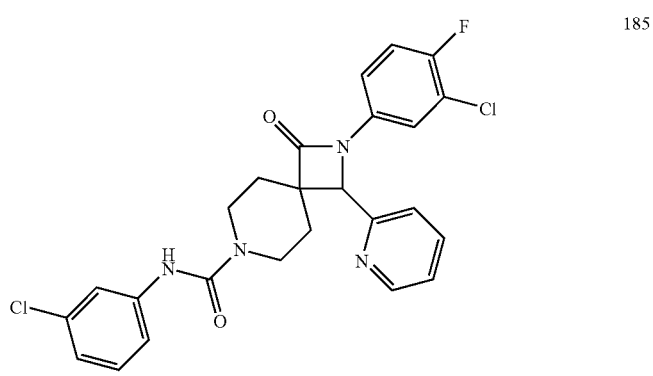 | 185 |

| isomer A | isomer B | Structure | IW hCav3 2 IC50 nM |
|---|---|---|---|
| | | 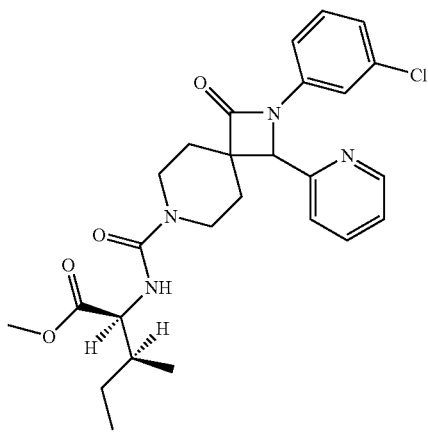 | 583.5 |
| | | 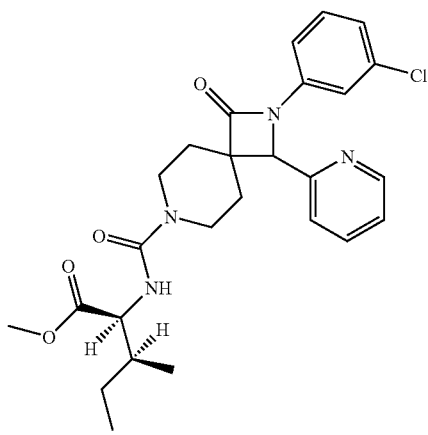 | 635 |
| | | 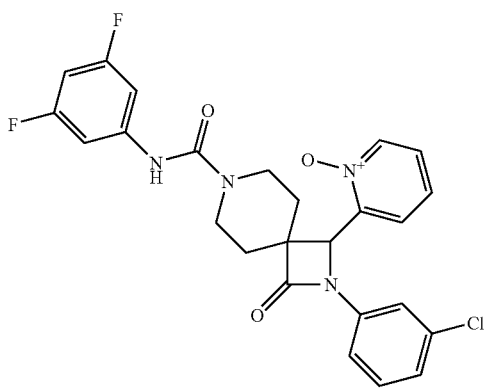 | 157 |

-continued
| isomer A | isomer B | Structure | IW hCav3 2 IC50 nM |
|---|---|---|---|
| | | 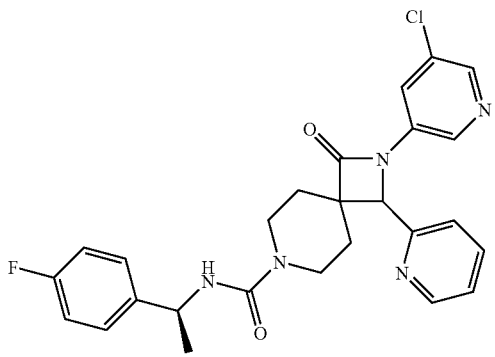 | 3240 |
| | | 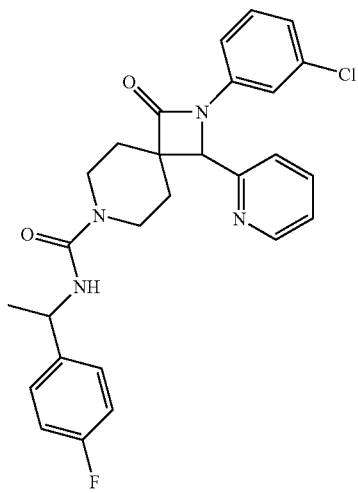 | 744.5 |
| | | 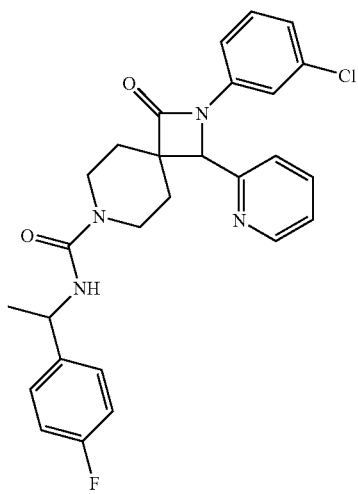 | 190.5 |

-continued
| isomer A | isomer B | Structure | IW hCav3 2 IC50 nM |
|---|---|---|---|
| | | 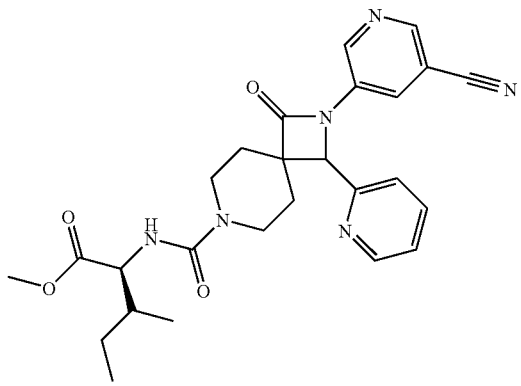 | |
| | | 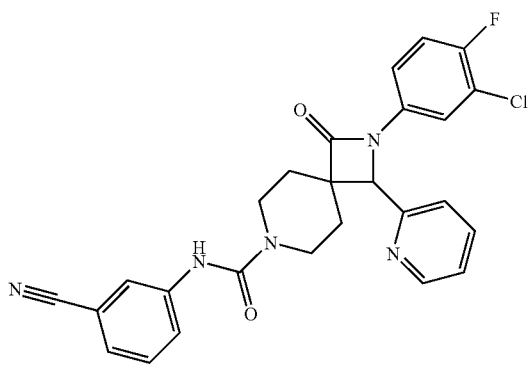 | 358 |
| | | 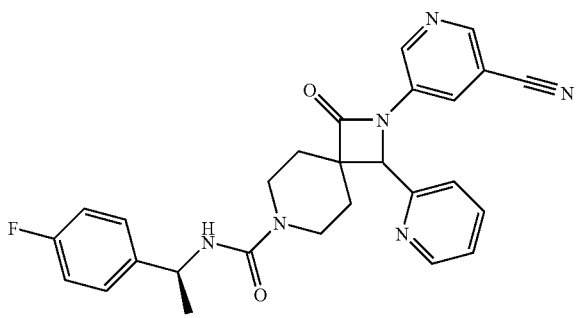 | |
| | | 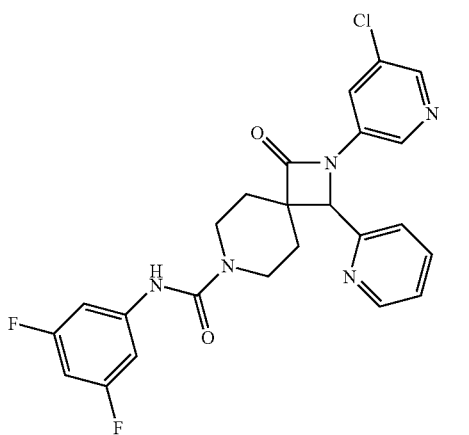 | 518.5 |

| isomer A | isomer B | Structure | IW hCav3 2 IC50 nM |
|---|---|---|---|
| | | 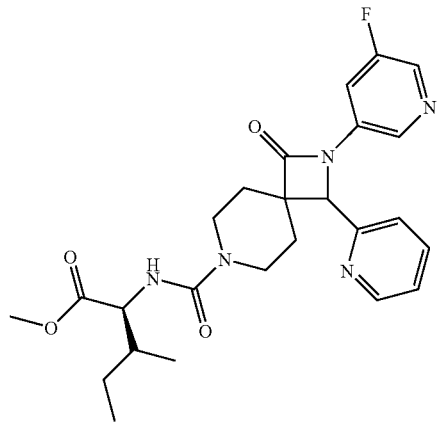 | |
| | | 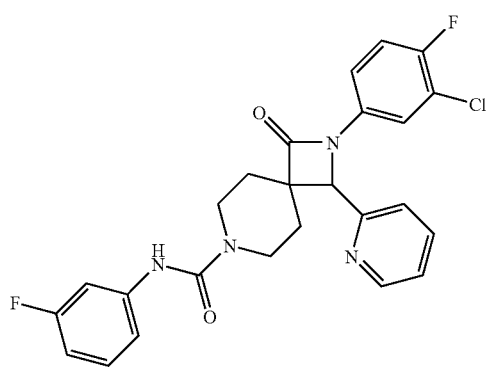 | 370.5 |
| | | 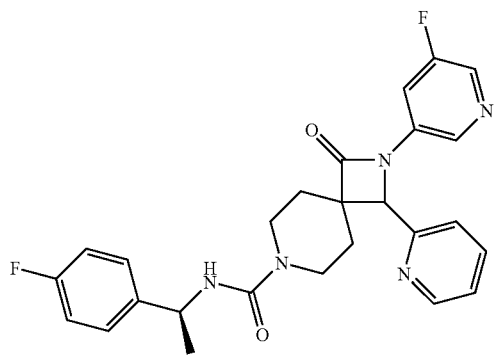 | |
| | | 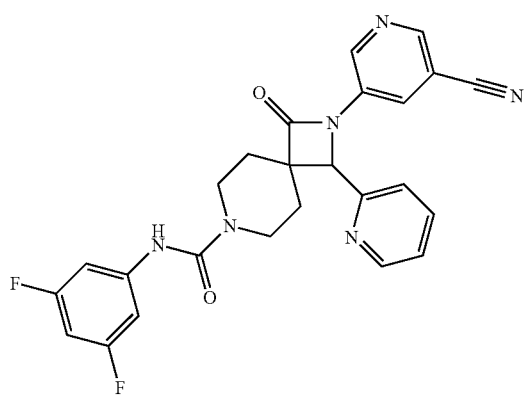 | 2376.5 |

| isomer A | isomer B | Structure | IW hCav3 2 IC50 nM |
|---|---|---|---|
| | | | 732 |
| | | | 247 |
| | | | 1481.5 |
| | | | 2104.5 |

-continued
| isomer A | isomer B | Structure | IW hCav3 2 IC50 nM |
|---|---|---|---|
| | | 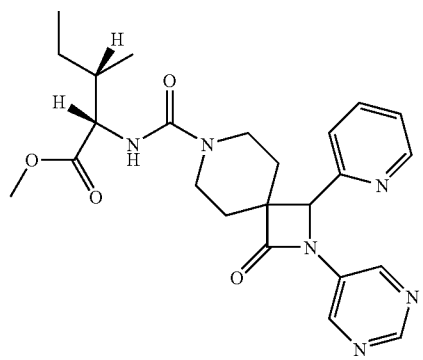 | 2607 |
| | | 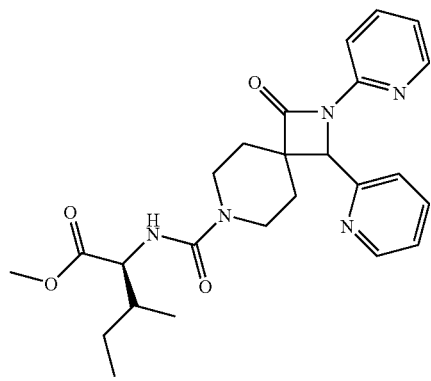 | |
| | | 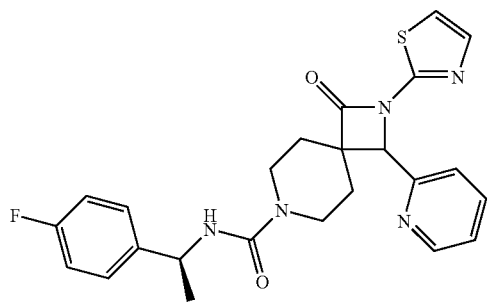 | |
| | | 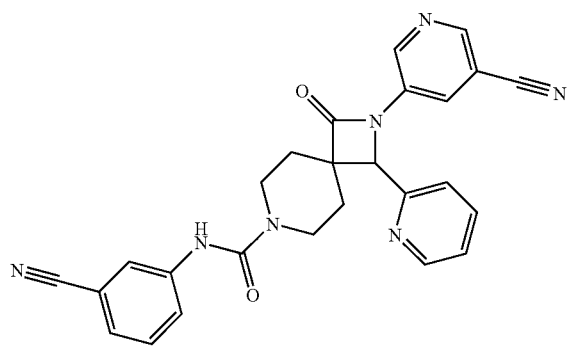 | |

-continued
| isomer A | isomer B | Structure | IW hCav3 2 IC50 nM |
|---|---|---|---|
| | | 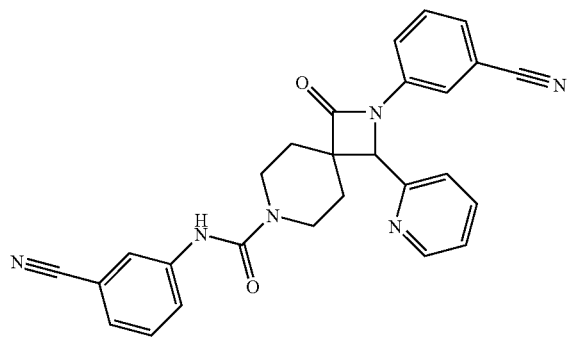 | 2913.5 |
| | | 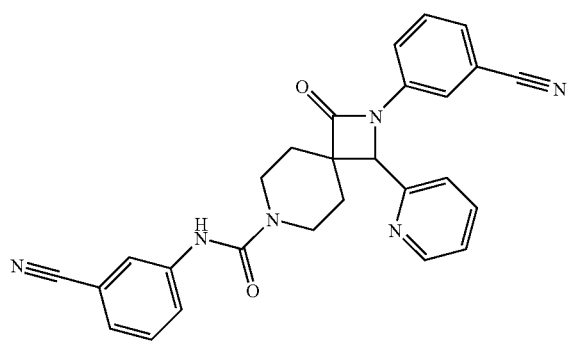 | 1174.5 |
| | | 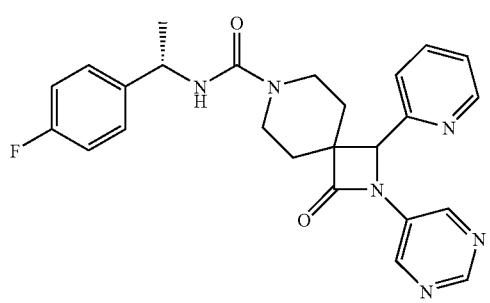 | 2014.75 |
| | | 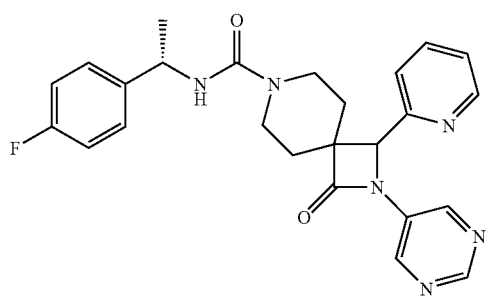 | |

| isomer A | isomer B | Structure | IW hCav3 2 IC50 nM |
|---|---|---|---|
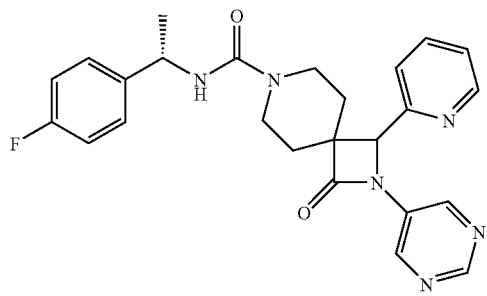
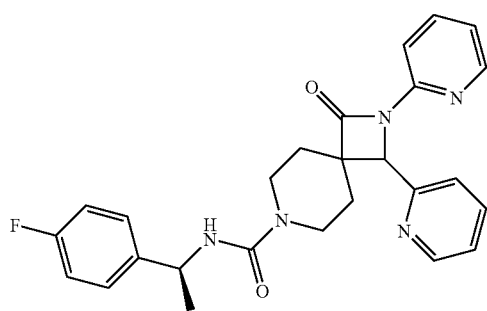
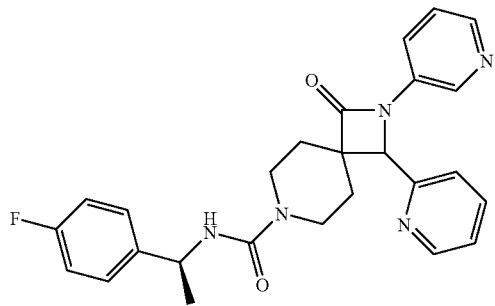
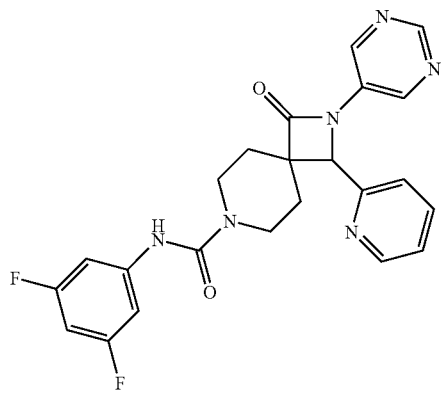

-continued
| isomer A | isomer B | Structure | IW hCav3 2 IC50 nM |
|---|---|---|---|
| | | 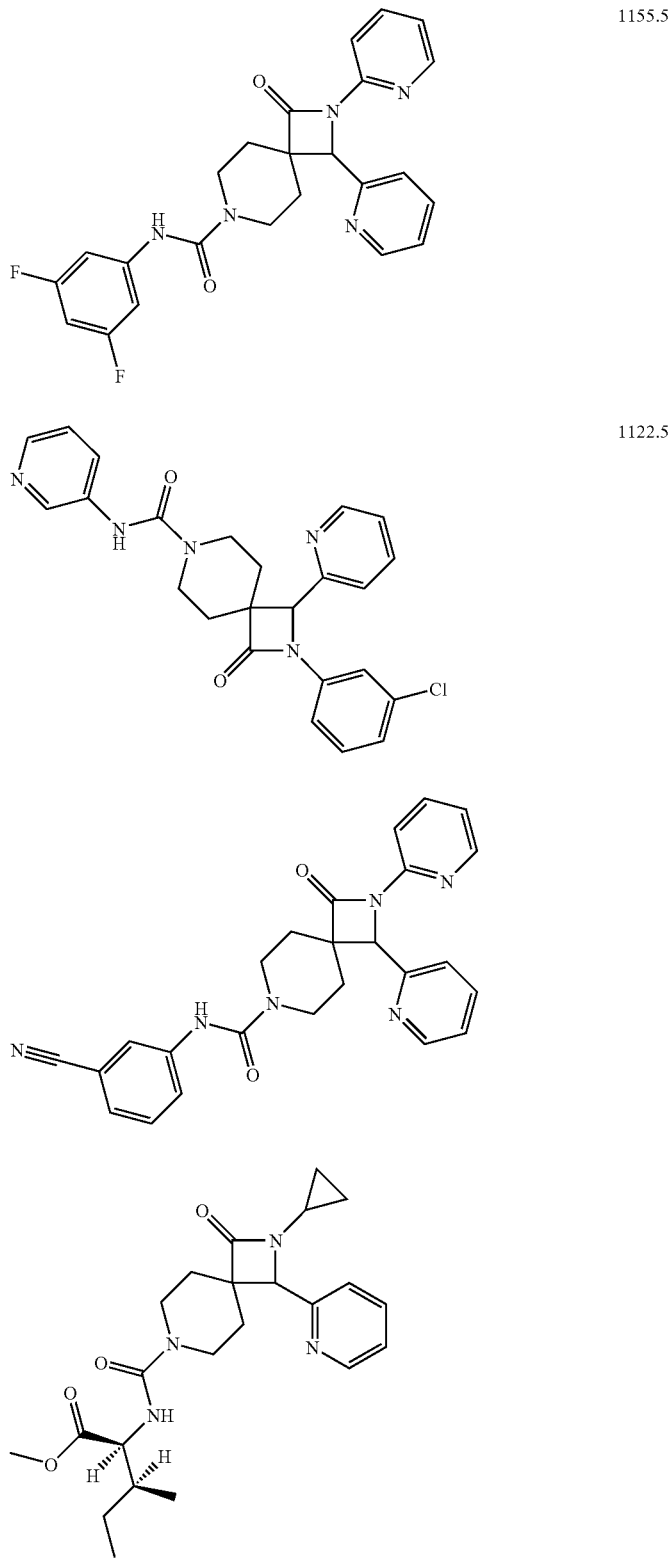 | 1155.5 |
| | | | 1122.5 |
| | | | |
| | | | |

| isomer A | isomer B | Structure | IW hCav3 2 IC50 nM |
|---|---|---|---|
| | | 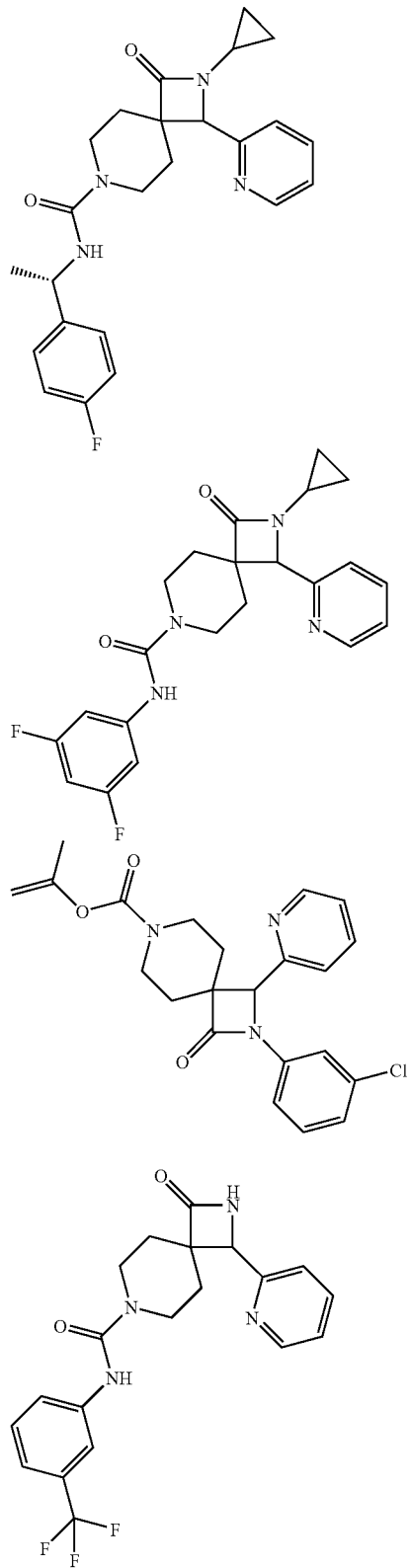 | |

| isomer A | isomer B | Structure | IW hCav3 2 IC50 nM |
|---|---|---|---|
| | | 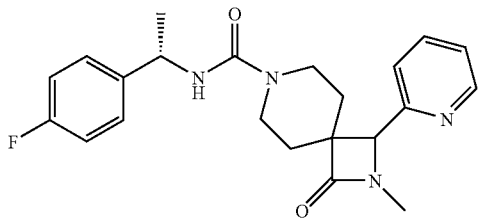 | |
| | | 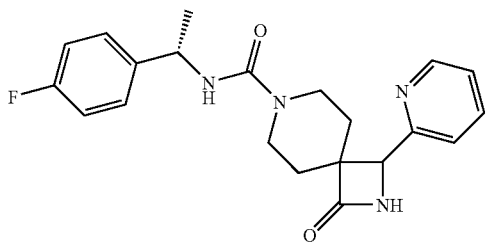 | 225 |
| | | 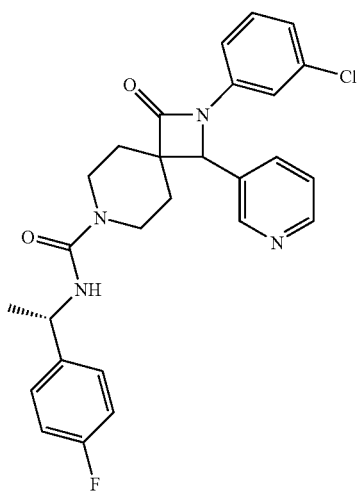 | 45 |
| | | 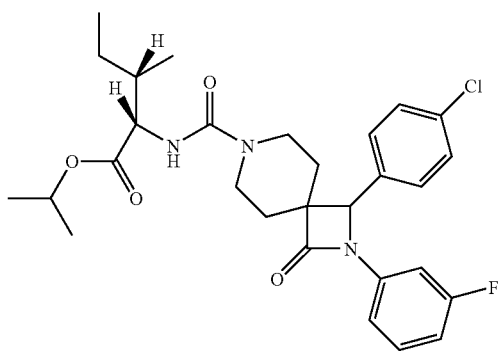 | |

-continued
| isomer A | isomer B | Structure | IW hCav3 2 IC50 nM |
|---|---|---|---|
| | | 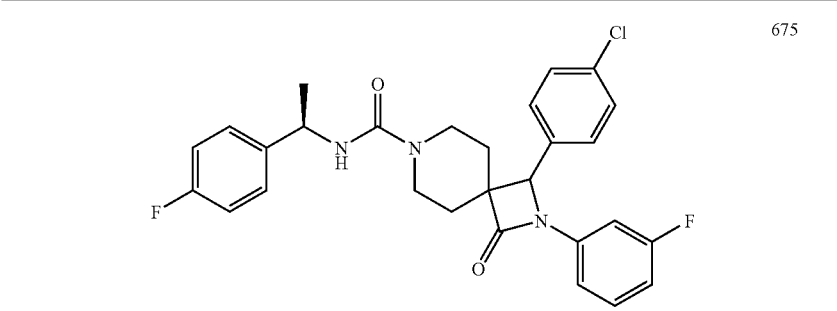 | 675 |
| | | 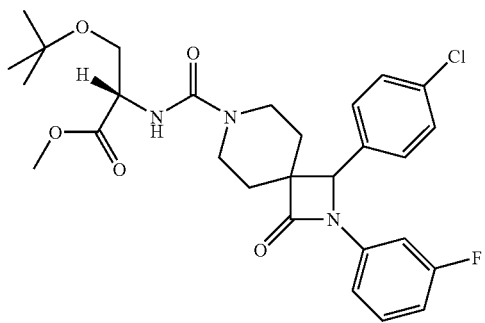 | 251 |
| | | 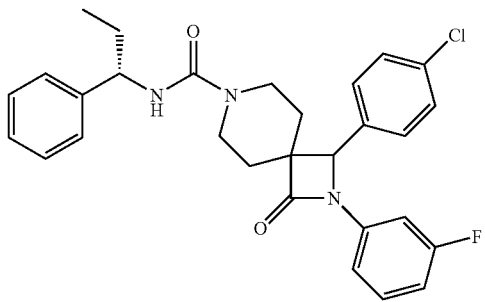 | 224 |
| | | 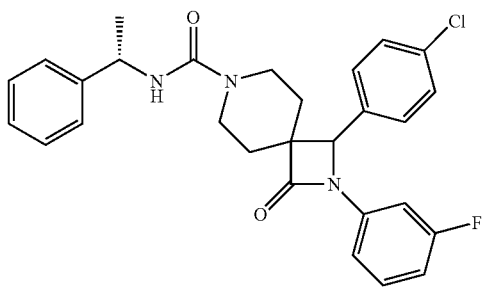 | 139 |

-continued
| isomer A | isomer B | Structure | IW hCav3 2 IC50 nM |
|---|---|---|---|
| | | 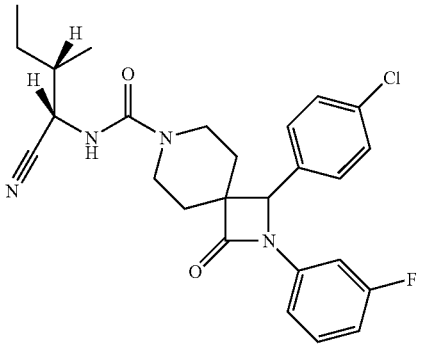 | 35 |
| | | 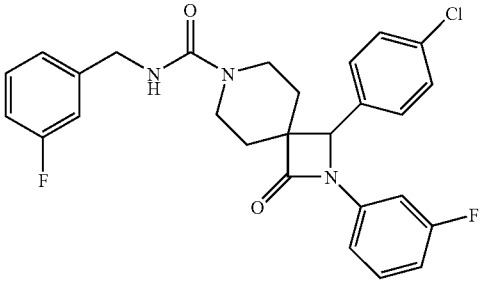 | 538 |
| | | 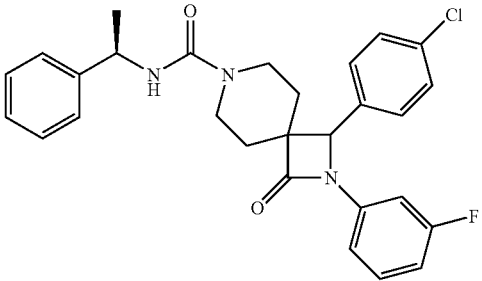 | 351 |
| | | 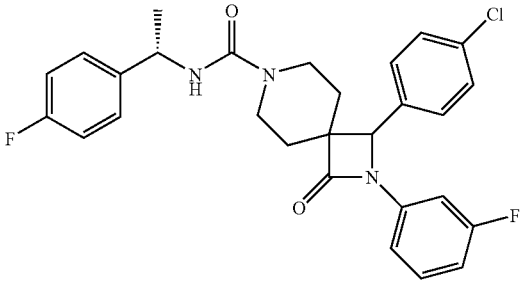 | 82 |
| | | 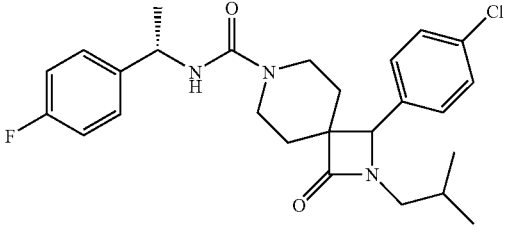 | 1830 |

-continued
| isomer A | isomer B | Structure | IW hCav3 2 IC50 nM |
|---|---|---|---|
| | | 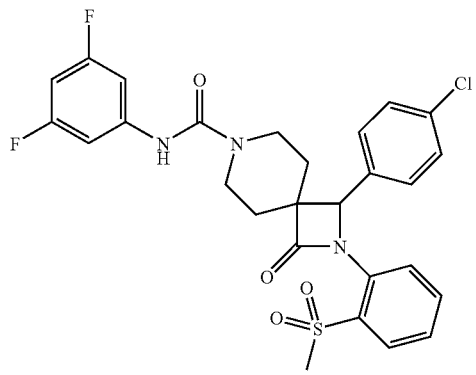 | 94 |
| | | 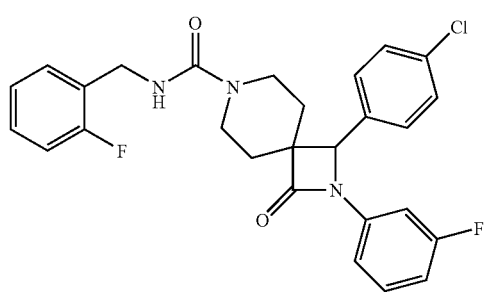 | 269 |
| | | 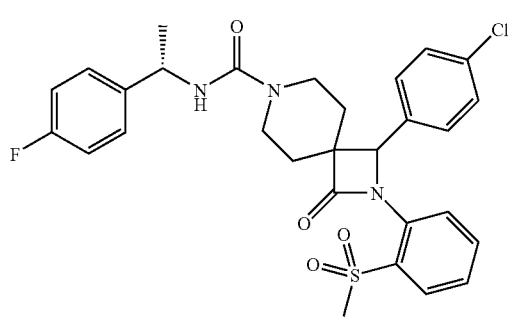 | 611 |
| | | 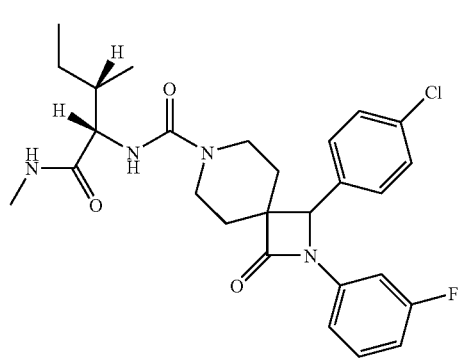 | 182 |

-continued
| isomer A | isomer B | Structure | IW hCav3 2 IC50 nM |
|---|---|---|---|
| | | 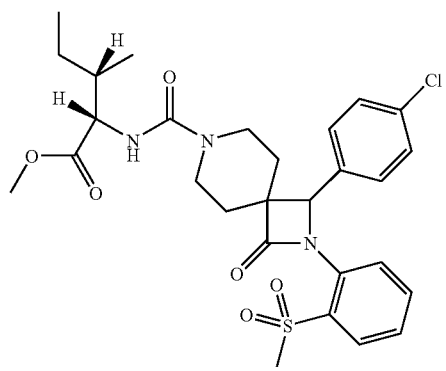 | 109 |
| | | 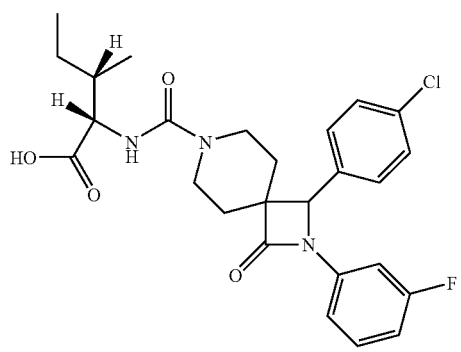 | 965 |
| | | 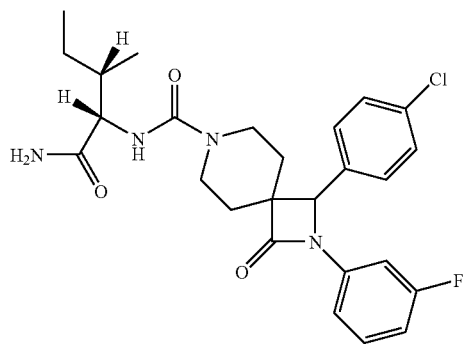 | 827 |
| | | 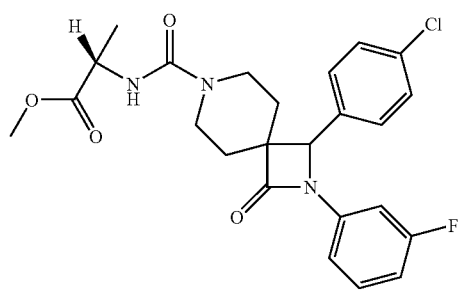 | |

-continued
| isomer A | isomer B | Structure | IW hCav3 2 IC50 nM |
|---|---|---|---|
| | | 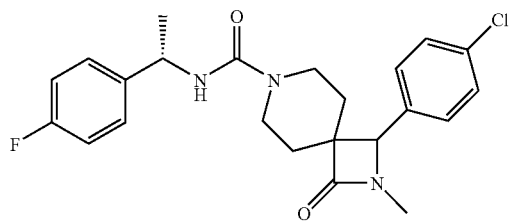 | |
| | | 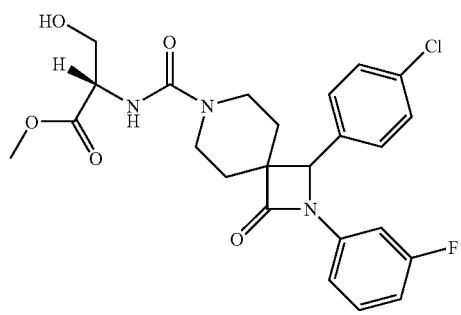 | |
| | | 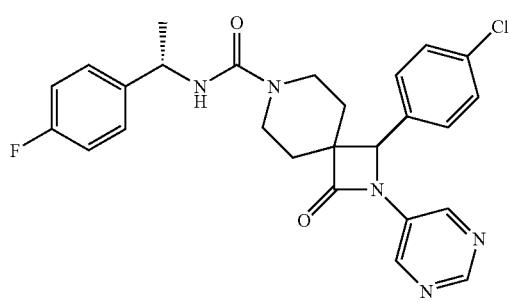 | 2330 |
| | | 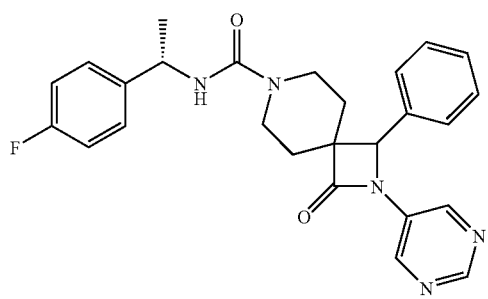 | |
| | | 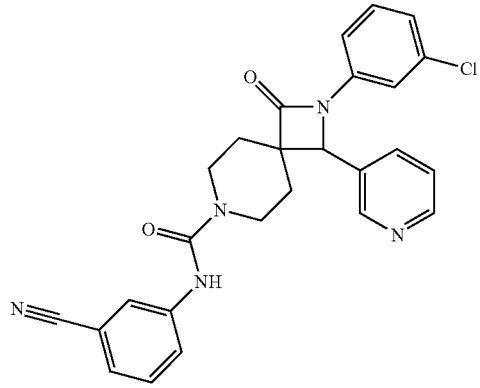 | 124 |

-continued
| isomer A | isomer B | Structure | IW hCav3 2 IC50 nM |
|---|---|---|---|
| | | 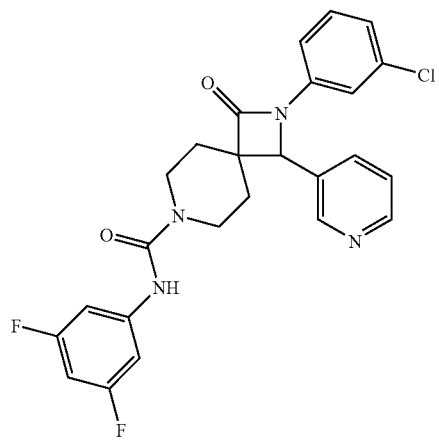 | 21 |
| | | 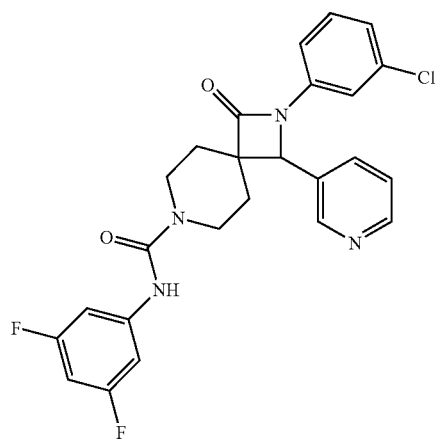 | 420 |
| | | 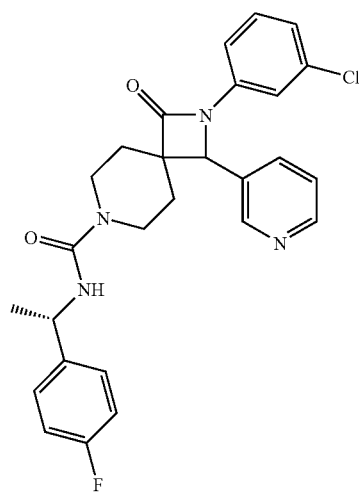 | 669 |

-continued
| isomer A | isomer B | Structure | IW hCav3 2 IC50 nM |
|---|---|---|---|
| | | 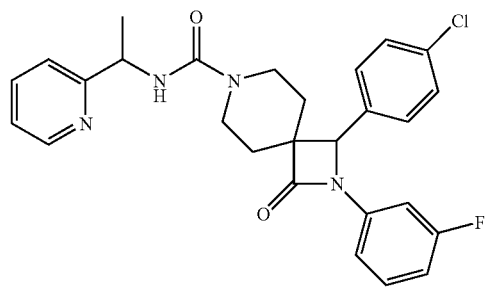 | 2174 |
| | | 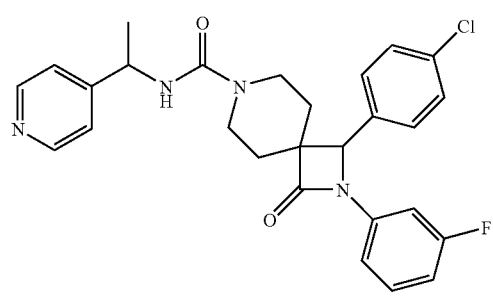 | 694 |
| | | 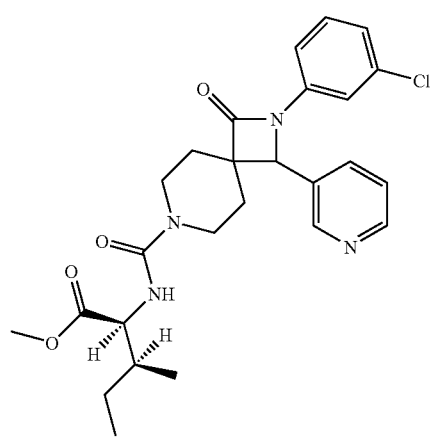 | 880 |
| | | 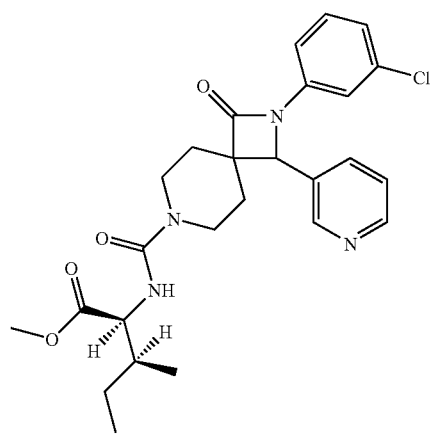 | 1297 |

-continued
| isomer A | isomer B | Structure | IW hCav3 2 IC50 nM |
|---|---|---|---|
| | | 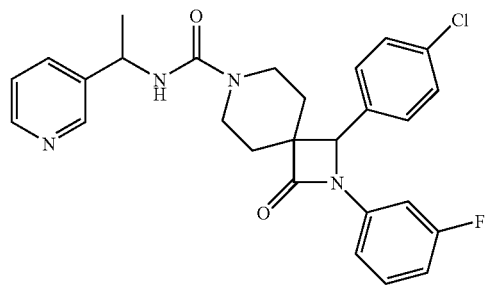 | 2458 |
| | | 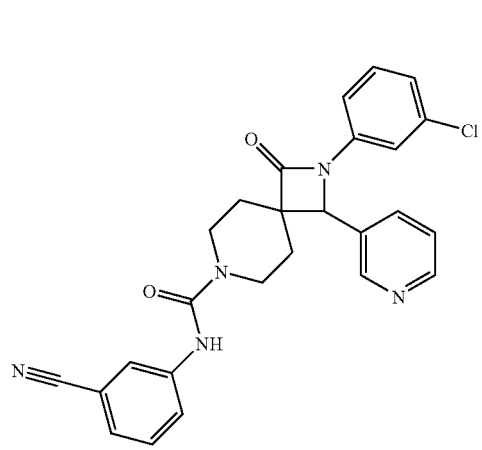 | 1660 |
| | | 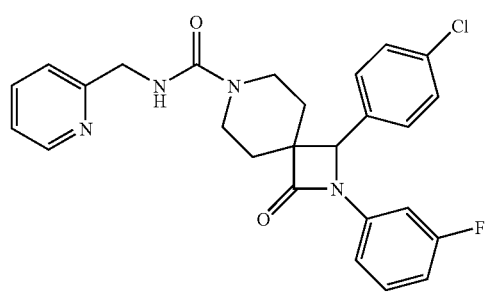 | 1333 |
| | | 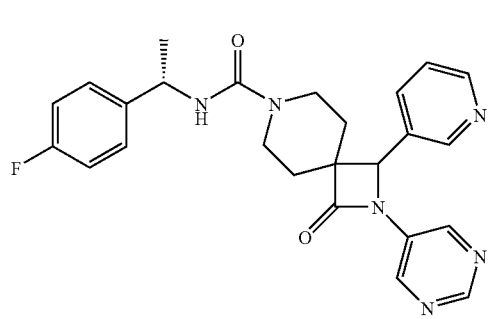 | 2588 |

-continued
| isomer A | isomer B | Structure | IW hCav3.2 IC50 nM |
|---|---|---|---|
| | | 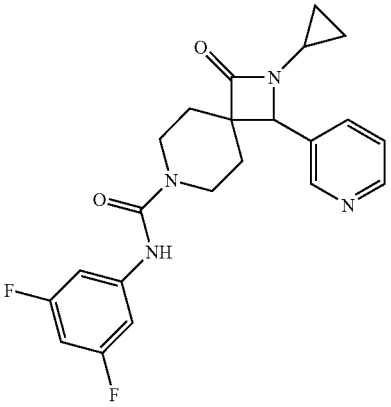 | |
| | | 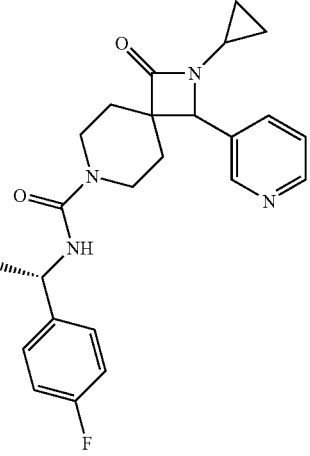 | |
| | | 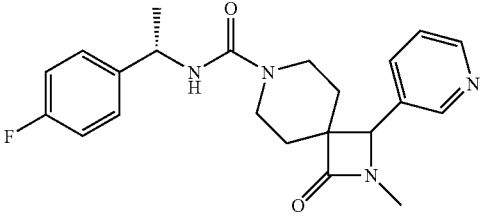 | |
| | | 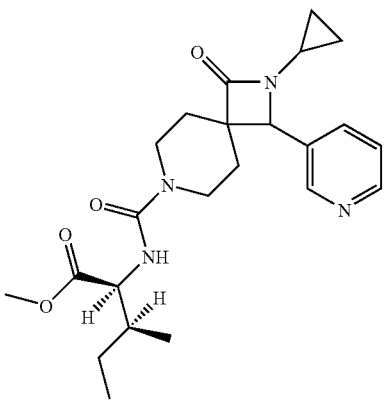 | |

Conventional Whole Cell Patch Clamp

Cells are plated onto 9 mm diameter circular coverglass in the appropriate growth medium and placed in a 37° C. incubator until used. Whole cell patch clamp studies are conducted at room temperature using conventional methods. PCLAMP software (v8 or 9) is used in conjunction with a compatible A/D D/A board, a Pentium III personal computer and either a Multiclamp 700 or an AxoPatch 1D amplifier can be used to generate voltage clamp protocols, acquire data and measure currents.

At the time of study, a piece of coverglass with attached cells is transferred to a recording chamber on the stage of an inverted microscope and the whole cell configuration of patch clamp is established. The recording chamber is gravity perfused with extracellular solution at a flow rate of approximately 3 mL/min. Patch electrodes should have resistances of 2-3 M$\Omega$ when filled with pipette solution. The extracellular solution used is a HEPES-buffered saline (NaCl (149 mM), HEPES-NaOH (10 mM, pH 7.4), glucose (10 mM), CsCl (5 mM), $MgCl_2$ (2 mM), $CaCl_2$ (5 mM). The pipette solution contained: CsCl (115 mM), HEPES-CsOH (10 mM, pH 7.3), MgATP (4 mM), EGTA (10 mM); osmolarity to 310 mM with sucrose. All solutions contain 0.1% DMSO.

The holding potential is -100 mV for all protocols. Interpulse interval is 15 seconds. The time course of $hCa_V3.2$ or $rCa_V3.2$ current is examined with a 200 millisecond test pulse to -35 mV. $Ca_V3.2$ currents are measured as the peak current 10-30 milliseconds after the voltage was stepped to -35 mV. P/N 4 leak subtraction is used. The amplifier low pass filter was set to 10 kHz and the data were sampled at 10 kHz. Data are filtered offline with a Gaussian filter with a -3 dB cutoff of 280 Hz. The voltage protocol for hCaV2.1 currents should differ only in terms of the voltage for the depolarizing test potential. For $hCa_V2.1$, currents are activated with a 200 millisecond step to 0 mV. $hCa_V2.1$ currents are measured from the leak-subtracted traces as the average current between 190 and 200 milliseconds after the step to 0 mV. The voltage protocol for sodium currents includes a 150 millisecond hyperpolarizing pulse to -140 mV to optimize channel availability, followed by a 20 millisecond test pulse to -20 mV. Sodium currents are measured from leak subtracted traces as the peak transient inward current.

All drug effects are measured after a steady-state effect is achieved. Concentration-effect relationships are derived by exposing each cell to only a single concentration of test article. For non-linear regression analysis the post-compound current amplitude is normalized to the pre-compound current amplitude for each cell. If a given current is inhibited by >50% at a concentration of 10 μM or less, the data for multiple concentrations of compound and corresponding vehicle and time control cells are entered into GraphPad Prism (v 4) for non-linear regression analysis to determine the $IC_{50}$.

Example 24

TRPV1 Screening Assay

Materials:
1) Cell line: HEK293-Tet$^{OFF}$-TRPV1
2) Media: MEM (Invitrogen)
3) 10% Tet-FBS (Clontech #8630-1)
4) Fungizone (Gibe #15290-018 (100X))
5) Penn/Strep (Gibco #15140-122 (100X))
6) Geneticin (Gibco #10131-027 (100X))
7) Hygromycin (Clontech #8057-1)
8) Doxycycline (Clontech #8634-1)
9) Trypsin/EDTA (Gibco #25200-056)
10) 100 mm cell culture plates (Falcon #3003)
11) 96-well poly-D-lysine plates (Fisher #08-774-256)
12) Hank's Balanced Salt Solution (HBSS) (GIBCO #14025-092)
13) HEPES Buffer (GIBCO #15630-080)
14) 30% BSA (Research Organics #1334A)
15) Probenecid (Sigma P-8761)
16) Fluo-4, AM (50 μg) (Molecular Probes F-23917)
17) Pluronic F-127 20% (Molecular Probes P-3000).
18) capsazepine (Sigma C-191)
19) capsaicin (Sigma M-2028)
20) compound plates (NUNC #442587)
21) black pipet tips 96-well FLIPR (Robbins Scientific 1043-24-0)
22) Additional reagents available from Fisher: methanol, DMSO, NaOH Reagent Preparation:

1) Cells: HEK293-Tet$^{OFF}$-TRPV11
   Growth Media: MEM
   10% Tet-FBS
   Fungizone
   Penn/Strep
   Geneticin Add fresh to culture: Hygromycin 25 μg/mL final
   and Doxycycline 2.5 μg/mL final (from a 1000× stock in PBS)
   Cells must be fed and/or split every 2-3 days (to maintain transcriptional repression with Doxycycline).
   Must be split no more than 1:5 (50-75% confluency) to maintain growth and viability.
   Grown on regular tissue culture plates (e.g Falcon 3003-100 mm)
   Split cells via Trypsin/EDTA: incubate with trypsin at room temperature no longer than 5 minutes (HEK293 cells have a tendency to ball up if over trypsinized).
   Two days prior to assay, the cells are split into 96-well plates in cell media in the absence of doxycycline at a concentration of 40,000 cells/well in a volume of 200 μL.

2) FLIPR buffer is prepared fresh:
   500 mL Hank's Balanced Salt Solution (HBSS)
   10 mL of 1M HEPES Buffer pH 7.2
   16.6 mL of 30% BSA
   Add 5 mL of Probenecid Solution, prepared as follows: 710 mg of probenecid (Sigma P-8761) is solubilized in 5 mL of 1N NaOH, 5 mL of above buffer is added for final volume of 10 mL. (of which 5 mL goes back into FLIPR buffer)

3) Dye Preparation:
   Fluo-4, AM (50 μg) is reconstituted in 22 μL of DMSO.
   22 μL of Pluronic F-127 20% is added.
   Combine 42 μL of dye mixture with 11 mL of FLIPR buffer/96-well plate.

4) Competitive Antagonist preparation:
   capsazepine (5 mg) in 1.3 mL of MeOH=10 mM solution ($IC_{50}$~500 nM).

5) Agonist Preparation:
   Stock solution of 0.1 M capsaicin is prepared in MeOH (50 mg+1.6 mL MeOH). Store 50 μL aliquots at -80° C.
   For assay:
   a) Dilute stock by adding 0.8 μL into 1 mL of MeOH (final=80 uM).

b) Add 50 μL of diluted stock to 20 mL of FLIPR buffer (final=0.2 uM)
c) Agonist solution is added 150 μL/well to 96-well plate.
d) Final agonist concentration on cells will be 50 nM. (~$EC_{80}$)

6) Compound Plate preparation:
   a) Compound plate is filled with 150 μL/well of FLIPR buffer
   b) 3 μL of compound mixtures (1 mg/mL) is added to each well (represents a 3× solution and final DMSO=0.67%)

Assay Procedure:
1) Media is removed from cells grown in 96-well dishes.
2) 100 μL of Fluo-4 containing FLIPR buffer in pipetted into each well.
3) Plates are incubated for 30-60 minutes at 37° C. in 5% $CO_2$ incubator.
4) Plates are then washed three times with 100 μL of FLIPR buffer.
5) 100 μL of FLIPR buffer is left in each well and plate is incubated at 37° C. for at least 20 minutes.
6) Signal of dye-labeled plate is initially determined using laser at 0.300 W with an exposure time of 0.4 seconds. Laser is adjusted upwards for an average signal≧10,000/well and less than 10% variability.

7) Compound addition conditions are as follows:
FLIPR setup (dual sequence parameters):
Sequence 1:
First interval 1 sec/60 counts
    Second interval 6 sec/50 counts
    Fluid addition=50 μL
    Pipettor height 110 μL
    Dispense Speed=30 μL/sec
Sequence 2:
Second interval 1 sec/60 counts
    Second interval 6 sec/40 counts
    Fluid addition=50 μL
    Pipettor height=140 μL
    Dispense Speed=50 μL/sec Data Analysis:
1) Data from both additions is reported as Max-Min for each well Using this method, the following data were obtained for the depicted Azetidinone Derivatives of the present invention:

| isomer | Structure | VR1 flipr PMA IC50 nM | VR1 flipr CAPSAICIN IC50 nM |
|---|---|---|---|
| | 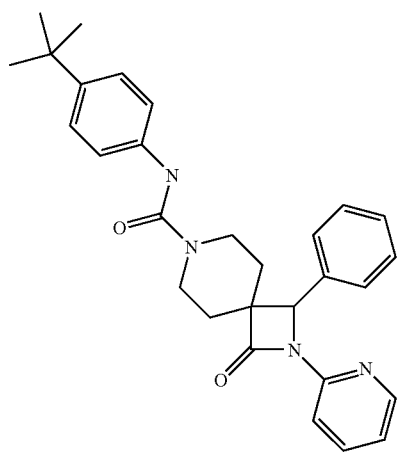 | | 1 |
| A | 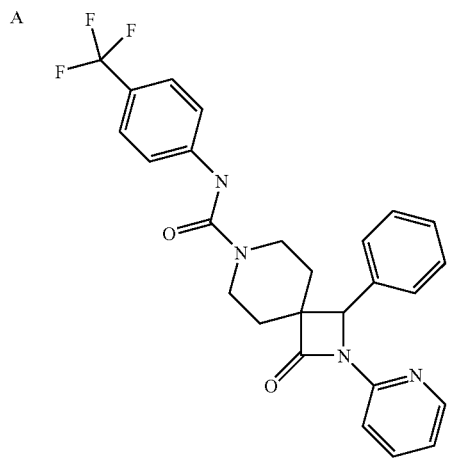 | 7 | 7 |

-continued
| isomer | Structure | VR1 flipr PMA IC50 nM | VR1 flipr CAPSAICIN IC50 nM |
|---|---|---|---|
| B | 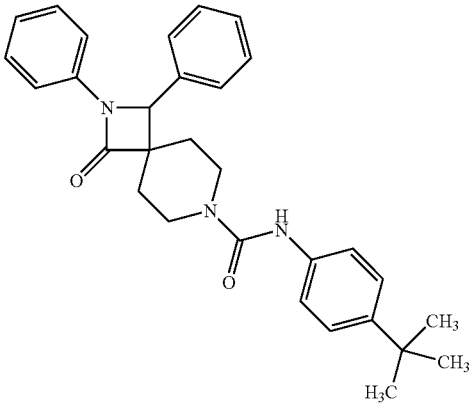 | 12 | 9 |
|  | 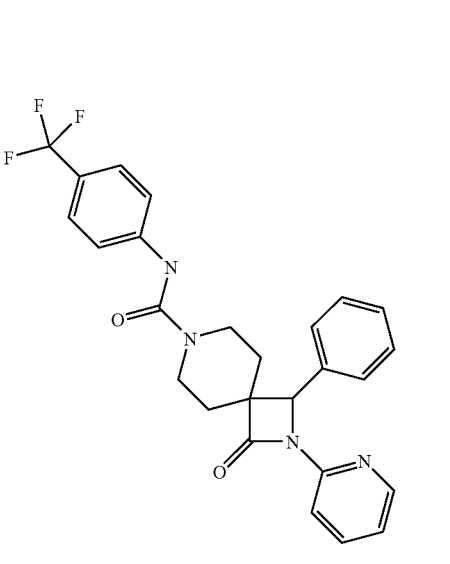 | 16 | 20 |
| A | 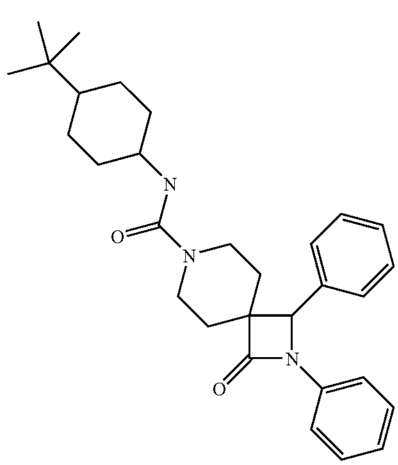 | 31 | 48 |

| isomer | Structure | VR1 flipr PMA IC50 nM | VR1 flipr CAPSAICIN IC50 nM |
|---|---|---|---|
|  | 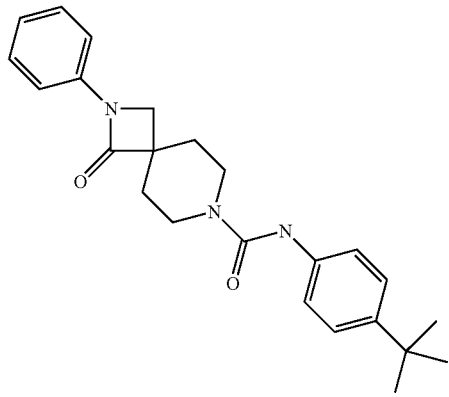 | 59 | 80 |
| A | 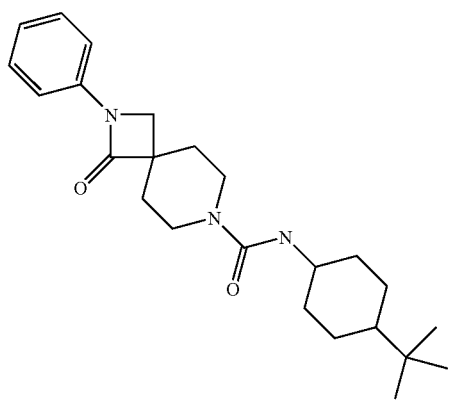 | 123 | 84 |
|  | 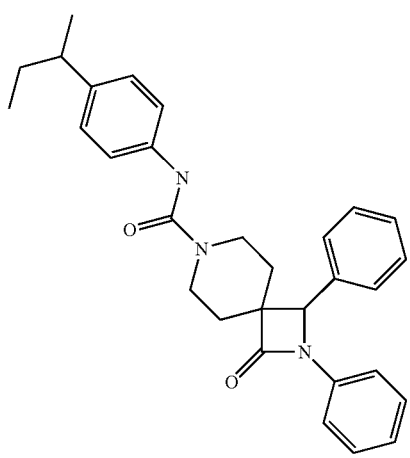 | 81 | 98 |

| isomer | Structure | VR1 flipr PMA IC50 nM | VR1 flipr CAPSAICIN IC50 nM |
|---|---|---|---|
| | | 205 | 315 |
| | | 5 | 504 |
Additional data obtained using this assay for selected compound of the present invention is provided in the following table:
| Structure | rat VR1 % activation @ 3.3 ug/ml compound |
|---|---|
| 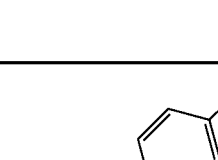 | 98 |

-continued

| Structure | rat VR1 % activation @ 3.3 ug/ml compound |
|---|---|
| (structure) | 61 |
| (structure) | 67 |
| (structure) | 61 |
| (structure) | 75 |

Example 25

Effects of the Azetidinone Derivatives on Pain

The actions of the Azetidinone Derivatives of the present invention for the treatment or prevention of pain can be assessed using various animal models, including but not limited to, those described below:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection, the mouse is immediately put back into the Plexiglas observation chamber (30×20×20 cm) and the nociceptive response of the animal to formalin injection is observed for a period of 60 minutes. The duration of licking and flinching of the injected paw is recorded and quantified every 5 minutes for the total observation period. The recording of the early phase (first phase) starts immediately and lasts for 5 minutes. The late phase (second phase) starts about 10-15 minutes after formalin injection.

L5 and L6 spinal nerve ligation of the sciatic nerve (neuropathic pain mode): The peripheral neuropathy is produced by ligating the L5 and L6 spinal nerves of the right sciatic nerve, based on the method previously described by Kim and Chung (1992). Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In the POST-TREATMENT protocol, rats are tested 3 hours after carrageenan treatment to establish the presence of hyperalgesia and then at different times after drug administration. In the PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioral test): Behavioral tests are conducted by observer blinded to the treatment during the light cycle to avoid circadian rhythm fluctuation. Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioral test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 seconds. The instrument cut-off is fixed at 21 seconds to prevent tissue damage.

Weight bearing (behavioral test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

Example 26

NPC1L1 Binding Assays

HEK-293 cells expressing human NPC1L1 were plated into 384-well black/clear plates (BD Biosciences, Bedford Mass.) for binding experiments the following day. Cell growth media (DMEM, 10% fetal calf serum, 1 mg/mL geneticin, 100 Units/mL penicillin) was aspirated. Cell growth media (20 mL) containing 250 nM BODIPY-labeled glucuronidated ezetimibe was added to each well. Cell growth media (20 mL) containing the indicated concentration of compound was then added to the wells. Unlabeled glucuronidated ezetimibe (100 mM) was used to determine non-specific binding. The binding reaction was allowed to proceed for 4 hours at 37° C. Subsequently the cell growth media was aspirated and the cells washed once with PBS. The remaining fluorescent labeled glucuronidated ezetimibe bound to the cells was quantified using a FlexStation plate reader (Molecular Devices, Sunnyvale Calif.) to measure fluorescence intensity. Ki values were determined from competition binding curves (n=4 for each point) using Prism and Activity Base software.

Using this method, the following data were obtained for the depicted Azetidinone Derivatives of the present invention:

| Compound | NPC1L1 binding rat (nM) | NPC1L1 binding human (nM) | isomer |
|---|---|---|---|
| 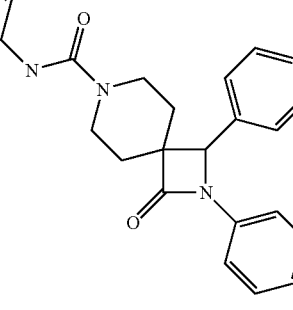 | 1520 | 2125 | |
| 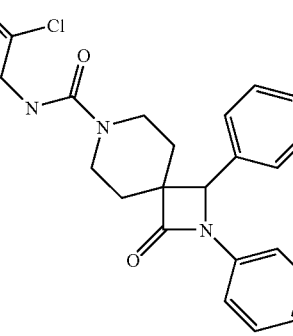 | 782 | 1570 | isomer A |
| 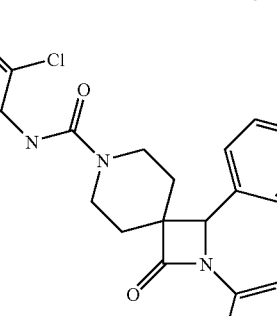 | 18050 | 17600 | isomer B |
| 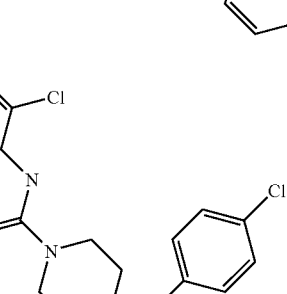 | 5950 | 10095 | |

-continued
| Compound | NPC1L1 binding rat (nM) | NPC1L1 binding human (nM) | isomer |
|---|---|---|---|
| 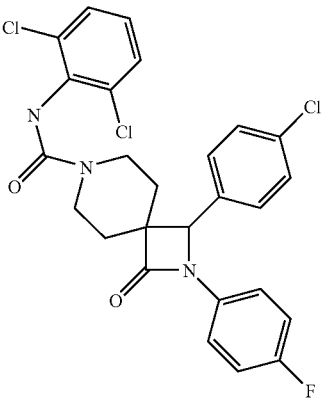 | 4840 | 6410 | |
| 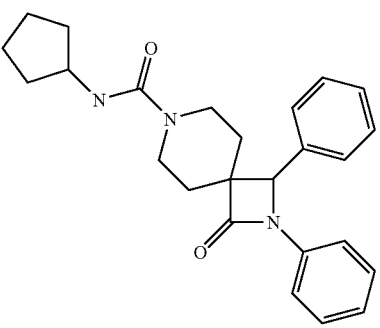 | | 31200 | |
| 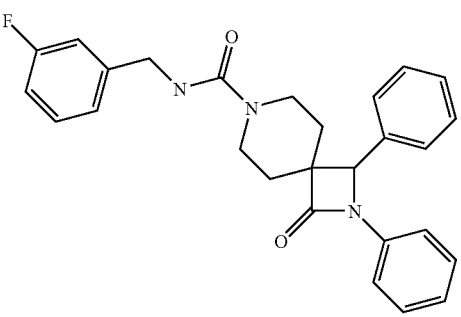 | | 26000 | |
| 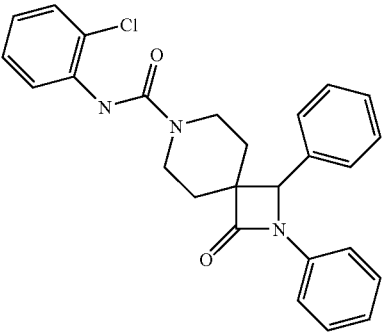 | | 8635 | |

-continued

| Compound | NPC1L1 binding rat (nM) | NPC1L1 binding human (nM) | isomer |
|---|---|---|---|
| [structure: 2-chlorobenzyl urea piperidine spiro azetidinone with phenyl groups] | | 17650 | |
| [structure: cyclohexyl urea piperidine spiro azetidinone with phenyl groups] | | 19700 | |

Example 27

GPR119 Screening Assay

Reagent Preparation

Stimulation Buffer: 100 mL HBSS (GIBCO # 14025-092)
 +100 mg BSA (MP Biomedicals faction V, #103703)=0.1%
 +500 μL 1M HEPES (Cellgro #25-060-Cl)=5 mM
 +75 μL RO-20 (Sigma B8279; 20 mM stock in DMSO stored in aliquots at −20° C.)=15 μM
 (made fresh daily)

B84 (N-[4-(methylsulfonyl)phenyl]-5-nitro-6-[4-(phenylthio)-1-piperidinyl]-4-pyrimidinamine, see WO 2004/065380): A 10 mM stock solution of the test compound in DMSO was prepared, aliquoted and stored at −20° C. For Totals—Dilute 1:33.3 in DMSO then 1:50 in Stimulation Buffer=6 μM in 2% DMSO (=3 μM B84 and 1% DMSO final). For Dose Response Curve–3 μL stock+7 μL DMSO+ 490 μL Stim Buffer=60 μM in 2% DMSO (=30 μM B84 and 1% DMSO final). (made fresh daily).

Cell Line

Human clone 3: HEK 293 cells stable transfected with human-SP9215 (GPR119)/pcDNA3.1 and also stable for pCRELuc, Stratagene. Cells are maintained in DMEM containing 10% FBS (Invitrogen #02-4006Dk, lot #1272302, heat inactivated), 1×MEM, 1× Pen/Strep, 0.1 mg/mL Hygromycin B, and 0.5 mg/mL G418. Cells are split 1:8 twice per week.

cAMP Kit: LANCE™ cAMP 384 kit, Perkin Elmer #AD0263

Compound Dilutions
1. Add DMSO to vials containing compounds to provide a 1 mg/mL solution.
2. Dilute compounds to 60 μM in Stimulation buffer. Make ½ log dilutions into stimulation buffer containing 2% DMSO using the epMotion robot. 10 point dose response curve 1 nM to 30 μM.
3. Compounds are run in quadruplicate, 2 separate dilutions for each, sets 1 and 1a.

Assay Procedure
1. The afternoon before the assay, replace the media in the flask of Human clone 3 cells with Optimem. (Gibco # 11058-021) NOTE: cells should be in culture 6-8 days.
2. Next morning, pipet the cells gently off the flask using HBSS (at room temperature).
3. Pellet the cells (1300 rpm, 7 minutes, room temperature) and resuspend in Stimulation Buffer at 2.5×10e6/mL (=5-8,000 cell/6 μL). Add 1:100 dilution of Alexa Fluor 647-anti cAMP antibody (provided in the kit) directly to the cell suspension.
4. Into white 384-well plates (Matrix) add 6 μL of 2×B84, cmpds or stim buffer for nsb. They all contain 2% DMSO (=1% DMSO final).
Add 6 μL of the cell suspension to the wells. Incubate 30 minutes at room temperature.
For the std curve add 6 μL cAMP std solution diluted in Stim Buffer+2% DMSO according to kit directions (1000-3 nM). Add 6 μL of 1:100 anti-cAMP dilution in Stim Buffer to std wells.

Make Detection Mix according to kit instructions and incubate 15 minutes at room temperature.

Add 12 μL Detection Mix to all the wells. Mix gently by tapping and incubate 2-3 hours at room temperature.

Read on the Envision under the protocol "Lance/Delphia cAMP"

Values (nM) for each sample are determined by extrapolation from the std curve. % Control, Fold and EC50 (Control=3 μM B84) are determined for each compound, averaging sets 1 and 1a.

Using this methods the following data were obtained for the depicted Azetidinone Derivatives of the present invention:

| Compound | GPR119 cAMP IC50 (nM) |
|---|---|
| (structure) | 1000 |
| (structure) | 2000 |
| (structure) | 2280 |

-continued

| Compound | GPR119 cAMP IC50 (nM) |
|---|---|
| (structure) | 2720 |
| (structure) | 3800 |
| (structure) | 4180 |
| (structure) | 4360 |

-continued

| Compound | GPR119 cAMP IC50 (nM) |
|---|---|
| 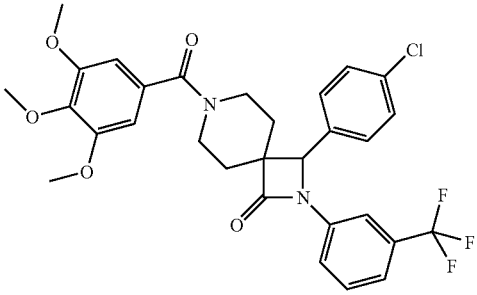 | 4400 |
| 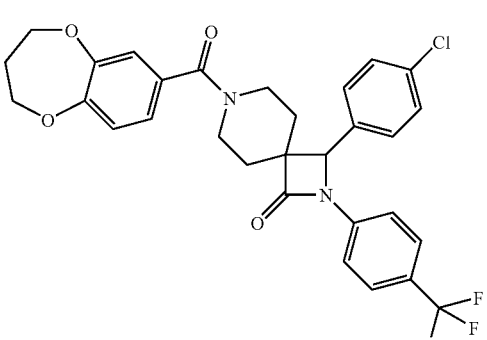 | 4460 |
| 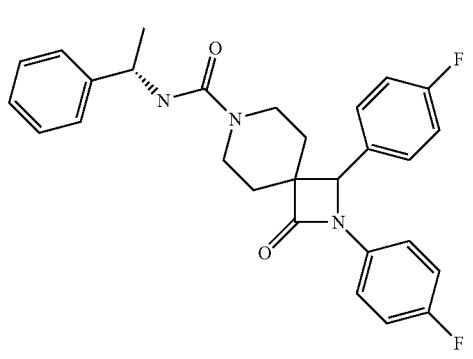 | 4680 |

Example 28

In Vivo Effects of the Azetidinone Derivatives on Inhibition of Cholesterol Absorption Male rats are dosed by oral gavage with 0.25 mL corn oil or test compound in corn oil-30 minutes after dosing, each rat is administered 0.25 mL of corn oil orally with 2 µCi $^{14}$C-Cholesterol, 1.0 mg cold cholesterol. 2 hours later, the rats are anesthetized with 100 mg/kg IP of Inactin, and a 10 mL blood sample is collected from the abdominal aorta. The small intestine is then removed, divided into 3 sections, each section is rinsed with 15 mL of cold saline and the rinses are pooled. The liver is then removed, weighed, and three ~350 mg aliquots are removed. 5 mL of 1N NaSH is added to each intestinal piece, 1 mL to each liver aliquot to dissolve at 40° C. overnight. 2×1 mL aliquots of the SI digests and the liver digests are neutralized with 0.25 mL 4N HCl and counted, 2×1 mL aliquots of plasma and intestinal rinses are counted.

Example 29

Hypothetical In Vivo Evaluation of Demyelination

An Azetidinone Derivative of the present invention can be administered to rodents which have been induced to develop experimental autoimmune encephalomyelitis ("EAE"), a model of human multiple sclerosis and demyelinating disease. Useful rodents include C57BL/6 mice (obtained from the Jackson Laboratory or Charles River Laboratories) immunized with myelin oligodendrocyte protein (MOG) 35-55 peptide, SJL/J (also available from Jackson Laboratory or Charles River Laboratories) mice immunized with proteolipid protein (PLP) peptides, or Lewis, B N or DA rats (obtained from Charles River Laboratories or Harlan Laboratories) immunized with guinea pig spinal cord homogenate or myelin basic protein (MBP). All immunizations are performed by emulsifying the inducing peptide in either incomplete Freund's adjuvant or complete Freund's adjuvant, with or without pertussis toxin administration (as described in *Current Protocols in Immunology*, Unit 15, John Wiley & Sons, Inc. NY, or Tran et al., *Eur. J. Immunol.* 30:1410, 2002 or H Butzkeuven et al., *Nat. Med.* 8:613, 2002).

Other rodents useful in this test include anti-MBP T cell receptor transgenic mice (as in Grewal et al., *Immunity* 14:2911 2001), which naturally develop EAE disease; rodents adoptively transferred with MBP-specific, PLP-specific or MOG-specific T cell lines (as described in *Current Protocols in Immunology*, Unit 15, John Wiley & Sons, Inc. NY); or SJL/J or C57BU6 mice which can be induced to develop a profound demyelinating disease by intracerebral inoculation with Theiler's murine encephalomyelitis virus (as described in Pope et al., *J. Immunol.* 156:4050, 1994) or by intraperitoneal injection of Simliki Forest virus (as described in Soilu-Hanninen et al., *J. Virol.* 68:6291, 1994).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed:

1. A compound having the formula:

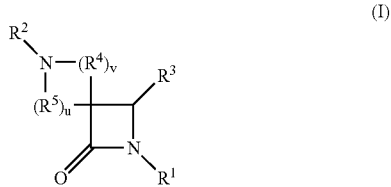

(I)

or a pharmaceutically acceptable salt, ester, prodrug or stereoisomer thereof, wherein:

$R^1$ is H, alkyl, aryl, arylalkyl, heteroaryl, heteroarylalkyl, diphenylmethyl, cycloalkylalkyl, cycloalkyl, cycloalkenyl, heterocycloalkyl, heterocycloalkenyl or -alkylene-C(O)N(alkyl)$_2$, wherein an alkyl, aryl or heteroaryl group can be optionally and independently substituted with one or more of the following groups: —(C=N—O-alkyl)CH₃, —NHC(O)NH₂, —NHC(O)NH(alkyl), —NHC(O)NH(alkyl)₂, —SO₂NH₂, —SO₂NH(alkyl), —SO₂N(alkyl)₂, —CF₃, —OH, -halo, —CN, -alkoxy, —C(O)O-alkyl, —S(O)alkyl, —SO₂-alkyl, or —P(O)(O-alkyl)₂, and an aryl group may further be optionally and independently substituted with one or more alkyl groups;

R² is H, alkyl, cycloalkyl, aryl, arylalkyl, heteroarylalkyl, heterocycloalkyl, heterocycloalkylalkyl, R⁶-A-, alkyl-O—C(O)—, (alkyl)₂N-alkylene-C(O)—, (alkyl)₂-N—C(O)-alkylene-C(O)—, CN-alkylene-C(O)—, alkyl-O-alkylene-C(O)—, alkyl-C(O)-alkylene-C(O)—, alkyl-C(O)—NH-alkylene-C(O)—, alkyl-NH—C(O)—, aryl-NH—C(O)—, alkyl-O—C(O)-alkylene-C(O)—, alkyl-O—C(O)-cycloalkylene-alkylene-, NH₂—C(O)—NH-alkylene-C(O)—, NH₂—C(O)-alkylene-C(O)—, alkyl-C(O)—NH-alkylene-S-alkylene-C(O)—, alkyl-O—C(O)-alkylene-C(O)—, alkyl-S-alkylene-C(O)—, alkyl-C(O)-cycloalkylene-alkylene-C(O)—, alkyl-S-alkyene-, (—NHC(O)alkyl)-C(O)—, alkyl(—C(O)Oalkyl)-NH—C(O)—, or —C(O)-alkylene-N(R⁶)₂—; or alkyl-S-alkylene(—NHC(O)alkyl)-C(O)—, wherein an alkyl or aryl group can be optionally and independently substituted with one or more of the following groups: —(C=N—O-alkyl)CH₃, —NH—C(O)NH-alkyl, —C(O)NH₂, —CN, —C(O)NH-alkyl, —C(O)O-alkyl, —C(O)H, —C(O)OH, —NHC(O)NH₂, —NHC(O)NH(alkyl), —NHC(O)N(alkyl)₂, —SO₂NH₂, —SO₂NH(alkyl), —SO₂N(alkyl)₂, —CF₃, —OH, -halo, haloalkyl, —CN, -alkoxy, —C(O)O-alkyl, —S(O)alkyl, —SO₂-alkyl, or —P(O)(O-alkyl)₂, and an aryl group may further be optionally and independently substituted with one or more alkyl groups;

R³ is H, alkyl, aryl, arylalkyl, arylalkenyl, arylalkynyl, NH-arylalkyl, arylalkoxy, arylthio, arylalkylthio, arylcarbonyl, aryloxy, cycloalkyl, arylsulfonyl, heteroaryl, heteroarylalkyl, heteroarylalkenyl, heteroarylalkynyl, heteroarylalkoxy, heteroaryloxy or heteroarylsulfonyl, wherein an alkyl or aryl group can be optionally and independently substituted with one or more of the following groups: —(C=N—O-alkyl)CH₃, —NHC(O)NH₂, —NHC(O)NH(alkyl), —NHC(O)N(alkyl)₂, —SO₂NH₂, —SO₂NH(alkyl), —SO₂N(alkyl)₂, —CF₃, —OH, -halo, —CN, -alkoxy, —C(O)O-alkyl, —S(O)alkyl, —SO₂-alkyl, or —P(O)(O-alkyl)₂, an aryl group can be optionally and independently substituted with one or more alkyl groups, and a heteroaryl group can be optionally and independently substituted with one or more aryl or heteroaryl groups each occurrence of R⁴ and R⁵ is independently —C(R⁷)₂—, wherein the ring carbon atom of one R⁴ group and the ring carbon atom of one R⁵ group may optionally be joined by a —CH₂—CH₂— group;

each occurrence of R⁶ is independently alkyl, alkenyl, aryl, heteroaryl, cycloalkyl, cycloalkylalkyl, heterocycloalkyl, cycloalkenyl, heterocycloalkenyl, benzofused cycloalkyl, benzofused heterocycloalkyl, or benzofused heterocycloalkenyl;

each occurrence of R⁷ is independently —H, -alkyl, —CN, or —OH;

A is —C(O)—, —OC(O)—, -alkylene-C(O)—, —O-alkylene-C(O)—, —C(O)-alkylene-C(O)—, —C(O)—NHCH₂—C(O)—, —C(O)—N(alkyl)-CH₂—C(O)—, -alkylene-, -alkenylene-, -alkenylene-C(O)—,

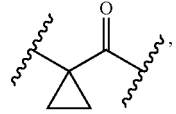

—O—C(O)-alkylene-C(O)—, -cycloalkylene-NH—C(O)—, —NHC(O)—, -alkylene-NHC(O)—, -alkylene-C(O)NH-alkylene-C(O)—, -alkylene-C(O)NH-alkylene-C(O)—, —C(O)—NH-alkylene-C(O)—, -alkylene-O-alkylene-C(O)—, -alkylene(alkoxy)-C(O)— or —S-alkylene-C(O)—, wherein an A group is joined to the nitrogen atom to which it is attached via a terminal C(O), alkylene, or alkenylene group;

u is an integer ranging from 0 to 3; and v is an integer ranging from 0 to 3; such that the sum of u and v is from 3 to 5, such that the compound of formula (I) is not a compound of formula (IA), (IB), (IC) or (ID) as set forth in the above specification.

2. A compound having the formula:

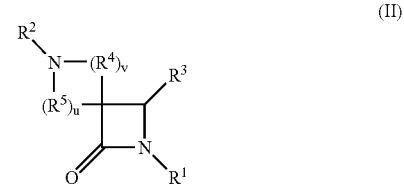

(II)

or a pharmaceutically acceptable salt, ester, prodrug or stereoisomer thereof, wherein:

R¹ is H, alkyl, aryl, arylalkyl, heteroaryl, heteroarylalkyl, cycloalkylalkyl, cycloalkyl, cycloalkenyl, heterocycloalkyl, heterocycloalkenyl, or -alkylene-C(O)N(alkyl)₂, wherein an alkyl or aryl group may be optionally and independently substituted with one or more of the following groups: —(C=N—O-alkyl)CH₃, —NHC(O)NH₂, —NHC(O)NH(alkyl), —NHC(O)N(alkyl)₂, —SO₂NH₂, —SO₂NH(alkyl), —SO₂N(alkyl)₂, —CF₃, —OH, -halo, —CN, -alkoxy, —C(O)O-alkyl, —C(O)N(R⁶)₂, —S(O)alkyl, —SO₂-alkyl, or —P(O)(O-alkyl)₂, an aryl group may further be optionally and independently substituted with one or more alkyl groups, and an alkyl group may further be optionally and independently substituted with one or more aryl groups;

R² is H, alkyl, cycloalkyl, aryl, arylalkyl, heteroarylalkyl, heterocycloalkyl, heterocycloalkylalkyl, R⁶-A-, alkyl-O—C(O)—, (alkyl)₂-N-alkylene-C(O)—, CN-alkylene-C(O)—, alkyl-O-alkylene-C(O)—, alkyl-C(O)-alkylene-C(O)—, alkyl-NH—C(O)— or alkyl-O—C(O)-alkylene-C(O)—, wherein an alkyl or aryl group may be optionally and independently substituted with one or more of the following groups: —(C=N—O-alkyl)CH₃, —NHC(O)NH₂, —NHC(O)NH(alkyl), —NHC(O)N(alkyl)₂, —SO₂NH₂, —SO₂NH(alkyl), —SO₂N(alkyl)₂, —CF₃, —OH, -halo, —CN, -alkoxy, —C(O)O-alkyl, —S(O)alkyl, —SO₂-alkyl, or —P(O)(O-alkyl)₂, and an aryl group may further be optionally and independently substituted with one or more alkyl groups;

R³ is H, alkyl, aryl, arylalkyl, arylalkenyl, arylalkynyl, —NH-arylalkyl, arylalkoxy, cycloalkyl, heteroaryl, heteroarylalkyl, heteroarylalkenyl or heteroarylalkynyl, wherein an alkyl or aryl group can be optionally and independently substituted with one or more of the following groups: —(C=N—O-alkyl)CH$_3$, —NH—C(O)NH-alkyl, —C(O)NH$_2$, —CN, —C(O)NH-alkyl, —C(O)O-alkyl, —C(O)H, —C(O)OH, —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, —CF$_3$, —OH, -halo, —CN, -alkoxy, —C(O)O-alkyl, —S(O)alkyl, —SO$_2$-alkyl, or —P(O)(O-alkyl)$_2$, an aryl group can be optionally and independently substituted with one or more alkyl groups, and a heteroaryl group can be optionally and independently substituted with one or more aryl or heteroaryl groups;

each occurrence of $R^4$ and $R^5$ is independently —C($R^7$)$_2$—, wherein the ring carbon atom of one $R^4$ group and the ring carbon atom of one $R^5$ group may optionally be joined by a —CH$_2$—CH$_2$— group;

each occurrence of $R^6$ is independently alkyl, alkenyl, aryl, heteroaryl, cycloalkyl, cycloalkylalkyl, heterocycloalkyl, cycloalkenyl, heterocycloalkenyl, benzofused cycloalkyl, benzofused heterocycloalkyl or benzofused heterocycloalkenyl;

each occurrence of $R^7$ is independently H, alkyl, —CN, or —OH;

A is —C(O)—, —OC(O)—, —NHC(O)—, -alkylene-C(O)—, —O-alkylene-C(O)—, —C(O)-alkylene-C(O)—, —C(O)—CH$_2$—NHC(O)—, -alkylene-, -alkenylene-, -alkenylene-C(O)—,

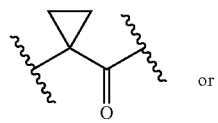

-alkylene-NHC(O)—, wherein an A group is joined to the nitrogen atom to which it is attached via a terminal C(O), alkylene, or alkenylene group;

u is an integer ranging from 0 to 3; and v is an integer ranging from 0 to 3; such that the sum of u and v is from 3 to 5, such that the compound of formula (II) is not a compound of formula (IA), (IB), (IC) or (ID) as set forth in the above specification.

3. A compound having the formula:

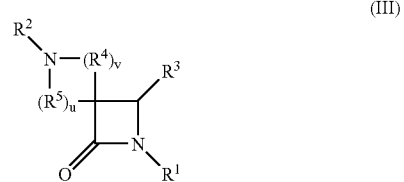

(III)

or a pharmaceutically acceptable salt, ester, prodrug or stereoisomer thereof, wherein:

$R^1$ is alkyl, aryl, cycloalkyl, —CH$_2$-cycloalkyl, —CH$_2$-aryl, —CH(aryl)$_2$, heteroaryl, wherein an aryl group may be optionally substituted with up to 3 substituents independently selected from alkyl, halo, —NO$_2$, —O-alkyl, —CN, —C(O)O-alkyl, —CF$_3$, —C(O)-alkyl or —S(O)$_2$-alkyl;

$R^2$ is H, —C(O)aryl, —C(O)NH-alkyl, —C(O)NH-alkylene-aryl, —C(O)NR$^6$-aryl, —C(O)NH-cycloalkyl, —C(O)NH—CH$_2$-aryl, —C(O)NH-heteroaryl, —C(O)NH-heterocycloalkyl, —C(O)NH-benzofused heterocycloalkyl, —C(O)O-alkyl or

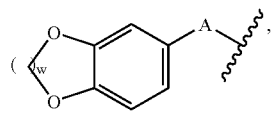

wherein an alkyl group may be optionally substituted with up to 2 substituents independently selected from —OH, —O-alkyl, —C(O)OR$^6$ or —C(O)N(R$^6$)$_2$; an aryl group may be optionally substituted with up to 3 substituents independently selected from alkyl, —O-alkyl, -halo, unsubstituted alkyl, —CN or —CF$_3$; and a cycloalkyl group may be may be optionally and independently substituted with up to 3 unsubstituted alkyl groups;

$R^3$ is H, aryl or heteroaryl, wherein an aryl group or may be optionally substituted with up to 2 substituents independently selected from alkyl, halo, —OH, or —O-benzyl;

each occurrence of $R^4$ and $R^5$ is independently —CH($R^7$)—, wherein the ring carbon atom of one $R^4$ group and the ring carbon atom of one $R^5$ group may optionally be joined by a —CH$_2$—CH$_2$— group;

each occurrence of $R^6$ is H or alkyl; each occurrence of $R^7$ is independently H, alkyl, —CN, or —OH;

A is —CH$_2$— or —C(O)—;

u and v are each 2; and w is an integer ranging from 1 to 3, such that the compound of formula (III) is not a compound of formula (IA), (IB), (IC) or (ID) as set forth in Tables 1-4 in the above specification.

4. The compound of claim 1, wherein $R^1$ is H, alkyl, aryl, substituted aryl, diphenylmethyl, heteroaryl, substituted heteroaryl, arylalkyl, cycloalkylalkyl or cycloalkyl.

5. The compound of claim 1, wherein $R^1$ is H, diphenylmethyl, methyl, isopropyl, —CH$_2$-cyclopropyl, benzyl, 2-chlorobenzyl, 2-pyridyl or phenyl, wherein a phenyl may be optionally and independently substituted with up to 2 substituents selected from Cl, Br, F, methoxy, —C(O)CH$_3$, —NO$_2$, —CN, —S(O)$_2$CH$_3$, —C(O)OCH$_3$ and —CF$_3$.

6. The compound of claim 1 wherein $R^2$ is $R^6$—C(O)—, $R^6$—NH—C(O)— or $R^6$—O—C(O)—, and $R^6$ is alkyl, aryl, heteroaryl, cycloalkyl, cycloalkylalkyl, heterocycloalkyl, cycloalkenyl, heterocycloalkenyl, benzofused cycloalkyl, benzofused heterocycloalkyl, or benzofused heterocycloalkenyl.

7. The compound of claim 1 wherein $R^2$ is alkyl-O—C(O)—.

8. The compound of claim 1 wherein $R^2$ is $R^6$—C(O)— and $R^6$ is phenyl, benzofused heterocycloalkyl, indolin-1-yl,

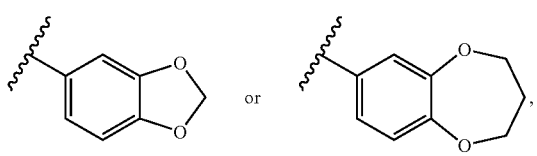

wherein a phenyl may be optionally and independently substituted with from 1-3 substitutents selected from halo, alkoxy or —C$_1$-C$_6$ alkyl.

9. The compound of claim 1 wherein $R^2$ is $R^6$—NH—C(O)— and $R^6$ is phenyl, naphthyl, benzyl, —$C_1$-$C_6$ alkyl, —CH($CH_3$)-phenyl, cyclopentyl, cyclohexyl, cycloheptyl, adamantyl, —CH(sec-butyl)-C(O)$OCH_3$, —CH(isobutyl)-C(O)$OCH_3$, —C(isopropyl)-C(O)$OCH_3$, —CH(sec-butyl)-C(O)$NH_2$, —CH($CH_2CH_3$)—$CH_2OCH_3$, —CH($CH_2CH_3$)—$CH_2OCH_3$, —CH(isobutyl)-$CH_2OH$, —CH(isopropyl)-$CH_2OH$,

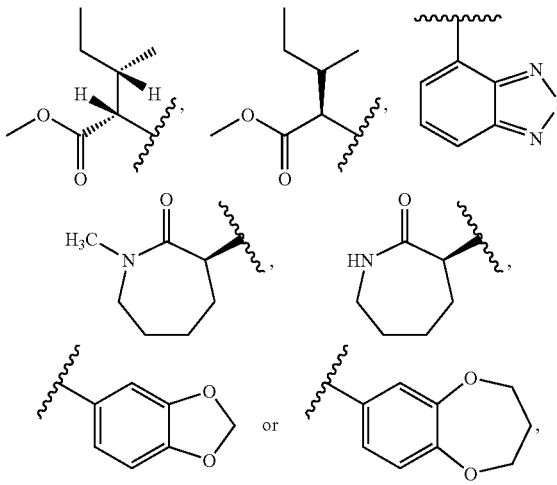

wherein a phenyl group or the phenyl moiety of a benzyl group may be optionally and independently substituted with from 1-3 substitutents selected from -halo, —$CF_3$, —CN, alkoxy or —$C_1$-$C_6$ alkyl, and wherein the methylene moiety of a benzyl group may be optionally substituted with a $C_1$-$C_6$ alkyl group, and wherein a cyclohexyl may be and independently substituted with a —$C_1$-$C_6$ alkyl group.

10. The compound of claim 1 wherein $R^2$ is H, alkyl, cycloalkyl, aryl, arylalkyl, heteroarylalkyl, heterocycloalkyl, heterocycloalkylalkyl, alkyl-O—C(O)—, (alkyl)$_2$N-alkylene-C(O)—, (alkyl)$_2$-N—C(O)-alkylene-C(O)—, CN-alkylene-C(O)—, alkyl-O-alkylene-C(O)—, alkyl-C(O)-alkylene-C(O)—, alkyl-C(O)—NH-alkylene-C(O)—, alkyl-NH—C(O)—, alkyl-O—C(O)-alkylene-C(O)—, alkyl-O—C(O)-cycloalkylene-alkylene-, $NH_2$—C(O)—NH-alkylene-C(O)—, $NH_2$—C(O)-alkylene-C(O)—, alkyl-C(O)—NH-alkylene-5-alkylene-C(O)—, alkyl-O—C(O)-alkylene-C(O)—, alkyl-5-alkylene-C(O)—, alkyl-C(O)-cycloalkylene-alkylene-C(O)—, alkyl-5-alkyene-, (—NHC(O)alkyl)-C(O)—, alkyl(—C(O)Oalkyl)-NH—C(O)—, or —C(O)-alkylene-N($R^6$)$_2$—; or alkyl-5-alkylene(—NHC(O)alkyl)-C(O)—, wherein an alkyl or aryl may be optionally and independently substituted with one or more of the following groups: —(C=N—O-alkyl)$CH_3$, —NHC(O)$NH_2$, —NHC(O)NH(alkyl), —NHC(O)N(alkyl)$_2$, —$SO_2NH_2$, —$SO_2$NH(alkyl), —$SO_2$N(alkyl)$_2$, —$CF_3$, —OH, halo, —CN, -alkoxy, —C(O)O-alkyl, —S(O)alkyl, —$SO_2$-alkyl, or —P(O)(O-alkyl)$_2$.

11. The compound of claim 1 wherein $R^2$ is H, alkyl, cycloalkyl, aryl, arylalkyl, heteroarylalkyl, heterocycloalkyl, heterocycloalkylalkyl or

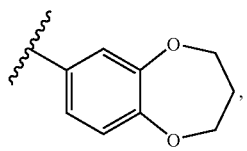

wherein an alkyl or aryl may be optionally and independently substituted with one or more of the following groups: —(C=N—O-alkyl)$CH_3$, —NHC(O)$NH_2$, —NHC(O)NH(alkyl), —NHC(O)N(alkyl)$_2$, —$SO_2NH_2$, —$SO_2$NH(alkyl), —$SO_2$N(alkyl)$_2$, —$CF_3$, —OH, -halo, —CN, -alkoxy, —C(O)O-alkyl, —S(O)alkyl, —$SO_2$-alkyl, or —P(O)(O-alkyl)$_2$.

12. The compound of claim 1, wherein u is 2, v is 2, each occurrence of $R^4$ is —$CH_2$— and each occurrence of $R^5$ is —$CH_2$—.

13. The compound of claim 1 wherein $R^3$ is H, aryl or heteroaryl, wherein an aryl group may be optionally substituted with up to 2 substituents independently selected from halo, —OH, phenyl, pyridyl or —O-benzyl.

14. The compound of claim 13, wherein $R^3$ is H, phenyl, 4-chlorophenyl, 4-fluorophenyl, 2-pyridyl, 4-hydroxyphenyl, 2,4-difluorophenyl, 4-bromophenyl, 4-(—O-benzyl)phenyl,

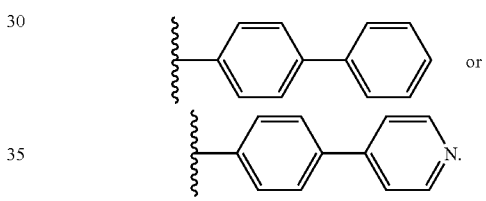

15. The compound of claim 3, wherein $R^1$ is H, diphenylmethyl, methyl, isopropyl, isobutyl, cyclopropyl, —$CH_2$-cyclopropyl, benzyl, 2-chlorobenzyl, 2-pyridyl or phenyl, wherein a phenyl may be optionally and independently substituted with up to 2 substituents selected from Cl, Br, F, methoxy, —C(O)$CH_3$, —$NO_2$, —CN, —S(O)$_2CH_3$, —C(O)$OCH_3$ and —$CF_3$.

16. The compound of claim 3, wherein $R^2$ is H, —C(O)aryl, —C(O)NH-alkyl, —C(O)NH-alkylene-aryl, —C(O)NH-aryl, —C(O)NH-cycloalkyl, —C(O)NH—$CH_2$-aryl, -C(O)NH-heteroaryl, —C(O)NH-heterocycloalkyl, —C(O)NH-benzofused heterocycloalkyl, —C(O)O-alkyl or

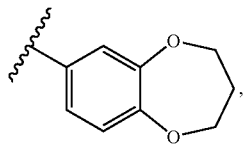

wherein an alkyl group may be optionally substituted with up to 2 substituents independently selected from —OH, —O-alkyl, —C(O)$OR^6$ or —C(O)N($R^6$)$_2$; an aryl group may be optionally substituted with up to 3 substituents independently selected from —O-alkyl, halo, unsubstituted alkyl, —CN or —$CF_3$; and a cycloalkyl or heterocycloalkyl group may be may be optionally and independently substituted with up to 3 unsubstituted alkyl groups.

17. The compound of claim 3, wherein $R^2$ is —C(O)phenyl, —C(O)NH-alkylene-phenyl, —C(O)NH-phenyl, —C(O)NH—CH$_2$-phenyl, wherein a phenyl group may be optionally substituted with up to 3 substituents independently selected from —O-alkyl, halo, unsubstituted alkyl, —CN or —CF$_3$.

18. The compound of claim 3 wherein $R^2$ is —C(O)NH—(C$_1$-C$_6$ alkyl), —C(O)NH-cyclopropyl, —C(O)NH-cycloheptyl, —C(O)NH-cyclopentyl, —C(O)NH-adamantyl or —C(O)NH-cyclohexyl, wherein a C$_1$-C$_6$ alkyl group may be optionally substituted with up to 2 substituents independently selected from —OH, —O-alkyl, phenyl, halo-substituted phenyl, —C(O)OR$^6$ or —C(O)N(R$^6$)$_2$, and a cycloalkyl group may be may be optionally and independently substituted with up to 3 unsubstituted alkyl groups.

19. The compound of claim 3, wherein $R^2$ is —C(O)NHCH(CH$_3$)— phenyl, —C(O)NHCH(sec-butyl)-C(O)OCH$_3$, —C(O)NHCH(isopropyl)-C(O)OCH$_3$, —C(O)NHCH(sec-butyl)-C(O)NH$_2$, —C(O)NHCH(CH$_2$CH$_3$)—CH$_2$OCH$_3$, —C(O)NHCH(isobutyl)-CH$_2$OH, —C(O)NHCH(isopropyl)-CH$_2$OH or

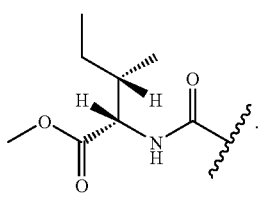

20. The compound of claim 3, wherein $R^2$ is

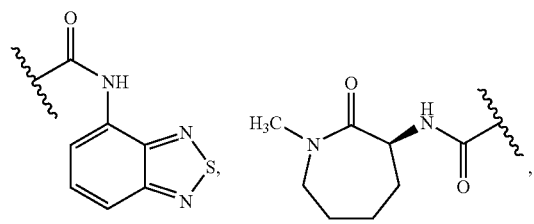

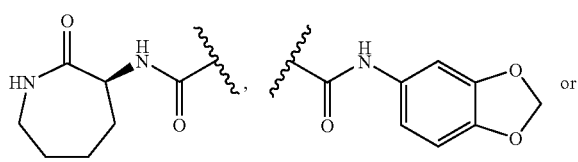

21. The compound of claim 3, wherein $R^3$ is H, phenyl, 4-chlorophenyl, 4-fluorophenyl, 2-pyridyl, 4-hydroxyphenyl, 2,4-difluorophenyl, 4-bromophenyl or 4-(—O-benzyl)phenyl.

22. A compound having the structure:

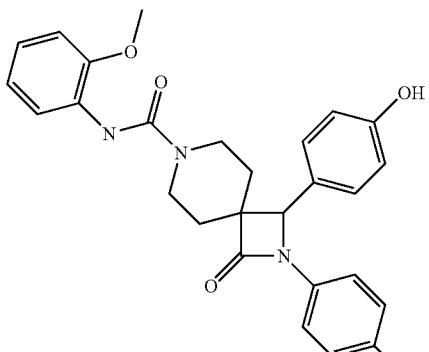

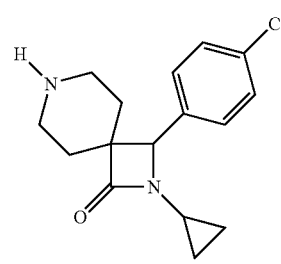

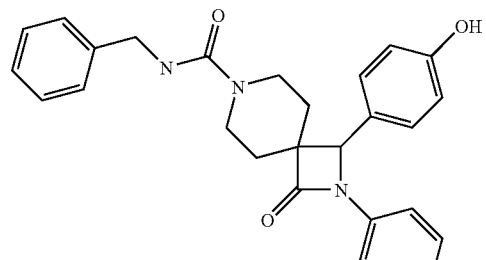

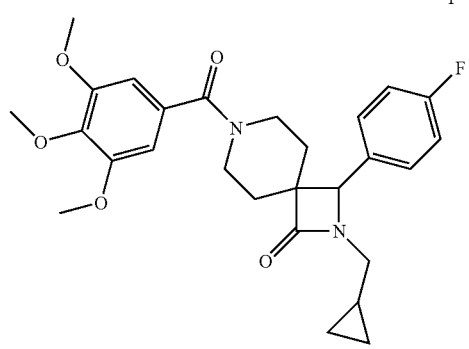

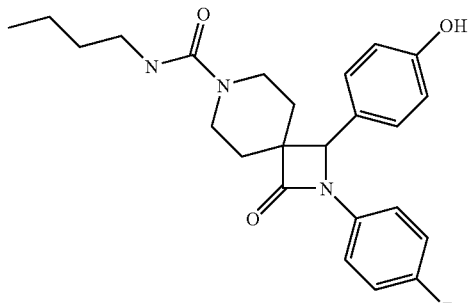

-continued
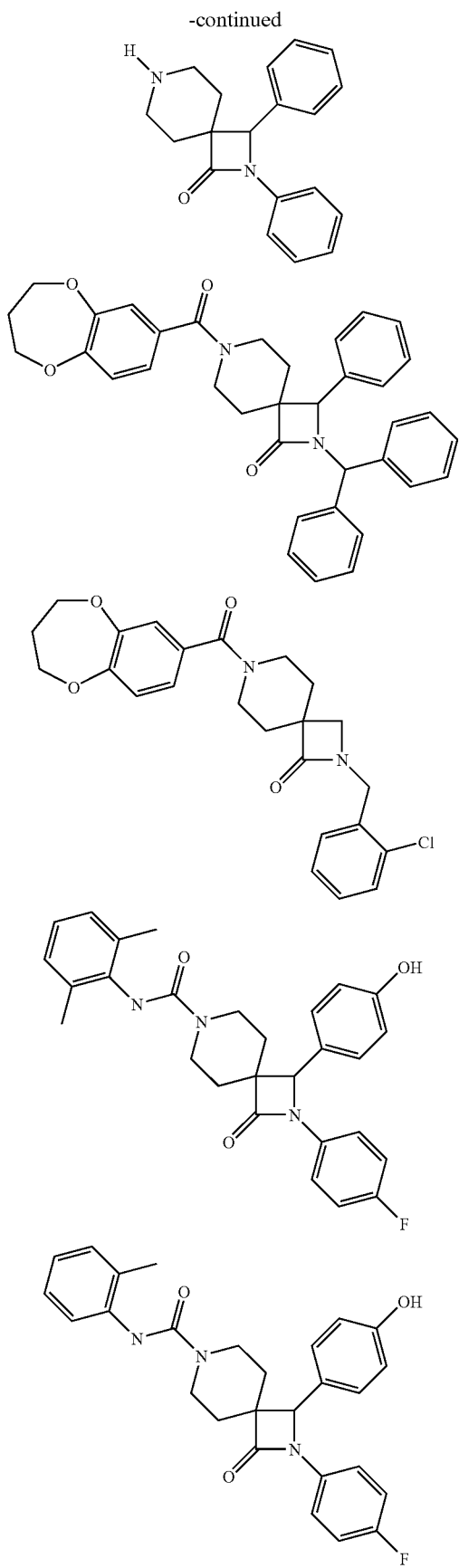
-continued
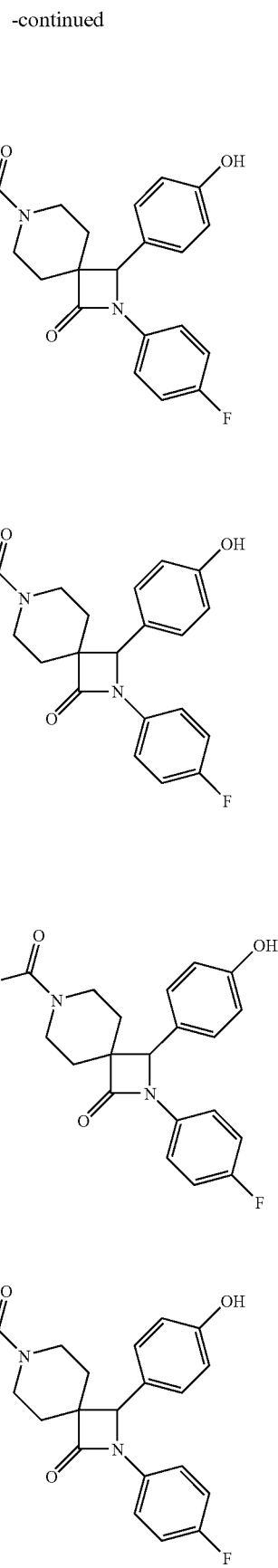

297
-continued
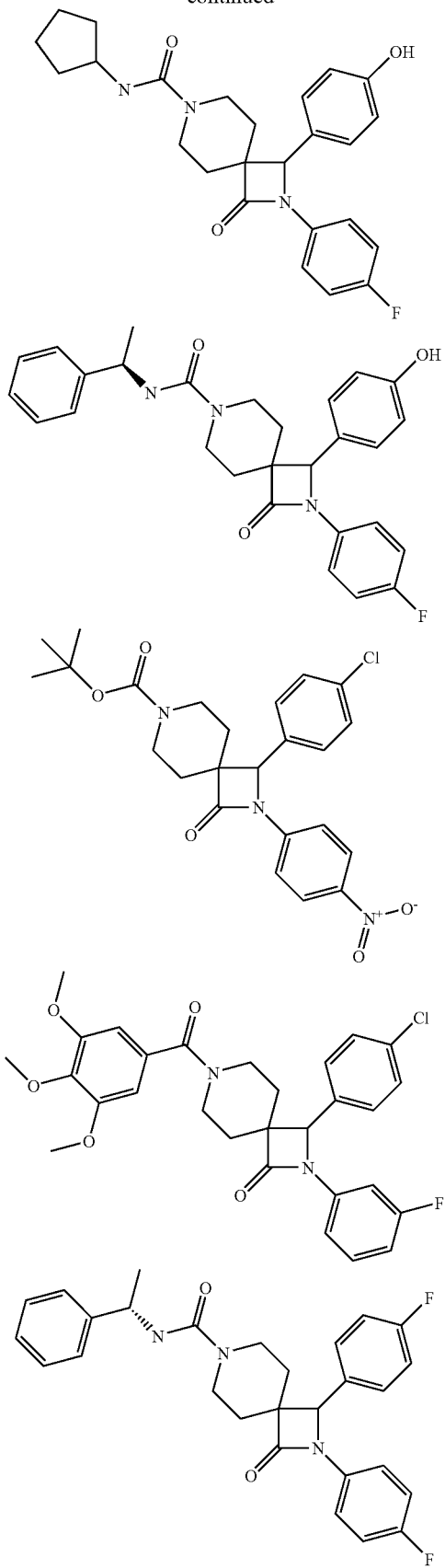
298
-continued
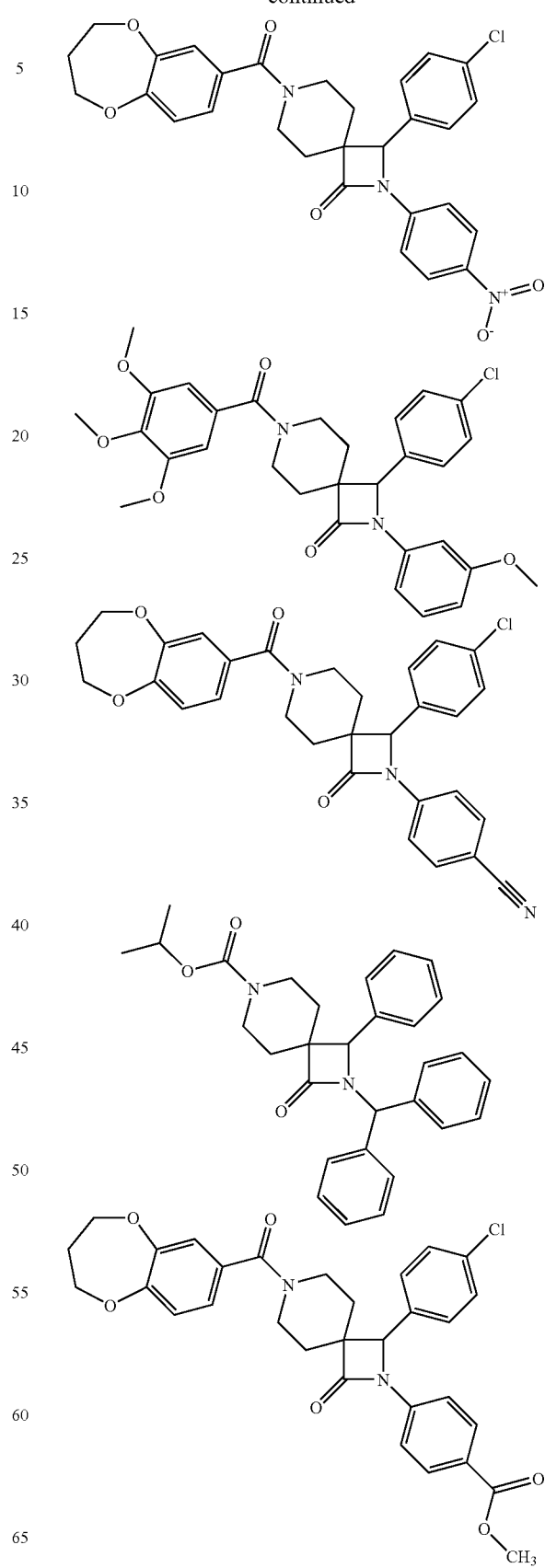

299
-continued
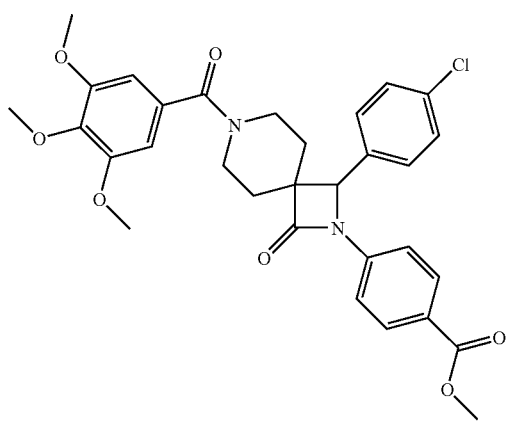
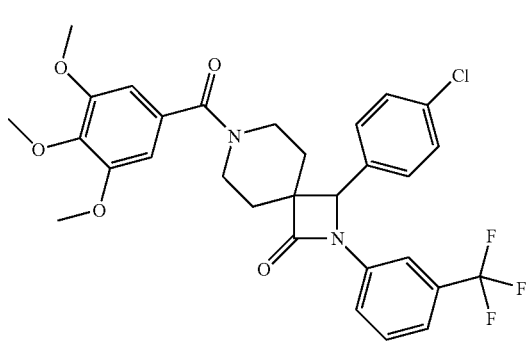
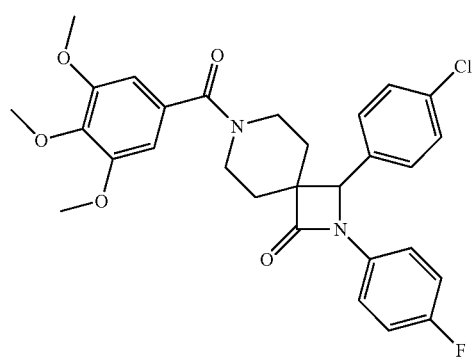
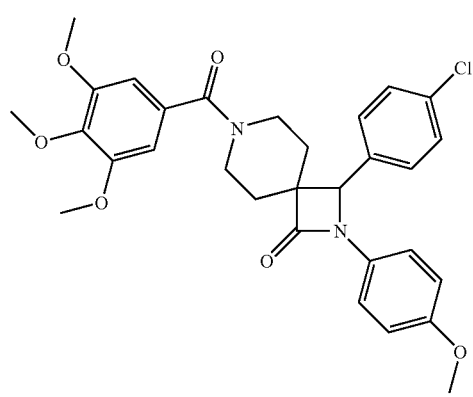
300
-continued
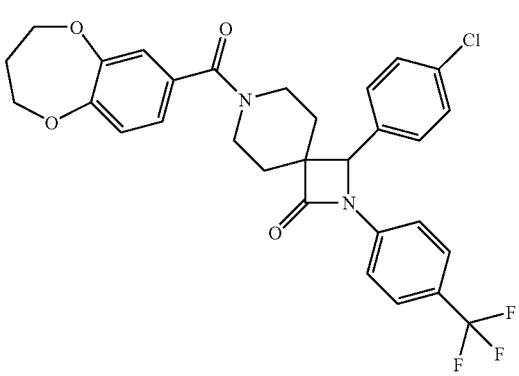
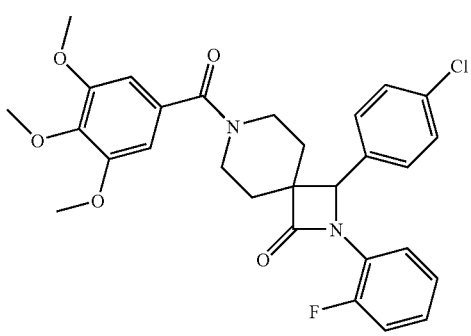
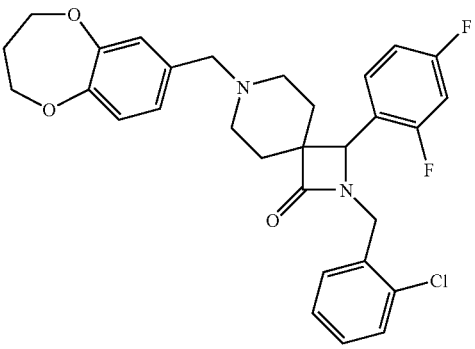
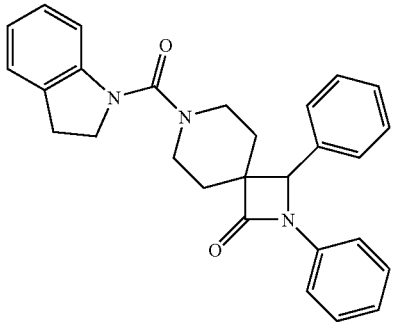

301
-continued
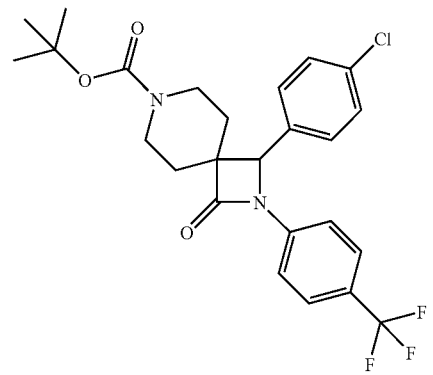
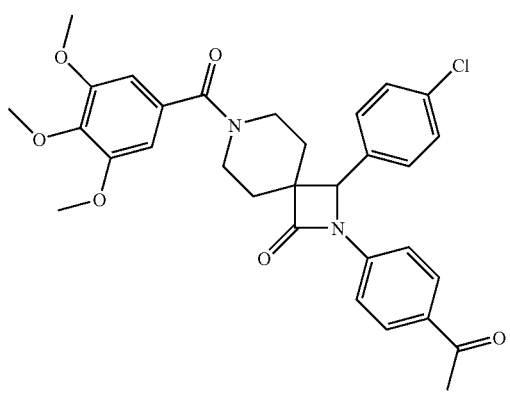
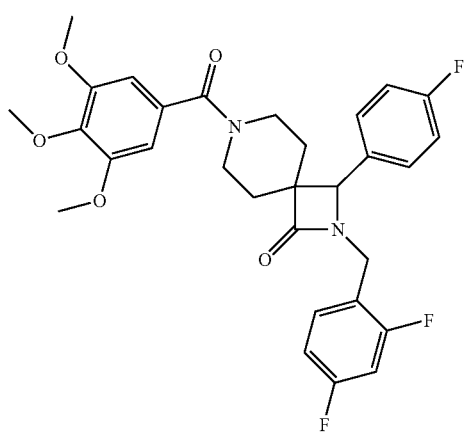
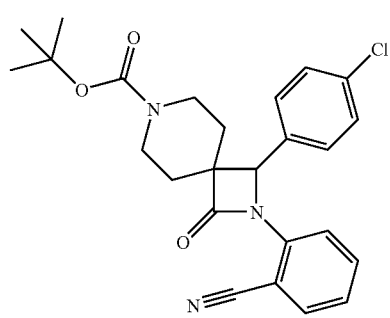
302
-continued
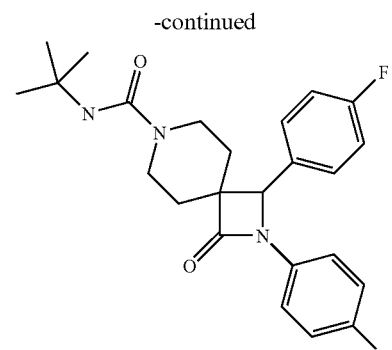
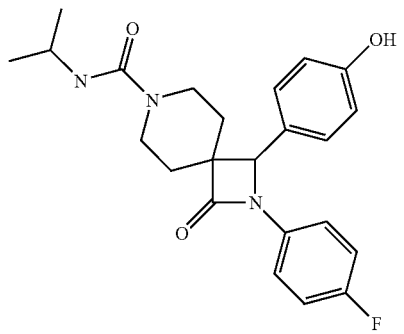
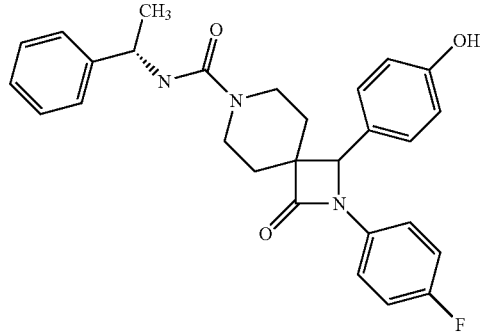
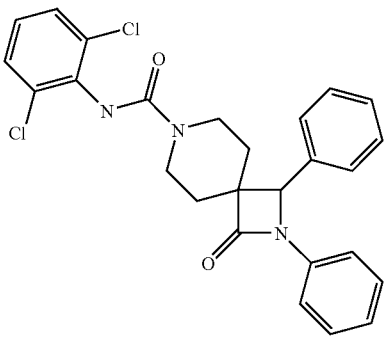
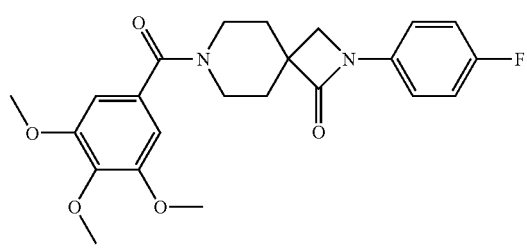

-continued
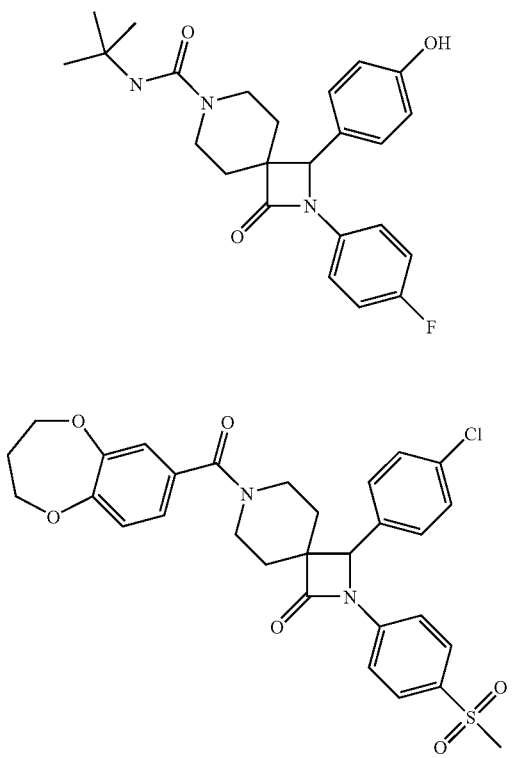
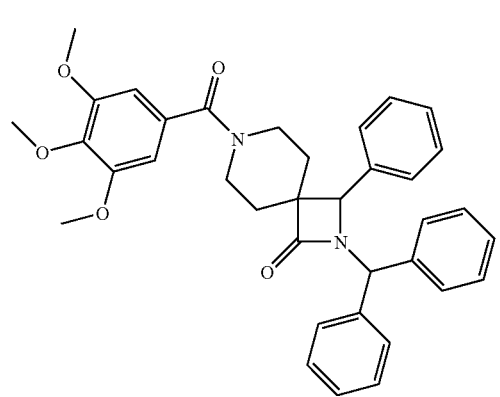
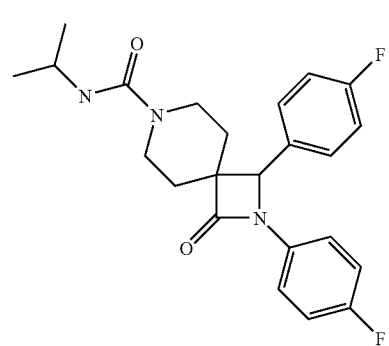
-continued
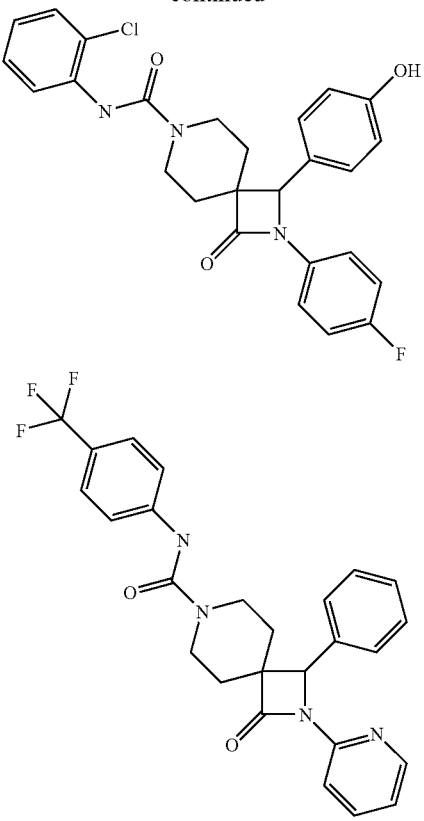
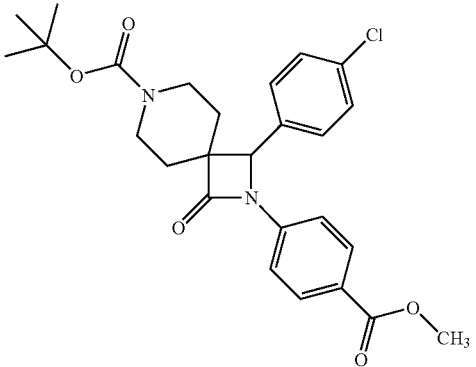

305
-continued
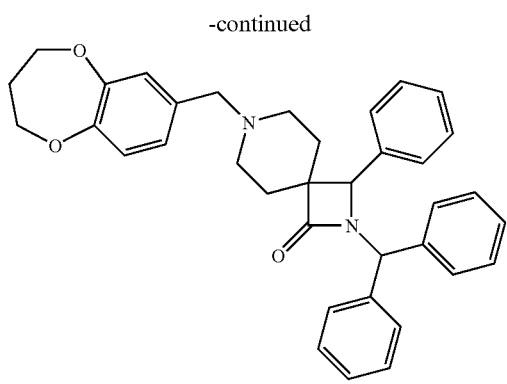
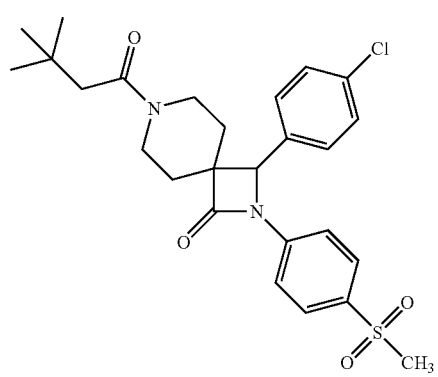
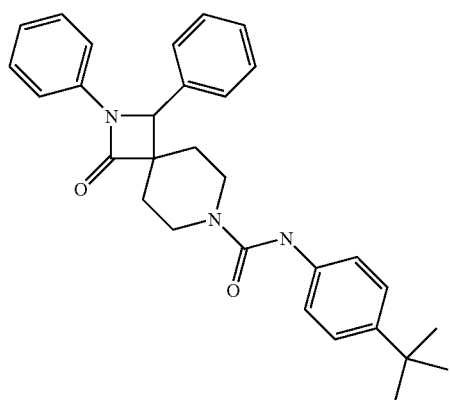
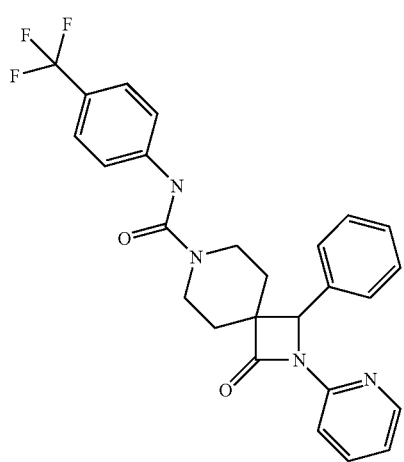
306
-continued
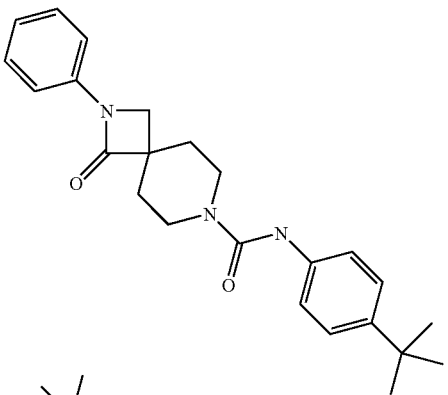
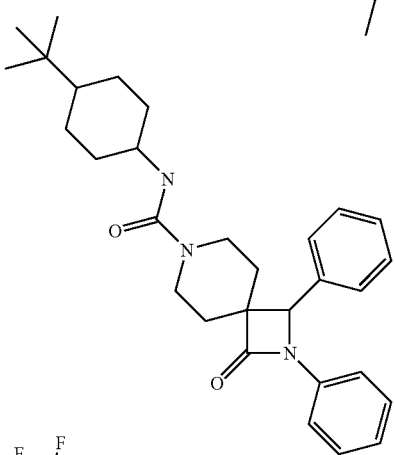
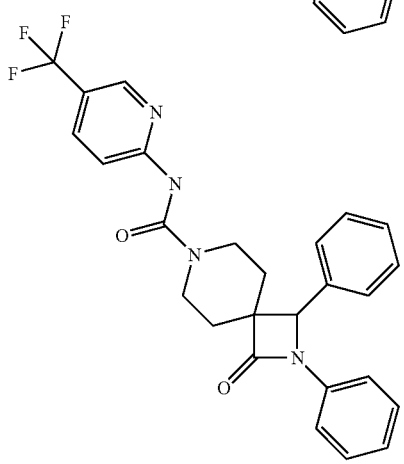
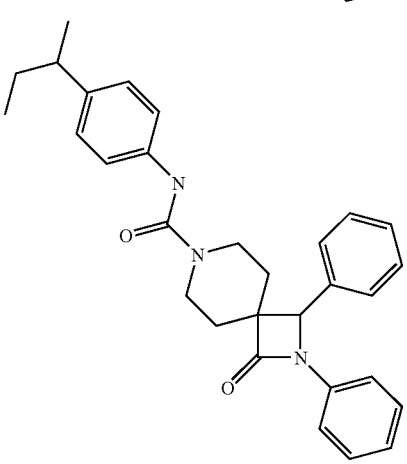

307
-continued
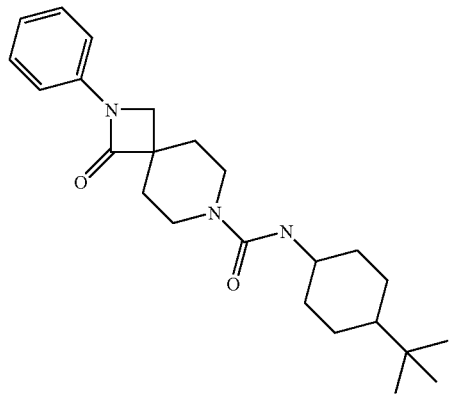
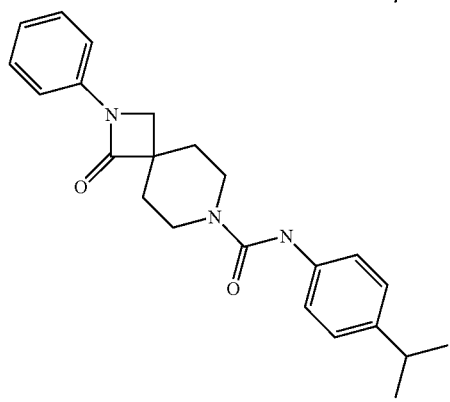
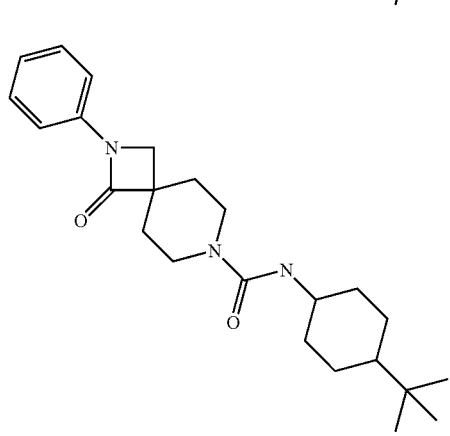
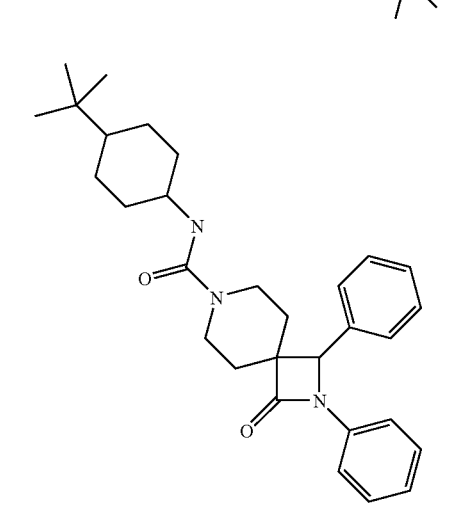
308
-continued
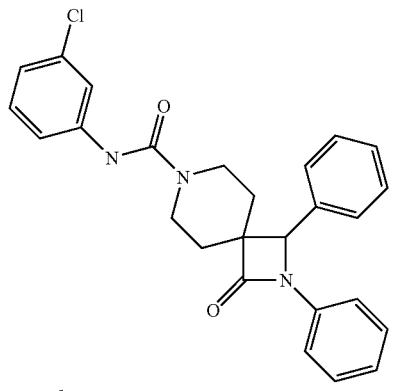
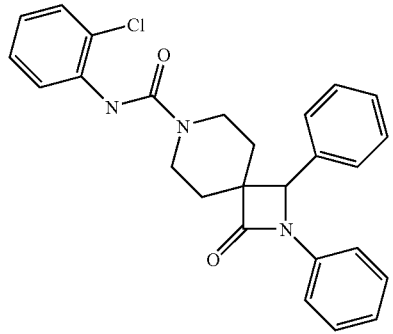
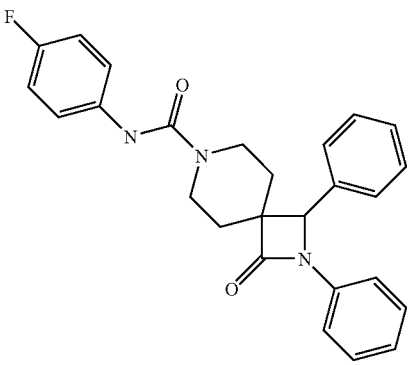
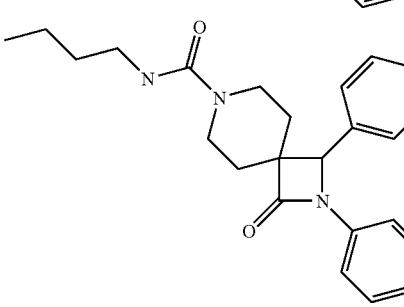
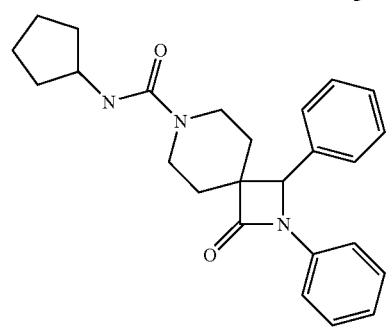

309 -continued
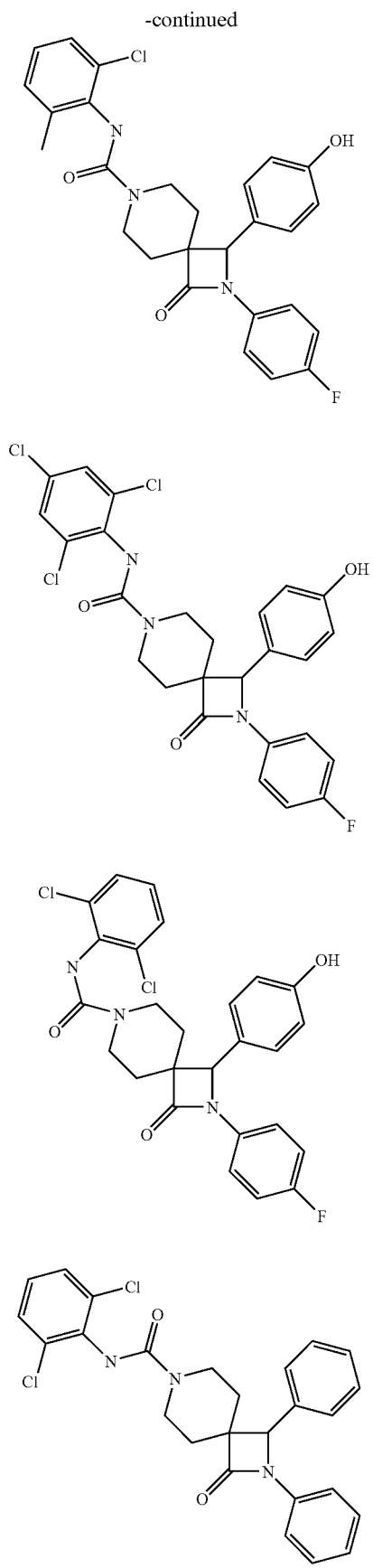
310 -continued
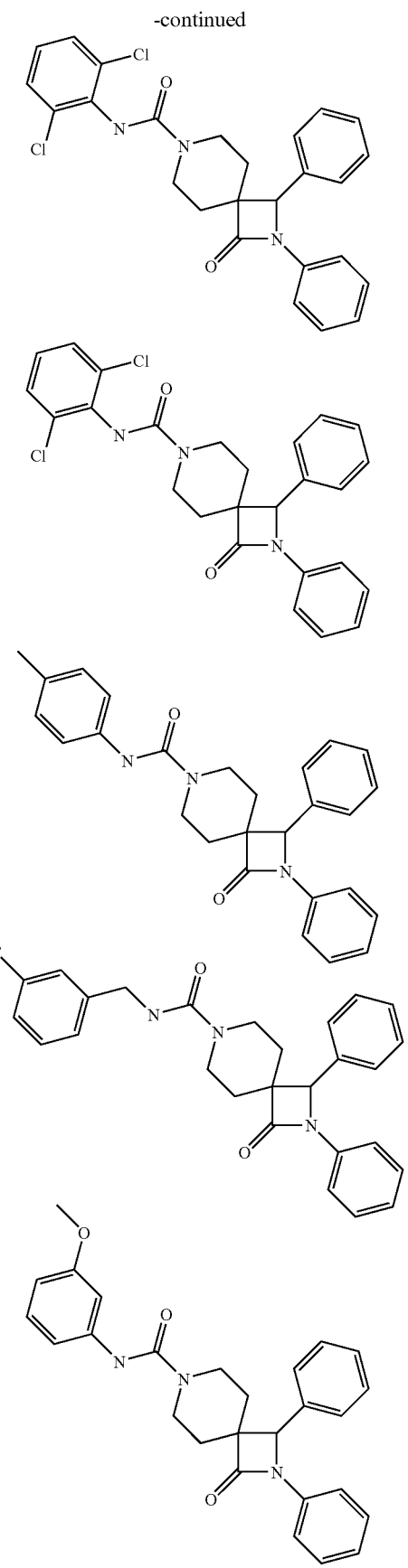

311
-continued
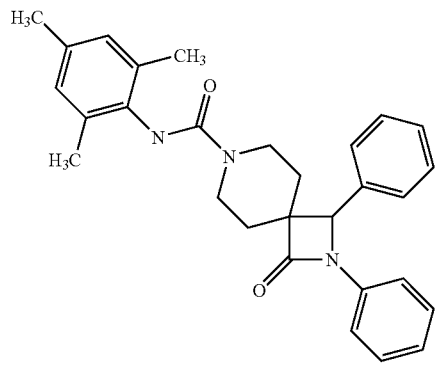
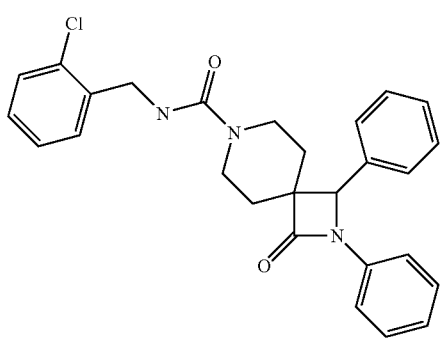
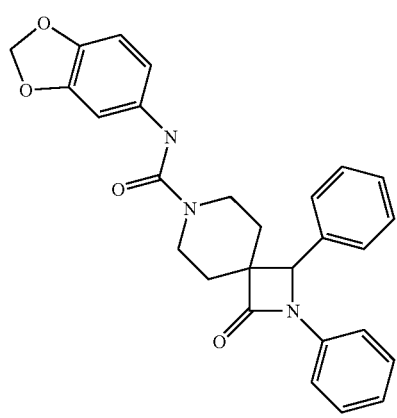
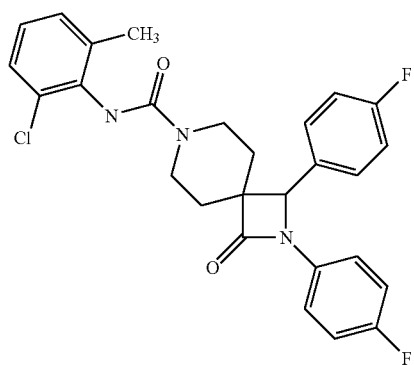
312
-continued
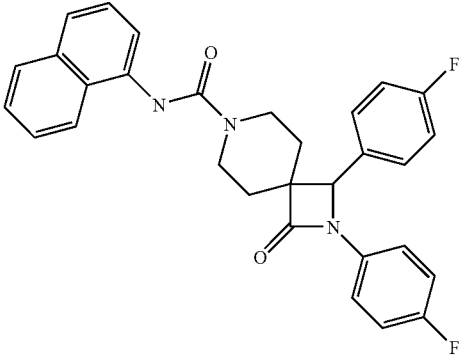
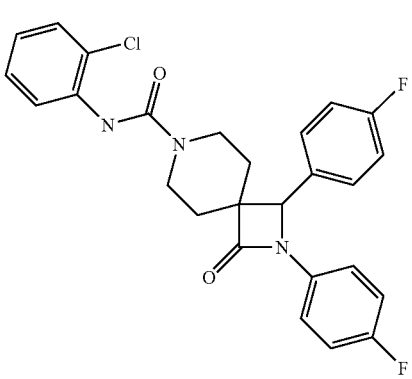
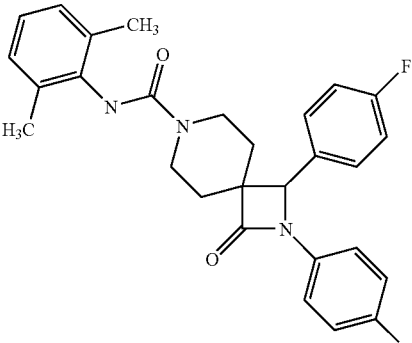
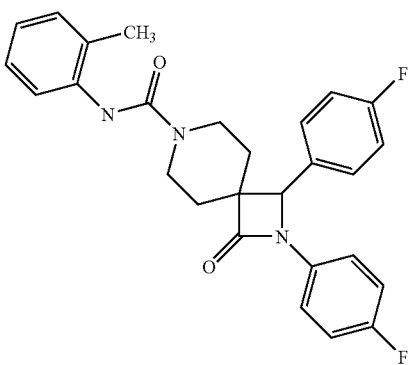

313
-continued
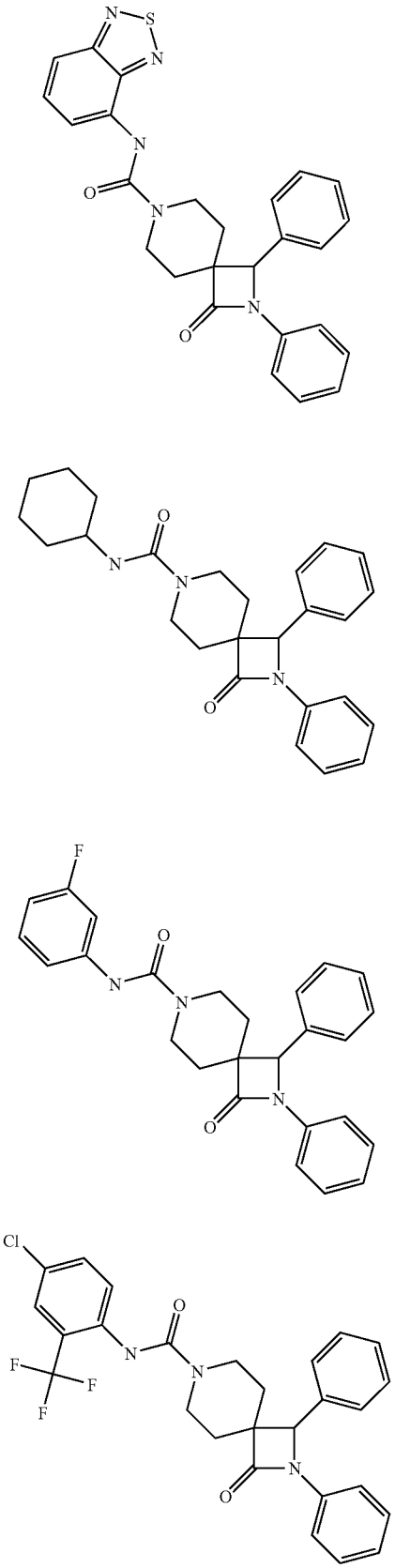
314
-continued
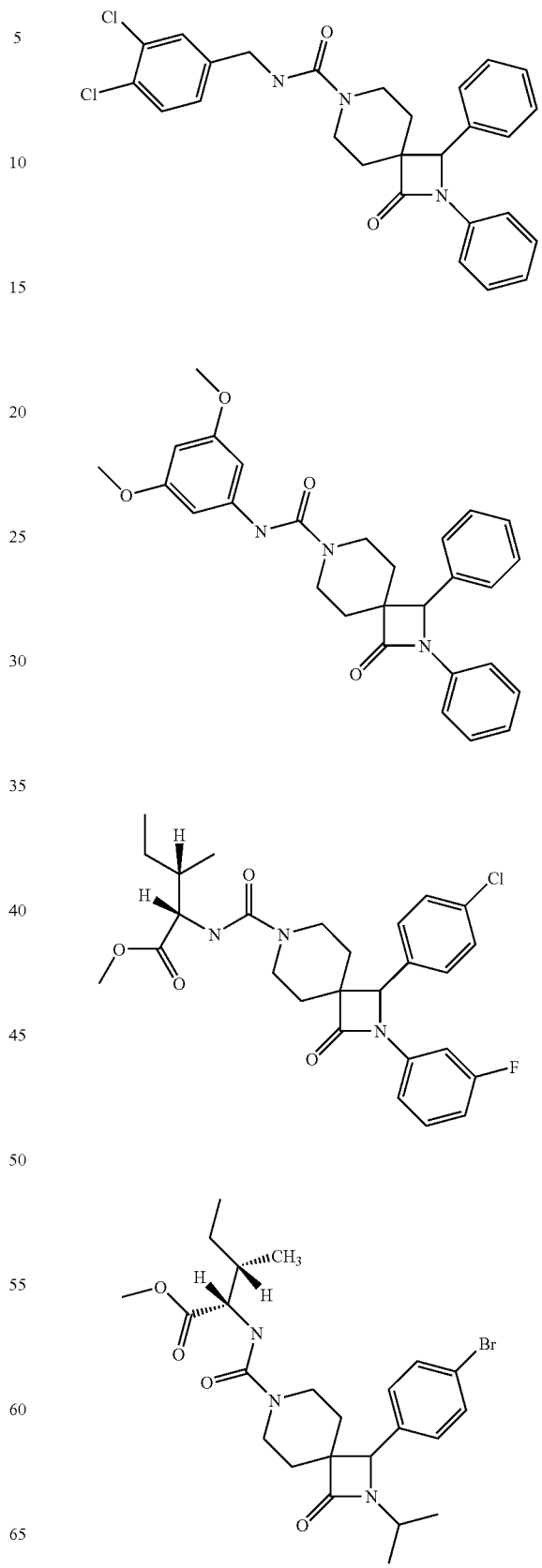

315
-continued
316
-continued
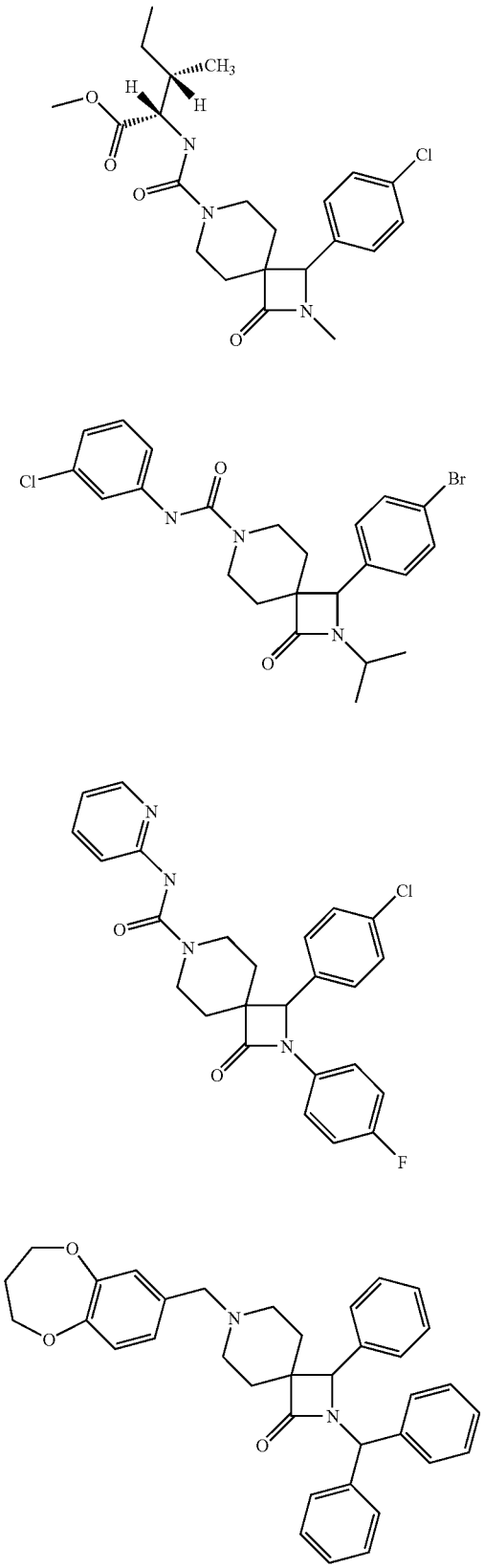
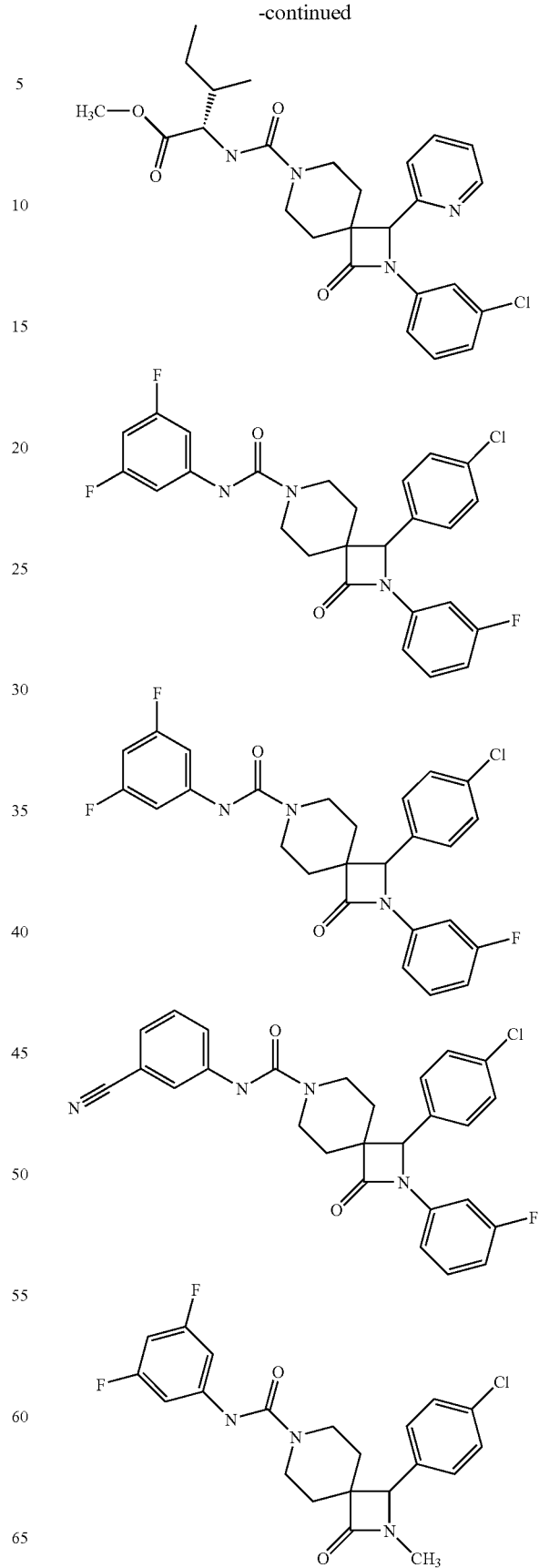

317
-continued
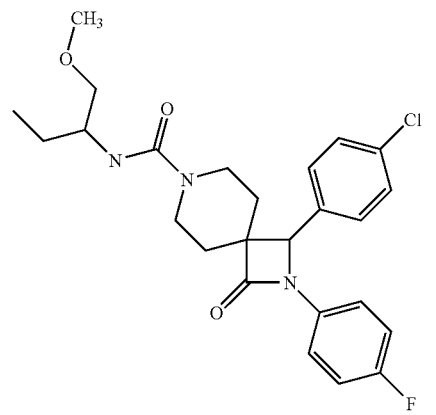
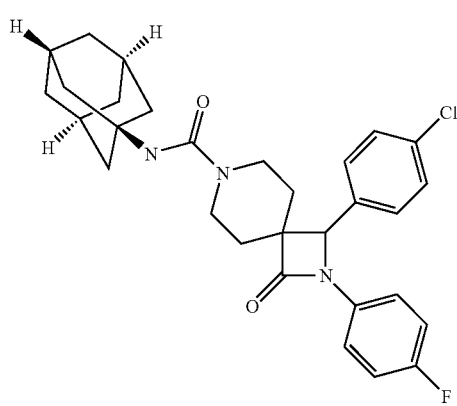
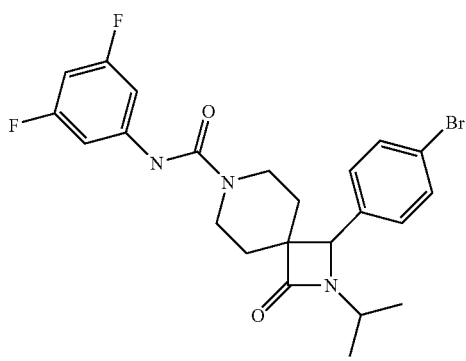
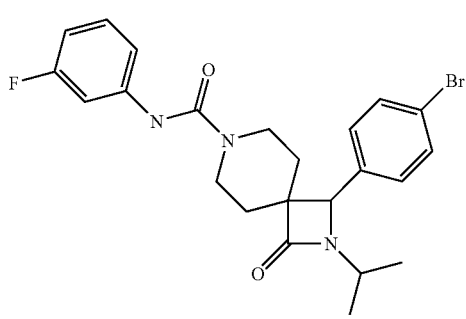
318
-continued
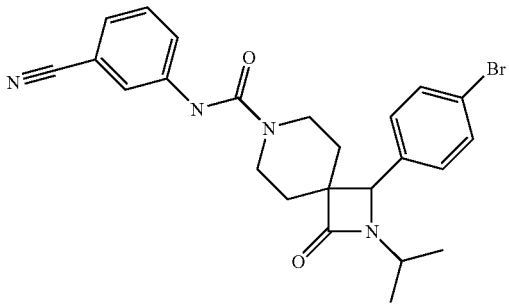
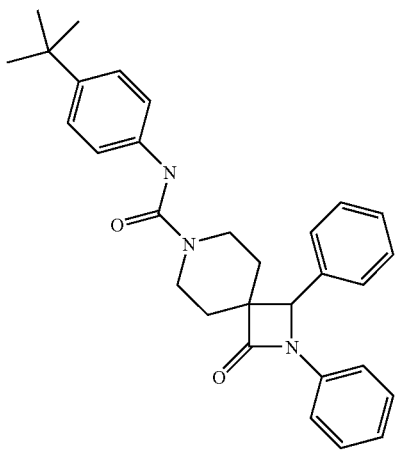
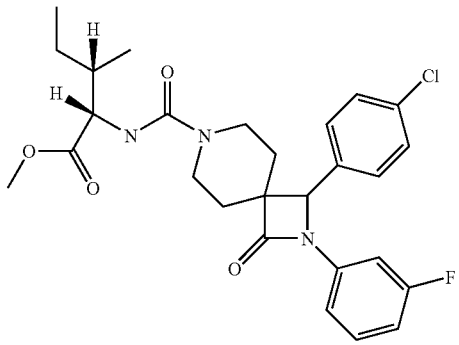
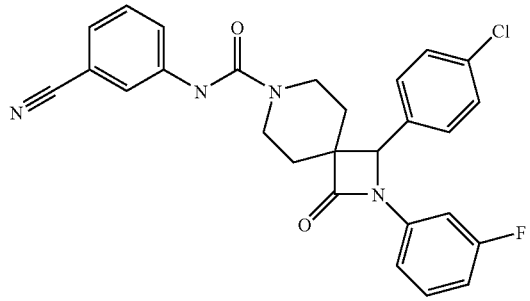
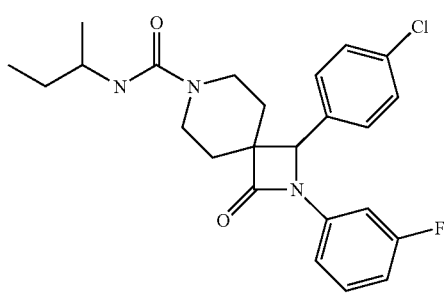

-continued
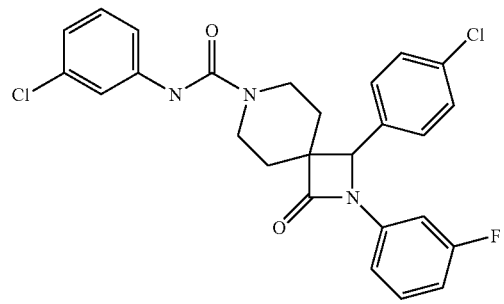
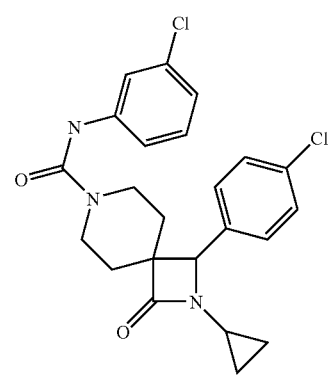
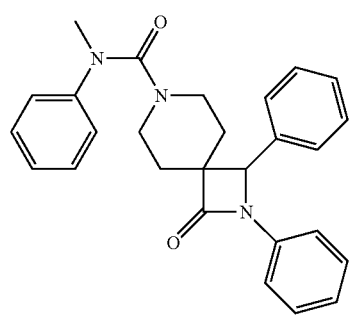
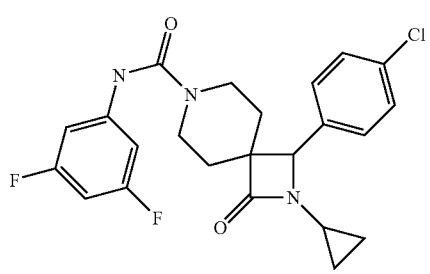
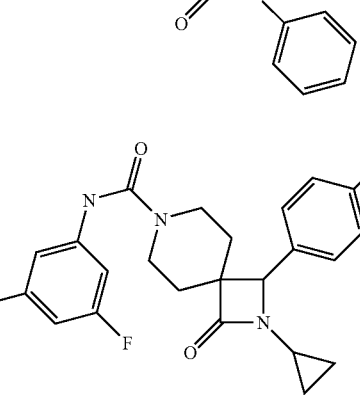
-continued
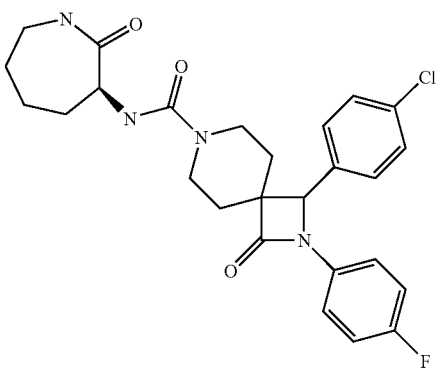
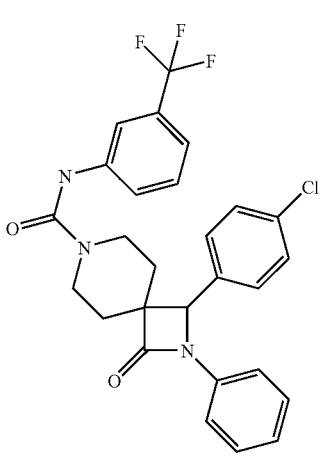
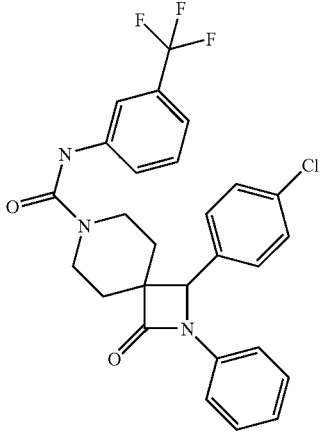
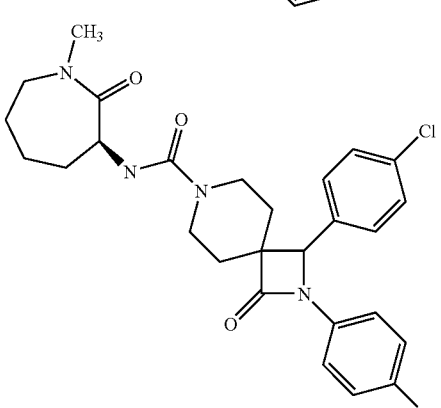

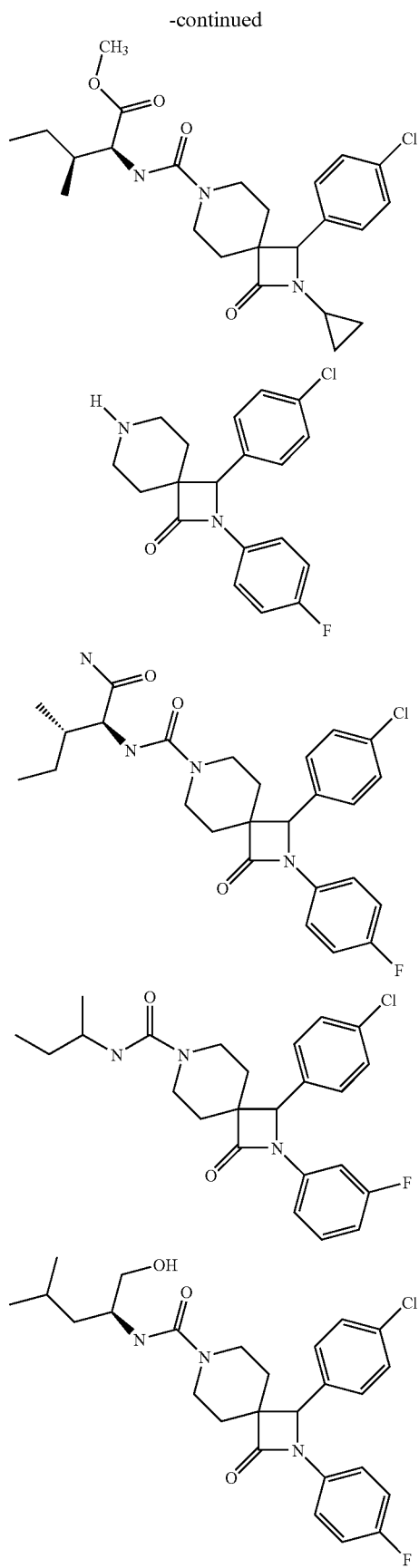
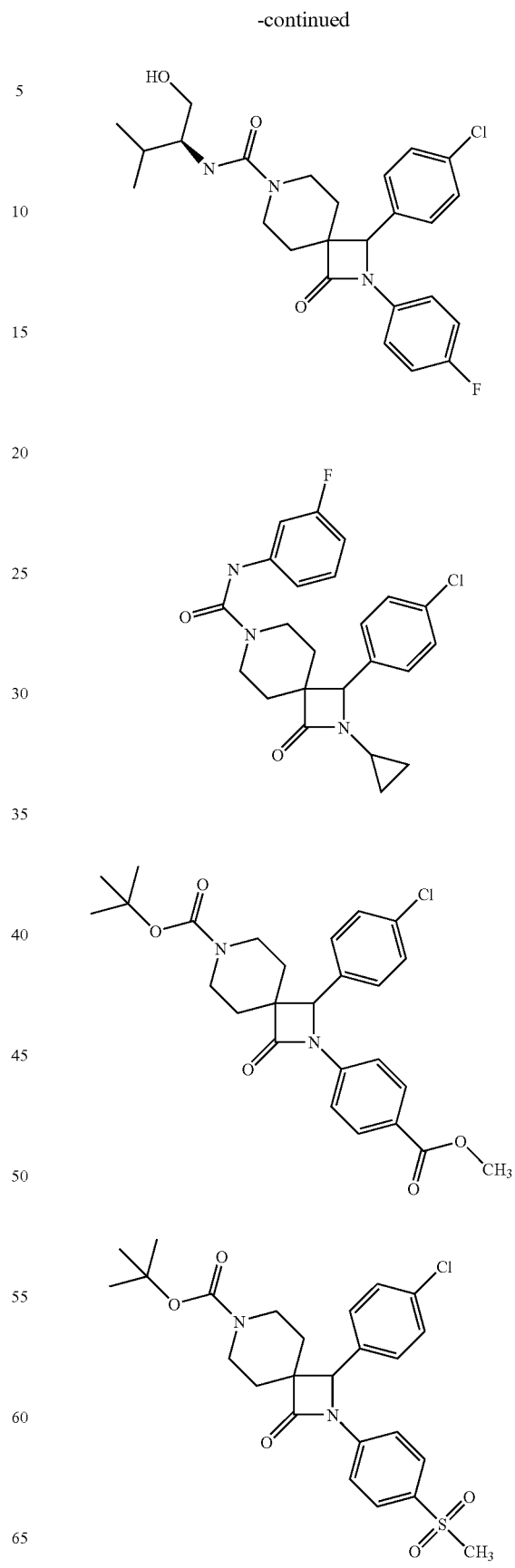

323
-continued
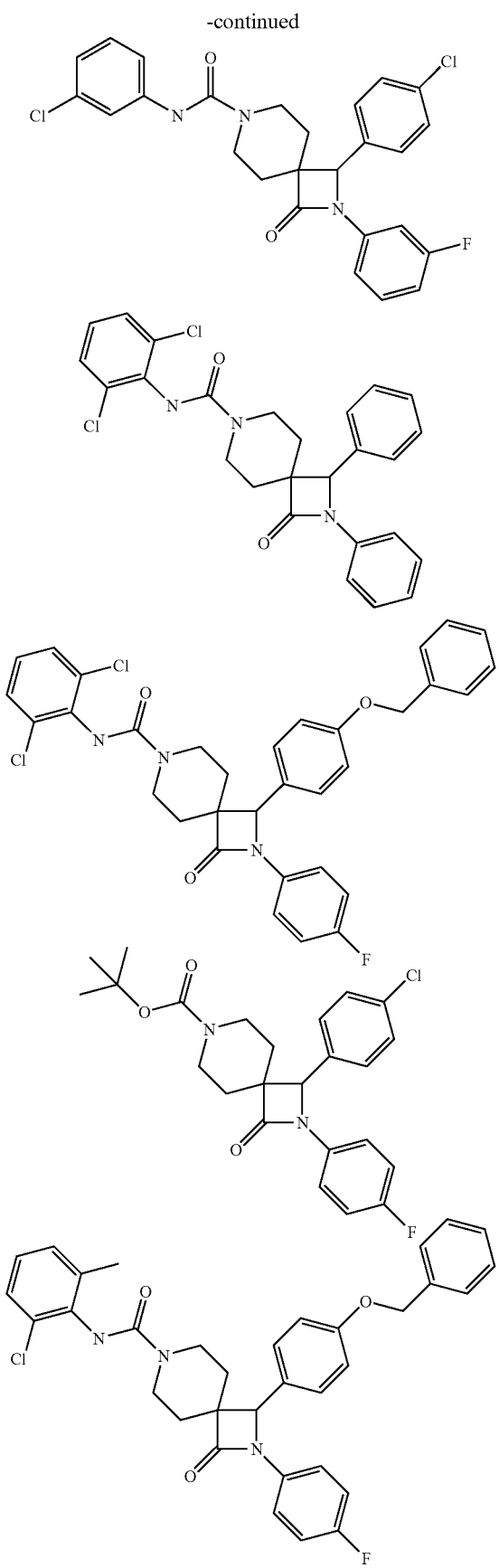
324
-continued
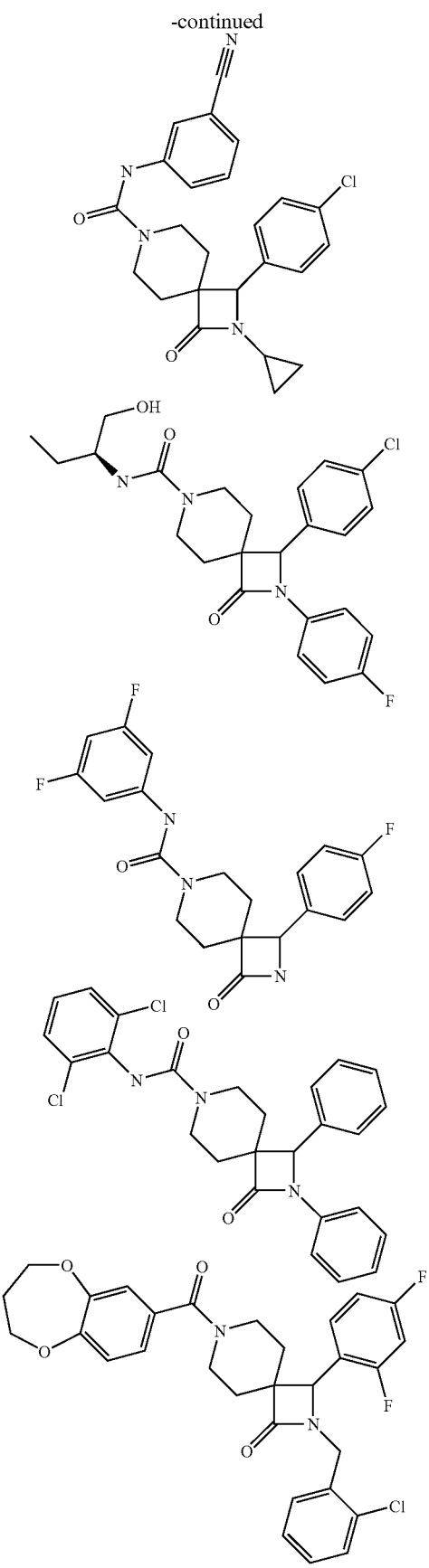

-continued
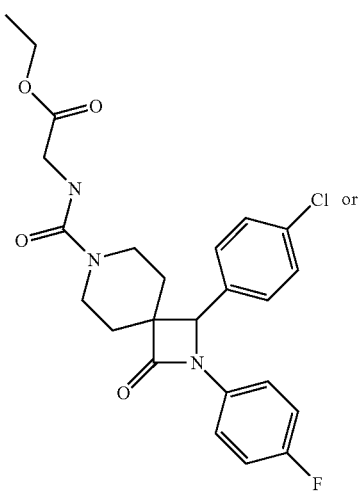
or
-continued
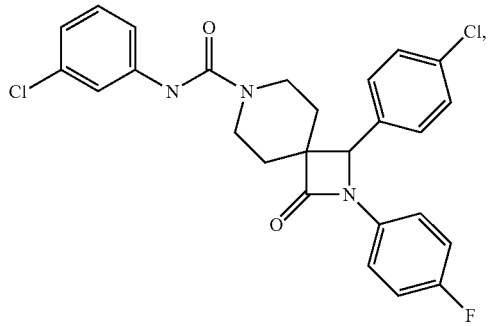
or a pharmaceutically acceptable salt, ester, prodrug or stereoisomer thereof.
23. A composition comprising a compound of claim 1 and a pharmaceutically acceptable carrier.
* * * * *